US012637685B2

(12) United States Patent
Meng

(10) Patent No.: US 12,637,685 B2
(45) Date of Patent: May 26, 2026

(54) METHOD FOR RAPID GENOME MODIFICATION IN RECALCITRANT PLANTS

(71) Applicant: KWS SAAT SE & Co. KGaA, Einbeck (DE)

(72) Inventor: Ling Meng, Saint Louis, MO (US)

(73) Assignee: KWS SAAT SE & Co. KGaA, Einbeck (DE)

( * ) Notice: Subject to any disclaimer, the term of this patent is extended or adjusted under 35 U.S.C. 154(b) by 211 days.

(21) Appl. No.: 17/800,696

(22) PCT Filed: Feb. 26, 2021

(86) PCT No.: PCT/EP2021/054805
§ 371 (c)(1),
(2) Date: Aug. 18, 2022

(87) PCT Pub. No.: WO2021/170787
PCT Pub. Date: Sep. 2, 2021

(65) Prior Publication Data
US 2024/0191248 A1     Jun. 13, 2024

Related U.S. Application Data

(60) Provisional application No. 62/982,979, filed on Feb. 28, 2020.

(51) Int. Cl.
*C12N 15/82*      (2006.01)

(52) U.S. Cl.
CPC ................................. *C12N 15/8262* (2013.01)

(58) Field of Classification Search
CPC ................................................. C12N 15/8262
USPC ........................................................ 800/278
See application file for complete search history.

(56) References Cited

U.S. PATENT DOCUMENTS

| | | | |
|---|---|---|---|
| 6,528,701 B1 | 3/2003 | Wang et al. |
| 6,825,397 B1 | 11/2004 | Lowe et al. |
| 7,763,774 B2 | 7/2010 | Hehl et al. |
| 7,767,801 B2 | 8/2010 | Hehl et al. |
| 7,960,612 B2 | 6/2011 | Zhang et al. |
| 9,476,057 B2 | 10/2016 | Samuel et al. |
| 2008/0229439 A1 | 9/2008 | La Rosa et al. |
| 2010/0162427 A1 | 6/2010 | Riechmann et al. |
| 2011/0165679 A1 | 7/2011 | Gordon-Kamm et al. |
| 2014/0219925 A1 | 8/2014 | Bertrand et al. |
| 2014/0237681 A1 | 8/2014 | Gordon-Kamm et al. |
| 2017/0121722 A1 | 5/2017 | Anand et al. |
| 2017/0233756 A1 | 8/2017 | Begemann et al. |
| 2018/0028686 A1 | 2/2018 | Brinker et al. |
| 2019/0225974 A1 | 7/2019 | D'Halluin et al. |
| 2021/0277407 A1 | 9/2021 | Kong et al. |
| 2022/0025388 A1 | 1/2022 | Meng |
| 2024/0417743 A1 | 12/2024 | Meng |

FOREIGN PATENT DOCUMENTS

| | | |
|---|---|---|
| CN | 101750487 A | 6/2010 |
| CN | 101849009 A | 9/2010 |
| CN | 109879944 A | 6/2019 |
| CN | 109983122 A | 7/2019 |
| EP | 2771468 B1 | 2/2015 |
| EP | 3159413 A1 | 4/2017 |
| EP | 3009511 B1 | 5/2017 |
| EP | 3252162 A1 | 12/2017 |
| EP | 3456825 A1 | 3/2019 |
| WO | 199418313 A1 | 8/1994 |
| WO | 199509233 A1 | 4/1995 |
| WO | 2003004659 A1 | 1/2003 |
| WO | 2003080809 A1 | 10/2003 |
| WO | 2010079430 A1 | 7/2010 |
| WO | 2011072246 A1 | 6/2011 |

(Continued)

OTHER PUBLICATIONS

Tsuwamoto et al., "Arabidopsis EMBRYOMAKER encoding an AP2 domain transcription factor plays a key role in developmental change from vegetative to embryonic phase", Plant Molecular Biology, 2010, vol. 73, pp. 481-492.
Yang et al., "Trichostatin A and 5-azacytidine both cause an increase in global histone H4 acetylation and a decrease in global DNA and H3K9 methylation during mitosis in maize", BMC Plant Biology, 2010, vol. 10, No. 178, 11 pages.
Prasad et al., "*Arabidopsis* PLETHORA transcription factors control phyllotaxis", Current Biology, 2011, vol. 21, No. 13, pp. 1123-1128.
Purwestri et al., "RWP-PK Domain 3 (OsRKD3) induces somatic embryogenesis in black rice", BMC Plant Biology, 2023, vol. 23, No. 202, 15 pages.

(Continued)

*Primary Examiner* — Li Zheng
(74) *Attorney, Agent, or Firm* — Troutman Pepper Locke LLP

(57) ABSTRACT

The present invention provides a method for plant genome modification, preferably for the targeted modification of at least one genomic target sequence, for obtaining at least one modified cell, wherein modification of a cell is achieved by providing a genome modification or editing system together with at least one regeneration booster, or a combination of regeneration boosters, which is/are transiently active in the cell and/or with at least one epigenetically regulating chemical. Preferably, the effector molecules are introduced by means of particle bombardment. Furthermore, the modified plant cell is regenerated to obtain a plant, which inherits the modification to its progeny. In addition, methods, tools, constructs and strategies are provided to effectively modify the genome of a plant cell or at least one genomic target site in a plant cell, to obtain said modified cell and to regenerate a plant tissue, organ, plant or seed from the modified cell. Finally, the present invention also relates to an improved method of regenerating a plant tissue, organ or a plant from a single plant cell.

18 Claims, 24 Drawing Sheets
Specification includes a Sequence Listing.

(56) References Cited

FOREIGN PATENT DOCUMENTS

| WO | 2011082310 A2 | 7/2011 | | |
|----|---------------|--------|---|---|
| WO | 2011082318 A2 | 7/2011 | | |
| WO | 2011146121 A1 | 11/2011 | | |
| WO | 2011154393 A1 | 12/2011 | | |
| WO | 2012001527 A1 | 1/2012 | | |
| WO | 2012093833 A1 | 7/2012 | | |
| WO | 2012104729 A1 | 8/2012 | | |
| WO | 2012138927 A1 | 10/2012 | | |
| WO | 2012138939 A1 | 10/2012 | | |
| WO | 2013103369 A1 | 7/2013 | | |
| WO | 2013103370 A1 | 7/2013 | | |
| WO | 2016021973 A1 | 2/2016 | | |
| WO | 2016146552 A1 | 9/2016 | | |
| WO | 2016184955 A2 | 11/2016 | | |
| WO | 2016184989 A1 | 11/2016 | | |
| WO | 2017074547 A1 | 5/2017 | | |
| WO | 2018042346 A2 | 3/2018 | | |
| WO | 2018236548 A1 | 12/2018 | | |
| WO | 2019/060383 A1 | 3/2019 | | |
| WO | WO-2019122360 A1 * | 6/2019 | ............ | A01H 4/005 |
| WO | 2019238909 A1 | 12/2019 | | |
| WO | 2019238911 A1 | 12/2019 | | |
| WO | WO-2019238908 A1 * | 12/2019 | ............ | A01H 4/008 |

OTHER PUBLICATIONS

Sprunck et al., "Elucidating small RNA pathways in *Arabidopsis thaliana* egg cells", BioRxiv, 2019, doi: https://doi.org/10.1101/525956, 39 pages.

Nardmann et al., Accession CAT02906, published 2009.

Kareem et al., "PLETHORA Genes Control Regeneration by a Two-step Mechanism", Curr Biol., 2015, vol. 25, No. 8, pp. 1017-1030.

Written Opinion issued in PCT/EP2021/054805 dated May 21, 2021.

Collins et al. Accession No. GO662999, 2010.

Hortsman et al., 2014, "Antigumenta-Like 5 protiends: hubs in a plethora of networks", Trends in Plant Science, vol. 19, No. 3, pp. 146-157.

Zhang et al., "Chemical probes in plant epigenetics studies", Plant Signaling & Behavoir, 2013, vol. 8, No. 9, e25364.

Nasti et al., 2022, Defining the Parameters to Improve Plant Regeneration with Developmental Regulators, BioRxiv.

Guo et al., 2004, "Protein tolerance to random amino acid change", Proceedings of the Naitonal Academy of Sciences, vol. 101, No. 25, pp. 9205-9210.

Horlbeck et al., 2016, "Nucleosomes impede Cas9 access to DNA in vivo and in vitro", elife, vol. 5, e12677.

Definition of derivative—NCI Dictionary of Cancer Terms—NCI (https://www.cancer.gov/publications/dictionaries/cancer-terms/def/derivative) viewed on Jan. 24, 2023 (Year: 2023).

Variant Definition & Meaning—Merriam-Webster (https://www.meriamp-webster.com/dictionary/variant) viewed on Jan. 24, 2023 (Year: 2023).

Zhang et al., "CRISPR ribonucleoprotein-mediated genetic engineering in plants", Plant Communications, Mar. 8, 2021, vol. 2, pp. 1-13.

Horstman et al., "A transcriptional view on somatic embryogenesis", Regeneration, 2017, vol. 4, No. 4, pp. 201-216.

Tanaka et al., "The *Arabidopsis* histone deacetylases HDA6 and HDA19 contribute to the repression of embryonic properities after germination", Plant Physiology, 2008, vol. 146, No. 1, pp. 149-161.

"RWP-RK domain containing protein [Triticum aestivum]", AEB26836.1, GenBank; Aug. 5, 2011.

Li et al., "Analysis of pepper RWP-RK transcription factors", Journal of Anhui Agricultural University, 2018, vol. 45, No. 1, pp. 187-194.

International Search Report issued in International Application No. PCT/EP2021/054805 dated May 21, 2021.

Lowe et al., "Morphogenic Regulators Baby boom and Wuschel Improve Monocot Transforamation", The Plant Cell, Sep. 2016, vol. 28(9), pp. 1998-2015.

Lowe et al., "Rapid genotype "independent" *Zea mays* L. (maize) transformation via direct somatic embryogenesis", In Vitro Cellular & Developmental Biology—Plant, 2018, vol. 54(8), pp. 240-252.

Komor, A., Kim, Y., Packer, M. et al. Programmable editing of a target base in genomic DNA without double-stranded DNA cleavage. Nature 2016, vol. 533, pp. 420-424. https://doi.org/10.1038/nature17946.

Gaudelli, N., Komor, A., Rees, H. et al., "Programmable base editing of A•T to G•C in genomic DNA without DNA cleavage", Nature, Nov. 1, 2017, vol. 551, pp. 464-471. https://doi.org/10.1038/nature24644.

Zong, Y., Wang, Y., Li, C. et al., "Precise base editing in rice, wheat and maize with a Cas9-cytidine deaminase fusion", Nat. Biotechnol., 2017, vol. 35, pp. 438-440. https://doi.org/10.1038/nbt.3811.

Yan et al., "Highly Efficient A•T to G•C Base Editing by Cas9n-Guided tRNA Adenosine Deaminase in Rice", Molecular Plant, Apr. 2, 2018, vol. 11, issue 4, pp. 631-634.

Hua et al., "Precise A T to G C Base Editing in the Rice Genome", Molecular Plant, Apr. 2018, vol. 11(4): pp. 627-630.

Anzalone et al., "Search and replace genome editing without double-strand breaks or donor DNA", Nature, Oct. 21, 2019, vol. 576, pp. 149-157.

Smith, T.F. & Waterman, M.S. "Identification of common molecular subsequences" Journal of Molecular Biology, 1981, vol. 147(1): pp. 195-197.

Andrews, A.J., and Luger, K., Nucleosome structure(s) and stability: Variations on a theme. Annu. Rev. Biophys, 2011, vol. 40, pp. 99-117.

Bannister AJ, Kouzarides T. 2011, Regulation of chromatin by histone modifications. Cell Res. 21: 381-395.

Mayer, K. F. et al., "Role of WUSCHEL in regulating stem cell fate in the *Arabidopsis* shoot meristem", Cell, Dec. 11, 1998, vol. 95, pp. 805-815.

Yadav, R. K. et al., "WUSCHEL protein movement mediates stem cell homeostasis in the *Arabidopsis* shoot apex", Genes Dev., 2011, vol. 25, pp. 2025-2030.

Laux, T., Mayer, K. F., Berger, J. & Jurgens, G., "The WUSCHEL gene is required for shoot and floral meristem integrity in *Arabidopsis*", Development, 1996, vol. 122, pp. 87-96.

Leibfried, A. et al., "WUSCHEL controls meristem function by direct regulation of cytokinin-inducible response regulators", Nature, Dec. 22, 2005, vol. 438(7071), pp. 1172-1175. doi: 10.1038/nature04270.

Hofmann, "A Breakthrough in Monocot Transformation Methods", The Plant Cell, Sep. 2016, vol. 28: p. 1989.

Nic-Can et al., "New Insights into Somatic Embryogenesis: Leafy COTYLEDON1, Baby BOOM1 and Wuschel-Related HOMEO-BOX4 are Epigenetically Regulated in Coffea canephora", PLoS One, Aug. 2013, vol. 8(8), 31 pages, e72160. PMID: 23977240.

Ling Min et al., "Leafy COTYLEDON1-CASEIN Kinase I-TCP15-PHYTOCHROME Interacting FACTOR4 Network Regulates Somatic Embryogenesis by Regulating Auxin Homeostasis", Plant Physiology, Dec. 2015, vol. 169, pp. 2805-2821.

A. Cagliari et al., "New insights on the evolution of Leafy cotyledon1 (LEC1) type genes in vascular plants", Genomics, 2014, vol. 103, pp. 380-387.

Kim et al., "The AtGRF family of putative transcription factors is involved in leaf and cotyledon growth in *Arabidopsis*", The Plant Journal, 2003, vol. 36, pp. 94-104. doi: 10.1046/j.1365-313X.2003.01862.x.

Choi et al., "Whole Genome Analysis of the OsGRF Gene Family Encoding Plant Specific Putative Transcription Activators in Rice (*Oryza sativa* L.)", Plant Cell Physiol, 2004, vol. 45(7): pp. 897-904.

Ellerstrom et al., "Etopic Expression of Effector of Transcription perturbs gibberellin-mediated plant developmental proceses", Plant Molecular Biology, 2005, vol. 59: pp. 663-681.

Aida, M., et al., "The PLETHORA genes mediate patterning of the *Arabidopsis* root stem cell niche", Cell, 2004, vol. 119: pp. 109-120.

(56)                References Cited

OTHER PUBLICATIONS

Mähönen, A.P., et al., "PLETHORA gradient formation mechanism separates auxin responses", Nature, 2014, vol. 515; pp. 125-129.

Santuari et al., "The PLETHORA Gene Regulatory Network Guides Growth and Cell Differentiation in *Arabidopsis* Roots", The Plant Cell, Dec. 2016, vol. 28: pp. 2937-2951 DOI: https://doi.org/10.1105/tpc.16.00656.

El Ouakfaoui, S. et al., "Control of somatic embryogenesis and embryo development by AP2 transcription factors", Plant Molecular Biology, 2010, vol. 74(4-5): pp. 313-326.

Ravi and Chan, "Haploid plants produced by centromere-mediated genome elimination", Nature, 2010, vol. 464, pp. 615-619. https://doi.org/10.1038/nature08842.

Helenius et al., "Gene delivery into intact plants using the HeliosTM Gene Gun", Plant Molecular Biology Reporter, 2000, vol. 18, No. 3, pp. 287a-2871.

Salan et al., "A rapid, generally applicable method to engineer zinc fingers illustrated by targeting the HIV-1 promoter", Nature Biotechnology, 2001, vol. 19, No. 7, pp. 656-660.

Liu et al. "Design of polydactyl zinc-finger proteins for unique addressing within complex genomes", Proceedings of the National Academy of Sciences, 1997, vol. 94, No. 11, pp. 5525-5530.

Boch et al., "Breaking the code of DNA binding specificity of TAL-type III effectors", Science, 2009, vol. 326, No. 5959, pp. 1509-1512.

Moscou et al., "A simple cipher governs DNA recognition by TAL effectors", Science, 2009, vol. 326, No. 5959, p. 1501.

Zetsche et al., "Cpf1 is a Single RNA-Guided Endonuclease of a Class 2 CRISPR-Cas System", Cell, 2015, vol. 163, pp. 759-771.

Makarova et al., "An updated evolutionary classification of CRISPR-Cas systems", Nature Rev. Microbiol., 2015, vol. 13, No. 11, pp. 722-736.

Jinek et al., "A programmable dual-RNA-guided DNA endonuclease in adaptive bacterial immunity", Science, 2012, vol. 337, No. 6096, pp. 816-821.

Burstein et al., "New CRISPR-Cas systems from uncultivated microbes", Nature, 2017, vol. 542, pp. 237-241.

Jore et al., "Structural basis for CRISPR RNA-guided DNA recognition by Cascadek", Nature Structural & Molecular Biology, 2011, vol. 18, No. 5, pp. 529-536.

Sterner et al., "Acetylation of histones and transcription-related factors", Microbiology and Molecular Biology Reviews, 2000, vol. 64, No. 2, pp. 435-459.

Zhang et al., "Transcription regulation by histone methylation: interplay between different covalent modifications of the core histone tails", Genes & Development, 2001, vol. 15, No. 18, pp. 2343-2360.

Shilatifard, "Chromatin modifications by methylation and ubiquitination: implications in the regulation of gene expression", Annu. Rev. Biochem., 2006, vol. 75, pp. 243-269.

Nowak et al., "Phosphorylation of histone H3: a balancing act between chromosome condensation and transcriptional activation", Trends in Genetics, 2004, vol. 20 , No. 4, pp. 214-220.

Nathan et al., "Histone sumoylation is a negative regulator in *Saccharomyces cerevisiae* and shows dynamic interplay with positive-acting histone modifications", Genes & Development, 2006, vol. 20, No. 8, pp. 966-976.

Hassa et al., "Nuclear ADP-ribosylation reactions in mammalian cells: where are we today and where are we going?", Microbiology and Molecular Biology Reviews, 2006, vol. 70, No. 3, pp. 789-829.

Zhang et al., "An epigenetic perspective on developmental regulation of seed genes", Molecular Plant, 2009, vol. 2, No. 4, pp. 610-627.

Miguel et al., "An epigenetic view of plant cells cultured in vitro: somaclonal variation and beyond", Journal of Experimental Botany, 2011, vol. 62, pp. 3713-3725.

Li et al., "The Histone Deacetylase Inhibitor Trichostatin A Promotes Totipotency in the Male Gametophyte", The Plant Cell, 2014, vol. 26, pp. 195-209.

Waki et al., "The *Arabidopsis* RWP-RK protein RKD4 triggers gene expression and pattern formation in early embryogenesis", Current Biology, 2011, vol. 21, No. 15, pp. 1277-1281.

Rice et al., "EMBOSS: The European Molecular Biology Open Software Suite", Trends in Genetics, 2000, vol. 16, No. 6, pp. 276-277.

U.S. Appl. No. 62/609,508, filed Dec. 22, 2017.

International Search Report and Written Opinion issued in International Application No. PCT/EP2019/065643 dated Oct. 2, 2019.

Svitashev et al., "Genome editing in maize directed by CRISPR-Cas9 ribonucleoprotein complexes", Nature Communications, vol. 7, 2016, p. 13274.

Bouchabke-Coussa et al., "Wuschel overexpression promotes somatic embryogenesis and induces organogenesis in cotton (*Gossypium hirsutum* L.) tissues cultured in vitro", Plant Cell Reports, 2013, vol. 32, No. 5, pp. 675-686.

International Search Report and Written Opinion issued in International Application No. PCT/EP2019/065645 dated Oct. 7, 2019.

Database EMBL [Online] May 1, 2009 (May 1, 2009), "Ginkgo biloba (maidenhair tree) putative wuschel homeobox protein WUS ID—CAT02906; sv 1.; linear; mRNA; STD; PLN; 786 BP", XP002794173, retrieved from EBI accession No. EMBL:CAT02906 sequence.

Database EMBL [Online] May 1, 2009 (May 1, 2009), "Ginkgo biloba mRNA for putative wuschel homeobox protein WUS (wus gene)", XP002794174, retrieved from EBI accession No. EMBL: FM882128 Database accession No. FM882128 sequence.

International Search Report and Written Opinion issued in International Application No. PCT/EP2019/065647 dated Nov. 29, 2019.

International Search Report and Written Opinion issued in International Application No. PCT/IB2020/000063 dated Jun. 16, 2020.

Koszegi et al., "Members of the RKD transcription factor family induce an egg cell-like gene expression program", The Plant Journal, 2011, vol. 67, No. 2, pp. 280-291.

Koi et al., "An Evolutionarily Conserved Plant RKD Factor Controls Germ Cell Differentiation", Current Biology, 2016, vol. 26, No. 13, pp. 1775-1781.

Zuo et al., "An estrogen receptor-based transactivator XVE mediates highly inducible gene expression in transgenic plants", The Plant Journal, 2000, vol. 24, No. 2, pp. 265-273.

Samalova et al., "pOp6/LhGR: a stringently regulated and highly responsive dexamethasone-inducible gene expression system for tobacco", The Plant Journal, 2005, vol. 41, No. 6, pp. 919-935.

Durr et al., "Highly efficient heritable targeted deletions of gene clusters and non-coding regulatory regions in *Arabidopsis* using CRISPR/Cas9", Scientific Reports, 2018, vol. 8, 4443, 11 pages.

Nardmann et al., "The Shoot Stem Cell Niche in Angiosperms: Expression Patterns of WUS Orthologues in Rice and Maize Imply Major Modifications in the Course of Mono- and Dicot Evolution", Molecular Biology and Evolution, 2006, vol. 23, No. 12, pp. 2492-2504.

Soderlund et al., "Sequencing, Mapping, and Analysis of 27,455 Maize Full-Length cDNAs", PLoS Genetics, 2009, vol. 5, Issue 11, e1000740, pp. 1-13.

Milne et al., "An Approach to gene-specific transcription inhibition using oligonucleotides complementary to the template strand of the open complex", PNAS, 2000, vol. 97, No. 7, pp. 3136-3141.

Zhang et al., "Predicting DNA Hybridization Kinetics from Sequence", Nature Chemistry, 2018, vol. 10, pp. 91-98.

Zhang et al., "A Two-Step Model for de Novo Activation of WUSCHEL during Plant Shoot Regeneration", The Plant Cell, 2017, vol. 29, pp. 1073-1087.

Zuo et al., "Chemical-inducible systems for regulated expression of plant genes", Current Opinion in Biotechnology, 2000, vol. 11, No. 2, pp. 146-151.

Craft et al., "New pOp/LhG4 vectors for stringent glucocorticoid—dependent transgene expression in *Arabidopsis*", The Plant Journal, 2005, vol. 41, No. 6, pp. 899-918.

Https://www.uniprot.org/uniprot/Q9S292; May 2009.

Du et al., "PLETHORA transcription factors orchestrate de novo organ patterning during *Arabidopsis* lateral root outgrowth", PNAS 2017, vol. 114, No. 44, pp. 11709-11714. https://doi.org/10.1073/pnas.1714410114.

(56)         References Cited

OTHER PUBLICATIONS

International Search Report and Written Opinion issued in International Application No. PCT/EP2021/054799 dated May 31, 2021.
Gordon-Kamm et al., "Using morphogenic genes to improve recovery and regeneration of transgenic plants", Plants, 2019, vol. 8, No. 2, p. 38; 18 pages.
Potsenkovskala et al., "Novel NF-Y genes expressed during somatic embryogenesis in Medicago truncatula", Plant Gene, 2022, vol. 31, 100364; 12 pages.
GenBank Accession AGL53583.1, "WUSCHEL homeobox protein WOX5 [*Picea abies*]" dated Jun. 20, 2013, https://www.ncbi.nlm.nih.gov/protein/AGL53583.1/.
Zhang et al., "Overexpression analysis of plant transcription factors", Current Opinion in Plant Biology, 2003, vol. 6, No. 5, pp. 430-440.
Eid et al., "CRISPR base editors: genome editing without double-stranded breaks", Biochemical Journal, 2018, vol. 475, No. 11, pp. 1955-1964.
Laforest et al., "Advances in Delivery Mechanisms of CRISPR Gene-Editing Reagents in Plants", Frontiers in Genome Editing, 2022, vol. 4, Article 830178; 10 pages.
Lv et al., "Nanoparticle-mediated gene transformation strategies for plant genetic engineering", The Plant Journal, 2020, vol. 104, pp. 880-891.
Sun et al., "Delivery of Abscisic Acid to Plants Using Glutathione Responsive Mesoporous Silica Nanoparticles", Journal of Nanoscience and Nanotechnology, 2018, vol. 18, No. 3, pp. 1615-1625.
Mukherjee et al., "A Comprehensive Classification and Evolutionary Analysis of Plant Homeobox Genes", Mol. Biol. Evol., 2009, vol. 26, No. 12, pp. 2775-2794.
Yuan et al., "Multifaceted roles of transcription factors during plant embryogenesis", Frontiers in Plant Science, 2024, vol. 14, 1322728.
Joshi et al., "Gold Nanoparticles as Carriers for Efficient Transmucosal Insulin Delivery", Langmuir, 2006, vol. 22, No. 1, pp. 300-305.
Klein et al., "Factors Influencing Gene Delivery into *Zea mays* Cells by High-Velocity Microprojectiles", Bio/Technology, 1988, vol. 6, pp. 559-563.
Ikeda et al., "Arabidopsis WUSCHEL Is a Bifunctional Transcription Factor That Acts as a Repressor in Stem Cell Regulation and as an Activator in Floral Patterning", The Plant Cell, 2009, vol. 21, pp. 3493-3505.
Bortesi et al., "The CRISPR/Cas9 system for plant genome editing and beyond", Biotechnology Advances, 2015, vol. 33, pp. 41-52.
Li et al., "Plant Specific Histone Deacetylases HDT1/2 Regulate Gibberellin 2-OXIDASE2 Expression to Control Arabidopsis Root Meristem Cell Number", The Plant Cell, 2017, vol. 29, pp. 2183-2196.
He et al., "Regulation and function of DNA methylation in plants and animals", Cell Research, 2011, vol. 21, pp. 442-465.
Ma et al., "Comprehensive insights on how 2,4-dichlorophenoxyacetic acid retards senescence in post-harvest citrus fruits using transcriptomic and proteomic approaches", Journal of Experimental Botany, 2014, vol. 65, No. 1, pp. 61-74.
Wang et al., "Chapter 13: Applications of Gold Nanoparticles in cancer Imaging and Treatment", in Book: Noble and Previous Metals-Properties, Nanoscale effects and applications, IntechOpen, 2017, pp. 291-309 http://dx.doi.org/10.5772/intechopen.70901.
Tsuji et al., "A New Antifungal Antibiotic, Trichostatin", The Journal of Antibiotics, 1976, vol. 29, No. 1, 49-14691, pp. 1-6.
Parveen et al., "Nanoparticles: a boon to drug delivery, therapeutics, diagnostics and imaging", Nanomedicine: Nanotechnology, Biology, and Medicine, 2012, vol. 8, pp. 147-166.

* cited by examiner

A

SDN-1 efficiency per regenerated T0 event (%)

No booster: 0
PLT5/RBP2: 7.10%
PLT5/RBP3: 48.70%
PLT5/RBP4: 26.30%
PLT5/RBP5: 17.90%
PLT5/RBP6: 14.70%
PLT5/RBP8: 50.00%

B

SDN-1 efficiency per immature embryo (%)

No booster: 0
PLT5/RBP2: 2.90%
PLT5/RBP3: 21.90%
PLT5/RBP4: 10.50%
PLT5/RBP5: 10.40%
PLT5/RBP6: 17.90%
PLT5/RBP8: 2.40%

A

B

A

Genome editing SDN-1 efficiency
(%) at target m7GEP1

Percent increase           61.5%

B

Genome editing SDN-1 efficiency
(%) at target m7GEP22

Percent increase           354.5%

SEQUENCE LISTING

<160> NUMBER OF SEQ ID NOS: 57

<210> SEQ ID NO 1
<211> LENGTH: 2219
<212> TYPE: DNA
<213> ORGANISM: Zea mays

<400> SEQUENCE: 1

```
gccgatcaca ggatgacaac cgggtcccgc gattgtctgg ccccgcggga cagtgggcaa      60
tgtgcccgtg gttgcggtga gaaaaggtcc cggccggtac gggaattcaa attgggaggc     120
gggtgcgggc cctcgctgcg cgggcagaat cgctgatatg cccttgggcc acgccttcct     180
tcttatcccc tgcgcctgcc ctcccctcct gcagcgcccg tcgcctccct ttccccttcc     240
ctccctccct ctccccgcgg gccgccagag gcaatttcgc cctcgattcg accccgattc     300
gtccgcccgc gaccgggatt ccctccgcca agcgcggatc tgaacgctgc gctccgtgtc     360
gccgctcgaa tccgccatga aggggccaa atccaagggc gccgccaagg ccgatgccaa     420
gtaagaaaaa cgaatctccg gttctcttct tccttgttcg tcccgtggat ctgttccgtg     480
gcgtccgaag cattcgattt ctgttattat gacatccgcc gccgcgagta gattttgacc     540
tttttttttc ccgtcgtcgt tgttttgctg tcgctgtctc tgtcgtcgtc gtcgtcgact     600
cgattgcttt ggcatctgca ggctggcggt gaagagcaag ggggcggaga agcccgccaa     660
gggcaggaaa gggaaggccg gcaaggaccc caacaagcct aagagggctc ccagcgcttt     720
cttcgtgttc atgtgagatg cgactttttt cgtcgtctct tttttttttgc tatatactta     780 tttctggatg cgactgttga ttcgatctat ttttggttgc cttttttatac agggaggaat     840 ttcgcaagga gttcaaggag aagaaccct agaacaagtc tgtcgctgcg gtaagaaccc     900
tgagagctgc tttatgaccg gccccatatt attactatct actttgactt ttcccttaat     960
gacgacttat tatttgattt actcgtcacg attcccctct cctggtcgaa cttttcaggt    1020
ggggaaagct gctggcgaca ggtggaaatc cctgagcgag tcggtaagct ccatcttctg    1080
tactaaagta gtagttgatt ggactagaaa tctcgtgctg attaattgtt ttacgcgtgc    1140
```

```
gtttgtgtgg attgtaggac aaggctccct atgtagccaa ggctaacaag ctcaagctcg     1200
agtacaacaa ggccatcgct gcctacaaca agggcgaggt agggaaactg atgcttcaat     1260
tgcgttgtta cttaatgtgt atatagactg ctcctgctgg tcatttattc aaatacgtat     1320
gcttactgaa ccatgtgttg tttgttcaga gcactgcagc taagaaggct cctgccaagg     1380
aggaagagga ggaagatgaa gaggagtctg acaagtccaa gtcggaggtc aatgacgagg     1440
atgatgaaga gggtagtgag gaggtataca aaatctattc ctgtcttctc catatttttt     1500
ccttagacaa aataccaatt aatccaggat acatagcatg ctcatgcatt aagcaagttg     1560
ctaaatttat cttcgaccac aatgtagacc tagtagtatt gtattggatt ccatcaatgc     1620
aaaacatatg cagatttgca tatgcaaccc tcttttgcaa gtcctcaata tgagcatttg     1680
tttggaacac ggtgcattgg ccttaggaag tctttaaaaa tatgtcttcc ctctgcttgc     1740
aggatgaaga tgatgacgag tgatggagct cctcgagaca atggaccgtg cttcatccaa     1800
caatggagcg gctacacaag gccccgtggc gatcacaaaa aaggagccta tatccatgta     1860
ctagaattat tcagtttcac tccacatcgt gatgttttat ttttacttttt gtcgtgctat     1920 aacggatagc gctcctcgtt ggcgccactg gcgggtggtt ctgcctctgg tctggtgtgt     1980
ttgtgtgtgg tcacacttgc cagccagcag aggcgcctgc ttgtacctag attactgttt     2040
ccattgtcgt catcatcggc taacattgtc ataatgtcag tttgggtaat gttagattaa     2100
gtaattattg tgttctgtat tcttgtttgt tgcccttctt ttgtgtgttt ttgttattgt     2160
tggtctgttt ccattgttgt tgctttggca ttgtcagtgc ccgccagccc tgaaaattg     2219
```

<210> SEQ ID NO 2
<211> LENGTH: 663
<212> TYPE: DNA
<213> ORGANISM: Zea mays

<400> SEQUENCE: 2

```
atgaaggggg ccaaatccaa gggcgccgcc aaggccgatg ccaagctggc ggtgaagagc      60 aaggggcgg agaagcccgc caagggcagg aaagggaagg ccggcaagga ccccaacaag     120
cctaagaggg ctcccagcgc tttcttcgtg ttcatggagg aatttcgcaa ggagttcaag     180
gagaagaacc ctaagaacaa gtctgtcgct gcggtgggga aagctgctgg cgacaggtgg     240
aaatccctga gcgagtcgga caaggctccc tatgtagcca aggctaacaa gctcaagctc     300
gagtacaaca aggccatcgc tgcctacaac aagggcgaga gcactgcagc taagaaggct     360
cctgccaagg aggaagagga ggaagatgaa gaggagtctg acaagtccaa gtcggaggtc     420
aatgacgagg atgatgaaga gggtagtgag gaggtataca aaatctattc ctgtcttctc     480
catatttttt ccttagacaa aataccaatt aatccaggat acatagcatg ttcatgcatt     540
aagcaagttg ctaaatttat cttcgaccac aatgtagacc tagtagtatt gtattggatt     600
ccatcaatgc aaaacatatg cagatttgca tatgcaaccc tcttttgcaa gtcctcaata     660
tga                                                                   663
```

<210> SEQ ID NO 3
<211> LENGTH: 220
<212> TYPE: PRT
<213> ORGANISM: Zea mays

<400> SEQUENCE: 3

```
Met Lys Gly Ala Lys Ser Lys Gly Ala Ala Lys Ala Asp Ala Lys Leu
1               5                   10                  15
```

```
Ala Val Lys Ser Lys Gly Ala Glu Lys Pro Ala Lys Gly Arg Lys Gly
            20                  25                  30

Lys Ala Gly Lys Asp Pro Asn Lys Pro Lys Arg Ala Pro Ser Ala Phe
            35                  40                  45

Phe Val Phe Met Glu Glu Phe Arg Lys Glu Phe Lys Glu Lys Asn Pro
        50                  55                  60

Lys Asn Lys Ser Val Ala Ala Val Gly Lys Ala Ala Gly Asp Arg Trp
65                  70                  75                  80

Lys Ser Leu Ser Glu Ser Asp Lys Ala Pro Tyr Val Ala Lys Ala Asn
                85                  90                  95

Lys Leu Lys Leu Glu Tyr Asn Lys Ala Ile Ala Ala Tyr Asn Lys Gly
            100                 105                 110

Glu Ser Thr Ala Ala Lys Lys Ala Pro Ala Lys Glu Glu Glu Glu Glu
            115                 120                 125

Asp Glu Glu Glu Ser Asp Lys Ser Lys Ser Glu Val Asn Asp Glu Asp
        130                 135                 140

Asp Glu Glu Gly Ser Glu Glu Val Tyr Lys Ile Tyr Ser Cys Leu Leu
145                 150                 155                 160

His Ile Phe Ser Leu Asp Lys Ile Pro Ile Asn Pro Gly Tyr Ile Ala
                165                 170                 175

Cys Ser Cys Ile Lys Gln Val Ala Lys Phe Ile Phe Asp His Asn Val
                180                 185                 190

Asp Leu Val Val Leu Tyr Trp Ile Pro Ser Met Gln Asn Ile Cys Arg
            195                 200                 205

Phe Ala Tyr Ala Thr Leu Phe Cys Lys Ser Ser Ile
        210                 215                 220

<210> SEQ ID NO 4
<211> LENGTH: 3282
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
cttcaccgcc attgcaaaaa ttgtcaataa atatttagag tgggtggcat cagaaaaaca      60
tctctagtgg actctcttcc tatcatagct actcgggctg tagatagaac gagggcacaa     120
gagttgggtg gcgtaggttt actcgtgacc tcaactcttt tggctgtgtc ttacgtctaa     180
gatgggtttg gcatgtgaga aacataggtc taagcaattc atgttagggc tgttgcattg     240
ttgttgcatc aaccaaatgt ccagatagca gttcatgcta catctagttg aaaaccctca     300
tcattaggcg gaacatgtgt tctttttttag catagtcaaa gtcagattgc ggcactcgct     360
catccacgga aagaattttc cctgtgcagg catctcgatc aaaagacgca aattaatttt     420
tgaatagcga tataacaata tctaattaac gtttcttgtt ttctgcgaaa tgtctttcat     480
cataaaatga gtcatctcga tgagcccaag tgacatagcc caacacccca ccccaccaat     540
aaaagtgaag aaaacatgtt gggaaaacta taccaagtaa aatacgagtt gttctaaaga     600
aaaagtaaag tacgagttag atcgcaccct gtcctggagt gtggcttgat gatccaactc     660
ctagcattgt atccctgttt ttggatgatg taactattat ttacaatgaa taaagaggtg     720
ttttactagt aaaaaaatct tgaggggagg agaaaaataat ggaggtcttt tttcaaaccg     780
atggactatt atttttagtg aaagagaata atattattgg aaaaattatt ctatccactt     840
```

-continued

```
attttatatt ggcagaatac aaagaatggt ggggtccacg cggaacttgc ggccccgaa    900 acctatcgag ggcgcggtac ccaagcaagg aacggaggaa acttgcgggg cccgaaacct    960
agtgataaaa ggcatatcat ccacacgatg aagatctgac ggaccatatc tcccaccacg   1020
gaaagccatc agacgaggat cagacggcca ggaaggaacc ctagcgcccg ccggtgccaa   1080
tataaagcgc cactctctct cgtcttaagc cccagcctct ccattcccct ctccctctcg   1140
ccgccgccgt ctccttctcc tactcccttc gaggtgtgtt gttcatccgt cccgaatcca   1200
tccatcccct cttcagatgt gttgttcatg gctctaatag ctctagatct gcttgtttgt   1260
gttgtttagc tctagatcta ctcgcgcgcg cttctctctc gatctcctgt agaacaattt   1320
tggttggttt tttgtgcata tccatggtaa ttttgtctgc aatatggagg aggctttcta   1380
agctcctacg tagcatcgat ctttagaatt ccctcggttt ctgtttattt cttcgcgagg   1440
gctctctgtt atctgtagga gtagctgtaa gcgcggttcg ttacggatta atcgtcatgc   1500
ttagttgaac ctatcggtcg aaggatttgt gtgggttgtc gtgtagaatt gacaccatct   1560
acttactgta ctgatatgcc gatctgtagg atactcttca ttacttttgt ttactgctag   1620
ttgtggtgta gatttagcat tctcaaaccc atgctgtagc gtttctaata ttgttacata   1680
gatctaccgg tgcctgttaa ttgtattcga tcgggcgttt ctacatctgt ccgcccacct   1740
agttttatat gtggtaatca aaattgcgtt gacttcgtga tgctgtctgt gtactgtttt   1800
taatcgctct tacttagatg atcaacatgg tgatggttac gatttactgt tttctaatcc   1860
ctgttacttc gatgctgcag tttggatcca tggagatgca acaacaatac ttcggggggg   1920
acggcgatgc ggactggttc catcaactcg cattgcttcc cccacttcca atctcatcgt   1980
ctctcccccc actcccgatg tcagagggct catgtctccc tatggcagca gcagctgcag   2040
ctgcactccc ccttggcgat tgctcgagcg ccctcatgat acgccctgag gaacagatgt   2100
cttgccttcc aatgaacccc tctccagcgg tcgtcgacga tgtctactct tcctacgcac   2160
cgaacaatgt cgacgtgttg ccgccattcc cggcaggact tgacgacgct ctgttgatgg   2220
agtctttttc tgacatcgac ctcgaggagt ttgctgacgc atttggccac aagatcaaga   2280 cagaaccccct cgacgatgcc atggtccccg cggaccacga cttcgcggct caagcccaac   2340
aggcctgccc tgtggtcatc atgaatcagc aacaactcaa cgcacccaga gacgtgcgcc   2400
tgctcattga cccggatgat gatgacagca ccgtggtggc cggggggctat gaagctgcag   2460 cggtgggggtg cgccgagcag aaacaggtca ggccagcacc acgtagggtg agaaagagct   2520
caggcggcgc aagaccagcc gcgggaggaa agtccctcga tcacatcgga ttcgaggaac   2580
tcaggaccta tttctatatg ccaatcacca aggcagcgag ggaaatgaac gtggggctga   2640
cagtcctgaa gaagagatgc cgggaactgg gggtggcgcg ctggccacac agaaagatga   2700
agtctctgag aagcctgatc ctcaacattc aggagatggg gaagggcgca acatctcccg   2760
cagccgtgca gggggaactt gaagcgcttg agaggtattg cgccattatg gaggagaacc   2820
cggctataga gctcaccgag caaacgaaga agctcaggca ggcttgtttc aaagagaatt   2880
ataagcggcg tagagccgcc gcttctgtta atcttctcga tcactgctat aacgatctgg   2940
catctcatga gcagcaaatg cctctcccac aaatgggatt ctttggattt tagaagcttaa  3000 cgcgtgtcga ctcgaatttc cccgatcgtt caaacatttg gcaataaagt ttcttaagat   3060
tgaatcctgt tgccggtctt gcgatgatta tcatataatt tctgttgaat tacgttaagc   3120
atgtaataat taacatgtaa tgcatgacgt tatttatgag atgggttttt atgattagag   3180
tcccgcaatt atacatttaa tacgcgatag aaaacaaaat atagcgcgca aactaggata   3240
```

```
aattatcgcg cgcggtgtca tctatgttac tagatcgctc ga                    3282

<210> SEQ ID NO 5
<211> LENGTH: 4224
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
cttcaccgcc attgcaaaaa ttgtcaataa atatttagag tgggtggcat cagaaaaaca     60
tctctagtgg actctcttcc tatcatagct actcgggctg tagatagaac gagggcacaa    120
gagttgggtg gcgtaggttt actcgtgacc tcaactcttt tggctgtgtc ttacgtctaa    180
gatgggtttg gcatgtgaga aacataggtc taagcaattc atgttagggc tgttgcattg    240
ttgttgcatc aaccaaatgt ccagatagca gttcatgcta catctagttg aaaaccctca    300
tcattaggcg gaacatgtgt tctttttag catagtcaaa gtcagattgc ggcactcgct    360
catccacgga aagaattttc cctgtgcagg catctcgatc aaaagacgca aattaatttt    420
tgaatagcga tataacaata tctaattaac gtttcttgtt ttctgcgaaa tgtctttcat    480
cataaaatga gtcatctcga tgagcccaag tgacatagcc caacacccca ccccaccaat    540
aaaagtgaag aaaacatgtt gggaaaacta taccaagtaa aatacgagtt gttctaaaga    600
aaaagtaaag tacgagttag atcgcaccct gtcctggagt gtggcttgat gatccaactc    660
ctagcattgt atccctgttt ttggatgatg taactattat ttacaatgaa taaagaggtg    720
ttttactagt aaaaaaatct tgaggggagg agaaaataat ggaggtcttt tttcaaaccg    780
atggactatt atttttagtg aaagagaata atattattgg aaaaattatt ctatccactt    840
attttatatt ggcagaatac aaagaatggt ggggtccacg cggaacttgc ggcccccgaa    900
acctatcgag ggcgcggtac ccaagcaagg aacggaggaa acttgcgggg cccgaaacct    960
agtgataaaa ggcatatcat ccacacgatg aagatctgac ggaccatatc tcccaccacg   1020
gaaagccatc agacgaggat cagacggcca ggaaggaacc ctagcgcccg ccggtgccaa   1080
tataaagcgc cactctctct cgtcttaagc cccagcctct ccattcccct ctccctctcg   1140
ccgccgccgt ctccttctcc tactcccttc gaggtgtgtt gttcatccgt cccgaatcca   1200
tccatcccct cttcagatgt gttgttcatg gctctaatag ctctagatct gcttgtttgt   1260
gttgtttagc tctagatcta ctcgcgcgcg cttctctctc gatctcctgt agaacaattt   1320
tggttggttt tttgtgcata tccatggtaa ttttgtctgc aatatggagg aggctttcta   1380
agctcctacg tagcatcgat ctttagaatt ccctcggttt ctgtttatttt cttcgcgagg   1440 gctctctgtt atctgtagga gtagctgtaa gcgcggttcg ttacggatta atcgtcatgc   1500
ttagttgaac ctatcggtcg aaggatttgt gtgggttgtc gtgtagaatt gacaccatct   1560
acttactgta ctgatatgcc gatctgtagg atactcttca ttacttttgt ttactgctag   1620
ttgtggtgta gatttagcat tctcaaaccc atgctgtagc gtttctaata ttgttacata   1680
gatctaccgg tgcctgttaa ttgtattcga tcgggcgttt ctacatctgt ccgcccacct   1740
agttttatat gtggtaatca aaattgcgtt gacttcgtga tgctgtctgt gtactgtttt   1800
taatcgctct tacttagatg atcaacatgg tgatggttac gatttactgt tttctaatcc   1860
ctgttacttc gatgctgcag tttggatccc ccgggatggc ttcagcgaac aactggctgg   1920
gcttctcgct ctcgggccag gataaacccgc agcctaacca ggatagctcg cctgccgccg   1980
```

-continued

```
gtatcgacat ctccggcgcc agcgacttct atggcctgcc cacgcagcag ggctccgacg   2040
ggcatctcgg cgtgccgggc ctgcgggacg atcacgcttc ttatggtatc atggaggcct   2100
acaacagggt tcctcaagaa acccaagatt ggaacatgag gggcttggac tacaacggcg   2160
gtggctcgga gctctcgatg cttgtggggt ccagcggcgg cggcggggc aacggcaaga    2220 gggccgtgga agacagcgag cccaagctcg aagatttcct cggcggcaac tcgttcgtct   2280
ccgatcaaga tcagtccggc ggttacctgt tctctggagt cccgatagcc agcagcgcca   2340
atagcaacag cgggagcaac accatggagc tatccatgat caagacctgg ctacggaaca   2400
accaggtggc ccagccccag ccgccagctc cacatcagcc gcagcctgag gaaatgagca   2460
ccgacgccag cggcagcagc tttggatgct cggattcgat gggaaggaac agcatggtgg   2520
cggctggtgg gagctcgcag agcctggcgc tctcgatgag cacgggctcg cacctgccca   2580
tggttgtggc cggcggcagc gccagcggag cggcctcgga gagcacgtcg tcggagaaca   2640
agcgagcgag cggtgccatg gattcgcccg gcagcgcggt agaagccgta ccgaggaagt   2700
ccatcgacac gttcgggcaa aggacctcta tatatcgagg tgtaacaagg catagatgga   2760
cagggcggta tgaggctcat ctatgggata atagttgtag aagagaaggg cagagtcgca   2820
agggtaggca agtttacctt ggtggctatg acaaggagga caaggcagca agggcttacg   2880
atttggcagc tctcaagtat tggggcacta cgacaacaac aaatttccct ataagcaact   2940
acgaaaagga gctagaagaa atgaaacata tgactagaca ggagtacatt gcatacctaa   3000
gaagaaatag cagtggattt tctcgtgggg cgtcaaagta tcgtggagta actagacatc   3060
atcagcatgg gagatggcaa gcaaggatag ggagagttgc aggaaacaag gatctctact   3120
tgggcacatt cagcaccgag gaggaggcgg cggaggccta cgacatcgcc gcgatcaagt   3180
tccgcggtct caacgccgtc accaacttcg acatgagccg ctacgacgtg aagagcatcc   3240
tcgagagcag cacactgcct gtcggcggcg cggccaggcg cctcaaggac gccgtggacc   3300
acgtggaggc cggcgccact atctggcgcg ccgacatgga cggcgccgtg atctcccagc   3360
tggccgaagc cgggatgggc ggctacgcct cgtacggcca ccacggctgg ccgaccatcg   3420
cgttccagca gccgtcgccg ctctccgtcc actacccgta cggccagccg tcccgcgggt   3480
ggtgcaaacc cgagcaggac gcggccgccg ccgcggccca cagcctgcag gacctccagc   3540
agctgcacct cggcagcgcg gcccacaact tcttccaggc gtcgtcgagc tccacagtct   3600
acaacggcgg cgccggcgcc agtggtgggt accagggcct cggtggtggt agctccttcc   3660
tcatgccgtc gagcactgtc gtggcggcgg ccgaccaggg gcacagcagc acggcaaacc   3720
aggggagcac gtgcagctac ggggacgacc accaggaggg gaagctcatc ggttacgacg   3780
ccgccatggt ggcgaccgca gctggtggag acccgtacgc tgcggcgagg aacgggtacc   3840
agttctcgca gggctcggga tccacggtga gcatcgcgag ggcgaacggg tacgctaaca   3900
actggagctc tcctttcaac aacggcatgg ggtgaaagct tacgcgtgtc gactcgaatt   3960
tccccgatcg ttcaaacatt tggcaataaa gtttcttaag attgaatcct gttgccggtc   4020
ttgcgatgat tatcatataa tttctgttga attacgttaa gcatgtaata attaacatgt   4080
aatgcatgac gttatttatg agatgggttt ttatgattag agtcccgcaa ttatacattt   4140
aatacgcgat agaaaacaaa atatagcgcg caaactagga taaattatcg cgcgcggtgt   4200
catctatgtt actagatcgc tcga                                          4224
```

<210> SEQ ID NO 6

<210> LENGTH: 3663
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
cttcaccgcc attgcaaaaa ttgtcaataa atatttagag tgggtggcat cagaaaaaca        60
tctctagtgg actctcttcc tatcatagct actcgggctg tagatagaac gagggcacaa       120
gagttgggtg gcgtaggttt actcgtgacc tcaactcttt tggctgtgtc ttacgtctaa       180
gatgggtttg gcatgtgaga aacataggtc taagcaattc atgttagggc tgttgcattg       240
ttgttgcatc aaccaaatgt ccagatagca gttcatgcta catctagttg aaaaccctca       300
tcattaggcg gaacatgtgt tctttttag catagtcaaa gtcagattgc ggcactcgct        360
catccacgga aagaattttc cctgtgcagg catctcgatc aaaagacgca aattaatttt       420
tgaatagcga tataacaata tctaattaac gtttcttgtt ttctgcgaaa tgtctttcat       480
cataaaatga gtcatctcga tgagcccaag tgacatagcc caacacccca ccccaccaat       540
aaaagtgaag aaaacatgtt gggaaaacta taccaagtaa aatacgagtt gttctaaaga       600
aaaagtaaag tacgagttag atcgcaccct gtcctggagt gtggcttgat gatccaactc       660
ctagcattgt atccctgttt ttggatgatg taactattat ttacaatgaa taaagaggtg       720
ttttactagt aaaaaaatct tgaggggagg agaaaataat ggaggtcttt tttcaaaccg       780
atggactatt attttttagtg aaagagaata atattattgg aaaaattatt ctatccactt      840
attttatatt ggcagaatac aaagaatggt ggggtccacg cggaacttgc ggcccccgaa       900
acctatcgag ggcgcggtac ccaagcaagg aacggaggaa acttgcgggg cccgaaacct       960
agtgataaaa ggcatatcat ccacacgatg aagatctgac ggaccatatc tcccaccacg      1020
gaaagccatc agacgaggat cagacggcca ggaaggaacc ctagcgcccg ccggtgccaa      1080
tataaagcgc cactctctct cgtcttaagc cccagcctct ccattcccct ctccctctcg      1140
ccgccgccgt ctccttctcc tactcccttc gaggtgtgtt gttcatccgt cccgaatcca      1200
tccatcccct cttcagatgt gttgttcatg gctctaatag ctctagatct gcttgtttgt      1260
gttgtttagc tctagatcta ctcgcgcgcg cttctctctc gatctcctgt agaacaattt      1320
tggttggttt tttgtgcata tccatggtaa ttttgtctgc aatatggagg aggctttcta      1380
agctcctacg tagcatcgat ctttagaatt ccctcggttt ctgtttattt cttcgcgagg      1440
gctctctgtt atctgtagga gtagctgtaa gcgcggttcg ttacggatta atcgtcatgc      1500
ttagttgaac ctatcggtcg aaggatttgt gtgggttgtc gtgtagaatt gacaccatct      1560
acttactgta ctgatatgcc gatctgtagg atactcttca ttacttttgt ttactgctag      1620
ttgtggtgta gatttagcat tctcaaaccc atgctgtagc gtttctaata ttgttacata      1680
gatctaccgg tgcctgttaa ttgtattcga tcggcgtttt ctacatctgt ccgcccacct      1740
agttttatat gtggtaatca aaattgcgtt gacttcgtga tgctgtctgt gtactgtttt      1800
taatcgctct tacttagatg atcaacatgg tgatggttac gatttactgt tttctaatcc      1860
ctgttacttc gatgctgcag tttggatcca tggacacctc gcaccactat catccatggc      1920
tcaacttctc cctcgcccac cactgtgacc tcgaggagga ggagagggggc gcggccgccg     1980 agctggccgc gatagccggc gccgcgccgc gccgaagct ggaggacttc ctcggcggag       2040
gcgtcgccac cggtggtccg gaggcggtgg cgcccgcgga gatgtacgac tcggacctca     2100

-continued

```
agttcatagc cgccgccggg ttccttggcg gctcggcggc ggcggcggcg acgtcgccgc    2160
tgtcctccct cgaccaggcc ggttccaagc tggccttgcc tgcggcggcg gctgctccgg    2220
cgccggagca gaggaaggcc gtcgactcct ttgggcagcg cacgtccatc taccgcggcg    2280
tcacacggca ccggtggact ggcaggtacg aggcacatct gtgggacaac agctgccgac    2340
gcgaagggca gagccgcaag ggccgccaag tatatttggg tggctatgat aaggaggaga    2400
aggctgccag ggcgtatgat cttgcagctt tgaagtactg gggttctagc accaccacca    2460
actttccggt tgctgagtat gagaaggagg tcgaggagat gaagaacatg acgcgacaag    2520
agtttgttgc ttcccttcga aggaagagca gtggattctc tcgggggtgct tccatctaca    2580 gaggtgtaac cagacatcac cagcatggac ggtggcaggc gaggatcgga agggtggccg    2640
gtaacaagga cctctacctt gggacgttca gcaccgagga ggaagctgca gaggcctacg    2700
acatagcggc catcaagttc agaggcctga acgccgtcac aaacttcgag atcagccggt    2760
acaacgtgga gaccataatg agcagcaacc ttccagtcgc gagcatgtcg tcgtcgtcgg    2820
cggcggcggc gggtggccgg agcagcaagg cgctggagtc ccctccgtcc ggctcgcttg    2880
acggcggcgg cggcatgcca gtcgtcgaag gcagcacggc accgccgctg ttcattccgg    2940
tgaagtacga ccagcagcag caggagtacc tgtcgatgct cgcgttgcag caccaccacc    3000
agcagcaaca agcagggaac ctgttgcagg ggccgctagt agggttcggc ggcctctact    3060
cctccggggt gaacctggat ttcgccaact cccacggcac ggcggctccg tcgtcgatgg    3120
cccaccactg ctacgccaat ggcaccgcgt ccgcctcgca tgagcaccag caccagcacc    3180
agatgcagca gggcggcgag aacgagacgc agccgcagcc gcagcagagc tccagcagct    3240
gctcctccct gccattcgcc accccggtcg cttttcaatgg gtcctatgaa agctccatca    3300
cggcggcagg cccctttgga tactcctacc caaatgtggc agcctttcag acgccgatct    3360
atggaatgga atgaaagctt acgcgtgtcg actcgaattt ccccgatcgt tcaaacattt    3420
ggcaataaag tttcttaaga ttgaatcctg ttgccggtct tgcgatgatt atcatataat    3480
ttctgttgaa ttacgttaag catgtaataa ttaacatgta atgcatgacg ttatttatga    3540
gatgggtttt tatgattaga gtcccgcaat tatacattta atacgcgata gaaaacaaaa    3600
tatagcgcgc aaactaggat aaattatcgc gcgcggtgtc atctatgtta ctagatcgct    3660
cga                                                                  3663
```

<210> SEQ ID NO 7
<211> LENGTH: 3648
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 7

```
cttcaccgcc attgcaaaaa ttgtcaataa atatttagag tgggtggcat cagaaaaaca     60
tctctagtgg actctcttcc tatcatagct actcgggctg tagatagaac gagggcacaa    120
gagttgggtg gcgtaggttt actcgtgacc tcaactcttt tggctgtgtc ttacgtctaa    180
gatgggtttg gcatgtgaga aacataggtc taagcaattc atgttagggc tgttgcattg    240
ttgttgcatc aaccaaatgt ccagatagca gttcatgcta catctagttg aaaaccctca    300
tcattaggcg gaacatgtgt ctttttttag catagtcaaa gtcagattgc ggcactcgct    360
catccacgga aagaattttc cctgtgcagg catctcgatc aaaagacgca aattaatttt    420
```

-continued

```
tgaatagcga tataacaata tctaattaac gtttcttgtt ttctgcgaaa tgtctttcat      480
cataaaatga gtcatctcga tgagcccaag tgacatagcc caacacccca ccccaccaat      540
aaaagtgaag aaaacatgtt gggaaaacta taccaagtaa aatacgagtt gttctaaaga      600
aaaagtaaag tacgagttag atcgcaccct gtcctggagt gtggcttgat gatccaactc      660
ctagcattgt atccctgttt ttggatgatg taactattat ttacaatgaa taaagaggtg      720
ttttactagt aaaaaaatct tgaggggagg agaaaataat ggaggtcttt tttcaaaccg      780
atggactatt atttttagtg aaagagaata atattattgg aaaaattatt ctatccactt      840
attttatatt ggcagaatac aaagaatggt ggggtccacg cggaacttgc ggcccccgaa      900
acctatcgag ggcgcggtac ccaagcaagg aacggaggaa acttgcgggg cccgaaacct      960
agtgataaaa ggcatatcat ccacacgatg aagatctgac ggaccatatc tcccaccacg     1020
gaaagccatc agacgaggat cagacggcca ggaaggaacc ctagcgcccg ccggtgccaa     1080
tataaagcgc cactctctct cgtcttaagc cccagcctct ccattcccct ctccctctcg     1140
ccgccgccgt ctccttctcc tactcccttc gaggtgtgtt gttcatccgt cccgaatcca     1200
tccatcccct cttcagatgt gttgttcatg gctctaatag ctctagatct gcttgtttgt     1260
gttgtttagc tctagatcta ctcgcgcgcg cttctctctc gatctcctgt agaacaattt     1320
tggttggttt tttgtgcata tccatggtaa ttttgtctgc aatatggagg aggctttcta     1380
agctcctacg tagcatcgat ctttagaatt ccctcggttt ctgtttattt cttcgcgagg     1440
gctctctgtt atctgtagga gtagctgtaa gcgcggttcg ttacggatta atcgtcatgc     1500
ttagttgaac ctatcggtcg aaggatttgt gtgggttgtc gtgtagaatt gacaccatct     1560
acttactgta ctgatatgcc gatctgtagg atactcttca ttacttttgt ttactgctag     1620
ttgtggtgta gatttagcat tctcaaaccc atgctgtagc gtttctaata ttgttacata     1680
gatctaccgg tgcctgttaa ttgtattcga tcgggcgttt ctacatctgt ccgcccacct     1740
agttttatat gtggtaatca aaattgcgtt gacttcgtga tgctgtctgt gtactgtttt     1800
taatcgctct tacttagatg atcaacatgg tgatggttac gatttactgt tttctaatcc     1860
ctgttacttc gatgctgcag tttggatcca tggacatgga catgagctca gcttatcccc     1920
accattggct ctccttctcc ctctccaaca actaccacca tggcctactc gaggccttct     1980
ctaactcctc cggtactcct cttggagacg agccgggcgc agtggaggag tccccgagga     2040
cggtggagga cttcctcggc ggcgtcggtg gcgccggcgc cccgccgcag ccggcggctg     2100
ctgcagatca ggatcaccag cttgtgtgcg gcgagctggg cagcatcaca gccaggttct     2160
tgcgccacta cccggcggcg ccagctggga cgacggtgga gaaccccggc gcggtgaccg     2220
tggcggccat gtcgtcgacg gacgtggcgg gggcggagtc cgaccaggcg aggcggcccg     2280
ccgagacgtt cggccagcgc acatccatct accgtggcgt caccaggcac cggtggacag     2340
ggagatatga ggcgcacttg tgggacaaca gctgccgccg ggagggccaa agccgcaaag     2400
gacgccaagt ctacctagga ggctatgaca aggaggagag ggcggctaga gcttacgacc     2460
tcgccgcgct caagtactgg gggcctacaa ccacgaccaa cttcccggtg tccaactacg     2520
agaaggagct ggaggagatg aagtccatga cgcggcagga gttcatcgcg tcgttgcgca     2580
ggaagagcag cggcttctca cgaggcgcct ccatctacag aggagtcaca aggcatcatc     2640
agcacggccg gtggcaggcg aggatcggca gggtggccgg aaacaaggac ctgtacttgg     2700
gcactttcag tactcaggaa gaggcggcgg aggcgtacga catcgctgcg atcaagttcc     2760
gcgggctcaa cgccgtcacc aacttcgaca tgagccgcta cgacgtggag agcatcctca     2820
```

```
gcagcgacct ccccgtcggg ggcggagcca ccgggcgcgc cgccaagttc ccgttggact   2880
cgctgcagcc ggggagcgct gctgcgatga tgctcgccgg ggctgctgcc gcttcgcagg   2940
ccaccatgcc gccgtccgag aaggactact ggtctctgct cgccctgcac taccagcagc   3000
agcaggagca ggagcggcag ttcccggctt ctgcttacga ggcttacggc tccggcggcg   3060
tgaacgtgga cttcacgatg ggcaccagta gcggcaacaa caacaacaac accggcagcg   3120
gcgtcatgtg gggcgccacc actggtgcag tagtagtggg acagcaagac agcagcggca   3180
agcagggcaa cggctatgcc agcaacattc cttatgctgc tgctgctgct atggtttctg   3240
gatctgctgg ctacgagggc tccaccggcg acaatggaac ctgggttact acgactatta   3300
ccagcagcaa caccggcacg gctccccact actacaacta tctcttcggg atggagtaga   3360
agcttacgcg tgtcgactcg aatttccccg atcgttcaaa catttggcaa taaagtttct   3420
taagattgaa tcctgttgcc ggtcttgcga tgattatcat ataatttctg ttgaattacg   3480
ttaagcatgt aataattaac atgtaatgca tgacgttatt tatgagatgg gttttttatga   3540 ttagagtccc gcaattatac atttaatacg cgatagaaaa caaaatatag cgcgcaaact   3600
aggataaatt atcgcgcgcg gtgtcatcta tgttactaga tcgctcga               3648
```

```
<210> SEQ ID NO 8
<211> LENGTH: 2961
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
```

```
cttcaccgcc attgcaaaaa ttgtcaataa atatttagag tgggtggcat cagaaaaaca     60
tctctagtgg actctcttcc tatcatagct actcgggctg tagatagaac gagggcacaa    120
gagttgggtg gcgtaggttt actcgtgacc tcaactcttt tggctgtgtc ttacgtctaa    180
gatgggtttg gcatgtgaga aacataggtc taagcaattc atgttagggc tgttgcattg    240
ttgttgcatc aaccaaatgt ccagatagca gttcatgcta catctagttg aaaaccctca    300
tcattaggcg gaacatgtgt tcttttttag catagtcaaa gtcagattgc ggcactcgct    360
catccacgga aagaattttc cctgtgcagg catctcgatc aaaagacgca aattaatttt    420
tgaatagcga tataacaata tctaattaac gtttcttgtt ttctgcgaaa tgtctttcat    480
cataaaatga gtcatctcga tgagcccaag tgacatagcc caacacccca ccccaccaat    540
aaaagtgaag aaaacatgtt gggaaaacta taccaagtaa aatacgagtt gttctaaaga    600
aaaagtaaag tacgagttag atcgcaccct gtcctggagt gtggcttgat gatccaactc    660
ctagcattgt atccctgttt ttggatgatg taactattat ttacaatgaa taaagaggtg    720
ttttactagt aaaaaaatct tgaggggagg agaaaataat ggaggtcttt tttcaaaccg    780
atggactatt attttttagtg aaagagaata atattattgg aaaaattatt ctatccactt    840
attttatatt ggcagaatac aaagaatggt ggggtccacg cggaacttgc ggccccccgaa    900 acctatcgag ggcgcggtac ccaagcaagg aacggaggaa acttgcgggg cccgaaacct    960
agtgataaaa ggcatatcat ccacacgatg aagatctgac ggaccatatc tcccaccacg   1020
gaaagccatc agacgaggat cagacggcca ggaaggaacc ctagcgcccg ccggtgccaa   1080
tataaagcgc cactctctct cgtcttaagc cccagcctct ccattcccct ctccctctcg   1140
ccgccgccgt ctccttctcc tactcccttc gaggtgtgtt gttcatccgt cccgaatcca   1200
```

-continued

```
tccatcccct cttcagatgt gttgttcatg gctctaatag ctctagatct gcttgtttgt    1260
gttgtttagc tctagatcta ctcgcgcgcg cttctctctc gatctcctgt agaacaattt    1320
tggttggttt tttgtgcata tccatggtaa ttttgtctgc aatatggagg aggctttcta    1380
agctcctacg tagcatcgat ctttagaatt ccctcggttt ctgtttatttt cttcgcgagg    1440 gctctctgtt atctgtagga gtagctgtaa gcgcggttcg ttacggatta atcgtcatgc    1500
ttagttgaac ctatcggtcg aaggatttgt gtgggttgtc gtgtagaatt gacaccatct    1560
acttactgta ctgatatgcc gatctgtagg atactcttca ttactttgt ttactgctag    1620 ttgtggtgta gatttagcat tctcaaaccc atgctgtagc gtttctaata ttgttacata    1680
gatctaccgg tgcctgttaa ttgtattcga tcgggcgttt ctacatctgt ccgcccacct    1740
agttttatat gtggtaatca aaattgcgtt gacttcgtga tgctgtctgt gtactgtttt    1800
taatcgctct tacttagatg atcaacatgg tgatggttac gatttactgt tttctaatcc    1860
ctgttacttc gatgctgcag tttggatcca tggagtcggg ctccgggacg gctgctggct    1920
ctggctatgt ttacagacag ccaggatcaa cgcggtggaa cccgacagct gaacaactgt    1980
ccttgcttag agaaatctac taccgcaacg gattgcggac cccgaccgcg gacgaaatca    2040
gacaaatcag ctcaaagctc tcaaggtacg gaaaaataga gggcaaaaac gtttacaact    2100
ggttccagaa tagacgcgca agagaaaagc gcaagcaacg gctctctaca atcggctgtg    2160
atccagcact gatcgagatg gggaatgtcg cttcactgga attcggtact gagagcgccc    2220
tggaatcgct gtcgtcagga ccatcctcag aactccgcga agcgccaacg agaaaatttt    2280
acgaaaaaaa gacggttgga gagaactcaa ctataataaa cccagtggaa caaaactgta    2340 cccttttcctg cggaacgtcc caagagttcc agtatgcggt cgattctcgg cgcgtcatga    2400
aagctatgga ggaaaagcag gcgacggacg atgaacccga cggaaataaa tggactgagt    2460
caaacagaca cgtcaagatt ctccagcttt tcccgctcca caataacgag gatcagacat    2520
tgataaagag cgacaaagaa atctattgtt tgggctcgtg cgagaagaaa atggatttgt    2580
caccgctggg tcattcaggc tctcagcgcg cttcggccct tgacttgtgc ctttcattgg    2640
gcaacgaatc ttgtgggctg catgataatt gaaagcttac gcgtgtcgac tcgaatttcc    2700
ccgatcgttc aaacatttgg caataaagtt tcttaagatt gaatcctgtt gccggtcttg    2760
cgatgattat catataattt ctgttgaatt acgttaagca tgtaataatt aacatgtaat    2820
gcatgacgtt atttatgaga tgggtttta tgattagagt cccgcaatta tacatttaat    2880
acgcgataga aaacaaaata tagcgcgcaa actaggataa attatcgcgc gcggtgtcat    2940
ctatgttact agatcgctcg a    2961
```

<210> SEQ ID NO 9
<211> LENGTH: 2961
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 9

```
cttcaccgcc attgcaaaaa ttgtcaataa atatttagag tgggtggcat cagaaaaaca      60
tctctagtgg actctcttcc tatcatagct actcgggctg tagatagaac gagggcacaa     120
gagttgggtg gcgtaggttt actcgtgacc tcaactcttt tggctgtgtc ttacgtctaa     180
gatgggtttg gcatgtgaga aacataggtc taagcaattc atgttagggc tgttgcattg     240
```

```
ttgttgcatc aaccaaatgt ccagatagca gttcatgcta catctagttg aaaaccctca      300
tcattaggcg gaacatgtgt tcttttttag catagtcaaa gtcagattgc ggcactcgct      360
catccacgga aagaattttc cctgtgcagg catctcgatc aaaagacgca aattaatttt      420
tgaatagcga tataacaata tctaattaac gtttcttgtt ttctgcgaaa tgtctttcat      480
cataaaatga gtcatctcga tgagcccaag tgacatagcc caacacccca ccccaccaat      540
aaaagtgaag aaaacatgtt gggaaaacta taccaagtaa aatacgagtt gttctaaaga      600
aaaagtaaag tacgagttag atcgcaccct gtcctggagt gtggcttgat gatccaactc      660
ctagcattgt atccctgttt ttggatgatg taactattat ttacaatgaa taaagaggtg      720
ttttactagt aaaaaaatct tgaggggagg agaaaataat ggaggtcttt tttcaaaccg      780
atggactatt attttttagtg aaagagaata atattattgg aaaaattatt ctatccactt      840
attttatatt ggcagaatac aaagaatggt ggggtccacg cggaacttgc ggcccccgaa      900
acctatcgag ggcgcggtac ccaagcaagg aacggaggaa acttgcgggg cccgaaacct      960
agtgataaaa ggcatatcat ccacacgatg aagatctgac ggaccatatc tcccaccacg     1020
gaaagccatc agacgaggat cagacggcca ggaaggaacc ctagcgcccg ccggtgccaa     1080
tataaagcgc cactctctct cgtcttaagc cccagcctct ccattcccct ctccctctcg     1140
ccgccgccgt ctccttctcc tactcccttc gaggtgtgtt gttcatccgt cccgaatcca     1200
tccatcccct cttcagatgt gttgttcatg gctctaatag ctctagatct gcttgtttgt     1260
gttgtttagc tctagatcta ctcgcgcgcg cttctctctc gatctcctgt agaacaattt     1320
tggttggttt tttgtgcata tccatggtaa ttttgtctgc aatatggagg aggctttcta     1380
agctcctacg tagcatcgat ctttagaatt ccctcggttt ctgtttatttt cttcgcgagg     1440 gctctctgtt atctgtagga gtagctgtaa gcgcggttcg ttacggatta atcgtcatgc     1500
ttagttgaac ctatcggtcg aaggatttgt gtgggttgtc gtgtagaatt gacaccatct     1560
acttactgta ctgatatgcc gatctgtagg atactcttca ttacttttgt ttactgctag     1620
ttgtggtgta gatttagcat tctcaaaccc atgctgtagc gtttctaata ttgttacata     1680
gatctaccgg tgcctgttaa ttgtattcga tcgggcgttt ctacatctgt ccgcccacct     1740
agttttatat gtggtaatca aaattgcgtt gacttcgtga tgctgtctgt gtactgtttt     1800
taatcgctct tacttagatg atcaacatgg tgatggttac gatttactgt tttctaatcc     1860
ctgttacttc gatgctgcag tttggatcca tggaatcggg ctccggcacg gcggcagggt     1920
ctggttatgt ctatcggcag agcggaagca cccggtggaa tccaacagca gaacagttgt     1980
cgctgctcaa ggaactttat taccggaatg gaattcggac accgtcggca gatcaaatta     2040
ggcaaatttc ggcccggctg tccagatacg gcaaaataga agggaaaaac gtcttttact     2100
ggtttcaaaa tcataaagca cgggaacggc agaagaaaag actttccacg gtcggctgcg     2160
accctgctct catagaaatg ggtaacgtcg cgagcttgga atttgggacc gaaagcgctc     2220
ttgaatctct cagctcaggc ccgtccagcg agttgcgcga ggctcctacc cgcaagtttt     2280
atgagaagaa aaccgttggt gagaacagca ccataatcaa tcctgttgag cagaactgca     2340
cactttcttg cggtacttcg caggaatttc agtatgctgt tgatagccgc cgggtgatga     2400
aggcaatgga agagaagcaa gcaacggatg atgaaccgga cggaaacaaa tggacggagt     2460
cgaacaggca tgtgaagacc ctccctcttt tccccttgca taataatgaa gatcagacct     2520
tgatcaagtc ggacaaggaa atttattgcc ttgggagctg tgaaaaaaaa atggatctgt     2580
```

-continued

```
ccccattggg acactcgggc tctcagaggg cgtcggcact ggatttgtgc ctgtctttgg      2640
gtaatgaatc ttgtggcctc cacgacaatt gaaagcttac gcgtgtcgac tcgaatttcc      2700
ccgatcgttc aaacatttgg caataaagtt tcttaagatt gaatcctgtt gccggtcttg      2760
cgatgattat catataattt ctgttgaatt acgttaagca tgtaataatt aacatgtaat      2820
gcatgacgtt atttatgaga tgggtttttta tgattagagt cccgcaatta tacatttaat      2880
acgcgataga aaacaaaata tagcgcgcaa actaggataa attatcgcgc gcggtgtcat      2940
ctatgttact agatcgctcg a                                                 2961
```

<210> SEQ ID NO 10
<211> LENGTH: 2655
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

```
cttcaccgcc attgcaaaaa ttgtcaataa atatttagag tgggtggcat cagaaaaaca        60
tctctagtgg actctcttcc tatcatagct actcgggctg tagatagaac gagggcacaa       120
gagttgggtg gcgtaggttt actcgtgacc tcaactcttt tggctgtgtc ttacgtctaa       180
gatgggtttg gcatgtgaga aacataggtc taagcaattc atgttagggc tgttgcattg       240
ttgttgcatc aaccaaatgt ccagatagca gttcatgcta catctagttg aaaaccctca       300
tcattaggcg gaacatgtgt tcttttttag catagtcaaa gtcagattgc ggcactcgct       360
catccacgga aagaattttc cctgtgcagg catctcgatc aaaagacgca aattaatttt       420
tgaatagcga tataacaata tctaattaac gtttcttgtt ttctgcgaaa tgtctttcat       480
cataaaatga gtcatctcga tgagcccaag tgacatagcc caacacccca ccccaccaat       540
aaaagtgaag aaaacatgtt gggaaaacta taccaagtaa aatacgagtt gttctaaaga       600
aaaagtaaag tacgagttag atcgcaccct gtcctggagt gtggcttgat gatccaactc       660
ctagcattgt atccctgttt ttggatgatg taactattat ttacaatgaa taaagaggtg       720
ttttactagt aaaaaaatct tgaggggagg agaaaataat ggaggtcttt tttcaaaccg       780
atggactatt attttttagtg aaagagaata atattattgg aaaaattatt ctatccactt       840
attttatatt ggcagaatac aaagaatggt ggggtccacg cggaacttgc ggcccccgaa       900
acctatcgag ggcgcggtac ccaagcaagg aacggaggaa acttgcgggg cccgaaacct       960
agtgataaaa ggcatatcat ccacacgatg aagatctgac ggaccatatc tcccaccacg      1020
gaaagccatc agacgaggat cagacggcca ggaaggaacc ctagcgcccg ccggtgccaa      1080
tataaagcgc cactctctct cgtcttaagc cccagcctct ccattcccct ctccctctcg      1140
ccgccgccgt ctccttctcc tactcccttc gaggtgtgtt gttcatccgt cccgaatcca      1200
tccatcccct cttcagatgt gttgttcatg gctctaatag ctctagatct gcttgtttgt      1260
gttgtttagc tctagatcta ctcgcgcgcg cttctctctc gatctcctgt agaacaattt      1320
tggttggttt tttgtgcata tccatggtaa ttttgtctgc aatatggagg aggctttcta      1380
agctcctacg tagcatcgat ctttagaatt ccctcggttt ctgtttattt cttcgcgagg      1440
gctctctgtt atctgtagga gtagctgtaa gcgcggttcg ttacggatta atcgtcatgc      1500
ttagttgaac ctatcggtcg aaggatttgt gtgggttgtc gtgtagaatt gacaccatct      1560
acttactgta ctgatatgcc gatctgtagg atactcttca ttacttttgt ttactgctag      1620
```

-continued

```
ttgtggtgta gatttagcat tctcaaaccc atgctgtagc gtttctaata ttgttacata    1680
gatctaccgg tgcctgttaa ttgtattcga tcgggcgttt ctacatctgt ccgcccacct    1740
agttttatat gtggtaatca aaattgcgtt gacttcgtga tgctgtctgt gtactgtttt    1800
taatcgctct tacttagatg atcaacatgg tgatggttac gatttactgt tttctaatcc    1860
ctgttacttc gatgctgcag tttggatcca tggttagcaa gggggaggag gttattaaag    1920
aattcccagg aagcacccgg tggaatccaa cggcggagca actttcgctc cttcgggaaa    1980
tttattacag gaatgggctg agaactccca ccgctgacga gatcagacag atttcatcaa    2040
aattgtcgcg gtatggtaag attgaaggga aaaatgtgta caactggttc cagaacagaa    2100
gagctaggga aaagagaaaa cagcggttgt caaccatagg ctgtggttcg gcggggtcgg    2160
ccgcagggag cggagagttt cgccatgtga agaccctgcc ccttttccct ttgcataata    2220
atgaggattc aggttcgttg gatctggagc tggaattggg ttttgcctct gctaccgcag    2280
ccgcgacttc tggttcacaa agggcgtcgg cattggatct ctgcctgtcc cttggaaatg    2340
agtcatgcgg tttgcatgac aactgaaagc ttacgcgtgt cgactcgaat ttccccgatc    2400
gttcaaacat ttggcaataa agtttcttaa gattgaatcc tgttgccggt cttgcgatga    2460
ttatcatata atttctgttg aattacgtta agcatgtaat aattaacatg taatgcatga    2520
cgttatttat gagatgggtt tttatgatta gagtcccgca attatacatt taatacgcga    2580
tagaaaacaa aatatagcgc gcaaactagg ataaattatc gcgcgcggtg tcatctatgt    2640
tactagatcg ctcga                                                     2655
```

<210> SEQ ID NO 11
<211> LENGTH: 2655
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

```
cttcaccgcc attgcaaaaa ttgtcaataa atatttagag tgggtggcat cagaaaaaca      60
tctctagtgg actctcttcc tatcatagct actcgggctg tagatagaac gagggcacaa     120
gagttgggtg gcgtaggttt actcgtgacc tcaactcttt tggctgtgtc ttacgtctaa     180
gatgggtttg gcatgtgaga aacataggtc taagcaattc atgttagggc tgttgcattg     240
ttgttgcatc aaccaaatgt ccagatagca gttcatgcta catctagttg aaaaccctca     300
tcattaggcg gaacatgtgt tctttttttag catagtcaaa gtcagattgc ggcactcgct     360
catccacgga aagaattttc cctgtgcagg catctcgatc aaaagacgca aattaatttt     420
tgaatagcga tataacaata tctaattaac gtttcttgtt ttctgcgaaa tgtctttcat     480
cataaaatga gtcatctcga tgagcccaag tgacatagcc caacacccca ccccaccaat     540
aaaagtgaag aaaacatgtt gggaaaacta taccaagtaa aatacgagtt gttctaaaga     600
aaaagtaaag tacgagttag atcgcaccct gtcctggagt gtggcttgat gatccaactc     660
ctagcattgt atccctgttt ttggatgatg taactattat ttacaatgaa taaagaggtg     720
ttttactagt aaaaaaatct tgaggggagg agaaaataat ggaggtcttt tttcaaaccg     780
atggactatt attttttagtg aaagagaata atattattgg aaaaattatt ctatccactt     840
attttatatt ggcagaatac aaagaatggt ggggtccacg cggaacttgc ggcccccgaa     900
acctatcgag ggcgcggtac ccaagcaagg aacggaggaa acttgcgggg cccgaaacct     960
```

-continued

```
agtgataaaa ggcatatcat ccacacgatg aagatctgac ggaccatatc tcccaccacg   1020
gaaagccatc agacgaggat cagacggcca ggaaggaacc ctagcgcccg ccggtgccaa   1080
tataaagcgc cactctctct cgtcttaagc cccagcctct ccattcccct ctccctctcg   1140
ccgccgccgt ctccttctcc tactcccttc gaggtgtgtt gttcatccgt cccgaatcca   1200
tccatcccct cttcagatgt gttgttcatg gctctaatag ctctagatct gcttgtttgt   1260
gttgtttagc tctagatcta ctcgcgcgcg cttctctctc gatctcctgt agaacaattt   1320
tggttggttt tttgtgcata tccatggtaa ttttgtctgc aatatggagg aggctttcta   1380
agctcctacg tagcatcgat ctttagaatt ccctcggttt ctgtttatatt cttcgcgagg   1440 gctctctgtt atctgtagga gtagctgtaa gcgcggttcg ttacggatta atcgtcatgc   1500
ttagttgaac ctatcggtcg aaggatttgt gtgggttgtc gtgtagaatt gacaccatct   1560
acttactgta ctgatatgcc gatctgtagg atactcttca ttacttttgt ttactgctag   1620
ttgtggtgta gatttagcat tctcaaaccc atgctgtagc gtttctaata ttgttacata   1680
gatctaccgg tgcctgttaa ttgtattcga tcgggcgttt ctacatctgt ccgcccacct   1740
agttttatat gtggtaatca aaattgcgtt gacttcgtga tgctgtctgt gtactgtttt   1800
taatcgctct tacttagatg atcaacatgg tgatggttac gatttactgt tttctaatcc   1860
ctgttacttc gatgctgcag tttggatcca tggtctcgaa aggagaagag gtcatcaaag   1920
aattttcagg cagcacccgc tggaatccga ctgcagaaca actttctctc ctcaaagagc   1980
tttattacag aaatgggatc agaacccctt cagcggacca gatacgccag ataagcgccc   2040
gcttgtcgag gtacggcaaa atcgagggga agaatgtttt ttactggttc caaaaccata   2100
aagcgaggga gcggcagaag aaaagactga gcactgtggg ttgtggatcg gcgggatcgg   2160
ctgccgggtc aggtgaattt cgccatgtta aaacgcttcc actgtttccc ttgcataata   2220
atgaagacag cggatcactt gacctggagc tggagttggg cttcgcttcc gcgacggctg   2280
ctgcaacatc cggctcgcag cgggcgtcgg cgctggattt gtgcctttcg ctgggaaatg   2340
agagctgcgg tcttcatgac aactgaaagc ttacgcgtgt cgactcgaat ttccccgatc   2400
gttcaaacat ttggcaataa agtttcttaa gattgaatcc tgttgccggt cttgcgatga   2460
ttatcatata atttctgttg aattacgtta agcatgtaat aattaacatg taatgcatga   2520
cgttatttat gagatgggtt tttatgatta gagtcccgca attatacatt taatacgcga   2580
tagaaaacaa aatatagcgc gcaaactagg ataaattatc gcgcgcggtg tcatctatgt   2640
tactagatcg ctcga                                                    2655
```

```
<210> SEQ ID NO 12
<211> LENGTH: 2679
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
cttcaccgcc attgcaaaaa ttgtcaataa atatttagag tgggtggcat cagaaaaaca     60
tctctagtgg actctcttcc tatcatagct actcgggctg tagatagaac gagggcacaa    120
gagttgggtg gcgtaggttt actcgtgacc tcaactcttt tggctgtgtc ttacgtctaa    180
gatgggtttg gcatgtgaga aacataggtc taagcaattc atgttagggc tgttgcattg    240
ttgttgcatc aaccaaatgt ccagatagca gttcatgcta catctagttg aaaaccctca    300
```

-continued

```
tcattaggcg gaacatgtgt tctttttttag catagtcaaa gtcagattgc ggcactcgct      360
catccacgga aagaattttc cctgtgcagg catctcgatc aaaagacgca aattaatttt      420
tgaatagcga tataacaata tctaattaac gtttcttgtt ttctgcgaaa tgtctttcat      480
cataaaatga gtcatctcga tgagcccaag tgacatagcc caacacccca ccccaccaat      540
aaaagtgaag aaaacatgtt gggaaaacta taccaagtaa aatacgagtt gttctaaaga      600
aaaagtaaag tacgagttag atcgcaccct gtcctggagt gtggcttgat gatccaactc      660
ctagcattgt atccctgttt ttggatgatg taactattat ttacaatgaa taaagaggtg      720
ttttactagt aaaaaaatct tgaggggagg agaaaataat ggaggtcttt tttcaaaccg      780
atggactatt attttttagtg aaagagaata atattattgg aaaaattatt ctatccactt      840
attttatatt ggcagaatac aaagaatggt ggggtccacg cggaacttgc ggcccccgaa      900
acctatcgag ggcgcggtac ccaagcaagg aacggaggaa acttgcgggg cccgaaacct      960
agtgataaaa ggcatatcat ccacacgatg aagatctgac ggaccatatc tcccaccacg     1020
gaaagccatc agacgaggat cagacggcca ggaaggaacc ctagcgcccg ccggtgccaa     1080
tataaagcgc cactctctct cgtcttaagc cccagcctct ccattcccct ctccctctcg     1140
ccgccgccgt ctccttctcc tactcccttc gaggtgtgtt gttcatccgt cccgaatcca     1200
tccatcccct cttcagatgt gttgttcatg gctctaatag ctctagatct gcttgtttgt     1260
gttgtttagc tctagatcta ctcgcgcgcg cttctctctc gatctcctgt agaacaattt     1320
tggttggttt tttgtgcata tccatggtaa ttttgtctgc aatatggagg aggctttcta     1380
agctcctacg tagcatcgat ctttagaatt ccctcggttt ctgtttattt cttcgcgagg     1440
gctctctgtt atctgtagga gtagctgtaa gcgcggttcg ttacggatta atcgtcatgc     1500
ttagttgaac ctatcggtcg aaggatttgt gtgggttgtc gtgtagaatt gacaccatct     1560
acttactgta ctgatatgcc gatctgtagg atactcttca ttacttttgt ttactgctag     1620
ttgtggtgta gatttagcat tctcaaaccc atgctgtagc gtttctaata ttgttacata     1680
gatctaccgg tgcctgttaa ttgtattcga tcgggcgttt ctacatctgt ccgcccacct     1740
agttttatat gtggtaatca aaattgcgtt gacttcgtga tgctgtctgt gtactgtttt     1800
taatcgctct tacttagatg atcaacatgg tgatggttac gatttactgt tttctaatcc     1860
ctgttacttc gatgctgcag tttggatcca tggtgtctaa aggggaagag gtcataaaag     1920
agttctcagg ttctactcgc tggaatccaa ctgcagaaca actctctctc ctgaaggagc     1980
tctactatcg gaacggaata cgcacgcctt cggcggacca aataaggcag atttcagccc     2040
gcctgtctag atacgggaaa atcgagggaa agaacgtgtt ttattggttc caaaaccata     2100
aggcaagaga gcggcagaaa aaacggctca gcacagtcgg ctgtgggtca gccggttcgg     2160
cggctggctc tggtgaattc cgccacgtca aaaccctgcc tctgttcccg ctccacaata     2220
atgtcgagac acttcccttg ttcccggagg attccgggtc tctcgacttg gagctcgaat     2280
tgggctttgc ctctgccact gcggcagcga ccagcggatc acagagagcc tccgcactgg     2340
atctgtgcct gtcacttgga aatgaatcgt gcggattgca cgacaattga aagcttacgc     2400
gtgtcgactc gaatttcccc gatcgttcaa acatttggca ataaagtttc ttaagattga     2460
atcctgttgc cggtcttgcg atgattatca tataatttct gttgaattac gttaagcatg     2520
taataattaa catgtaatgc atgacgttat ttatgagatg ggtttttatg attagagtcc     2580
cgcaattata catttaatac gcgatagaaa acaaaatata gcgcgcaaac taggataaat     2640
tatcgcgcgc ggtgtcatct atgttactag atcgctcga                           2679
```

-continued

<210> SEQ ID NO 13
<211> LENGTH: 2949
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

```
cttcaccgcc attgcaaaaa ttgtcaataa atatttagag tgggtggcat cagaaaaaca      60
tctctagtgg actctcttcc tatcatagct actcgggctg tagatagaac gagggcacaa     120
gagttgggtg gcgtaggttt actcgtgacc tcaactcttt tggctgtgtc ttacgtctaa     180
gatgggtttg gcatgtgaga aacataggtc taagcaattc atgttagggc tgttgcattg     240
ttgttgcatc aaccaaatgt ccagatagca gttcatgcta catctagttg aaaaccctca     300
tcattaggcg gaacatgtgt tcttttttag catagtcaaa gtcagattgc ggcactcgct     360
catccacgga aagaattttc cctgtgcagg catctcgatc aaaagacgca aattaatttt     420
tgaatagcga tataacaata tctaattaac gtttcttgtt ttctgcgaaa tgtctttcat     480
cataaaatga gtcatctcga tgagcccaag tgacatagcc caacacccca ccccaccaat     540
aaaagtgaag aaaacatgtt gggaaaacta taccaagtaa aatacgagtt gttctaaaga     600
aaaagtaaag tacgagttag atcgcaccct gtcctggagt gtggcttgat gatccaactc     660
ctagcattgt atccctgttt ttggatgatg taactattat ttacaatgaa taaagaggtg     720
ttttactagt aaaaaaatct tgaggggagg agaaaataat ggaggtcttt tttcaaaccg     780
atggactatt attttagtg aaagagaata atattattgg aaaaattatt ctatccactt     840
attttatatt ggcagaatac aaagaatggt ggggtccacg cggaacttgc ggcccccgaa     900
acctatcgag ggcgcggtac ccaagcaagg aacggaggaa acttgcgggg cccgaaacct     960
agtgataaaa ggcatatcat ccacacgatg aagatctgac ggaccatatc tcccaccacg    1020
gaaagccatc agacgaggat cagacggcca ggaaggaacc ctagcgcccg ccggtgccaa    1080
tataaagcgc cactctctct cgtcttaagc cccagcctct ccattcccct ctccctctcg    1140
ccgccgccgt ctccttctcc tactcccttc gaggtgtgtt gttcatccgt cccgaatcca    1200
tccatcccct cttcagatgt gttgttcatg gctctaatag ctctagatct gcttgtttgt    1260
gttgtttagc tctagatcta ctcgcgcgcg cttctctctc gatctcctgt agaacaattt    1320
tggttggttt tttgtgcata tccatggtaa ttttgtctgc aatatggagg aggctttcta    1380
agctcctacg tagcatcgat ctttagaatt ccctcggttt ctgtttattt cttcgcgagg    1440
gctctctgtt atctgtagga gtagctgtaa gcgcggttcg ttacggatta atcgtcatgc    1500
ttagttgaac ctatcggtcg aaggatttgt gtgggttgtc gtgtagaatt gacaccatct    1560
acttactgta ctgatatgcc gatctgtagg atactcttca ttacttttgt ttactgctag    1620
ttgtggtgta gatttagcat tctcaaaccc atgctgtagc gtttctaata ttgttacata    1680
gatctaccgg tgcctgttaa ttgtattcga tcgggcgttt ctacatctgt ccgcccacct    1740
agttttatat gtggtaatca aaattgcgtt gacttcgtga tgctgtctgt gtactgtttt    1800
taatcgctct tacttagatg atcaacatgg tgatggttac gatttactgt tttctaatcc    1860
ctgttacttc gatgctgcag tttggatcca tggtgtctaa aggcgaagag gtcattaagg    1920
agttcagcgg ctctactaga tggaatccaa cggccgagca acttagcctg ctcaaagaac    1980
tctattatcg caatgggata cgcacgccct ctgcagatca gatacgccaa atctcagcgc    2040
```

-continued

```
gcctgtccag gtatgggaag attgagggta aaaacgtctt ttactggttc caaaatcaca    2100
aagcgcgcga gagacagaag aaaagactca gcaccgttgg ttgtgaccct gctctcatcg    2160
agatggggaa tgttgcttcc ctggagtttg gcacagagag cgctttggaa tcactctctt    2220
ccggcccctc aagcgaactc agagaggctc ccactcggaa gttttacgag aaaaaaaccg    2280
tcggagaaaa cagcacgatt atcaacccog tcgagcagaa ctgcaccctc tcatgcggca    2340
cgtcccagga gtttcagtac gccgtcgact cgaggagagt gatgaaggcg atggaggaaa    2400
agcaagcaac tgacgacgag cccgacggaa acaagtggac tgaatccaat cgccatgtta    2460
aaacgttgcc tttgttcccg ctccataaca atgtggagac gttgccactc ttcccggagg    2520
actcgggatc tctggacttg gagctggaac tgggctttgc ttcggctacc gcagcagcca    2580
cctcgggttc ccagagagcc tcggctcttg atctctgcct gtcactgggt aacgaatctt    2640
gcggactgca cgataattag aagcttacgc gtgtcgactc gaatttcccc gatcgttcaa    2700
acatttggca ataaagtttc ttaagattga atcctgttgc cggtcttgcg atgattatca    2760
tataatttct gttgaattac gttaagcatg taataattaa catgtaatgc atgacgttat    2820
ttatgagatg ggtttttatg attagagtcc cgcaattata catttaatac gcgatagaaa    2880
acaaaatata gcgcgcaaac taggataaat tatcgcgcgc ggtgtcatct atgttactag    2940
atcgctcga                                                           2949
```

<210> SEQ ID NO 14
<211> LENGTH: 3018
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
cttcaccgcc attgcaaaaa ttgtcaataa atatttagag tgggtggcat cagaaaaaca      60
tctctagtgg actctcttcc tatcatagct actcgggctg tagatagaac gagggcacaa     120
gagttgggtg gcgtaggttt actcgtgacc tcaactcttt tggctgtgtc ttacgtctaa     180
gatgggtttg gcatgtgaga aacataggtc taagcaattc atgttagggc tgttgcattg     240
ttgttgcatc aaccaaatgt ccagatagca gttcatgcta catctagttg aaaaccctca     300
tcattaggcg gaacatgtgt tcttttttag catagtcaaa gtcagattgc ggcactcgct     360
catccacgga aagaattttc cctgtgcagg catctcgatc aaaagacgca aattaatttt     420
tgaatagcga tataacaata tctaattaac gtttcttgtt ttctgcgaaa tgtctttcat     480
cataaaatga gtcatctcga tgagcccaag tgacatagcc caacacccca ccccaccaat     540
aaaagtgaag aaaacatgtt gggaaaacta taccaagtaa aatacgagtt gttctaaaga     600
aaaagtaaag tacgagttag atcgcaccct gtcctggagt gtggcttgat gatccaactc     660
ctagcattgt atccctgttt ttggatgatg taactattat ttacaatgaa taaagaggtg     720
ttttactagt aaaaaaatct tgaggggagg agaaaataat ggaggtcttt tttcaaaccg     780
atggactatt attttttagtg aaagagaata atattattgg aaaaattatt ctatccactt     840
attttatatt ggcagaatac aaagaatggt ggggtccacg cggaacttgc ggcccccgaa     900
acctatcgag ggcgcggtac ccaagcaagg aacggaggaa acttgcgggg ccgaaacct     960 agtgataaaa ggcatatcat ccacacgatg aagatctgac ggaccatatc tcccaccacg    1020
gaaagccatc agacgaggat cagacggcca ggaaggaacc ctagcgcccg ccggtgccaa    1080
```

-continued

```
tataaagcgc cactctctct cgtcttaagc cccagcctct ccattcccct ctccctctcg    1140
ccgccgccgt ctccttctcc tactcccttc gaggtgtgtt gttcatccgt cccgaatcca    1200
tccatcccct cttcagatgt gttgttcatg gctctaatag ctctagatct gcttgtttgt    1260
gttgtttagc tctagatcta ctcgcgcgcg cttctctctc gatctcctgt agaacaattt    1320
tggttggttt tttgtgcata tccatggtaa ttttgtctgc aatatggagg aggctttcta    1380
agctcctacg tagcatcgat ctttagaatt ccctcggttt ctgtttattt cttcgcgagg    1440
gctctctgtt atctgtagga gtagctgtaa gcgcggttcg ttacggatta atcgtcatgc    1500
ttagttgaac ctatcggtcg aaggatttgt gtgggttgtc gtgtagaatt gacaccatct    1560
acttactgta ctgatatgcc gatctgtagg atactcttca ttacttttgt ttactgctag    1620
ttgtggtgta gatttagcat tctcaaaccc atgctgtagc gtttctaata ttgttacata    1680
gatctaccgg tgcctgttaa ttgtattcga tcgggcgttt ctacatctgt ccgcccacct    1740
agttttatat gtggtaatca aaattgcgtt gacttcgtga tgctgtctgt gtactgtttt    1800
taatcgctct tacttagatg atcaacatgg tgatggttac gatttactgt tttctaatcc    1860
ctgttacttc gatgctgcag tttggatcca tggtttcaaa gggggaggag gtcataaaag    1920
aattttctgg cagcactaga tggaatccga ctgctgagca gttgtctctc ctcaaagaac    1980
tttactatag gaacggtatc cgcactccgt ccgctgatca aattcgccaa atttcggcca    2040
gactgtccag atacgggaaa attgagggaa aaaatgtttt ctactggttc cagaatcata    2100
aggcgcgcga aaggcagaaa aagagacttt cgaccgtcgg atgtgaccct gcacttatcg    2160
aaatgggcaa tgtcgcgtcg ttggagtttg gcaccgaatc cgctctcgaa tctcttagct    2220
cgggcccctc atcggaactc agagaggccc ctaccagaaa attttatgag aaaaagacag    2280
tgggagagaa ctctacaatc attaaccccg tcgagcagaa ctgcacattg agctgtggaa    2340
catcgcagga gtttcaatac gcggtggatt cgcgccgcgt tatgaaggca atggaggaga    2400
agcaggcaac agatgatgag ccagacggca ataaatggac cgaatctaac agacatgtca    2460
agacactgcc acttttccct ctccacaaca atgtcgagac actccctctg tttcccgagg    2520
attcgggaag cctggatctt gagctggaac ttggctttgc atcaggtgga tctgccgggt    2580
cagttgacac gctgccattg tttcctagag aggctgcggg ttctggggaa tttgccactg    2640
cggctgcgac tagcggatca cagcgcgcat cggcgctcga cctctgcctt tctttgggta    2700
acgagtcttg cggcctgcat gacaactgaa agcttacgcg tgtcgactcg aatttccccg    2760
atcgttcaaa catttggcaa taaagtttct taagattgaa tcctgttgcc ggtcttgcga    2820
tgattatcat ataatttctg ttgaattacg ttaagcatgt aataattaac atgtaatgca    2880
tgacgttatt tatgagatgg gttttttatga ttagagtccc gcaattatac atttaatacg    2940
cgatagaaaa caaaatatag cgcgcaaact aggataaatt atcgcgcgcg gtgtcatcta    3000
tgttactaga tcgctcga                                                  3018
```

```
<210> SEQ ID NO 15
<211> LENGTH: 2676
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
cttcaccgcc attgcaaaaa ttgtcaataa atatttagag tgggtggcat cagaaaaaca      60
```

```
tctctagtgg actctcttcc tatcatagct actcgggctg tagatagaac gagggcacaa     120
gagttgggtg gcgtaggttt actcgtgacc tcaactcttt tggctgtgtc ttacgtctaa     180
gatgggtttg gcatgtgaga aacataggtc taagcaattc atgttagggc tgttgcattg     240
ttgttgcatc aaccaaatgt ccagatagca gttcatgcta catctagttg aaaaccctca     300
tcattaggcg gaacatgtgt tctttttttag catagtcaaa gtcagattgc ggcactcgct     360
catccacgga aagaattttc cctgtgcagg catctcgatc aaaagacgca aattaatttt     420
tgaatagcga tataacaata tctaattaac gtttcttgtt ttctgcgaaa tgtctttcat     480
cataaaatga gtcatctcga tgagcccaag tgacatagcc caacacccca ccccaccaat     540
aaaagtgaag aaaacatgtt gggaaaacta taccaagtaa aatacgagtt gttctaaaga     600
aaaagtaaag tacgagttag atcgcaccct gtcctggagt gtggcttgat gatccaactc     660
ctagcattgt atccctgttt ttggatgatg taactattat ttacaatgaa taaagaggtg     720
ttttactagt aaaaaaatct tgaggggagg agaaaataat ggaggtcttt tttcaaaccg     780
atggactatt atttttagtg aaagagaata atattattgg aaaaattatt ctatccactt     840
attttatatt ggcagaatac aaagaatggt ggggtccacg cggaacttgc ggcccccgaa     900
acctatcgag ggcgcggtac ccaagcaagg aacggaggaa acttgcgggg cccgaaacct     960
agtgataaaa ggcatatcat ccacacgatg aagatctgac ggaccatatc tcccaccacg    1020
gaaagccatc agacgaggat cagacggcca ggaaggaacc ctagcgcccg ccggtgccaa    1080
tataaagcgc cactctctct cgtcttaagc cccagcctct ccattcccct ctccctctcg    1140
ccgccgccgt ctccttctcc tactcccttc gaggtgtgtt gttcatccgt cccgaatcca    1200
tccatcccct cttcagatgt gttgttcatg gctctaatag ctctagatct gcttgtttgt    1260
gttgtttagc tctagatcta ctcgcgcgcg cttctctctc gatctcctgt agaacaattt    1320
tggttggttt tttgtgcata tccatggtaa ttttgtctgc aatatggagg aggctttcta    1380
agctcctacg tagcatcgat ctttagaatt ccctcggttt ctgtttattt cttcgcgagg    1440
gctctctgtt atctgtagga gtagctgtaa gcgcggttcg ttacggatta atcgtcatgc    1500
ttagttgaac ctatcggtcg aaggatttgt gtgggttgtc gtgtagaatt gacaccatct    1560
acttactgta ctgatatgcc gatctgtagg atactcttca ttacttttgt ttactgctag    1620
ttgtggtgta gatttagcat tctcaaaccc atgctgtagc gtttctaata ttgttacata    1680
gatctaccgg tgcctgttaa ttgtattcga tcgggcgttt ctacatctgt ccgcccacct    1740
agttttatat gtggtaatca aaattgcgtt gacttcgtga tgctgtctgt gtactgtttt    1800
taatcgctct tacttagatg atcaacatgg tgatggttac gatttactgt tttctaatcc    1860
ctgttacttc gatgctgcag tttggatcca tggtttcgaa gggggaagaa gtcattaaag    1920
agttttcagg gtctacgcgc tggaacccta ccgctgaaca agtcaaggtt ttgagggaaa    1980
tatattaccg cgcgggtctt aggacgccat ccgcggatca gatccgccaa atatcctcac    2040
agctgaaacg gtatggaaag gtggaaggaa aaaacgtgtt ttattggttc cagaaccata    2100
aagcgcggga aagacaaaaa aagcggctca gcaccgttgg gagcgctggc tcagcagcgg    2160
gttcaggtga gttcaggcac gttaaaacac tgcccttgtt ccctttgcac aataatgaag    2220
actcagggag cggtttggac ttggatctga accttgagtt gcgcctgtcg gcgactgctg    2280
ctgccacttc gggctcacag cgggcgtctg ccctcgatct ggacttggag ctcagactcg    2340
gtttcgcgct tggtaatgag tcgtgtggac tgcacgacaa ctagtgaaag cttacgcgtg    2400
```

-continued

```
tcgactcgaa tttccccgat cgttcaaaca tttggcaata aagtttctta agattgaatc    2460
ctgttgccgg tcttgcgatg attatcatat aatttctgtt gaattacgtt aagcatgtaa    2520
taattaacat gtaatgcatg acgttattta tgagatgggt ttttatgatt agagtcccgc    2580
aattatacat ttaatacgcg atagaaaaca aaatatagcg cgcaaactag gataaattat    2640
cgcgcgcggt gtcatctatg ttactagatc gctcga                              2676
```

```
<210> SEQ ID NO 16
<211> LENGTH: 1104
<212> TYPE: DNA
<213> ORGANISM: Triticum aestivum

<400> SEQUENCE: 16
atggagatgc aacaacaata cttcgggggg gacggcgatg cggactggtt ccatcaactc      60
gcattgcttc ccccacttcc aatctcatcg tctctccccc cactcccgat gtcagagggc     120
tcatgtctcc ctatggcagc agcagctgca gctgcactcc cccttggcga ttgctcgagc     180
gccctcatga tacgccctga ggaacagatg tcttgccttc caatgaaccc ctctccagcg     240
gtcgtcgacg atgtctactc ttcctacgca ccgaacaatg tcgacgtgtt gccgccattc     300
ccggcaggac ttgacgacgc tctgttgatg gagtcttttt ctgacatcga cctcgaggag     360
tttgctgacg catttggcca caagatcaag acagaacccc tcgacgatgc catggtcccc     420
gcggaccacg acttcgcggc tcaagcccaa caggcctgcc ctgtggtcat catgaatcag     480
caacaactca acgcacccag agacgtgcgc ctgctcattg acccggatga tgatgacagc     540
accgtggtgg ccgggggcta tgaagctgca gcggtggggt gcgccgagca gaaacaggtc     600
aggccagcac cacgtagggt gagaaagagc tcaggcggcg caagaccagc cgcgggagga     660
aagtccctcg atcacatcgg attcgaggaa ctcaggacct atttctatat gccaatcacc     720
aaggcagcga gggaaatgaa cgtggggctg acagtcctga agaagagatg ccgggaactg     780
ggggtggcgc gctggccaca cagaaagatg aagtctctga gaagcctgat cctcaacatt     840
caggagatgg ggaagggcgc aacatctccc gcagccgtgc aggggaact tgaagcgctt      900 gagaggtatt cgccattat ggaggagaac ccggctatag agctcaccga gcaaacgaag      960
aagctcaggc aggcttgttt caaagagaat tataagcggc gtagagccgc cgcttctgtt     1020
aatcttctcg atcactgcta taacgatctg gcatctcatg agcagcaaat gcctctccca     1080
caaatgggat tctttggatt ttag                                           1104
```

```
<210> SEQ ID NO 17
<211> LENGTH: 2040
<212> TYPE: DNA
<213> ORGANISM: Zea mays

<400> SEQUENCE: 17
atggcttcag cgaacaactg gctgggcttc tcgctctcgg ccaggataa cccgcagcct       60 aaccaggata gctcgcctgc cgccggtatc gacatctccg gcgccagcga cttctatggc     120
ctgcccacgc agcagggctc cgacgggcat ctcggcgtgc cgggcctgcg ggacgatcac     180
gcttcttatg gtatcatgga ggcctacaac agggttcctc aagaaaccca agattggaac     240
atgaggggct tggactacaa cggcggtggc tcggagctct cgatgcttgt ggggtccagc     300
ggcggcggcg ggggcaacgg caagagggcc gtggaagaca gcgagcccaa gctcgaagat     360
ttcctcggcg gcaactcgtt cgtctccgat caagatcagt ccggcggtta cctgttctct     420
ggagtcccga tagccagcag cgccaatagc aacagcggga gcaacaccat ggagctatcc     480
```

-continued

```
atgatcaaga cctggctacg gaacaaccag gtggcccagc cccagccgcc agctccacat      540
cagccgcagc ctgaggaaat gagcaccgac gccagcggca gcagctttgg atgctcggat      600
tcgatgggaa ggaacagcat ggtggcggct ggtgggagct cgcagagcct ggcgctctcg      660
atgagcacgg gctcgcacct gcccatggtt gtggccggcg gcagcgccag cggagcggcc      720
tcggagagca cgtcgtcgga gaacaagcga gcgagcggtg ccatggattc gcccggcagc      780
gcggtagaag ccgtaccgag gaagtccatc gacacgttcg ggcaaaggac ctctatatat      840
cgaggtgtaa caaggcatag atggacaggg cggtatgagg ctcatctatg ggataatagt      900
tgtagaagaa aagggcagag tcgcaagggt aggcaagttt accttggtgg ctatgacaag      960
gaggacaagg cagcaagggc ttacgatttg gcagctctca agtattgggg cactacgaca     1020
acaacaaatt tccctataag caactacgaa aaggagctag aagaaatgaa acatatgact     1080
agacaggagt acattgcata cctaagaaga aatagcagtg gattttctcg tggggcgtca     1140
aagtatcgtg gagtaactag acatcatcag catgggagat ggcaagcaag gataggggaga     1200 gttgcaggaa acaaggatct ctacttgggc acattcagca ccgaggagga ggcggcggag     1260
gcctacgaca tcgccgcgat caagttccgc ggtctcaacg ccgtcaccaa cttcgacatg     1320
agccgctacg acgtgaagag catcctcgag agcagcacac tgcctgtcgg cggcgcggcc     1380
aggcgcctca aggacgccgt ggaccacgtg gaggccggcg ccactatctg gcgcgccgac     1440
atggacggcg ccgtgatctc ccagctggcc gaagccggga tgggcggcta cgcctcgtac     1500
ggccaccacg gctggccgac catcgcgttc agcagccgt cgccgctctc cgtccactac     1560
ccgtacggcc agccgtcccg cgggtggtgc aaacccgagc aggacgcggc cgccgccgcg     1620
gcccacagcc tgcaggacct ccagcagctg cacctcggca gcgcggccca caacttcttc     1680
caggcgtcgt cgagctccac agtctacaac ggcggcgccg gcgccagtgg tgggtaccag     1740
ggcctcggtg gtggtagctc cttcctcatg ccgtcgagca ctgtcgtggc ggcggccgac     1800
caggggcaca gcagcacggc aaaccagggg agcacgtgca gctacgggga cgaccaccag     1860 gagggggaagc tcatcggtta cgacgccgcc atggtggcga ccgcagctgg tggagacccg     1920
tacgctgcgg cgaggaacgg gtaccagttc tcgcagggct cgggatccac ggtgagcatc     1980
gcgagggcga acgggtacgc taacaactgg agctctcctt tcaacaacgg catggggtga     2040
```

```
<210> SEQ ID NO 18
<211> LENGTH: 1485
<212> TYPE: DNA
<213> ORGANISM: Zea mays

<400> SEQUENCE: 18
```

```
atggacacct cgcaccacta tcatccatgg ctcaacttct ccctcgccca ccactgtgac       60
ctcgaggagg aggagagggg cgcggccgcc gagctggccg cgatagccgg cgccgcgccg      120
ccgccgaagc tggaggactt cctcggcgga ggcgtcgcca ccggtggtcc ggaggcggtg      180
gcgcccgcgg agatgtacga ctcggacctc aagttcatag ccgccgccgg gttccttggc      240
ggctcggcgg cggcggcggc gacgtcgccg ctgtcctccc tcgaccaggc cggttccaag      300
ctggccttgc ctgcggcggc ggctgctccg gcgccggagc agaggaaggc cgtcgactcc      360
tttgggcagc gcacgtccat ctaccgcggc gtcacacggc accggtggac tggcaggtac      420
gaggcacatc tgtgggacaa cagctgccga cgcgaagggc agagccgcaa gggccgccaa      480
gtatatttgg gtggctatga taaggaggag aaggctgcca gggcgtatga tcttgcagct      540
```

-continued

```
ttgaagtact ggggttctag caccaccacc aactttccgg ttgctgagta tgagaaggag      600
gtcgaggaga tgaagaacat gacgcgacaa gagtttgttg cttcccttcg aaggaagagc      660
agtggattct ctcggggtgc ttccatctac agaggtgtaa ccagacatca ccagcatgga      720
cggtggcagg cgaggatcgg aagggtggcc ggtaacaagg acctctacct tgggacgttc      780
agcaccgagg aggaagctgc agaggcctac gacatagcgg ccatcaagtt cagaggcctg      840
aacgccgtca caaacttcga gatcagccgg tacaacgtgg agaccataat gagcagcaac      900
cttccagtcg cgagcatgtc gtcgtcgtcg gcggcggcgg cgggtggccg gagcagcaag      960
gcgctggagt cccctccgtc cggctcgctt gacggcggcg gcggcatgcc agtcgtcgaa     1020
ggcagcacgg caccgccgct gttcattccg gtgaagtacg accagcagca gcaggagtac     1080
ctgtcgatgc tcgcgttgca gcaccaccac cagcagcaac aagcagggaa cctgttgcag     1140
gggccgctag tagggttcgg cggcctctac tcctccgggg tgaacctgga tttcgccaac     1200
tcccacggca cggcggctcc gtcgtcgatg gcccaccact gctacgccaa tggcaccgcg     1260
tccgcctcgc atgagcacca gcaccagcac cagatgcagc agggcggcga gaacgagacg     1320
cagccgcagc cgcagcagag ctccagcagc tgctcctccc tgccattcgc cacccccggtc    1380 gctttcaatg ggtcctatga aagctccatc acggcggcag gcccctttgg atactcctac     1440
ccaaatgtgg cagcctttca gacgccgatc tatggaatgg aatga                    1485

<210> SEQ ID NO 19
<211> LENGTH: 1470
<212> TYPE: DNA
<213> ORGANISM: Zea mays

<400> SEQUENCE: 19
atggacatgg acatgagctc agcttatccc caccattggc tctccttctc cctctccaac       60
aactaccacc atggcctact cgaggccttc tctaactcct ccggtactcc tcttggagac      120
gagccgggcg cagtggagga gtccccgagg acggtggagg acttcctcgg cggcgtcggt      180
ggcgccggcg ccccgccgca gccggcggct gctgcagatc aggatcacca gcttgtgtgc      240
ggcgagctgg gcagcatcac agccaggttc ttgcgccact acccggcggc gccagctggg      300
acgacggtgg agaaccccgg cgcggtgacc gtggcggcca tgtcgtcgac ggacgtggcg      360
ggggcggagt ccgaccaggc gaggcggccc gccgagacgt tcggccagcg cacatccatc      420
taccgtggcg tcaccaggca ccggtggaca gggagatatg aggcgcactt gtgggacaac      480
agctgccgcc gggagggcca aagccgcaaa ggacgccaag tctacctagg aggctatgac      540
aaggaggaga aggcggctag agcttacgac ctcgccgcgc tcaagtactg ggggcctaca      600
accacgacca acttcccggt gtccaactac gagaaggagc tggaggagat gaagtccatg      660
acgcggcagg agttcatcgc gtcgttgcgc aggaagagca gcggcttctc acgaggcgcc      720
tccatctaca gaggagtcac aaggcatcat cagcacggcc ggtggcaggc gaggatcggc      780
agggtggccg gaaacaagga cctgtacttg ggcactttca gtactcagga gagagcggcg      840
gaggcgtacg acatcgctgc gatcaagttc cgcgggctca cgccgtcac caacttcgac       900 atgagccgct acgacgtgga gagcatcctc agcagcgacc tccccgtcgg gggcggagcc      960
accgggcgcg ccgccaagtt cccgttggac tcgctgcagc cggggagcgc tgctgcgatg     1020
atgctcgccg gggctgctgc cgcttcgcag gccaccatgc cgccgtccga gaaggactac     1080
tggtctctgc tcgccctgca ctaccagcag cagcaggagc aggagcggca gttcccggct     1140
tctgcttacg aggcttacgg ctccggcggc gtgaacgtgg acttcacgat gggcaccagt     1200
```

-continued

```
agcggcaaca acaacaacaa caccggcagc ggcgtcatgt ggggcgccac cactggtgca    1260
gtagtagtgg gacagcaaga cagcagcggc aagcagggca acggctatgc cagcaacatt    1320
ccttatgctg ctgctgctgc tatggtttct ggatctgctg gctacgaggg ctccaccggc    1380
gacaatggaa cctgggttac tacgactatt accagcagca acaccggcac ggctccccac    1440
tactacaact atctcttcgg gatggagtag                                     1470

<210> SEQ ID NO 20
<211> LENGTH: 783
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
atggagtcgg gctccgggac ggctgctggc tctggctatg tttacagaca gccaggatca     60
acgcggtgga acccgacagc tgaacaactg tccttgctta gagaaatcta ctaccgcaac    120
ggattgcgga ccccgaccgc ggacgaaatc agacaaatca gctcaaagct ctcaaggtac    180
ggaaaaatag agggcaaaaa cgtttacaac tggttccaga atagacgcgc aagagaaaag    240
cgcaagcaac ggctctctac aatcggctgt gatccagcac tgatcgagat ggggaatgtc    300
gcttcactgg aattcggtac tgagagcgcc ctggaatcgc tgtcgtcagg accatcctca    360
gaactccgcg aagcgccaac gagaaaattt tacgaaaaaa agacggttgg agagaactca    420
actataataa acccagtgga acaaaactgt acccttcct gcggaacgtc ccaagagttc    480
cagtatgcgg tcgattctcg gcgcgtcatg aaagctatgg aggaaaagca ggcgacggac    540
gatgaacccg acggaaataa atggactgag tcaaacagac acgtcaagat tctccagctt    600
ttcccgctcc acaataacga ggatcagaca ttgataaaga gcgacaaaga aatctattgt    660
ttgggctcgt gcgagaagaa aatggatttg tcaccgctgg gtcattcagg ctctcagcgc    720
gcttcggccc ttgacttgtg cctttcattg ggcaacgaat cttgtgggct gcatgataat    780
tga                                                                   783

<210> SEQ ID NO 21
<211> LENGTH: 783
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
atggaatcgg gctccggcac ggcggcaggg tctggttatg tctatcggca gagcggaagc     60
acccggtgga atccaacagc agaacagttg tcgctgctca aggaacttta ttaccggaat    120
ggaattcgga caccgtcggc agatcaaatt aggcaaattt cggcccggct gtccagatac    180
ggcaaaatag aagggaaaaa cgtcttttac tggtttcaaa atcataaagc acgggaacgg    240
cagaagaaaa gactttccac ggtcggctgc gaccctgctc tcatagaaat gggtaacgtc    300
gcgagcttgg aatttgggac cgaaagcgct cttgaatctc tcagctcagg cccgtccagc    360
gagttgcgcg aggctcctac ccgcaagttt tatgagaaga aaaccgttgg tgagaacagc    420
accataatca atcctgttga gcagaactgc acactttctt gcggtacttc gcaggaattt    480
cagtatgctg ttgatagccg ccgggtgatg aaggcaatgg aagagaagca agcaacggat    540
```

-continued

```
gatgaaccgg acggaaacaa atggacggag tcgaacaggc atgtgaagac cctccctctt      600
ttccccttgc ataataatga agatcagacc ttgatcaagt cggacaagga aatttattgc      660
cttgggagct gtgaaaaaaa aatggatctg tccccattgg acactcgggg ctctcagagg      720
gcgtcggcac tggatttgtg cctgtctttg ggtaatgaat cttgtggcct ccacgacaat      780
tga                                                                    783

<210> SEQ ID NO 22
<211> LENGTH: 477
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
atggttagca aggggagga ggttattaaa gaattcccag gaagcacccg gtggaatcca       60
acggcggagc aactttcgct ccttcgggaa atttattaca ggaatgggct gagaactccc      120
accgctgacg agatcagaca gatttcatca aaattgtcgc ggtatggtaa gattgaaggg      180
aaaaatgtgt acaactggtt ccagaacaga gagctagggg aaaagagaaa acagcggttg      240
tcaaccatag gctgtggttc ggcggggtcg gccgcaggga gcggagagtt tcgccatgtg      300
aagaccctgc cccttttccc tttgcataat aatgaggatt caggttcgtt ggatctggag      360
ctggaattgg gttttgcctc tgctaccgca gccgcgactt ctggttcaca aagggcgtcg      420
gcattggatc tctgcctgtc ccttggaaat gagtcatgcg gtttgcatga caactga       477

<210> SEQ ID NO 23
<211> LENGTH: 477
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
atggtctcga aaggagaaga ggtcatcaaa gaattttcag gcagcacccg ctggaatccg       60
actgcagaac aactttctct cctcaaagag ctttattaca gaaatgggat cagaacccct      120
tcagcggacc agatacgcca gataagcgcc cgcttgtcga ggtacggcaa aatcgagggg      180
aagaatgttt tttactggtt ccaaaaccat aaagcgaggg agcggcagaa gaaaagactg      240
agcactgtgg gttgtggatc ggcgggatcg gctgccgggt caggtgaatt tcgccatgtt      300
aaaacgcttc cactgtttcc cttgcataat aatgaagaca gcggatcact tgacctggag      360
ctggagttgg gcttcgcttc cgcgacggct gctgcaacat ccggctcgca gcgggcgtcg      420
gcgctggatt tgtgcctttc gctgggaaat gagagctgcg gtcttcatga caactga       477

<210> SEQ ID NO 24
<211> LENGTH: 501
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
atggtgtcta aaggggaaga ggtcataaaa gagttctcag ttctactcg ctggaatcca        60 actgcagaac aactctctct cctgaaggag ctctactatc ggaacggaat acgcacgcct      120
```

-continued

```
tcggcggacc aaataaggca gatttcagcc cgcctgtcta gatacgggaa aatcgaggga    180
aagaacgtgt tttattggtt ccaaaaccat aaggcaagag agcggcagaa aaaacggctc    240
agcacagtcg gctgtgggtc agccggttcg gcggctggct ctggtgaatt ccgccacgtc    300
aaaaccctgc ctctgttccc gctccacaat aatgtcgaga cacttccctt gttcccggag    360
gattccgggt ctctcgactt ggagctcgaa ttgggctttg cctctgccac tgcggcagcg    420
accagcggat cacagagagc ctccgcactg gatctgtgcc tgtcacttgg aaatgaatcg    480
tgcggattgc acgacaattg a    501
```

<210> SEQ ID NO 25
<211> LENGTH: 771
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

```
atggtgtcta aaggcgaaga ggtcattaag gagttcagcg gctctactag atggaatcca    60
acggccgagc aacttagcct gctcaaagaa ctctattatc gcaatgggat acgcacgccc    120
tctgcagatc agatacgcca aatctcagcg cgcctgtcca ggtatgggaa gattgagggt    180
aaaaacgtct tttactggtt ccaaaatcac aaagcgcgcg agagacagaa gaaaagactc    240
agcaccgttg gttgtgaccc tgctctcatc gagatgggga atgttgcttc cctggagttt    300
ggcacagaga gcgctttgga atcactctct tccggcccct caagcgaact cagagaggct    360
cccactcgga agttttacga gaaaaaaacc gtcggagaaa acagcacgat tatcaacccc    420
gtcgagcaga actgcaccct ctcatgcggc acgtcccagg agtttcagta cgccgtcgac    480
tcgaggagag tgatgaaggc gatggaggaa aagcaagcaa ctgacgacga gcccgacgga    540
aacaagtgga ctgaatccaa tcgccatgtt aaaacgttgc ctttgttccc gctccataac    600
aatgtggaga cgttgccact cttcccggag gactcgggat ctctggactt ggagctggaa    660
ctgggctttg cttcggctac cgcagcagcc acctcgggtt cccagagagc ctcggctctt    720
gatctctgcc tgtcactggg taacgaatct tgcggactgc acgataatta g    771
```

<210> SEQ ID NO 26
<211> LENGTH: 840
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

```
atggtttcaa agggggagga ggtcataaaa gaattttctg gcagcactag atggaatccg    60
actgctgagc agttgtctct cctcaaagaa ctttactata ggaacggtat ccgcactccg    120
tccgctgatc aaaattcgcca aatttcggcc agactgtcca gatacgggaa aattgaggga    180
aaaaatgttt tctactggtt ccagaatcat aaggcgcgcg aaaggcagaa aaagagactt    240
tcgaccgtcg gatgtgaccc tgcacttatc gaaatgggca atgtcgcgtc gttggagttt    300
ggcaccgaat ccgctctcga atctcttagc tcgggcccct catcggaact cagagaggcc    360
cctaccagaa aattttatga gaaaaagaca gtgggagaga actctacaat cattaacccc    420
gtcgagcaga actgcacatt gagctgtgga acatcgcagg agtttcaata cgcggtggat    480
tcgcgccgcg ttatgaaggc aatggaggag aagcaggcaa cagatgatga gccagacggc    540
```

```
aataaatgga ccgaatctaa cagacatgtc aagacactgc cactttttcc tctccacaac      600
aatgtcgaga cactccctct gtttcccgag gattcgggaa gcctggatct tgagctggaa      660
cttggctttg catcaggtgg atctgccggg tcagttgaca cgctgccatt gtttcctaga      720
gaggctgcgg gttctgggga atttgccact gcggctgcga ctagcggatc acagcgcgca      780
tcggcgctcg acctctgcct ttctttgggt aacgagtctt gcggcctgca tgacaactga      840

<210> SEQ ID NO 27
<211> LENGTH: 498
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
atggtttcga aggggggaaga agtcattaaa gagtttttcag ggtctacgcg ctggaaccct      60
accgctgaac aagtcaaggt tttgagggaa atatattacc gcgcgggtct taggacgcca     120
tccgcggatc agatccgcca aatatcctca cagctgaaac ggtatggaaa ggtggaagga     180
aaaaacgtgt tttattggtt ccagaaccat aaagcgcggg aaagacaaaa aaagcggctc     240
agcaccgttg ggagcgctgg ctcagcagcg ggttcaggtg agttcaggca cgttaaaaca     300
ctgcccttgt tcctttgca caataatgaa gactcaggga gcggtttgga cttggatctg     360
aaccttgagt tgcgcctgtc ggcgactgct gctgccactt cgggctcaca gcgggcgtct     420
gccctcgatc tggacttgga gctcagactc ggtttcgcgc ttggtaatga gtcgtgtgga     480
ctgcacgaca actagtga                                                   498

<210> SEQ ID NO 28
<211> LENGTH: 367
<212> TYPE: PRT
<213> ORGANISM: Triticum aestivum

<400> SEQUENCE: 28

Met Glu Met Gln Gln Gln Tyr Phe Gly Gly Asp Gly Asp Ala Asp Trp
1               5                   10                  15

Phe His Gln Leu Ala Leu Leu Pro Pro Leu Pro Ile Ser Ser Ser Leu
            20                  25                  30

Pro Pro Leu Pro Met Ser Glu Gly Ser Cys Leu Pro Met Ala Ala Ala
        35                  40                  45

Ala Ala Ala Ala Leu Pro Leu Gly Asp Cys Ser Ser Ala Leu Met Ile
    50                  55                  60

Arg Pro Glu Glu Gln Met Ser Cys Leu Pro Met Asn Pro Ser Pro Ala
65                  70                  75                  80

Val Val Asp Asp Val Tyr Ser Ser Tyr Ala Pro Asn Asn Val Asp Val
                85                  90                  95

Leu Pro Pro Phe Pro Ala Gly Leu Asp Asp Ala Leu Leu Met Glu Ser
            100                 105                 110

Phe Ser Asp Ile Asp Leu Glu Glu Phe Ala Asp Ala Phe Gly His Lys
        115                 120                 125

Ile Lys Thr Glu Pro Leu Asp Asp Ala Met Val Pro Ala Asp His Asp
    130                 135                 140

Phe Ala Ala Gln Ala Gln Gln Ala Cys Pro Val Val Ile Met Asn Gln
145                 150                 155                 160

Gln Gln Leu Asn Ala Pro Arg Asp Val Arg Leu Leu Ile Asp Pro Asp
```

-continued

```
              165              170              175

Asp Asp Asp Ser Thr Val Val Ala Gly Gly Tyr Glu Ala Ala Ala Val
             180              185              190

Gly Cys Ala Glu Gln Lys Gln Val Arg Pro Ala Pro Arg Arg Val Arg
             195              200              205

Lys Ser Ser Gly Gly Ala Arg Pro Ala Ala Gly Gly Lys Ser Leu Asp
             210              215              220

His Ile Gly Phe Glu Glu Leu Arg Thr Tyr Phe Tyr Met Pro Ile Thr
225              230              235              240

Lys Ala Ala Arg Glu Met Asn Val Gly Leu Thr Val Leu Lys Lys Arg
             245              250              255

Cys Arg Glu Leu Gly Val Ala Arg Trp Pro His Arg Lys Met Lys Ser
             260              265              270

Leu Arg Ser Leu Ile Leu Asn Ile Gln Glu Met Gly Lys Gly Ala Thr
             275              280              285

Ser Pro Ala Ala Val Gln Gly Glu Leu Glu Ala Leu Glu Arg Tyr Cys
             290              295              300

Ala Ile Met Glu Glu Asn Pro Ala Ile Glu Leu Thr Glu Gln Thr Lys
305              310              315              320

Lys Leu Arg Gln Ala Cys Phe Lys Glu Asn Tyr Lys Arg Arg Arg Ala
             325              330              335

Ala Ala Ser Val Asn Leu Leu Asp His Cys Tyr Asn Asp Leu Ala Ser
             340              345              350

His Glu Gln Gln Met Pro Leu Pro Gln Met Gly Phe Phe Gly Phe
             355              360              365

<210> SEQ ID NO 29
<211> LENGTH: 679
<212> TYPE: PRT
<213> ORGANISM: Zea mays

<400> SEQUENCE: 29

Met Ala Ser Ala Asn Asn Trp Leu Gly Phe Ser Leu Ser Gly Gln Asp
1               5               10              15

Asn Pro Gln Pro Asn Gln Asp Ser Ser Pro Ala Ala Gly Ile Asp Ile
             20              25              30

Ser Gly Ala Ser Asp Phe Tyr Gly Leu Pro Thr Gln Gln Gly Ser Asp
             35              40              45

Gly His Leu Gly Val Pro Gly Leu Arg Asp Asp His Ala Ser Tyr Gly
     50              55              60

Ile Met Glu Ala Tyr Asn Arg Val Pro Gln Glu Thr Gln Asp Trp Asn
65              70              75              80

Met Arg Gly Leu Asp Tyr Asn Gly Gly Gly Ser Glu Leu Ser Met Leu
             85              90              95

Val Gly Ser Ser Gly Gly Gly Gly Asn Gly Lys Arg Ala Val Glu
             100             105             110

Asp Ser Glu Pro Lys Leu Glu Asp Phe Leu Gly Gly Asn Ser Phe Val
             115             120             125

Ser Asp Gln Asp Gln Ser Gly Gly Tyr Leu Phe Ser Gly Val Pro Ile
             130             135             140

Ala Ser Ser Ala Asn Ser Asn Ser Gly Ser Asn Thr Met Glu Leu Ser
145             150             155             160

Met Ile Lys Thr Trp Leu Arg Asn Asn Gln Val Ala Gln Pro Gln Pro
             165             170             175
```

-continued

Pro Ala Pro His Gln Pro Gln Pro Glu Glu Met Ser Thr Asp Ala Ser
                180                 185                 190

Gly Ser Ser Phe Gly Cys Ser Asp Ser Met Gly Arg Asn Ser Met Val
            195                 200                 205

Ala Ala Gly Gly Ser Ser Gln Ser Leu Ala Leu Ser Met Ser Thr Gly
    210                 215                 220

Ser His Leu Pro Met Val Val Ala Gly Gly Ser Ala Ser Gly Ala Ala
225                 230                 235                 240

Ser Glu Ser Thr Ser Ser Glu Asn Lys Arg Ala Ser Gly Ala Met Asp
                245                 250                 255

Ser Pro Gly Ser Ala Val Glu Ala Val Pro Arg Lys Ser Ile Asp Thr
            260                 265                 270

Phe Gly Gln Arg Thr Ser Ile Tyr Arg Gly Val Thr Arg His Arg Trp
            275                 280                 285

Thr Gly Arg Tyr Glu Ala His Leu Trp Asp Asn Ser Cys Arg Arg Glu
    290                 295                 300

Gly Gln Ser Arg Lys Gly Arg Gln Val Tyr Leu Gly Gly Tyr Asp Lys
305                 310                 315                 320

Glu Asp Lys Ala Ala Arg Ala Tyr Asp Leu Ala Ala Leu Lys Tyr Trp
                325                 330                 335

Gly Thr Thr Thr Thr Thr Asn Phe Pro Ile Ser Asn Tyr Glu Lys Glu
                340                 345                 350

Leu Glu Glu Met Lys His Met Thr Arg Gln Glu Tyr Ile Ala Tyr Leu
            355                 360                 365

Arg Arg Asn Ser Ser Gly Phe Ser Arg Gly Ala Ser Lys Tyr Arg Gly
    370                 375                 380

Val Thr Arg His His Gln His Gly Arg Trp Gln Ala Arg Ile Gly Arg
385                 390                 395                 400

Val Ala Gly Asn Lys Asp Leu Tyr Leu Gly Thr Phe Ser Thr Glu Glu
                405                 410                 415

Glu Ala Ala Glu Ala Tyr Asp Ile Ala Ala Ile Lys Phe Arg Gly Leu
            420                 425                 430

Asn Ala Val Thr Asn Phe Asp Met Ser Arg Tyr Asp Val Lys Ser Ile
            435                 440                 445

Leu Glu Ser Ser Thr Leu Pro Val Gly Gly Ala Ala Arg Arg Leu Lys
    450                 455                 460

Asp Ala Val Asp His Val Glu Ala Gly Ala Thr Ile Trp Arg Ala Asp
465                 470                 475                 480

Met Asp Gly Ala Val Ile Ser Gln Leu Ala Glu Ala Gly Met Gly Gly
                485                 490                 495

Tyr Ala Ser Tyr Gly His His Gly Trp Pro Thr Ile Ala Phe Gln Gln
            500                 505                 510

Pro Ser Pro Leu Ser Val His Tyr Pro Tyr Gly Gln Pro Ser Arg Gly
            515                 520                 525

Trp Cys Lys Pro Glu Gln Asp Ala Ala Ala Ala Ala His Ser Leu
    530                 535                 540

Gln Asp Leu Gln Gln Leu His Leu Gly Ser Ala Ala His Asn Phe Phe
545                 550                 555                 560

Gln Ala Ser Ser Ser Ser Thr Val Tyr Asn Gly Gly Ala Gly Ala Ser
            565                 570                 575

Gly Gly Tyr Gln Gly Leu Gly Gly Gly Ser Ser Phe Leu Met Pro Ser
            580                 585                 590

Ser Thr Val Val Ala Ala Ala Asp Gln Gly His Ser Ser Thr Ala Asn

-continued

```
            595                 600                 605

Gln Gly Ser Thr Cys Ser Tyr Gly Asp Asp His Gln Glu Gly Lys Leu
        610                 615                 620

Ile Gly Tyr Asp Ala Ala Met Val Ala Thr Ala Ala Gly Gly Asp Pro
625                 630                 635                 640

Tyr Ala Ala Ala Arg Asn Gly Tyr Gln Phe Ser Gln Gly Ser Gly Ser
                645                 650                 655

Thr Val Ser Ile Ala Arg Ala Asn Gly Tyr Ala Asn Asn Trp Ser Ser
                660                 665                 670

Pro Phe Asn Asn Gly Met Gly
        675

<210> SEQ ID NO 30
<211> LENGTH: 494
<212> TYPE: PRT
<213> ORGANISM: Zea mays

<400> SEQUENCE: 30

Met Asp Thr Ser His His Tyr His Pro Trp Leu Asn Phe Ser Leu Ala
1               5                   10                  15

His His Cys Asp Leu Glu Glu Glu Glu Arg Gly Ala Ala Ala Glu Leu
            20                  25                  30

Ala Ala Ile Ala Gly Ala Ala Pro Pro Pro Lys Leu Glu Asp Phe Leu
            35                  40                  45

Gly Gly Gly Val Ala Thr Gly Gly Pro Glu Ala Val Ala Pro Ala Glu
        50                  55                  60

Met Tyr Asp Ser Asp Leu Lys Phe Ile Ala Ala Ala Gly Phe Leu Gly
65                  70                  75                  80

Gly Ser Ala Ala Ala Ala Ala Thr Ser Pro Leu Ser Ser Leu Asp Gln
                85                  90                  95

Ala Gly Ser Lys Leu Ala Leu Pro Ala Ala Ala Ala Pro Ala Pro
            100                 105                 110

Glu Gln Arg Lys Ala Val Asp Ser Phe Gly Gln Arg Thr Ser Ile Tyr
            115                 120                 125

Arg Gly Val Thr Arg His Arg Trp Thr Gly Arg Tyr Glu Ala His Leu
        130                 135                 140

Trp Asp Asn Ser Cys Arg Arg Glu Gly Gln Ser Arg Lys Gly Arg Gln
145                 150                 155                 160

Val Tyr Leu Gly Gly Tyr Asp Lys Glu Glu Lys Ala Ala Arg Ala Tyr
                165                 170                 175

Asp Leu Ala Ala Leu Lys Tyr Trp Gly Ser Ser Thr Thr Thr Asn Phe
            180                 185                 190

Pro Val Ala Glu Tyr Glu Lys Glu Val Glu Glu Met Lys Asn Met Thr
            195                 200                 205

Arg Gln Glu Phe Val Ala Ser Leu Arg Arg Lys Ser Ser Gly Phe Ser
        210                 215                 220

Arg Gly Ala Ser Ile Tyr Arg Gly Val Thr Arg His His Gln His Gly
225                 230                 235                 240

Arg Trp Gln Ala Arg Ile Gly Arg Val Ala Gly Asn Lys Asp Leu Tyr
                245                 250                 255

Leu Gly Thr Phe Ser Thr Glu Glu Glu Ala Ala Glu Ala Tyr Asp Ile
            260                 265                 270

Ala Ala Ile Lys Phe Arg Gly Leu Asn Ala Val Thr Asn Phe Glu Ile
            275                 280                 285
```

```
Ser Arg Tyr Asn Val Glu Thr Ile Met Ser Ser Asn Leu Pro Val Ala
    290             295                 300

Ser Met Ser Ser Ser Ser Ala Ala Ala Ala Gly Gly Arg Ser Ser Lys
305             310                 315                 320

Ala Leu Glu Ser Pro Pro Ser Gly Ser Leu Asp Gly Gly Gly Gly Met
            325                 330                 335

Pro Val Val Glu Gly Ser Thr Ala Pro Pro Leu Phe Ile Pro Val Lys
            340                 345                 350

Tyr Asp Gln Gln Gln Gln Glu Tyr Leu Ser Met Leu Ala Leu Gln His
            355                 360                 365

His His Gln Gln Gln Gln Ala Gly Asn Leu Leu Gln Gly Pro Leu Val
            370                 375                 380

Gly Phe Gly Gly Leu Tyr Ser Ser Gly Val Asn Leu Asp Phe Ala Asn
385             390                 395                 400

Ser His Gly Thr Ala Ala Pro Ser Ser Met Ala His His Cys Tyr Ala
            405                 410                 415

Asn Gly Thr Ala Ser Ala Ser His Glu His Gln His Gln His Gln Met
            420                 425                 430

Gln Gln Gly Gly Glu Asn Glu Thr Gln Pro Gln Pro Gln Gln Ser Ser
            435                 440                 445

Ser Ser Cys Ser Ser Leu Pro Phe Ala Thr Pro Val Ala Phe Asn Gly
    450                 455                 460

Ser Tyr Glu Ser Ser Ile Thr Ala Ala Gly Pro Phe Gly Tyr Ser Tyr
465                 470                 475                 480

Pro Asn Val Ala Ala Phe Gln Thr Pro Ile Tyr Gly Met Glu
            485                 490
```

```
<210> SEQ ID NO 31
<211> LENGTH: 489
<212> TYPE: PRT
<213> ORGANISM: Zea mays

<400> SEQUENCE: 31
```

```
Met Asp Met Asp Met Ser Ser Ala Tyr Pro His His Trp Leu Ser Phe
1               5                   10                  15

Ser Leu Ser Asn Asn Tyr His His Gly Leu Leu Glu Ala Phe Ser Asn
            20                  25                  30

Ser Ser Gly Thr Pro Leu Gly Asp Glu Pro Gly Ala Val Glu Glu Ser
        35                  40                  45

Pro Arg Thr Val Glu Asp Phe Leu Gly Gly Val Gly Gly Ala Gly Ala
    50                  55                  60

Pro Pro Gln Pro Ala Ala Ala Ala Asp Gln Asp His Gln Leu Val Cys
65                  70                  75                  80

Gly Glu Leu Gly Ser Ile Thr Ala Arg Phe Leu Arg His Tyr Pro Ala
            85                  90                  95

Ala Pro Ala Gly Thr Thr Val Glu Asn Pro Gly Ala Val Thr Val Ala
            100                 105                 110

Ala Met Ser Ser Thr Asp Val Ala Gly Ala Glu Ser Asp Gln Ala Arg
        115                 120                 125

Arg Pro Ala Glu Thr Phe Gly Gln Arg Thr Ser Ile Tyr Arg Gly Val
    130                 135                 140

Thr Arg His Arg Trp Thr Gly Arg Tyr Glu Ala His Leu Trp Asp Asn
145                 150                 155                 160

Ser Cys Arg Arg Glu Gly Gln Ser Arg Lys Gly Arg Gln Val Tyr Leu
            165                 170                 175
```

-continued

```
Gly Gly Tyr Asp Lys Glu Glu Lys Ala Ala Arg Ala Tyr Asp Leu Ala
            180                 185                 190

Ala Leu Lys Tyr Trp Gly Pro Thr Thr Thr Thr Asn Phe Pro Val Ser
            195                 200                 205

Asn Tyr Glu Lys Glu Leu Glu Glu Met Lys Ser Met Thr Arg Gln Glu
            210                 215                 220

Phe Ile Ala Ser Leu Arg Arg Lys Ser Ser Gly Phe Ser Arg Gly Ala
225                 230                 235                 240

Ser Ile Tyr Arg Gly Val Thr Arg His His Gln His Gly Arg Trp Gln
            245                 250                 255

Ala Arg Ile Gly Arg Val Ala Gly Asn Lys Asp Leu Tyr Leu Gly Thr
            260                 265                 270

Phe Ser Thr Gln Glu Glu Ala Ala Glu Ala Tyr Asp Ile Ala Ala Ile
            275                 280                 285

Lys Phe Arg Gly Leu Asn Ala Val Thr Asn Phe Asp Met Ser Arg Tyr
    290                 295                 300

Asp Val Glu Ser Ile Leu Ser Ser Asp Leu Pro Val Gly Gly Gly Ala
305                 310                 315                 320

Thr Gly Arg Ala Ala Lys Phe Pro Leu Asp Ser Leu Gln Pro Gly Ser
            325                 330                 335

Ala Ala Ala Met Met Leu Ala Gly Ala Ala Ala Ala Ser Gln Ala Thr
            340                 345                 350

Met Pro Pro Ser Glu Lys Asp Tyr Trp Ser Leu Leu Ala Leu His Tyr
            355                 360                 365

Gln Gln Gln Gln Glu Gln Glu Arg Gln Phe Pro Ala Ser Ala Tyr Glu
    370                 375                 380

Ala Tyr Gly Ser Gly Gly Val Asn Val Asp Phe Thr Met Gly Thr Ser
385                 390                 395                 400

Ser Gly Asn Asn Asn Asn Thr Gly Ser Gly Val Met Trp Gly Ala
            405                 410                 415

Thr Thr Gly Ala Val Val Val Gly Gln Gln Asp Ser Ser Gly Lys Gln
            420                 425                 430

Gly Asn Gly Tyr Ala Ser Asn Ile Pro Tyr Ala Ala Ala Ala Ala Met
            435                 440                 445

Val Ser Gly Ser Ala Gly Tyr Glu Gly Ser Thr Gly Asp Asn Gly Thr
    450                 455                 460

Trp Val Thr Thr Thr Ile Thr Ser Ser Asn Thr Gly Thr Ala Pro His
465                 470                 475                 480

Tyr Tyr Asn Tyr Leu Phe Gly Met Glu
            485
```

```
<210> SEQ ID NO 32
<211> LENGTH: 260
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Met Glu Ser Gly Ser Gly Thr Ala Ala Gly Ser Gly Tyr Val Tyr Arg
1               5                   10                  15

Gln Pro Gly Ser Thr Arg Trp Asn Pro Thr Ala Glu Gln Leu Ser Leu
            20                  25                  30

Leu Arg Glu Ile Tyr Tyr Arg Asn Gly Leu Arg Thr Pro Thr Ala Asp
```

-continued

```
            35                  40                  45
Glu Ile Arg Gln Ile Ser Ser Lys Leu Ser Arg Tyr Gly Lys Ile Glu
        50                  55                  60
Gly Lys Asn Val Tyr Asn Trp Phe Gln Asn Arg Arg Ala Arg Glu Lys
65                  70                  75                  80
Arg Lys Gln Arg Leu Ser Thr Ile Gly Cys Asp Pro Ala Leu Ile Glu
                85                  90                  95
Met Gly Asn Val Ala Ser Leu Glu Phe Gly Thr Glu Ser Ala Leu Glu
                100                 105                 110
Ser Leu Ser Ser Gly Pro Ser Ser Glu Leu Arg Glu Ala Pro Thr Arg
                115                 120                 125
Lys Phe Tyr Glu Lys Lys Thr Val Gly Glu Asn Ser Thr Ile Ile Asn
        130                 135                 140
Pro Val Glu Gln Asn Cys Thr Leu Ser Cys Gly Thr Ser Gln Glu Phe
145                 150                 155                 160
Gln Tyr Ala Val Asp Ser Arg Arg Val Met Lys Ala Met Glu Glu Lys
                165                 170                 175
Gln Ala Thr Asp Asp Glu Pro Asp Gly Asn Lys Trp Thr Glu Ser Asn
                180                 185                 190
Arg His Val Lys Ile Leu Gln Leu Phe Pro Leu His Asn Asn Glu Asp
                195                 200                 205
Gln Thr Leu Ile Lys Ser Asp Lys Glu Ile Tyr Cys Leu Gly Ser Cys
        210                 215                 220
Glu Lys Lys Met Asp Leu Ser Pro Leu Gly His Ser Gly Ser Gln Arg
225                 230                 235                 240
Ala Ser Ala Leu Asp Leu Cys Leu Ser Leu Gly Asn Glu Ser Cys Gly
                245                 250                 255
Leu His Asp Asn
                260

<210> SEQ ID NO 33
<211> LENGTH: 260
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Met Glu Ser Gly Ser Gly Thr Ala Ala Gly Ser Gly Tyr Val Tyr Arg
1               5                   10                  15
Gln Ser Gly Ser Thr Arg Trp Asn Pro Thr Ala Glu Gln Leu Ser Leu
                20                  25                  30
Leu Lys Glu Leu Tyr Tyr Arg Asn Gly Ile Arg Thr Pro Ser Ala Asp
        35                  40                  45
Gln Ile Arg Gln Ile Ser Ala Arg Leu Ser Arg Tyr Gly Lys Ile Glu
        50                  55                  60
Gly Lys Asn Val Phe Tyr Trp Phe Gln Asn His Lys Ala Arg Glu Arg
65                  70                  75                  80
Gln Lys Lys Arg Leu Ser Thr Val Gly Cys Asp Pro Ala Leu Ile Glu
                85                  90                  95
Met Gly Asn Val Ala Ser Leu Glu Phe Gly Thr Glu Ser Ala Leu Glu
                100                 105                 110
Ser Leu Ser Ser Gly Pro Ser Ser Glu Leu Arg Glu Ala Pro Thr Arg
                115                 120                 125
```

-continued

```
Lys Phe Tyr Glu Lys Lys Thr Val Gly Glu Asn Ser Thr Ile Ile Asn
    130                 135                 140

Pro Val Glu Gln Asn Cys Thr Leu Ser Cys Gly Thr Ser Gln Glu Phe
145                 150                 155                 160

Gln Tyr Ala Val Asp Ser Arg Arg Val Met Lys Ala Met Glu Glu Lys
                165                 170                 175

Gln Ala Thr Asp Asp Glu Pro Asp Gly Asn Lys Trp Thr Glu Ser Asn
                180                 185                 190

Arg His Val Lys Thr Leu Pro Leu Phe Pro Leu His Asn Asn Glu Asp
            195                 200                 205

Gln Thr Leu Ile Lys Ser Asp Lys Glu Ile Tyr Cys Leu Gly Ser Cys
    210                 215                 220

Glu Lys Lys Met Asp Leu Ser Pro Leu Gly His Ser Gly Ser Gln Arg
225                 230                 235                 240

Ala Ser Ala Leu Asp Leu Cys Leu Ser Leu Gly Asn Glu Ser Cys Gly
                245                 250                 255

Leu His Asp Asn
            260
```

<210> SEQ ID NO 34
<211> LENGTH: 158
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

```
Met Val Ser Lys Gly Glu Glu Val Ile Lys Glu Phe Pro Gly Ser Thr
1               5                   10                  15

Arg Trp Asn Pro Thr Ala Glu Gln Leu Ser Leu Leu Arg Glu Ile Tyr
            20                  25                  30

Tyr Arg Asn Gly Leu Arg Thr Pro Thr Ala Asp Glu Ile Arg Gln Ile
        35                  40                  45

Ser Ser Lys Leu Ser Arg Tyr Gly Lys Ile Glu Gly Lys Asn Val Tyr
    50                  55                  60

Asn Trp Phe Gln Asn Arg Arg Ala Arg Glu Lys Arg Lys Gln Arg Leu
65                  70                  75                  80

Ser Thr Ile Gly Cys Gly Ser Ala Gly Ser Ala Ala Gly Ser Gly Glu
                85                  90                  95

Phe Arg His Val Lys Thr Leu Pro Leu Phe Pro Leu His Asn Asn Glu
                100                 105                 110

Asp Ser Gly Ser Leu Asp Leu Glu Leu Glu Leu Gly Phe Ala Ser Ala
        115                 120                 125

Thr Ala Ala Ala Thr Ser Gly Ser Gln Arg Ala Ser Ala Leu Asp Leu
    130                 135                 140

Cys Leu Ser Leu Gly Asn Glu Ser Cys Gly Leu His Asp Asn
145                 150                 155
```

<210> SEQ ID NO 35
<211> LENGTH: 158
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

-continued

```
Met Val Ser Lys Gly Glu Glu Val Ile Lys Glu Phe Ser Gly Ser Thr
1               5                   10                  15

Arg Trp Asn Pro Thr Ala Glu Gln Leu Ser Leu Leu Lys Glu Leu Tyr
                20                  25                  30

Tyr Arg Asn Gly Ile Arg Thr Pro Ser Ala Asp Gln Ile Arg Gln Ile
            35                  40                  45

Ser Ala Arg Leu Ser Arg Tyr Gly Lys Ile Glu Gly Lys Asn Val Phe
        50                  55                  60

Tyr Trp Phe Gln Asn His Lys Ala Arg Glu Arg Gln Lys Lys Arg Leu
65                  70                  75                  80

Ser Thr Val Gly Cys Gly Ser Ala Gly Ser Ala Ala Gly Ser Gly Glu
                85                  90                  95

Phe Arg His Val Lys Thr Leu Pro Leu Phe Pro Leu His Asn Asn Glu
                100                 105                 110

Asp Ser Gly Ser Leu Asp Leu Glu Leu Glu Leu Gly Phe Ala Ser Ala
            115                 120                 125

Thr Ala Ala Ala Thr Ser Gly Ser Gln Arg Ala Ser Ala Leu Asp Leu
        130                 135                 140

Cys Leu Ser Leu Gly Asn Glu Ser Cys Gly Leu His Asp Asn
145                 150                 155
```

```
<210> SEQ ID NO 36
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36
```

```
Met Val Ser Lys Gly Glu Glu Val Ile Lys Glu Phe Ser Gly Ser Thr
1               5                   10                  15

Arg Trp Asn Pro Thr Ala Glu Gln Leu Ser Leu Leu Lys Glu Leu Tyr
                20                  25                  30

Tyr Arg Asn Gly Ile Arg Thr Pro Ser Ala Asp Gln Ile Arg Gln Ile
            35                  40                  45

Ser Ala Arg Leu Ser Arg Tyr Gly Lys Ile Glu Gly Lys Asn Val Phe
        50                  55                  60

Tyr Trp Phe Gln Asn His Lys Ala Arg Glu Arg Gln Lys Lys Arg Leu
65                  70                  75                  80

Ser Thr Val Gly Cys Gly Ser Ala Gly Ser Ala Ala Gly Ser Gly Glu
                85                  90                  95

Phe Arg His Val Lys Thr Leu Pro Leu Phe Pro Leu His Asn Asn Val
                100                 105                 110

Glu Thr Leu Pro Leu Phe Pro Glu Asp Ser Gly Ser Leu Asp Leu Glu
            115                 120                 125

Leu Glu Leu Gly Phe Ala Ser Ala Thr Ala Ala Ala Thr Ser Gly Ser
        130                 135                 140

Gln Arg Ala Ser Ala Leu Asp Leu Cys Leu Ser Leu Gly Asn Glu Ser
145                 150                 155                 160

Cys Gly Leu His Asp Asn
                165
```

```
<210> SEQ ID NO 37
<211> LENGTH: 256
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 37

Met Val Ser Lys Gly Glu Glu Val Ile Lys Glu Phe Ser Gly Ser Thr
1               5                   10                  15

Arg Trp Asn Pro Thr Ala Glu Gln Leu Ser Leu Leu Lys Glu Leu Tyr
                20                  25                  30

Tyr Arg Asn Gly Ile Arg Thr Pro Ser Ala Asp Gln Ile Arg Gln Ile
        35                  40                  45

Ser Ala Arg Leu Ser Arg Tyr Gly Lys Ile Glu Gly Lys Asn Val Phe
    50                  55                  60

Tyr Trp Phe Gln Asn His Lys Ala Arg Glu Arg Gln Lys Lys Arg Leu
65                  70                  75                  80

Ser Thr Val Gly Cys Asp Pro Ala Leu Ile Glu Met Gly Asn Val Ala
                85                  90                  95

Ser Leu Glu Phe Gly Thr Glu Ser Ala Leu Glu Ser Leu Ser Ser Gly
            100                 105                 110

Pro Ser Ser Glu Leu Arg Glu Ala Pro Thr Arg Lys Phe Tyr Glu Lys
            115                 120                 125

Lys Thr Val Gly Glu Asn Ser Thr Ile Ile Asn Pro Val Glu Gln Asn
    130                 135                 140

Cys Thr Leu Ser Cys Gly Thr Ser Gln Glu Phe Gln Tyr Ala Val Asp
145                 150                 155                 160

Ser Arg Arg Val Met Lys Ala Met Glu Glu Lys Gln Ala Thr Asp Asp
                165                 170                 175

Glu Pro Asp Gly Asn Lys Trp Thr Glu Ser Asn Arg His Val Lys Thr
            180                 185                 190

Leu Pro Leu Phe Pro Leu His Asn Asn Val Glu Thr Leu Pro Leu Phe
            195                 200                 205

Pro Glu Asp Ser Gly Ser Leu Asp Leu Glu Leu Glu Leu Gly Phe Ala
            210                 215                 220

Ser Ala Thr Ala Ala Ala Thr Ser Gly Ser Gln Arg Ala Ser Ala Leu
225                 230                 235                 240

Asp Leu Cys Leu Ser Leu Gly Asn Glu Ser Cys Gly Leu His Asp Asn
                245                 250                 255

<210> SEQ ID NO 38
<211> LENGTH: 279
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Val Ser Lys Gly Glu Glu Val Ile Lys Glu Phe Ser Gly Ser Thr
1               5                   10                  15

Arg Trp Asn Pro Thr Ala Glu Gln Leu Ser Leu Leu Lys Glu Leu Tyr
                20                  25                  30

Tyr Arg Asn Gly Ile Arg Thr Pro Ser Ala Asp Gln Ile Arg Gln Ile
        35                  40                  45

Ser Ala Arg Leu Ser Arg Tyr Gly Lys Ile Glu Gly Lys Asn Val Phe
    50                  55                  60

Tyr Trp Phe Gln Asn His Lys Ala Arg Glu Arg Gln Lys Lys Arg Leu
65                  70                  75                  80
```

-continued

```
Ser Thr Val Gly Cys Asp Pro Ala Leu Ile Glu Met Gly Asn Val Ala
                85                  90                  95

Ser Leu Glu Phe Gly Thr Glu Ser Ala Leu Glu Ser Leu Ser Ser Gly
               100                 105                 110

Pro Ser Ser Glu Leu Arg Glu Ala Pro Thr Arg Lys Phe Tyr Glu Lys
               115                 120                 125

Lys Thr Val Gly Glu Asn Ser Thr Ile Ile Asn Pro Val Glu Gln Asn
           130                 135                 140

Cys Thr Leu Ser Cys Gly Thr Ser Gln Glu Phe Gln Tyr Ala Val Asp
145                 150                 155                 160

Ser Arg Arg Val Met Lys Ala Met Glu Glu Lys Gln Ala Thr Asp Asp
               165                 170                 175

Glu Pro Asp Gly Asn Lys Trp Thr Glu Ser Asn Arg His Val Lys Thr
               180                 185                 190

Leu Pro Leu Phe Pro Leu His Asn Asn Val Glu Thr Leu Pro Leu Phe
               195                 200                 205

Pro Glu Asp Ser Gly Ser Leu Asp Leu Glu Leu Glu Leu Gly Phe Ala
           210                 215                 220

Ser Gly Gly Ser Ala Gly Ser Val Asp Thr Leu Pro Leu Phe Pro Arg
225                 230                 235                 240

Glu Ala Ala Gly Ser Gly Glu Phe Ala Thr Ala Ala Ala Thr Ser Gly
               245                 250                 255

Ser Gln Arg Ala Ser Ala Leu Asp Leu Cys Leu Ser Leu Gly Asn Glu
               260                 265                 270

Ser Cys Gly Leu His Asp Asn
           275
```

```
<210> SEQ ID NO 39
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39
```

```
Met Val Ser Lys Gly Glu Glu Val Ile Lys Glu Phe Ser Gly Ser Thr
1               5                  10                  15

Arg Trp Asn Pro Thr Ala Glu Gln Val Lys Val Leu Arg Glu Ile Tyr
               20                  25                  30

Tyr Arg Ala Gly Leu Arg Thr Pro Ser Ala Asp Gln Ile Arg Gln Ile
           35                  40                  45

Ser Ser Gln Leu Lys Arg Tyr Gly Lys Val Glu Gly Lys Asn Val Phe
           50                  55                  60

Tyr Trp Phe Gln Asn His Lys Ala Arg Glu Arg Gln Lys Lys Arg Leu
65                  70                  75                  80

Ser Thr Val Gly Ser Ala Gly Ser Ala Ala Gly Ser Gly Glu Phe Arg
                85                  90                  95

His Val Lys Thr Leu Pro Leu Phe Pro Leu His Asn Asn Glu Asp Ser
               100                 105                 110

Gly Ser Gly Leu Asp Leu Asp Leu Asn Leu Glu Leu Arg Leu Ser Ala
               115                 120                 125

Thr Ala Ala Ala Thr Ser Gly Ser Gln Arg Ala Ser Ala Leu Asp Leu
           130                 135                 140

Asp Leu Glu Leu Arg Leu Gly Phe Ala Leu Gly Asn Glu Ser Cys Gly
```

-continued 145               150               155               160

Leu His Asp Asn

<210> SEQ ID NO 40
<211> LENGTH: 6186
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
agcttacgcg tgtcgactcg aatttccccg atcgttcaaa catttggcaa taaagtttct      60
taagattgaa tcctgttgcc ggtcttgcga tgattatcat ataatttctg ttgaattacg     120
ttaagcatgt aataattaac atgtaatgca tgacgttatt tatgagatgg gtttttatga     180
ttagagtccc gcaattatac atttaatacg cgatagaaaa caaaatatag cgcgcaaact     240
aggataaatt atcgcgcgcg gtgtcatcta tgttactaga tcgctcgacg cggccgccat     300
ggccagatcg tacccaattc gccctatagt gagtcgtatt acaattcact ggccgtcgtt     360
ttacaacgtc gtgactggga aaaccctggc gttacccaac ttaatcgcct tgcagcacat     420
ccccctttcg ccagctggcg taatagcgaa gaggcccgca ccgatcgccc ttcccaacag     480
ttgcgcagcc tgaatggcga atggaaattg taagcgttaa tattttgtta aaattcgcgt     540 taaattttg ttaaatcagc tcattttta accataggc cgaaatcggc aaaatccctt      600
ataaatcaaa agaatagacc gagatagggt tgagtgttgt tccagtttgg aacaagagtc     660
cactattaaa gaacgtggac tccaacgtca aagggcgaaa aaccgtctat cagggcgatg     720
gcccactacg tgaaccatca ccctaatcaa gttttttggg gtcgaggtgc cgtaaagcac     780
taaatcggaa ccctaaaggg agcccccgat ttagagcttg acgggaaag ccggcgaacg      840 tggcgagaaa ggaagggaag aaagcgaaag gagcgggcgc tagggcgctg gcaagtgtag     900
cggtcacgct gcgcgtaacc accacacccg ccgcgcttaa tgcgccgcta cagggcgcgt     960
caggtggcac ttttcgggga atgtgcgcg gaacccctat ttgtttattt ttctaaatac     1020
attcaaatat gtatccgctc atgagacaat aaccctgata aatgcttcaa taatattgaa     1080
aaaggaagag tatgagtatt caacatttcc gtgtcgccct tattcccttt tttgcggcat     1140
tttgccttcc tgttttgct cacccagaaa cgctggtgaa agtaaaagat gctgaagatc      1200
agttgggtgc acgagtgggt tacatcgaac tggatctcaa cagcggtaag atccttgaga     1260
gttttcgccc cgaagaacgt tttccaatga tgagcacttt taaagttctg ctatgtggcg     1320
cggtattatc ccgtattgac gccgggcaag agcaactcgg tcgccgcata cactattctc     1380
agaatgactt ggttgagtac tcaccagtca cagaaaagca tcttacggat ggcatgacag     1440
taagagaatt atgcagtgct gccataacca tgagtgataa cactgcggcc aacttacttc     1500
tgacaacgat cggaggaccg aaggagctaa ccgcttttt gcacaacatg ggggatcatg      1560
taactcgcct tgatcgttgg gaaccggagc tgaatgaagc cataccaaac gacgagcgtg     1620
acaccacgat gcctgtagca atggcaacaa cgttgcgcaa actattaact ggcgaactac     1680
ttactctagc ttcccggcaa caattaatag actggatgga ggcggataaa gttgcaggac     1740
cacttctgcg ctcggccctt ccggctggct ggtttattgc tgataaatct ggagccggtg     1800
agcgtgggtc tcgcggtatc attgcagcac tggggccaga tggtaagccc tcccgtatcg     1860
tagttatcta cacgacgggg agtcaggcaa ctatggatga acgaaataga cagatcgctg     1920

-continued

```
agataggtgc ctcactgatt aagcattggt aactgtcaga ccaagtttac tcatatatac    1980
tttagattga tttaaaactt catttttaat ttaaaaggat ctaggtgaag atcctttttg    2040
ataatctcat gaccaaaatc ccttaacgtg agttttcgtt ccactgagcg tcagaccccg    2100
tagaaaagat caaaggatct tcttgagatc ctttttttct gcgcgtaatc tgctgcttgc    2160
aaacaaaaaa accaccgcta ccagcggtgg tttgtttgcc ggatcaagag ctaccaactc    2220 ttttttccgaa ggtaactggc ttcagcagag cgcagatacc aaatactgtc cttctagtgt    2280
agccgtagtt aggccaccac ttcaagaact ctgtagcacc gcctacatac ctcgctctgc    2340
taatcctgtt accagtggct gctgccagtg gcgataagtc gtgtcttacc gggttggact    2400
caagacgata gttaccggat aaggcgcagc ggtcgggctg aacggggggt tcgtgcacac    2460
agcccagctt ggagcgaacg acctacaccg aactgagata cctacagcgt gagctatgag    2520
aaagcgccac gcttcccgaa gggagaaagg cggacaggta tccggtaagc ggcagggtcg    2580
gaacaggaga gcgcacgagg gagcttccag ggggaaacgc ctggtatctt tatagtcctg    2640
tcgggtttcg ccacctctga cttgagcgtc gatttttgtg atgctcgtca ggggggcgga    2700
gcctatggaa aaacgccagc aacgcggcct ttttacggtt cctggccttt tgctggcctt    2760
ttgctcacat gttctttcct gcgttatccc ctgattctgt ggataaccgt attaccgcct    2820
ttgagtgagc tgataccgct cgccgcagcc gaacgaccga gcgcagcgag tcagtgagcg    2880
aggaagcgga agagcgccca atacgcaaac cgcctctccc cgcgcgttgg ccgattcatt    2940
aatgcagctg gcacgacagg tttcccgact ggaaagcggg cagtgagcgc aacgcaatta    3000
atgtgagtta gctcactcat taggcacccc aggctttaca ctttatgctt ccggctcgta    3060
tgttgtgtgg aattgtgagc ggataacaat ttcacacagg aaacagctat gaccatgatt    3120
acgccaagct cgaaattaac cctcactaaa gggaacaaaa gctggactag aggcccttaa    3180
ggccttacta gacttcaccg ccattgcaaa aattgtcaat aaatatttag agtgggtggc    3240
atcagaaaaa catctctagt ggactctctt cctatcatag ctactcgggc tgtagataga    3300
acgagggcac aagagttggg tggcgtaggt ttactcgtga cctcaactct tttggctgtg    3360
tcttacgtct aagatgggtt tggcatgtga gaaacatagg tctaagcaat tcatgttagg    3420
gctgttgcat tgttgttgca tcaaccaaat gtccagatag cagttcatgc tacatctagt    3480
tgaaaaccct catcattagg cggaacatgt gttctttttt agcatagtca aagtcagatt    3540
gcggcactcg ctcatccacg gaaagaattt tccctgtgca ggcatctcga tcaaaagacg    3600
caaattaatt tttgaatagc gatataacaa tatctaatta acgtttcttg ttttctgcga    3660
aatgtctttc atcataaaat gagtcatctc gatgagccca agtgacatag cccaacaccc    3720
caccccacca ataaaagtga agaaacatg ttgggaaaac tataccaagt aaaatacgag    3780
ttgttctaaa gaaaaagtaa agtacgagtt agatcgcacc ctgtcctgga gtgtggcttg    3840
atgatccaac tcctagcatt gtatccctgt ttttggatga tgtaactatt atttacaatg    3900
aataaagagg tgttttacta gtaaaaaaat cttgaggggga ggagaaaata atggaggtct    3960
tttttcaaac cgatggacta ttattttttag tgaaagagaa taatattatt ggaaaaatta    4020
ttctatccac ttattttata ttggcagaat acaaagaatg gtggggtcca cgcggaactt    4080
gcggcccccg aaacctatcg agggcgcggt acccaagcaa ggaacggagg aaacttgcgg    4140
ggcccgaaac ctagtgataa aaggcatatc atccacacga tgaagatctg acggaccata    4200
tctcccacca cggaaagcca tcagacgagg atcagacggc caggaaggaa ccctagcgcc    4260
cgccggtgcc aatataaagc gccactctct ctcgtcttaa gccccagcct ctccattccc    4320
```

-continued

```
ctctccctct cgccgccgcc gtctccttct cctactccct tcgaggtgtg ttgttcatcc      4380
gtcccgaatc catccatccc ctcttcagat gtgttgttca tggctctaat agctctagat      4440
ctgcttgttt gtgttgttta gctctagatc tactcgcgcg cgcttctctc tcgatctcct      4500
gtagaacaat tttggttggt tttttgtgca tatccatggt aattttgtct gcaatatgga      4560
ggaggctttc taagctccta cgtagcatcg atctttagaa ttccctcggt ttctgtttat      4620
ttcttcgcga gggctctctg ttatctgtag gagtagctgt aagcgcggtt cgttacggat      4680
taatcgtcat gcttagttga acctatcggt cgaaggattt gtgtgggttg tcgtgtagaa      4740
ttgacaccat ctacttactg tactgatatg ccgatctgta ggatactctt cattactttt      4800
gtttactgct agttgtggtg tagatttagc attctcaaac ccatgctgta gcgtttctaa      4860
tattgttaca tagatctacc ggtgcctgtt aattgtattc gatcgggcgt ttctacatct      4920
gtccgcccac ctagtttat atgtggtaat caaaattgcg ttgacttcgt gatgctgtct      4980
gtgtactgtt tttaatcgct cttacttaga tgatcaacat ggtgatggtt acgatttact      5040
gttttctaat ccctgttact tcgatgctgc agtttggatc catggagatg caacaacaat      5100
acttcggggg ggacggcgat gcggactggt tccatcaact cgcattgctt cccccacttc      5160
caatctcatc gtctctcccc ccactcccga tgtcagaggg ctcatgtctc cctatggcag      5220
cagcagctgc agctgcactc ccccttggcg attgctcgag cgccctcatg atacgccctg      5280
aggaacagat gtcttgcctt ccaatgaacc cctctccagc ggtcgtcgac gatgtctact      5340
cttcctacgc accgaacaat gtcgacgtgt tgccgccatt cccggcagga cttgacgacg      5400
ctctgttgat ggagtctttt tctgacatcg acctcgagga gtttgctgac gcatttggcc      5460
acaagatcaa gacagaaccc ctcgacgatg ccatggtccc cgcggaccac gacttcgcgg      5520
ctcaagccca acaggcctgc cctgtggtca tcatgaatca gcaacaactc aacgcaccca      5580
gagacgtgcg cctgctcatt gacccggatg atgatgacag caccgtggtg gccgggggct      5640
atgaagctgc agcggtgggg tgcgccgagc agaaacaggt caggccagca ccacgtaggg      5700
tgagaaagag ctcaggcggc gcaagaccag ccgcgggagg aaagtccctc gatcacatcg      5760
gattcgagga actcaggacc tatttctata tgccaatcac caaggcagcg agggaaatga      5820
acgtggggct gacagtcctg aagaagagat gccgggaact gggggtggcg cgctggccac      5880
acagaaagat gaagtctctg agaagcctga tcctcaacat tcaggagatg gggaaggggcg      5940 caacatctcc cgcagccgtg caggggggaac ttgaagcgct tgagaggtat tgcgccatta      6000
tggaggagaa cccggctata gagctcaccg agcaaacgaa gaagctcagg caggcttgtt      6060
tcaaagagaa ttataagcgg cgtagagccg ccgcttctgt taatcttctc gatcactgct      6120
ataacgatct ggcatctcat gagcagcaaa tgcctctccc acaaatggga ttctttggat      6180
tttaga                                                                 6186
```

<210> SEQ ID NO 41
<211> LENGTH: 7128
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41

```
gatcccccgg gatggcttca gcgaacaact ggctgggctt ctcgctctcg ggccaggata        60
acccgcagcc taaccaggat agctcgcctg ccgccggtat cgacatctcc ggcgccagcg       120
```

```
acttctatgg cctgcccacg cagcagggct ccgacgggca tctcggccgtg ccgggcctgc      180 gggacgatca cgcttcttat ggtatcatgg aggcctacaa cagggttcct caagaaaccc      240
aagattggaa catgaggggc ttggactaca acggcggtgg ctcggagctc tcgatgcttg      300
tggggtccag cggcggcggc gggggcaacg gcaagagggc cgtggaagac agcgagccca      360
agctcgaaga tttcctcggc ggcaactcgt tcgtctccga tcaagatcag tccggcggtt      420
acctgttctc tggagtcccg atagccagca gcgccaatag caacagcggg agcaacacca      480
tggagctatc catgatcaag acctggctac ggaacaacca ggtggcccag ccccagccgc      540
cagctccaca tcagccgcag cctgaggaaa tgagcaccga cgccagcggc agcagctttg      600
gatgctcgga ttcgatggga aggaacagca tggtggcggc tggtgggagc tcgcagagcc      660
tggcgctctc gatgagcacg ggctcgcacc tgcccatggt tgtggccggc ggcagcgcca      720
gcggagcggc ctcggagagc acgtcgtcgg agaacaagcg agcgagcggt gccatggatt      780
cgcccggcag cgcggtagaa gccgtaccga ggaagtccat cgacacgttc gggcaaagga      840
cctctatata tcgaggtgta acaaggcata gatggacagg gcggtatgag gctcatctat      900
gggataatag ttgtagaaga gaagggcaga gtcgcaaggg taggcaagtt taccttggtg      960
gctatgacaa ggaggacaag gcagcaaggg cttacgattt ggcagctctc aagtattggg     1020
gcactacgac aacaacaaat ttccctataa gcaactacga aaaggagcta gaagaaatga     1080
aacatatgac tagacaggag tacattgcat acctaagaag aaatagcagt ggattttctc     1140
gtggggcgtc aaagtatcgt ggagtaacta gacatcatca gcatgggaga tggcaagcaa     1200
ggatagggag agttgcagga aacaaggatc tctacttggg cacattcagc accgaggagg     1260
aggcggcgga ggcctacgac atcgccgcga tcaagttccg cggtctcaac gccgtcacca     1320
acttcgacat gagccgctac gacgtgaaga gcatcctcga gagcagcaca ctgcctgtcg     1380
gcggcgcggc caggcgcctc aaggacgccg tggaccacgt ggaggccggc gccactatct     1440
ggcgcgccga catggacggc gccgtgatct cccagctggc cgaagccggg atgggcggct     1500
acgcctcgta cggccaccac ggctggccga ccatcgcgtt ccagcagccg tcgccgctct     1560
ccgtccacta cccgtacggc cagccgtccc gcgggtggtg caaacccgag caggacgcgg     1620
ccgccgccgc ggcccacagc ctgcaggacc tccagcagct gcacctcggc agcgcggccc     1680
acaacttctt ccaggcgtcg tcgagctcca cagtctacaa cggcggcgcc ggcgccagtg     1740
gtgggtacca gggcctcggt ggtggtagct ccttcctcat gccgtcgagc actgtcgtgg     1800
cggcggccga ccagggcac agcagcacg caaaccaggg gagcacgtgc agctacgggg     1860
acgaccacca ggaggggaag ctcatcggtt acgacgccgc catggtggcg accgcagctg     1920
gtggagaccc gtacgctgcg gcgaggaacg ggtaccagtt ctcgcagggc tcgggatcca     1980
cggtgagcat cgcgagggcg aacgggtacg ctaacaactg gagctctcct ttcaacaacg     2040
gcatggggtg aaagcttacg cgtgtcgact cgaatttccc cgatcgttca aacatttggc     2100
aataaagttt cttaagattg aatcctgttg ccggtcttgc gatgattatc atataatttc     2160
tgttgaatta cgttaagcat gtaataatta acatgtaatg catgacgtta tttatgagat     2220
gggtttttat gattagagtc ccgcaattat acatttaata cgcgatagaa aacaaaatat     2280
agcgcgcaaa ctaggataaa ttatcgcgcg cggtgtcatc tatgttacta gatcgctcga     2340
cgcggccgcc atggccagat cgtacccaat tcgccctata gtgagtcgta ttacaattca     2400
ctggccgtcg ttttacaacg tcgtgactgg gaaaaccctg gcgttaccca acttaatcgc     2460
```

-continued

```
cttgcagcac atcccccttt cgccagctgg cgtaatagcg aagaggcccg caccgatcgc   2520
ccttcccaac agttgcgcag cctgaatggc gaatggaaat tgtaagcgtt aatattttgt   2580
taaaattcgc gttaaatttt tgttaaatca gctcattttt taaccaatag gccgaaatcg   2640
gcaaaatccc ttataaatca aaagaataga ccgagatagg gttgagtgtt gttccagttt   2700
ggaacaagag tccactatta aagaacgtgg actccaacgt caaagggcga aaaaccgtct   2760
atcagggcga tggcccacta cgtgaaccat caccctaatc aagttttttg gggtcgaggt   2820
gccgtaaagc actaaatcgg aaccctaaag ggagccccg atttagagct tgacggggaa   2880
agccggcgaa cgtggcgaga aaggaaggga agaaagcgaa aggagcgggc gctagggcgc   2940
tggcaagtgt agcggtcacg ctgcgcgtaa ccaccacacc cgccgcgctt aatgcgccgc   3000
tacagggcgc gtcaggtggc acttttcggg gaaatgtgcg cggaacccct atttgtttat   3060
ttttctaaat acattcaaat atgtatccgc tcatgagaca ataaccctga taaatgcttc   3120
aataatattg aaaaggaag agtatgagta ttcaacattt ccgtgtcgcc cttattccct   3180
tttttgcggc attttgcctt cctgtttttg ctcacccaga aacgctggtg aaagtaaaag   3240
atgctgaaga tcagttgggt gcacgagtgg gttacatcga actggatctc aacagcggta   3300
agatccttga gagttttcgc cccgaagaac gttttccaat gatgagcact tttaaagttc   3360
tgctatgtgg cgcggtatta tcccgtattg acgccgggca agagcaactc ggtcgccgca   3420
tacactattc tcagaatgac ttggttgagt actcaccagt cacagaaaag catcttacgg   3480
atggcatgac agtaagagaa ttatgcagtg ctgccataac catgagtgat aacactgcgg   3540
ccaacttact tctgacaacg atcggaggac cgaaggagct aaccgctttt ttgcacaaca   3600
tgggggatca tgtaactcgc cttgatcgtt gggaaccgga gctgaatgaa gccataccaa   3660
acgacgagcg tgacaccacg atgcctgtag caatggcaac aacgttgcgc aaactattaa   3720
ctggcgaact acttactcta gcttcccggc aacaattaat agactggatg gaggcggata   3780
aagttgcagg accacttctg cgctcggccc ttccggctgg ctggtttatt gctgataaat   3840
ctggagccgg tgagcgtggg tctcgcggta tcattgcagc actggggcca gatggtaagc   3900
cctcccgtat cgtagttatc tacacgacgg ggagtcaggc aactatggat gaacgaaata   3960
gacagatcgc tgagataggt gcctcactga ttaagcattg gtaactgtca gaccaagttt   4020
actcatatat actttagatt gatttaaaac ttcattttta atttaaaagg atctaggtga   4080
agatcctttt tgataatctc atgaccaaaa tcccttaacg tgagttttcg ttccactgag   4140
cgtcagaccc cgtagaaaag atcaaaggat cttcttgaga tccttttttt ctgcgcgtaa   4200
tctgctgctt gcaaacaaaa aaaccaccgc taccagcggt ggtttgtttg ccggatcaag   4260
agctaccaac tctttttccg aaggtaactg gcttcagcag agcgcagata ccaaatactg   4320
tccttctagt gtagccgtag ttaggccacc acttcaagaa ctctgtagca ccgcctacat   4380
acctcgctct gctaatcctg ttaccagtgg ctgctgccag tggcgataag tcgtgtctta   4440
ccgggttgga ctcaagacga tagttaccgg ataaggcgca gcggtcgggc tgaacggggg   4500
gttcgtgcac acagcccagc ttggagcgaa cgacctacac cgaactgaga tacctacagc   4560
gtgagctatg agaaagcgcc acgcttcccg aagggagaaa ggcggacagg tatccggtaa   4620
gcggcagggt cggaacagga gagcgcacga gggagcttcc aggggggaaac gcctggtatc   4680 tttatagtcc tgtcgggttt cgccacctct gacttgagcg tcgatttttg tgatgctcgt   4740
caggggggcg gagcctatgg aaaaacgcca gcaacgcggc cttttacgg ttcctggcct   4800 tttgctggcc ttttgctcac atgttctttc ctgcgttatc ccctgattct gtggataacc   4860
```

```
gtattaccgc ctttgagtga gctgataccg ctcgccgcag ccgaacgacc gagcgcagcg        4920
agtcagtgag cgaggaagcg gaagagcgcc caatacgcaa accgcctctc cccgcgcgtt        4980
ggccgattca ttaatgcagc tggcacgaca ggtttcccga ctggaaagcg ggcagtgagc        5040
gcaacgcaat taatgtgagt tagctcactc attaggcacc ccaggcttta cactttatgc        5100
ttccggctcg tatgttgtgt ggaattgtga gcggataaca atttcacaca ggaaacagct        5160
atgaccatga ttacgccaag ctcgaaatta accctcacta aagggaacaa aagctggact        5220
agaggccctt aaggccttac tagacttcac cgccattgca aaaattgtca ataaatattt        5280
agagtgggtg gcatcagaaa aacatctcta gtggactctc ttcctatcat agctactcgg        5340
gctgtagata gaacgagggc acaagagttg ggtggcgtag gtttactcgt gacctcaact        5400
cttttggctg tgtcttacgt ctaagatggg tttggcatgt gagaaacata ggtctaagca        5460
attcatgtta gggctgttgc attgttgttg catcaaccaa atgtccagat agcagttcat        5520
gctacatcta gttgaaaacc ctcatcatta ggcggaacat gtgttctttt ttagcatagt        5580
caaagtcaga ttgcggcact cgctcatcca cggaaagaat tttccctgtg caggcatctc        5640
gatcaaaaga cgcaaattaa tttttgaata gcgatataac aatatctaat taacgtttct        5700
tgttttctgc gaaatgtctt tcatcataaa atgagtcatc tcgatgagcc caagtgacat        5760
agcccaacac cccaccccac caataaaagt gaagaaaaca tgttgggaaa actataccaa        5820
gtaaaatacg agttgttcta aagaaaaagt aaagtacgag ttagatcgca ccctgtcctg        5880
gagtgtggct tgatgatcca actcctagca ttgtatccct gttttttggat gatgtaacta        5940 ttatttacaa tgaataaaga ggtgttttac tagtaaaaaa atcttgaggg gaggagaaaa        6000
taatggaggt cttttttcaa accgatggac tattattttt agtgaaagag aataatatta        6060
ttggaaaaat tattctatcc acttatttta tattggcaga atacaaagaa tggtggggtc        6120
cacgcggaac ttgcggcccc cgaaacctat cgagggcgcg gtacccaagc aaggaacgga        6180
ggaaacttgc ggggcccgaa acctagtgat aaaaggcata tcatccacac gatgaagatc        6240
tgacggacca tatctcccac cacggaaagc catcagacga ggatcagacg gccaggaagg        6300
aaccctagcg cccgccggtg ccaatataaa gcgccactct ctctcgtctt aagccccagc        6360
ctctccattc ccctctccct ctcgccgccg ccgtctcctt ctcctactcc cttcgaggtg        6420
tgttgttcat ccgtcccgaa tccatccatc ccctcttcag atgtgttgtt catggctcta        6480
atagctctag atctgcttgt ttgtgttgtt tagctctaga tctactcgcg cgcgcttctc        6540
tctcgatctc ctgtagaaca attttggttg gtttttttgtg catatccatg gtaattttgt        6600
ctgcaatatg gaggaggctt tctaagctcc tacgtagcat cgatctttag aattccctcg        6660
gtttctgttt atttcttcgc gagggctctc tgttatctgt aggagtagct gtaagcgcgg        6720
ttcgttacgg attaatcgtc atgcttagtt gaacctatcg gtcgaaggat ttgtgtgggt        6780
tgtcgtgtag aattgacacc atctacttac tgtactgata tgccgatctg taggatactc        6840
ttcattactt ttgtttactg ctagttgtgg tgtagattta gcattctcaa acccatgctg        6900
tagcgtttct aatattgtta catagatcta ccggtgcctg ttaattgtat tcgatcgggc        6960
gtttctacat ctgtccgccc acctagtttt atatgtggta atcaaaattg cgttgacttc        7020
gtgatgctgt ctgtgtactg tttttaatcg ctcttactta gatgatcaac atggtgatgg        7080
ttacgattta ctgttttcta atccctgtta cttcgatgct gcagtttg                     7128
```

<210> SEQ ID NO 42

<211> LENGTH: 6567
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42

```
agcttacgcg tgtcgactcg aatttccccg atcgttcaaa catttggcaa taaagtttct      60
taagattgaa tcctgttgcc ggtcttgcga tgattatcat ataatttctg ttgaattacg     120
ttaagcatgt aataattaac atgtaatgca tgacgttatt tatgagatgg gttttttatga    180 ttagagtccc gcaattatac atttaatacg cgatagaaaa caaaatatag cgcgcaaact     240
aggataaatt atcgcgcgcg gtgtcatcta tgttactaga tcgctcgacg cggccgccat     300
ggccagatcg tacccaattc gccctatagt gagtcgtatt acaattcact ggccgtcgtt     360
ttacaacgtc gtgactggga aaaccctggc gttacccaac ttaatcgcct tgcagcacat     420 cccccttctcg ccagctggcg taatagcgaa gaggcccgca ccgatcgccc ttcccaacag    480
ttgcgcagcc tgaatggcga atggaaattg taagcgttaa tattttgtta aaattcgcgt     540
taaatttttg ttaaatcagc tcatttttta accaataggc cgaaatcggc aaaatccctt     600
ataaatcaaa agaatagacc gagatagggt tgagtgttgt tccagtttgg aacaagagtc     660
cactattaaa gaacgtggac tccaacgtca aagggcgaaa aaccgtctat cagggcgatg     720
gcccactacg tgaaccatca ccctaatcaa gttttttggg gtcgaggtgc cgtaaagcac     780
taaatcggaa ccctaaaggg agcccccgat ttagagcttg acggggaaag ccggcgaacg     840
tggcgagaaa ggaagggaag aaagcgaaag gagcgggcgc tagggcgctg gcaagtgtag     900
cggtcacgct gcgcgtaacc accacacccg ccgcgcttaa tgcgccgcta cagggcgcgt     960
caggtggcac ttttcgggga aatgtgcgcg gaacccctat ttgtttattt ttctaaatac    1020
attcaaatat gtatccgctc atgagacaat aaccctgata aatgcttcaa taatattgaa    1080
aaaggaagag tatgagtatt caacatttcc gtgtcgccct tattcccttt tttgcggcat    1140
tttgccttcc tgtttttgct cacccagaaa cgctggtgaa agtaaaagat gctgaagatc    1200
agttgggtgc acgagtgggt tacatcgaac tggatctcaa cagcggtaag atccttgaga    1260
gttttcgccc cgaagaacgt tttccaatga tgagcacttt taaagttctg ctatgtggcg    1320
cggtattatc ccgtattgac gccgggcaag agcaactcgg tcgccgcata cactattctc    1380
agaatgactt ggttgagtac tcaccagtca cagaaaagca tcttacggat ggcatgacag    1440
taagagaatt atgcagtgct gccataacca tgagtgataa cactgcggcc aacttacttc    1500
tgacaacgat cggaggaccg aaggagctaa ccgcttttttt gcacaacatg ggggatcatg    1560
taactcgcct tgatcgttgg gaaccggagc tgaatgaagc cataccaaac gacgagcgtg    1620
acaccacgat gcctgtagca atggcaacaa cgttgcgcaa actattaact ggcgaactac    1680
ttactctagc ttcccggcaa caattaatag actggatgga ggcggataaa gttgcaggac    1740
cacttctgcg ctcggccctt ccggctggct ggtttattgc tgataaatct ggagccggtg    1800
agcgtgggtc tcgcggtatc attgcagcac tggggccaga tggtaagccc tcccgtatcg    1860
tagttatcta cacgacgggg agtcaggcaa ctatggatga acgaaataga cagatcgctg    1920
agataggtgc ctcactgatt aagcattggt aactgtcaga ccaagtttac tcatatatac    1980
tttagattga tttaaaactt catttttaat ttaaaaggat ctaggtgaag atcctttttg    2040
ataatctcat gaccaaaatc ccttaacgtg agttttcgtt ccactgagcg tcagacccccg    2100
```

```
tagaaaagat caaaggatct tcttgagatc cttttttttct gcgcgtaatc tgctgcttgc   2160
aaacaaaaaa accaccgcta ccagcggtgg tttgtttgcc ggatcaagag ctaccaactc   2220
tttttccgaa ggtaactggc ttcagcagag cgcagatacc aaatactgtc cttctagtgt   2280
agccgtagtt aggccaccac ttcaagaact ctgtagcacc gcctacatac ctcgctctgc   2340
taatcctgtt accagtggct gctgccagtg gcgataagtc gtgtcttacc gggttggact   2400
caagacgata gttaccggat aaggcgcagc ggtcgggctg aacggggggt tcgtgcacac   2460
agcccagctt ggagcgaacg acctacaccg aactgagata cctacagcgt gagctatgag   2520
aaagcgccac gcttcccgaa gggagaaagg cggacaggta tccggtaagc ggcagggtcg   2580
gaacaggaga gcgcacgagg gagcttccag ggggaaacgc ctggtatctt tatagtcctg   2640
tcgggtttcg ccacctctga cttgagcgtc gatttttgtg atgctcgtca gggggggcgga   2700 gcctatggaa aaacgccagc aacgcggcct ttttacggtt cctggccttt tgctggcctt   2760
ttgctcacat gttctttcct gcgttatccc ctgattctgt ggataaccgt attaccgcct   2820
ttgagtgagc tgataccgct cgccgcagcc gaacgaccga gcgcagcgag tcagtgagcg   2880
aggaagcgga agagcgccca atacgcaaac cgcctctccc cgcgcgttgg ccgattcatt   2940
aatgcagctg gcacgacagg tttcccgact ggaaagcggg cagtgagcgc aacgcaatta   3000
atgtgagtta gctcactcat taggcacccc aggctttaca ctttatgctt ccggctcgta   3060
tgttgtgtgg aattgtgagc ggataacaat ttcacacagg aaacagctat gaccatgatt   3120
acgccaagct cgaaattaac cctcactaaa gggaacaaaa gctggactag aggcccttaa   3180
ggccttacta gacttcaccg ccattgcaaa aattgtcaat aaatatttag agtgggtggc   3240
atcagaaaaa catctctagt ggactctctt cctatcatag ctactcgggc tgtagataga   3300
acgagggcac aagagttggg tggcgtaggt ttactcgtga cctcaactct tttggctgtg   3360
tcttacgtct aagatgggtt tggcatgtga gaaacatagg tctaagcaat tcatgttagg   3420
gctgttgcat tgttgttgca tcaaccaaat gtccagatag cagttcatgc tacatctagt   3480 tgaaaccct catcattagg cggaacatgt gttctttttt agcatagtca aagtcagatt   3540
gcggcactcg ctcatccacg gaaagaattt tccctgtgca ggcatctcga tcaaaagacg   3600
caaattaatt tttgaatagc gatataacaa tatctaatta acgtttcttg ttttctgcga   3660
aatgtctttc atcataaaat gagtcatctc gatgagccca agtgacatag cccaacaccc   3720
caccccacca ataaaagtga agaaacatg ttgggaaaac tataccaagt aaaatacgag   3780
ttgttctaaa gaaaaagtaa agtacgagtt agatcgcacc ctgtcctgga gtgtggcttg   3840
atgatccaac tcctagcatt gtatccctgt ttttggatga tgtaactatt atttacaatg   3900
aataaagagg tgtttactta gtaaaaaaat cttgaggga ggagaaaata atggaggtct   3960
tttttcaaac cgatggacta ttattttttag tgaaagagaa taatattatt ggaaaaatta   4020
ttctatccac ttattttata ttggcagaat acaaagaatg gtggggtcca cgcggaactt   4080
gcggcccccg aaacctatcg agggcgcggt acccaagcaa ggaacggagg aaacttgcgg   4140
ggcccgaaac ctagtgataa aaggcatatc atccacacga tgaagatctg acggaccata   4200
tctcccacca cggaaagcca tcagacgagg atcagacggc caggaaggaa ccctagcgcc   4260
cgccggtgcc aatataaagc gccactctct ctcgtcttaa gccccagcct ctccattccc   4320
ctctccctct cgccgccgcc gtctccttct cctactccct tcgaggtgtg ttgttcatcc   4380
gtcccgaatc catccatccc ctcttcagat gtgttgttca tggctctaat agctctagat   4440
ctgcttgttt gtgttgttta gctctagatc tactcgcgcg cgcttctctc tcgatctcct   4500
```

```
gtagaacaat tttggttggt tttttgtgca tatccatggt aattttgtct gcaatatgga   4560
ggaggctttc taagctccta cgtagcatcg atctttagaa ttccctcggt ttctgtttat   4620
ttcttcgcga gggctctctg ttatctgtag gagtagctgt aagcgcggtt cgttacggat   4680
taatcgtcat gcttagttga acctatcggt cgaaggattt gtgtgggttg tcgtgtagaa   4740
ttgacaccat ctacttactg tactgatatg ccgatctgta ggatactctt cattactttt   4800
gtttactgct agttgtggtg tagatttagc attctcaaac ccatgctgta gcgtttctaa   4860
tattgttaca tagatctacc ggtgcctgtt aattgtattc gatcgggcgt ttctacatct   4920
gtccgcccac ctagttttat atgtggtaat caaaattgcg ttgacttcgt gatgctgtct   4980
gtgtactgtt tttaatcgct cttacttaga tgatcaacat ggtgatggtt acgatttact   5040
gttttctaat ccctgttact tcgatgctgc agtttggatc catggacacc tcgcaccact   5100
atcatccatg gctcaacttc tccctcgccc accactgtga cctcgaggag gaggagaggg   5160
gcgcggccgc cgagctggcc gcgatagccg gcgccgcgcc gccgccgaag ctggaggact   5220
tcctcggcgg aggcgtcgcc accggtggtc cggaggcggt ggcgcccgcg gagatgtacg   5280
actcggacct caagttcata gccgccgccg ggttccttgg cggctcggcg gcggcggcgg   5340
cgacgtcgcc gctgtcctcc ctcgaccagg ccggttccaa gctggccttg cctgcggcgg   5400
cggctgctcc ggcgccggag cagaggaagg ccgtcgactc ctttgggcag cgcacgtcca   5460
tctaccgcgg cgtcacacgg caccggtgga ctggcaggta cgaggcacat ctgtgggaca   5520
acagctgccg acgcgaaggg cagagccgca agggccgcca agtatatttg ggtggctatg   5580
ataaggagga gaaggctgcc agggcgtatg atcttgcagc tttgaagtac tggggttcta   5640
gcaccaccac caactttccg gttgctgagt atgagaagga ggtcgaggag atgaagaaca   5700
tgacgcgaca agagtttgtt gcttcccttc gaaggaagag cagtggattc tctcggggtg   5760
cttccatcta cagaggtgta accagacatc accagcatgg acggtggcag gcgaggatcg   5820
gaagggtggc cggtaacaag gacctctacc ttgggacgtt cagcaccgag gaggaagctg   5880
cagaggccta cgacatagcg gccatcaagt tcagaggcct gaacgccgtc acaaacttcg   5940
agatcagccg gtacaacgtg gagaccataa tgagcagcaa ccttccagtc gcgagcatgt   6000
cgtcgtcgtc ggcggcggcg gcgggtggcc ggagcagcaa ggcgctggag tcccctccgt   6060
ccggctcgct tgacggcggc ggcggcatgc cagtcgtcga aggcagcacg gcaccgccgc   6120
tgttcattcc ggtgaagtac gaccagcagc agcaggagta cctgtcgatg ctcgcgttgc   6180
agcaccacca ccagcagcaa caagcaggga acctgttgca ggggccgcta gtagggttcg   6240
gcggcctcta ctcctccggg gtgaacctgg atttcgccaa ctcccacggc acggcggctc   6300
cgtcgtcgat ggcccaccac tgctacgcca atggcaccgc gtccgcctcg catgagcacc   6360
agcaccagca ccagatgcag cagggcggcg agaacgagac gcagccgcag ccgcagcaga   6420
gctccagcag ctgctcctcc ctgccattcg ccaccccggt cgctttcaat gggtcctatg   6480
aaagctccat cacggcggca ggcccctttg gatactccta cccaaatgtg gcagcctttc   6540
agacgccgat ctatggaatg gaatgaa                                        6567
```

<210> SEQ ID NO 43
<211> LENGTH: 6552
<212> TYPE: DNA
<213> ORGANISM: Artificial Sequence
<220> FEATURE:
<223> OTHER INFORMATION: Description of Artificial Sequence: Synthetic
      polynucleotide -continued

<400> SEQUENCE: 43

```
agcttacgcg tgtcgactcg aatttcccccg atcgttcaaa catttggcaa taaagtttct        60
taagattgaa tcctgttgcc ggtcttgcga tgattatcat ataatttctg ttgaattacg       120
ttaagcatgt aataattaac atgtaatgca tgacgttatt tatgagatgg gtttttatga       180
ttagagtccc gcaattatac atttaatacg cgatagaaaa caaaatatag cgcgcaaact       240
aggataaatt atcgcgcgcg gtgtcatcta tgttactaga tcgctcgacg cggccgccat       300
ggccagatcg tacccaattc gccctatagt gagtcgtatt acaattcact ggccgtcgtt       360
ttacaacgtc gtgactggga aaaccctggc gttacccaac ttaatcgcct tgcagcacat       420
ccccctttcg ccagctggcg taatagcgaa gaggcccgca ccgatcgccc ttcccaacag       480
ttgcgcagcc tgaatggcga atggaaattg taagcgttaa tattttgtta aaattcgcgt       540 taaattttg ttaaatcagc tcatttttta accaataggc cgaaatcggc aaaatccctt       600
ataaatcaaa agaatagacc gagatagggt tgagtgttgt tccagtttgg aacaagagtc       660
cactattaaa gaacgtggac tccaacgtca aagggcgaaa aaccgtctat cagggcgatg       720
gcccactacg tgaaccatca ccctaatcaa gttttttggg gtcgaggtgc cgtaaagcac       780
taaatcggaa ccctaaaggg agcccccgat ttagagcttg acggggaaag ccggcgaacg       840
tggcgagaaa ggaagggaag aaagcgaaag gagcgggcgc tagggcgctg gcaagtgtag       900
cggtcacgct gcgcgtaacc accacacccg ccgcgcttaa tgcgccgcta cagggcgcgt       960
caggtggcac ttttcgggga aatgtgcgcg gaacccctat ttgtttattt ttctaaatac      1020
attcaaatat gtatccgctc atgagacaat aaccctgata aatgcttcaa taatattgaa      1080
aaaggaagag tatgagtatt caacatttcc gtgtcgccct tattcccttt tttgcggcat      1140
tttgccttcc tgtttttgct cacccagaaa cgctggtgaa agtaaaagat gctgaagatc      1200
agttgggtgc acgagtgggt tacatcgaac tggatctcaa cagcggtaag atccttgaga      1260
gttttcgccc cgaagaacgt tttccaatga tgagcacttt taaagttctg ctatgtggcg      1320
cggtattatc ccgtattgac gccgggcaag agcaactcgg tcgccgcata cactattctc      1380
agaatgactt ggttgagtac tcaccagtca cagaaaagca tcttacggat ggcatgacag      1440
taagagaatt atgcagtgct gccataacca tgagtgataa cactgcggcc aacttacttc      1500
tgacaacgat cggaggaccg aaggagctaa ccgcttttttt gcacaacatg ggggatcatg      1560
taactcgcct tgatcgttgg gaaccggagc tgaatgaagc cataccaaac gacgagcgtg      1620
acaccacgat gcctgtagca atggcaacaa cgttgcgcaa actattaact ggcgaactac      1680
ttactctagc ttcccggcaa caattaatag actggatgga ggcggataaa gttgcaggac      1740
cacttctgcg ctcggccctt ccggctggct ggtttattgc tgataaatct ggagccggtg      1800
agcgtgggtc tcgcggtatc attgcagcac tggggccaga tggtaagccc tcccgtatcg      1860
tagttatcta cacgacgggg agtcaggcaa ctatggatga acgaaataga cagatcgctg      1920
agataggtgc ctcactgatt aagcattggt aactgtcaga ccaagtttac tcatatatac      1980
tttagattga tttaaaactt cattttttaat ttaaaaggat ctaggtgaag atccttttttg      2040 ataatctcat gaccaaaatc ccttaacgtg agttttcgtt ccactgagcg tcagaccccg      2100
tagaaaagat caaaggatct tcttgagatc cttttttttct gcgcgtaatc tgctgcttgc      2160
aaacaaaaaa accaccgcta ccagcggtgg tttgtttgcc ggatcaagag ctaccaactc      2220 ttttttccgaa ggtaactggc ttcagcagag cgcagatacc aaatactgtc cttctagtgt      2280
```

```
agccgtagtt aggccaccac ttcaagaact ctgtagcacc gcctacatac ctcgctctgc    2340
taatcctgtt accagtggct gctgccagtg gcgataagtc gtgtcttacc gggttggact    2400
caagacgata gttaccggat aaggcgcagc ggtcgggctg aacggggggt tcgtgcacac    2460
agcccagctt ggagcgaacg acctacaccg aactgagata cctacagcgt gagctatgag    2520
aaagcgccac gcttcccgaa gggagaaagg cggacaggta tccggtaagc ggcagggtcg    2580
gaacaggaga gcgcacgagg gagcttccag ggggaaacgc ctggtatctt tatagtcctg    2640
tcgggtttcg ccacctctga cttgagcgtc gattttgtg atgctcgtca ggggggcgga    2700
gcctatggaa aaacgccagc aacgcggcct ttttacggtt cctggccttt tgctggcctt    2760
ttgctcacat gttctttcct gcgttatccc ctgattctgt ggataaccgt attaccgcct    2820
ttgagtgagc tgataccgct cgccgcagcc gaacgaccga gcgcagcgag tcagtgagcg    2880
aggaagcgga agagcgccca atacgcaaac cgcctctccc cgcgcgttgg ccgattcatt    2940
aatgcagctg gcacgacagg tttcccgact ggaaagcggg cagtgagcgc aacgcaatta    3000
atgtgagtta gctcactcat taggcacccc aggctttaca ctttatgctt ccggctcgta    3060
tgttgtgtgg aattgtgagc ggataacaat ttcacacagg aaacagctat gaccatgatt    3120
acgccaagct cgaaattaac cctcactaaa gggaacaaaa gctggactag aggcccttaa    3180
ggccttacta gacttcaccg ccattgcaaa aattgtcaat aaatatttag agtgggtggc    3240
atcagaaaaa catctctagt ggactctctt cctatcatag ctactcgggc tgtagataga    3300
acgagggcac aagagttggg tggcgtaggt ttactcgtga cctcaactct tttggctgtg    3360
tcttacgtct aagatgggtt tggcatgtga gaaacatagg tctaagcaat tcatgttagg    3420
gctgttgcat tgttgttgca tcaaccaaat gtccagatag cagttcatgc tacatctagt    3480
tgaaaaccct catcattagg cggaacatgt gttctttttt agcatagtca aagtcagatt    3540
gcggcactcg ctcatccacg gaaagaattt tccctgtgca ggcatctcga tcaaaagacg    3600
caaattaatt tttgaatagc gatataacaa tatctaatta acgtttcttg ttttctgcga    3660
aatgtctttc atcataaaat gagtcatctc gatgagccca agtgacatag cccaacaccc    3720 cacccaccaca ataaaagtga agaaaacatg ttgggaaaac tataccaagt aaaatacgag    3780
ttgttctaaa gaaaaagtaa agtacgagtt agatcgcacc ctgtcctgga gtgtggcttg    3840
atgatccaac tcctagcatt gtatccctgt ttttggatga tgtaactatt atttacaatg    3900
aataaagagg tgttttacta gtaaaaaaat cttgaggggg ggagaaaata atggaggtct    3960
tttttcaaac cgatggacta ttatttttag tgaaagagaa taatattatt ggaaaaatta    4020
ttctatccac ttattttata ttggcagaat acaaagaatg gtggggtcca cgcggaactt    4080
gcggcccccg aaacctatcg agggcgcggt acccaagcaa ggaacggagg aaacttgcgg    4140
ggcccgaaac ctagtgataa aaggcatatc atccacacga tgaagatctg acggaccata    4200
tctcccacca cggaaagcca tcagacgagg atcagacggc caggaaggaa ccctagcgcc    4260
cgccggtgcc aatataaagc gccactctct ctcgtcttaa gccccagcct ctccattccc    4320
ctctccctct cgccgccgcc gtctccttct cctactccct tcgaggtgtg ttgttcatcc    4380
gtcccgaatc catccatccc ctcttcagat gtgttgttca tggctctaat agctctagat    4440
ctgcttgttt gtgttgttta gctctagatc tactcgcgcg cgcttctctc tcgatctcct    4500
gtagaacaat tttggttggt tttttgtgca tatccatggt aattttgtct gcaatatgga    4560
ggaggctttc taagctccta cgtagcatcg atctttagaa ttccctcggt ttctgtttat    4620
ttcttcgcga gggctctctg ttatctgtag gagtagctgt aagcgcggtt cgttacggat    4680
```

```
taatcgtcat gcttagttga acctatcggt cgaaggattt gtgtgggttg tcgtgtagaa   4740
ttgacaccat ctacttactg tactgatatg ccgatctgta ggatactctt cattactttt   4800
gtttactgct agttgtggtg tagatttagc attctcaaac ccatgctgta gcgtttctaa   4860
tattgttaca tagatctacc ggtgcctgtt aattgtattc gatcgggcgt ttctacatct   4920
gtccgcccac ctagttttat atgtggtaat caaaattgcg ttgacttcgt gatgctgtct   4980
gtgtactgtt tttaatcgct cttacttaga tgatcaacat ggtgatggtt acgatttact   5040
gttttctaat ccctgttact tcgatgctgc agtttggatc catggacatg gacatgagct   5100
cagcttatcc ccaccattgg ctctccttct ccctctccaa caactaccac catggcctac   5160
tcgaggcctt ctctaactcc tccggtactc ctcttggaga cgagccgggc gcagtggagg   5220
agtccccgag gacggtggag gacttcctcg gcggcgtcgg tggcgccggc gccccgccgc   5280
agccggcggc tgctgcagat caggatcacc agcttgtgtg cggcgagctg ggcagcatca   5340
cagccaggtt cttgcgccac tacccggcgg cgccagctgg gacgacggtg gagaaccccg   5400
gcgcggtgac cgtggcggcc atgtcgtcga cggacgtggc ggggggcggag tccgaccagg   5460 cgaggcggcc cgccgagacg ttcggccagc gcacatccat ctaccgtggc gtcaccaggc   5520
accggtggac agggagatat gaggcgcact tgtgggacaa cagctgccgc cgggagggcc   5580
aaagccgcaa aggacgccaa gtctacctag gaggctatga caaggaggag aaggcggcta   5640
gagcttacga cctcgccgcg ctcaagtact gggggcctac aaccacgacc aacttcccgg   5700
tgtccaacta cgagaaggag ctggaggaga tgaagtccat gacgcggcag gagttcatcg   5760
cgtcgttgcg caggaagagc agcggcttct cacgaggcgc ctccatctac agaggagtca   5820
caaggcatca tcagcacggc cggtggcagg cgaggatcgg cagggtggcc ggaaacaagg   5880
acctgtactt gggcactttc agtactcagg aagaggcggc ggaggcgtac gacatcgctg   5940
cgatcaagtt ccgcgggctc aacgccgtca ccaacttcga catgagccgc tacgacgtgg   6000
agagcatcct cagcagcgac ctccccgtcg ggggcggagc caccgggcgc gccgccaagt   6060
tcccgttgga ctcgctgcag ccggggagcc ctgctgcgat gatgctcgcc ggggctgctg   6120
ccgcttcgca ggccaccatg ccgccgtccg agaaggacta ctggtctctg ctcgccctgc   6180
actaccagca gcagcaggag caggagcggc agttcccggc ttctgcttac gaggcttacg   6240
gctccggcgg cgtgaacgtg gacttcacga tgggcaccag tagcggcaac aacaacaaca   6300
acaccggcag cggcgtcatg tggggcgcca ccactggtgc agtagtagtg ggacagcaag   6360
acagcagcgc caagcagggc aacggctatg ccagcaacat tccttatgct gctgctgctg   6420
ctatggtttc tggatctgct ggctacgagg ctccaccgg cgacaatgga acctgggtta   6480
ctacgactat taccagcagc aacaccggca cggctcccca ctactacaac tatctcttcg   6540
ggatggagta ga                                                      6552
```

```
<210> SEQ ID NO 44
<211> LENGTH: 5865
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
agcttacgcg tgtcgactcg aatttccccg atcgttcaaa catttggcaa taaagtttct     60
taagattgaa tcctgttgcc ggtcttgcga tgattatcat ataatttctg ttgaattacg    120
```

```
ttaagcatgt aataattaac atgtaatgca tgacgttatt tatgagatgg gttttttatga      180 ttagagtccc gcaattatac atttaatacg cgatagaaaa caaaatatag cgcgcaaact      240
aggataaatt atcgcgcgcg gtgtcatcta tgttactaga tcgctcgacg cggccgccat      300
ggccagatcg tacccaattc gccctatagt gagtcgtatt acaattcact ggccgtcgtt      360
ttacaacgtc gtgactggga aaaccctggc gttacccaac ttaatcgcct tgcagcacat      420
ccccctttcg ccagctggcg taatagcgaa gaggcccgca ccgatcgccc ttcccaacag      480
ttgcgcagcc tgaatggcga atggaaattg taagcgttaa tattttgtta aaattcgcgt      540
taaatttttg ttaaatcagc tcattttttta accataggc cgaaatcggc aaaatccctt      600
ataaatcaaa agaatagacc gagatagggt tgagtgttgt tccagtttgg aacaagagtc      660
cactattaaa gaacgtggac tccaacgtca aagggcgaaa aaccgtctat cagggcgatg      720
gcccactacg tgaaccatca ccctaatcaa gttttttggg gtcgaggtgc cgtaaagcac      780
taaatcggaa ccctaaaggg agcccccgat ttagagcttg acggggaaag ccggcgaacg      840
tggcgagaaa ggaagggaag aaagcgaaag gagcgggcgc tagggcgctg gcaagtgtag      900
cggtcacgct gcgcgtaacc accacacccg ccgcgcttaa tgcgccgcta cagggcgcgt      960
caggtggcac ttttcgggga aatgtgcgcg gaacccctat ttgtttattt ttctaaatac     1020
attcaaatat gtatccgctc atgagacaat aaccctgata aatgcttcaa taatattgaa     1080
aaaggaagag tatgagtatt caacatttcc gtgtcgccct tattccctt tttgcggcat     1140 tttgccttcc tgtttttgct cacccagaaa cgctggtgaa agtaaaagat gctgaagatc     1200
agttgggtgc acgagtgggt tacatcgaac tggatctcaa cagcggtaag atccttgaga     1260
gttttcgccc cgaagaacgt tttccaatga tgagcacttt taaagttctg ctatgtggcg     1320
cggtattatc ccgtattgac gccgggcaag agcaactcgg tcgccgcata cactattctc     1380
agaatgactt ggttgagtac tcaccagtca cagaaaagca tcttacggat ggcatgacag     1440
taagagaatt atgcagtgct gccataacca tgagtgataa cactgcggcc aacttacttc     1500
tgacaacgat cggaggaccg aaggagctaa ccgctttttt gcacaacatg ggggatcatg     1560
taactcgcct tgatcgttgg gaaccggagc tgaatgaagc cataccaaac gacgagcgtg     1620
acaccacgat gcctgtagca atggcaacaa cgttgcgcaa actattaact ggcgaactac     1680
ttactctagc ttcccggcaa caattaatag actggatgga ggcggataaa gttgcaggac     1740
cacttctgcg ctcggccctt ccggctggct ggtttattgc tgataaatct ggagccggtg     1800
agcgtgggtc tcgcggtatc attgcagcac tggggccaga tggtaagccc tcccgtatcg     1860
tagttatcta cacgacgggg agtcaggcaa ctatggatga acgaaataga cagatcgctg     1920
agataggtgc ctcactgatt aagcattggt aactgtcaga ccaagtttac tcatatatac     1980
tttagattga tttaaaactt catttttaat ttaaaaggat ctaggtgaag atcctttttg     2040
ataatctcat gaccaaaatc ccttaacgtg agttttcgtt ccactgagcg tcagaccccg     2100
tagaaaagat caaaggatct tcttgagatc ctttttttct gcgcgtaatc tgctgcttgc     2160
aaacaaaaaa accaccgcta ccagcggtgg tttgtttgcc ggatcaagag ctaccaactc     2220
tttttccgaa ggtaactggc ttcagcagag cgcagatacc aaatactgtc cttctagtgt     2280
agccgtagtt aggccaccac ttcaagaact ctgtagcacc gcctacatac ctcgctctgc     2340
taatcctgtt accagtggct gctgccagtg gcgataagtc gtgtcttacc gggttggact     2400
caagacgata gttaccggat aaggcgcagc ggtcgggctg aacggggggt tcgtgcacac     2460
```

-continued

```
agcccagctt ggagcgaacg acctacaccg aactgagata cctacagcgt gagctatgag      2520
aaagcgccac gcttcccgaa gggagaaagg cggacaggta tccggtaagc ggcagggtcg      2580
gaacaggaga gcgcacgagg gagcttccag ggggaaacgc ctggtatctt tatagtcctg      2640
tcgggtttcg ccacctctga cttgagcgtc gatttttgtg atgctcgtca gggggggcgga     2700 gcctatggaa aaacgccagc aacgcggcct ttttacggtt cctggccttt tgctggcctt      2760
ttgctcacat gttctttcct gcgttatccc ctgattctgt ggataaccgt attaccgcct      2820
ttgagtgagc tgataccgct cgccgcagcc gaacgaccga gcgcagcgag tcagtgagcg      2880
aggaagcgga agagcgccca atacgcaaac cgcctctccc cgcgcgttgg ccgattcatt      2940
aatgcagctg gcacgacagg tttcccgact ggaaagcggg cagtgagcgc aacgcaatta      3000
atgtgagtta gctcactcat taggcacccc aggctttaca ctttatgctt ccggctcgta      3060
tgttgtgtgg aattgtgagc ggataacaat ttcacacagg aaacagctat gaccatgatt      3120
acgccaagct cgaaattaac cctcactaaa gggaacaaaa gctggactag aggcccttaa      3180
ggccttacta gacttcaccg ccattgcaaa aattgtcaat aaatatttag agtgggtggc      3240
atcagaaaaa catctctagt ggactctctt cctatcatag ctactcgggc tgtagataga      3300
acgagggcac aagagttggg tggcgtaggt ttactcgtga cctcaactct tttggctgtg      3360
tcttacgtct aagatgggtt tggcatgtga gaaacatagg tctaagcaat tcatgttagg      3420 gctgttcat tgttgttgca tcaaccaaat gtccagatag cagttcatgc tacatctagt       3480
tgaaaaccct catcattagg cggaacatgt gttctttttt agcatagtca aagtcagatt      3540
gcggcactcg ctcatccacg gaaagaattt tccctgtgca ggcatctcga tcaaaagacg      3600
caaattaatt tttgaatagc gatataacaa tatctaatta acgtttcttg ttttctgcga      3660
aatgtctttc atcataaaat gagtcatctc gatgagccca agtgacatag cccaacaccc      3720 cacccccacca ataaaagtga agaaacatg ttgggaaaac tataccaagt aaaatacgag      3780
ttgttctaaa gaaaaagtaa agtacgagtt agatcgcacc ctgtcctgga gtgtggcttg      3840
atgatccaac tcctagcatt gtatccctgt ttttggatga tgtaactatt atttacaatg      3900
aataaagagg tgtttactta gtaaaaaaat cttgaggggga ggagaaaata atggaggtct     3960
tttttcaaac cgatggacta ttattttttag tgaaagagaa taatattatt ggaaaaatta     4020
ttctatccac ttattttata ttggcagaat acaaagaatg gtggggtcca cgcggaactt      4080
gcggcccccg aaacctatcg agggcgcggt acccaagcaa ggaacggagg aaacttgcgg      4140
ggcccgaaac ctagtgataa aaggcatatc atccacacga tgaagatctg acggaccata      4200
tctcccacca cggaaagcca tcagacgagg atcagacggc caggaaggaa ccctagcgcc      4260
cgccggtgcc aatataaagc gccactctct ctcgtcttaa gccccagcct ctccattccc      4320
ctctccctct cgccgccgcc gtctccttct cctactccct tcgaggtgtg ttgttcatcc      4380
gtcccgaatc catccatccc ctcttcagat gtgttgttca tggctctaat agctctagat      4440
ctgcttgttt gtgttgttta gctctagatc tactcgcgcg cgcttctctc tcgatctcct      4500
gtagaacaat tttggttggt tttttgtgca tatccatggt aattttgtct gcaatatgga      4560
ggaggctttc taagctccta cgtagcatcg atctttagaa ttccctcggt ttctgtttat      4620
ttcttcgcga gggctctctg ttatctgtag gagtagctgt aagcgcggtt cgttacggat      4680
taatcgtcat gcttagttga acctatcggt cgaaggattt gtgtgggttg tcgtgtagaa      4740
ttgacaccat ctacttactg tactgatatg ccgatctgta ggatactctt cattactttt      4800
gtttactgct agttgtggtg tagatttagc attctcaaac ccatgctgta gcgtttctaa      4860
```

```
tattgttaca tagatctacc ggtgcctgtt aattgtattc gatcgggcgt ttctacatct    4920
gtccgcccac ctagtttat atgtggtaat caaaattgcg ttgacttcgt gatgctgtct     4980
gtgtactgtt tttaatcgct cttacttaga tgatcaacat ggtgatggtt acgatttact    5040
gttttctaat ccctgttact tcgatgctgc agtttggatc catggagtcg ggctccggga    5100
cggctgctgg ctctggctat gtttacagac agccaggatc aacgcggtgg aacccgacag    5160
ctgaacaact gtccttgctt agagaaatct actaccgcaa cggattgcgg accccgaccg    5220
cggacgaaat cagacaaatc agctcaaagc tctcaaggta cggaaaaata gagggcaaaa    5280
acgtttacaa ctggttccag aatagacgcg caagagaaaa gcgcaagcaa cggctctcta    5340
caatcggctg tgatccagca ctgatcgaga tggggaatgt cgcttcactg gaattcggta    5400
ctgagagcgc cctggaatcg ctgtcgtcag gaccatcctc agaactccgc gaagcgccaa    5460
cgagaaaatt ttacgaaaaa aagacggttg gagagaactc aactataata aacccagtgg    5520
aacaaaactg tacccttcc tgcggaacgt cccaagagtt ccagtatgcg gtcgattctc     5580
ggcgcgtcat gaaagctatg gaggaaaagc aggcgacgga cgatgaaccc gacggaaata    5640
aatggactga gtcaaacaga cacgtcaaga ttctccagct tttcccgctc cacaataacg    5700
aggatcagac attgataaag agcgacaaag aaatctattg tttgggctcg tgcgagaaga    5760
aaatggattt gtcaccgctg ggtcattcag gctctcagcg cgcttcggcc cttgacttgt    5820
gcctttcatt gggcaacgaa tcttgtgggc tgcatgataa ttgaa                    5865
```

<210> SEQ ID NO 45
<211> LENGTH: 5865
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45

```
agcttacgcg tgtcgactcg aatttccccg atcgttcaaa catttggcaa taaagtttct     60
taagattgaa tcctgttgcc ggtcttgcga tgattatcat ataatttctg ttgaattacg    120
ttaagcatgt aataattaac atgtaatgca tgacgttatt tatgagatgg gttttttatga   180 ttagagtccc gcaattatac atttaatacg cgatagaaaa caaaatatag cgcgcaaact    240
aggataaatt atcgcgcgcg gtgtcatcta tgttactaga tcgctcgacg cggccgccat    300
ggccagatcg tacccaattc gccctatagt gagtcgtatt acaattcact ggccgtcgtt    360
ttacaacgtc gtgactggga aaaccctggc gttacccaac ttaatcgcct tgcagcacat    420
ccccctttcg ccagctggcg taatagcgaa gaggcccgca ccgatcgccc ttcccaacag    480
ttgcgcagcc tgaatggcga atggaaattg taagcgttaa tattttgtta aaattcgcgt    540 taaattttg ttaaatcagc tcatttttta accaataggc cgaaatcggc aaaatccctt     600
ataaatcaaa agaatagacc gagatagggt tgagtgttgt tccagtttgg aacaagagtc    660
cactattaaa gaacgtggac tccaacgtca aagggcgaaa aaccgtctat cagggcgatg    720
gcccactacg tgaaccatca ccctaatcaa gttttttggg gtcgaggtgc cgtaaagcac    780
taaatcggaa ccctaaaggg agcccccgat ttagagcttg acggggaaag ccggcgaacg    840
tggcgagaaa ggaagggaag aaagcgaaag gagcgggcgc tagggcgctg gcaagtgtag    900
cggtcacgct gcgcgtaacc accacacccg ccgcgcttaa tgcgccgcta cagggcgcgt    960
caggtggcac ttttcgggga aatgtgcgcg gaacccctat ttgtttattt ttctaaatac    1020
```

-continued

```
attcaaatat gtatccgctc atgagacaat aaccctgata aatgcttcaa taatattgaa   1080
aaaggaagag tatgagtatt caacatttcc gtgtcgccct tattcccttt tttgcggcat   1140
tttgccttcc tgttttttgct cacccagaaa cgctggtgaa agtaaaagat gctgaagatc   1200
agttgggtgc acgagtgggt tacatcgaac tggatctcaa cagcggtaag atccttgaga   1260
gttttcgccc cgaagaacgt tttccaatga tgagcacttt taaagttctg ctatgtggcg   1320
cggtattatc ccgtattgac gccgggcaag agcaactcgg tcgccgcata cactattctc   1380
agaatgactt ggttgagtac tcaccagtca cagaaaagca tcttacggat ggcatgacag   1440
taagagaatt atgcagtgct gccataacca tgagtgataa cactgcggcc aacttacttc   1500
tgacaacgat cggaggaccg aaggagctaa ccgcttttttt gcacaacatg ggggatcatg   1560
taactcgcct tgatcgttgg gaaccggagc tgaatgaagc cataccaaac gacgagcgtg   1620
acaccacgat gcctgtagca atggcaacaa cgttgcgcaa actattaact ggcgaactac   1680
ttactctagc ttcccggcaa caattaatag actggatgga ggcggataaa gttgcaggac   1740
cacttctgcg ctcggccctt ccggctggct ggtttattgc tgataaatct ggagccggtg   1800
agcgtgggtc tcgcggtatc attgcagcac tggggccaga tggtaagccc tcccgtatcg   1860
tagttatcta cacgacgggg agtcaggcaa ctatggatga acgaaataga cagatcgctg   1920
agataggtgc ctcactgatt aagcattggt aactgtcaga ccaagtttac tcatatatac   1980
tttagattga tttaaaactt catttttaat ttaaaaggat ctaggtgaag atcctttttg   2040
ataatctcat gaccaaaatc ccttaacgtg agttttcgtt ccactgagcg tcagacccccg   2100 tagaaaagat caaaggatct tcttgagatc cttttttttct gcgcgtaatc tgctgcttgc   2160
aaacaaaaaa accaccgcta ccagcggtgg tttgtttgcc ggatcaagag ctaccaactc   2220
tttttccgaa ggtaactggc ttcagcagag cgcagatacc aaatactgtc cttctagtgt   2280
agccgtagtt aggccaccac ttcaagaact ctgtagcacc gcctacatac ctcgctctgc   2340
taatcctgtt accagtggct gctgccagtg gcgataagtc gtgtcttacc gggttggact   2400
caagacgata gttaccggat aaggcgcagc ggtcgggctg aacggggggt tcgtgcacac   2460
agcccagctt ggagcgaacg acctacaccg aactgagata cctacagcgt gagctatgag   2520
aaagcgccac gcttcccgaa gggagaaagg cggacaggta tccggtaagc ggcagggtcg   2580
gaacaggaga gcgcacgagg gagcttccag ggggaaacgc ctggtatctt tatagtcctg   2640
tcgggtttcg ccacctctga cttgagcgtc gatttttgtg atgctcgtca gggggggcgga   2700 gcctatggaa aaacgccagc aacgcggcct ttttacggtt cctggccttt tgctggcctt   2760
ttgctcacat gttctttcct gcgttatccc ctgattctgt ggataaccgt attaccgcct   2820
ttgagtgagc tgataccgct cgccgcagcc gaacgaccga cgcagcgag tcagtgagcg   2880 aggaagcgga agagcgccca atacgcaaac cgcctctccc cgcgcgttgg ccgattcatt   2940
aatgcagctg gcacgacagg tttcccgact ggaaagcggg cagtgagcgc aacgcaatta   3000
atgtgagtta gctcactcat taggcacccc aggctttaca ctttatgctt ccggctcgta   3060
tgttgtgtgg aattgtgagc ggataacaat ttcacacagg aaacagctat gaccatgatt   3120
acgccaagct cgaaattaac cctcactaaa gggaacaaaa gctggactag aggcccttaa   3180
ggccttacta gacttcaccg ccattgcaaa aattgtcaat aaatatttag agtgggtggc   3240
atcagaaaaa catctctagt ggactctctt cctatcatag ctactcgggc tgtagataga   3300
acgagggcac aagagttggg tggcgtaggt ttactcgtga cctcaactct tttggctgtg   3360
```

-continued

```
tcttacgtct aagatgggtt tggcatgtga gaaacatagg tctaagcaat tcatgttagg   3420
gctgttgcat tgttgttgca tcaaccaaat gtccagatag cagttcatgc tacatctagt   3480
tgaaaaccct catcattagg cggaacatgt gttctttttt agcatagtca aagtcagatt   3540
gcggcactcg ctcatccacg gaaagaattt tccctgtgca ggcatctcga tcaaaagacg   3600
caaattaatt tttgaatagc gatataacaa tatctaatta acgtttcttg ttttctgcga   3660
aatgtctttc atcataaaat gagtcatctc gatgagccca agtgacatag cccaacaccc   3720
caccccacca ataaaagtga agaaacatg ttgggaaaac tataccaagt aaaatacgag   3780
ttgttctaaa gaaaagtaa agtacgagtt agatcgcacc ctgtcctgga gtgtggcttg   3840
atgatccaac tcctagcatt gtatccctgt ttttggatga tgtaactatt atttacaatg   3900
aataaagagg tgttttacta gtaaaaaaat cttgaggggga ggagaaaata atggaggtct   3960
tttttcaaac cgatggacta ttattttttag tgaaagagaa taatattatt ggaaaaatta   4020
ttctatccac ttattttata ttggcagaat acaaagaatg gtggggtcca cgcggaactt   4080
gcggcccccg aaacctatcg agggcgcggt acccaagcaa ggaacggagg aaacttgcgg   4140
ggcccgaaac ctagtgataa aaggcatatc atccacacga tgaagatctg acggaccata   4200
tctcccacca cggaaagcca tcagacgagg atcagacggc caggaaggaa ccctagcgcc   4260
cgccggtgcc aatataaagc gccactctct ctcgtcttaa gccccagcct ctccattccc   4320
ctctccctct cgccgccgcc gtctccttct cctactccct tcgaggtgtg ttgttcatcc   4380
gtcccgaatc catccatccc ctcttcagat gtgttgttca tggctctaat agctctagat   4440
ctgcttgttt gtgttgttta gctctagatc tactcgcgcg cgcttctctc tcgatctcct   4500
gtagaacaat tttggttggt tttttgtgca tatccatggt aattttgtct gcaatatgga   4560
ggaggctttc taagctccta cgtagcatcg atctttagaa ttccctcggt ttctgtttat   4620
ttcttcgcga gggctctctg ttatctgtag gagtagctgt aagcgcggtt cgttacggat   4680
taatcgtcat gcttagttga acctatcggt cgaaggattt gtgtgggttg tcgtgtagaa   4740
ttgacaccat ctacttactg tactgatatg ccgatctgta ggatactctt cattacttttt   4800 gtttactgct agttgtggtg tagatttagc attctcaaac ccatgctgta gcgtttctaa   4860
tattgttaca tagatctacc ggtgcctgtt aattgtattc gatcgggcgt ttctacatct   4920
gtccgcccac ctagttttat atgtggtaat caaaattgcg ttgacttcgt gatgctgtct   4980
gtgtactgtt tttaatcgct cttacttaga tgatcaacat ggtgatggtt acgatttact   5040
gttttctaat ccctgttact tcgatgctgc agtttggatc catggaatcg ggctccggca   5100
cggcggcagg gtctggttat gtctatcggc agagcggaag cacccggtgg aatccaacag   5160
cagaacagtt gtcgctgctc aaggaacttt attaccggaa tggaattcgg acaccgtcgg   5220
cagatcaaat taggcaaatt tcggcccggc tgtccagata cggcaaaata gaagggaaaa   5280
acgtctttta ctggtttcaa aatcataaag cacgggaacg gcagaagaaa agactttcca   5340
cggtcggctg cgaccctgct ctcatagaaa tgggtaacgt cgcgagcttg gaatttggga   5400
ccgaaagcgc tcttgaatct ctcagctcag gcccgtccag cgagttgcgc gaggctccta   5460
cccgcaagtt ttatgagaag aaaaccgttg gtgagaacag caccataatc aatcctgttg   5520
agcagaactg cacactttct tgcggtactt cgcaggaatt tcagtatgct gttgatagcc   5580
gccgggtgat gaaggcaatg gaagagaagc aagcaacgga tgatgaaccg gacggaaaca   5640
aatgacggga gtcgaacagg catgtgaaga ccctccctct tttccccttg cataataatg   5700
aagatcagac cttgatcaag tcggacaagg aaatttattg ccttgggagc tgtgaaaaaa   5760
```
aaatggatct gtccccattg ggacactcgg gctctcagag ggcgtcggca ctggatttgt      5820
gcctgtcttt gggtaatgaa tcttgtggcc tccacgacaa ttgaa                      5865

<210> SEQ ID NO 46
<211> LENGTH: 5559
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
agcttacgcg tgtcgactcg aatttccccg atcgttcaaa catttggcaa taaagtttct        60
taagattgaa tcctgttgcc ggtcttgcga tgattatcat ataatttctg ttgaattacg       120
ttaagcatgt aataattaac atgtaatgca tgacgttatt tatgagatgg gttttttatga      180 ttagagtccc gcaattatac atttaatacg cgatagaaaa caaaatatag cgcgcaaact       240
aggataaatt atcgcgcgcg gtgtcatcta tgttactaga tcgctcgacg cggccgccat       300
ggccagatcg tacccaattc gccctatagt gagtcgtatt acaattcact ggccgtcgtt       360
ttacaacgtc gtgactggga aaaccctggc gttacccaac ttaatcgcct tgcagcacat       420
ccccctttcg ccagctggcg taatagcgaa gaggcccgca ccgatcgccc ttcccaacag       480
ttgcgcagcc tgaatggcga atggaaattg taagcgttaa tattttgtta aaattcgcgt       540
taaatttttg ttaaatcagc tcatttttta accataggc cgaaatcggc aaaatccctt        600
ataaatcaaa agaatagacc gagatagggt tgagtgttgt tccagtttgg aacaagagtc       660
cactattaaa gaacgtggac tccaacgtca aagggcgaaa aaccgtctat cagggcgatg       720
gcccactacg tgaaccatca ccctaatcaa gttttttggg gtcgaggtgc cgtaaagcac       780
taaatcggaa ccctaaaggg agcccccgat ttagagcttg acgggaaag ccggcgaacg        840 tggcgagaaa ggaagggaag aaagcgaaag gagcgggcgc tagggcgctg gcaagtgtag       900
cggtcacgct gcgcgtaacc accacacccg ccgcgcttaa tgcgccgcta cagggcgcgt       960
caggtggcac ttttcgggga aatgtgcgcg gaacccctat ttgtttattt ttctaaatac      1020
attcaaatat gtatccgctc atgagacaat aaccctgata aatgcttcaa taatattgaa      1080
aaaggaagag tatgagtatt caacatttcc gtgtcgccct tattcccttt tttgcggcat      1140
tttgccttcc tgttttttgct cacccagaaa cgctggtgaa agtaaaagat gctgaagatc     1200
agttgggtgc acgagtgggt tacatcgaac tggatctcaa cagcggtaag atccttgaga      1260
gttttcgccc cgaagaacgt tttccaatga tgagcacttt taaagttctg ctatgtggcg      1320
cggtattatc ccgtattgac gccgggcaag agcaactcgg tcgccgcata cactattctc      1380
agaatgactt ggttgagtac tcaccagtca cagaaaagca tcttacggat ggcatgacag      1440
taagagaatt atgcagtgct gccataacca tgagtgataa cactgcggcc aacttacttc      1500
tgacaacgat cggaggaccg aaggagctaa ccgcttttt gcacaacatg ggggatcatg       1560
taactcgcct tgatcgttgg gaaccggagc tgaatgaagc cataccaaac gacgagcgtg      1620
acaccacgat gcctgtagca atggcaacaa cgttgcgcaa actattaact ggcgaactac      1680
ttactctagc ttcccggcaa caattaatag actggatgga ggcggataaa gttgcaggac      1740
cacttctgcg ctcggccctt ccggctggct ggtttattgc tgataaatct ggagccggtg      1800
agcgtgggtc tcgcggtatc attgcagcac tggggccaga tggtaagccc tcccgtatcg      1860
tagttatcta cacgacgggg agtcaggcaa ctatggatga acgaaataga cagatcgctg      1920

-continued

```
agataggtgc ctcactgatt aagcattggt aactgtcaga ccaagtttac tcatatatac   1980
tttagattga tttaaaactt catttttaat ttaaaaggat ctaggtgaag atcctttttg   2040
ataatctcat gaccaaaatc ccttaacgtg agttttcgtt ccactgagcg tcagaccccg   2100
tagaaaagat caaaggatct tcttgagatc ctttttttct gcgcgtaatc tgctgcttgc   2160
aaacaaaaaa accaccgcta ccagcggtgg tttgtttgcc ggatcaagag ctaccaactc   2220
tttttccgaa ggtaactggc ttcagcagag cgcagatacc aaatactgtc cttctagtgt   2280
agccgtagtt aggccaccac ttcaagaact ctgtagcacc gcctacatac ctcgctctgc   2340
taatcctgtt accagtggct gctgccagtg gcgataagtc gtgtcttacc gggttggact   2400
caagacgata gttaccggat aaggcgcagc ggtcgggctg aacggggggt cgtgcacac   2460 agcccagctt ggagcgaacg acctacaccg aactgagata cctacagcgt gagctatgag   2520
aaagcgccac gcttcccgaa gggagaaagg cggacaggta tccggtaagc ggcagggtcg   2580
gaacaggaga gcgcacgagg gagcttccag ggggaaacgc ctggtatctt tatagtcctg   2640
tcgggtttcg ccacctctga cttgagcgtc gatttttgtg atgctcgtca gggggcgga   2700 gcctatggaa aaacgccagc aacgcggcct ttttacggtt cctggccttt gctggcctt   2760 ttgctcacat gttctttcct gcgttatccc ctgattctgt ggataaccgt attaccgcct   2820
ttgagtgagc tgataccgct cgccgcagcc gaacgaccga gcgcagcgag tcagtgagcg   2880
aggaagcgga agagcgccca atacgcaaac cgcctctccc cgcgcgttgg ccgattcatt   2940
aatgcagctg gcacgacagg tttcccgact ggaaagcggg cagtgagcgc aacgcaatta   3000
atgtgagtta gctcactcat taggcacccc aggctttaca ctttatgctt ccggctcgta   3060
tgttgtgtgg aattgtgagc ggataacaat ttcacacagg aaacagctat gaccatgatt   3120
acgccaagct cgaaattaac cctcactaaa gggaacaaaa gctggactag aggcccttaa   3180
ggccttacta gacttcaccg ccattgcaaa aattgtcaat aaatatttag agtgggtggc   3240
atcagaaaaa catctctagt ggactctctt cctatcatag ctactcgggc tgtagataga   3300
acgagggcac aagagttggg tggcgtaggt ttactcgtga cctcaactct tttggctgtg   3360
tcttacgtct aagatgggtt tggcatgtga gaaacatagg tctaagcaat tcatgttagg   3420
gctgttgcat tgttgttgca tcaaccaaat gtccagatag cagttcatgc tacatctagt   3480
tgaaacccct catcattagg cggaacatgt gttctttttt agcatagtca aagtcagatt   3540
gcggcactcg ctcatccacg gaaagaattt tccctgtgca ggcatctcga tcaaaagacg   3600
caaattaatt tttgaatagc gatataacaa tatctaatta acgtttcttg ttttctgcga   3660
aatgtctttc atcataaaat gagtcatctc gatgagccca agtgacatag cccaacaccc   3720
cacccaccaa ataaaagtga agaaaacatg ttgggaaaac tataccaagt aaaatacgag   3780
ttgttctaaa gaaaaagtaa agtacgagtt agatcgcacc ctgtcctgga gtgtggcttg   3840
atgatccaac tcctagcatt gtatccctgt ttttggatga tgtaactatt atttacaatg   3900
aataaagagg tgtttactac gtaaaaaaat cttgaggggga ggagaaaata atggaggtct   3960
tttttcaaac cgatggacta ttatttttag tgaaagagaa taatattatt ggaaaaatta   4020
ttctatccac ttatttttata ttggcagaat acaaagaatg gtggggtcca cgcggaactt   4080 gcggccccg aaacctatcg agggcgcggt acccaagcaa ggaacggagg aaacttgcgg   4140
ggcccgaaac ctagtgataa aaggcatatc atccacacga tgaagatctg acggaccata   4200
tctcccacca cggaaagcca tcagacgagg atcagacggc caggaaggaa ccctagcgcc   4260
```

-continued

```
cgccggtgcc aatataaagc gccactctct ctcgtcttaa gccccagcct ctccattccc    4320
ctctccctct cgccgccgcc gtctccttct cctactccct tcgaggtgtg ttgttcatcc    4380
gtcccgaatc catccatccc ctcttcagat gtgttgttca tggctctaat agctctagat    4440
ctgcttgttt gtgttgttta gctctagatc tactcgcgcg cgcttctctc tcgatctcct    4500
gtagaacaat tttggttggt tttttgtgca tatccatggt aattttgtct gcaatatgga    4560
ggaggctttc taagctccta cgtagcatcg atctttagaa ttccctcggt ttctgtttat    4620
ttcttcgcga gggctctctg ttatctgtag gagtagctgt aagcgcggtt cgttacggat    4680
taatcgtcat gcttagttga acctatcggt cgaaggattt gtgtgggttg tcgtgtagaa    4740
ttgacaccat ctacttactg tactgatatg ccgatctgta ggatactctt cattactttt    4800
gtttactgct agttgtggtg tagatttagc attctcaaac ccatgctgta gcgtttctaa    4860
tattgttaca tagatctacc ggtgcctgtt aattgtattc gatcgggcgt ttctacatct    4920
gtccgcccac ctagttttat atgtggtaat caaaattgcg ttgacttcgt gatgctgtct    4980
gtgtactgtt tttaatcgct cttacttaga tgatcaacat ggtgatggtt acgatttact    5040
gttttctaat ccctgttact tcgatgctgc agtttggatc catggttagc aaggggggagg    5100 aggttattaa agaattccca ggaagcaccc ggtggaatcc aacggcggag caactttcgc    5160
tccttcggga aatttattac aggaatgggc tgagaactcc caccgctgac gagatcagac    5220
agatttcatc aaaattgtcg cggtatggta agattgaagg gaaaaatgtg tacaactggt    5280
tccagaacag aagagctagg gaaaagagaa aacagcggtt gtcaaccata ggctgtggtt    5340 cggcgggtc ggccgcaggg agcggagagt ttcgccatgt gaagaccctg cccctttttcc    5400 ctttgcataa taatgaggat tcaggttcgt tggatctgga gctggaattg ggttttgcct    5460
ctgctaccgc agccgcgact tctggttcac aaagggcgtc ggcattggat ctctgcctgt    5520
cccttggaaa tgagtcatgc ggtttgcatg acaactgaa                          5559
```

<210> SEQ ID NO 47
<211> LENGTH: 5559
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47

```
agcttacgcg tgtcgactcg aatttccccg atcgttcaaa catttggcaa taaagtttct      60
taagattgaa tcctgttgcc ggtcttgcga tgattatcat ataatttctg ttgaattacg     120
ttaagcatgt aataattaac atgtaatgca tgacgttatt tatgagatgg gttttttatga    180 ttagagtccc gcaattatac atttaatacg cgatagaaaa caaaatatag cgcgcaaact     240
aggataaatt atcgcgcgcg gtgtcatcta tgttactaga tcgctcgacg cggccgccat     300
ggccagatcg tacccaattc gccctatagt gagtcgtatt acaattcact ggccgtcgtt     360
ttacaacgtc gtgactggga aaaccctggc gttacccaac ttaatcgcct tgcagcacat     420
ccccctttcg ccagctggcg taatagcgaa gaggcccgca ccgatcgccc ttcccaacag     480
ttgcgcagcc tgaatggcga atggaaattg taagcgttaa tattttgtta aaattcgcgt     540
taaatttttg ttaaatcagc tcatttttta accataggc cgaaatcggc aaaatccctt     600
ataaatcaaa agaatagacc gagatagggt tgagtgttgt tccagtttgg aacaagagtc     660
cactattaaa gaacgtggac tccaacgtca aagggcgaaa aaccgtctat cagggcgatg     720
```

-continued

```
gcccactacg tgaaccatca ccctaatcaa gttttttggg gtcgaggtgc cgtaaagcac    780
taaatcggaa ccctaaaggg agcccccgat ttagagcttg acggggaaag ccggcgaacg    840
tggcgagaaa ggaagggaag aaagcgaaag gagcgggcgc tagggcgctg gcaagtgtag    900
cggtcacgct gcgcgtaacc accacacccg ccgcgcttaa tgcgccgcta cagggcgcgt    960
caggtggcac ttttcgggga aatgtgcgcg gaacccctat ttgtttattt ttctaaatac    1020
attcaaatat gtatccgctc atgagacaat aaccctgata aatgcttcaa taatattgaa    1080
aaaggaagag tatgagtatt caacatttcc gtgtcgccct tattcccttt tttgcggcat    1140
tttgccttcc tgtttttgct cacccagaaa cgctggtgaa agtaaaagat gctgaagatc    1200
agttgggtgc acgagtgggt tacatcgaac tggatctcaa cagcggtaag atccttgaga    1260
gttttcgccc cgaagaacgt tttccaatga tgagcacttt taaagttctg ctatgtggcg    1320
cggtattatc ccgtattgac gccgggcaag agcaactcgg tcgccgcata cactattctc    1380
agaatgactt ggttgagtac tcaccagtca cagaaaagca tcttacggat ggcatgacag    1440
taagagaatt atgcagtgct gccataacca tgagtgataa cactgcggcc aacttacttc    1500
tgacaacgat cggaggaccg aaggagctaa ccgctttttt gcacaacatg ggggatcatg    1560
taactcgcct tgatcgttgg gaaccggagc tgaatgaagc cataccaaac gacgagcgtg    1620
acaccacgat gcctgtagca atggcaacaa cgttgcgcaa actattaact ggcgaactac    1680
ttactctagc ttcccggcaa caattaatag actggatgga ggcggataaa gttgcaggac    1740
cacttctgcg ctcggccctt ccggctggct ggtttattgc tgataaatct ggagccggtg    1800
agcgtgggtc tcgcggtatc attgcagcac tggggccaga tggtaagccc tcccgtatcg    1860
tagttatcta cacgacgggg agtcaggcaa ctatggatga acgaaataga cagatcgctg    1920
agataggtgc ctcactgatt aagcattggt aactgtcaga ccaagtttac tcatatatac    1980
tttagattga tttaaaactt catttttaat ttaaaaggat ctaggtgaag atcctttttg    2040
ataatctcat gaccaaaatc ccttaacgtg agttttcgtt ccactgagcg tcagaccccg    2100
tagaaaagat caaaggatct tcttgagatc ctttttttct gcgcgtaatc tgctgcttgc    2160
aaacaaaaaa accaccgcta ccagcggtgg tttgtttgcc ggatcaagag ctaccaactc    2220
tttttccgaa ggtaactggc ttcagcagag cgcagatacc aaatactgtc cttctagtgt    2280
agccgtagtt aggccaccac ttcaagaact ctgtagcacc gcctacatac ctcgctctgc    2340
taatcctgtt accagtggct gctgccagtg gcgataagtc gtgtcttacc gggttggact    2400
caagacgata gttaccggat aaggcgcagc ggtcgggctg aacggggggt tcgtgcacac    2460
agcccagctt ggagcgaacg acctacaccg aactgagata cctacagcgt gagctatgag    2520
aaagcgccac gcttcccgaa gggagaaagg cggacaggta tccggtaagc ggcagggtcg    2580
gaacaggaga gcgcacgagg gagcttccag ggggaaacgc ctggtatctt tatagtcctg    2640
tcgggtttcg ccacctctga cttgagcgtc gatttttgtg atgctcgtca ggggggcgga    2700
gcctatggaa aaacgccagc aacgcggcct ttttacggtt cctggccttt tgctggcctt    2760
ttgctcacat gttctttcct gcgttatccc ctgattctgt ggataaccgt attaccgcct    2820
ttgagtgagc tgataccgct cgccgcagcc gaacgaccga cgcagcgag tcagtgagcg    2880 aggaagcgga agagcgccca atacgcaaac cgcctctccc cgcgcgttgg ccgattcatt    2940
aatgcagctg gcacgacagg tttcccgact ggaaagcggg cagtgagcgc aacgcaatta    3000
atgtgagtta gctcactcat taggcacccc aggctttaca ctttatgctt ccggctcgta    3060
tgttgtgtgg aattgtgagc ggataacaat ttcacacagg aaacagctat gaccatgatt    3120
```

-continued

```
acgccaagct cgaaattaac cctcactaaa gggaacaaaa gctggactag aggcccttaa   3180
ggccttacta gacttcaccg ccattgcaaa aattgtcaat aaatatttag agtgggtggc   3240
atcagaaaaa catctctagt ggactctctt cctatcatag ctactcgggc tgtagataga   3300
acgagggcac aagagttggg tggcgtaggt ttactcgtga cctcaactct tttggctgtg   3360
tcttacgtct aagatgggtt tggcatgtga gaaacatagg tctaagcaat tcatgttagg   3420
gctgttgcat tgttgttgca tcaaccaaat gtccagatag cagttcatgc tacatctagt   3480
tgaaaaccct catcattagg cggaacatgt gttctttttt agcatagtca aagtcagatt   3540
gcggcactcg ctcatccacg gaaagaattt tccctgtgca ggcatctcga tcaaaagacg   3600
caaattaatt tttgaatagc gatataacaa tatctaatta acgtttcttg ttttctgcga   3660
aatgtctttc atcataaaat gagtcatctc gatgagccca agtgacatag cccaacaccc   3720 cacccaccc ataaaagtga agaaacatg ttgggaaaac tataccaagt aaaatacgag   3780
ttgttctaaa gaaaaagtaa agtacgagtt agatcgcacc ctgtcctgga gtgtggcttg   3840
atgatccaac tcctagcatt gtatccctgt ttttggatga tgtaactatt atttacaatg   3900
aataaagagg tgttttacta gtaaaaaaat cttgaggggga ggagaaaata atggaggtct   3960
tttttcaaac cgatggacta ttattttttag tgaaagagaa taatattatt ggaaaaatta   4020
ttctatccac ttattttata ttggcagaat acaaagaatg gtggggtcca cgcggaactt   4080
gcggcccccg aaacctatcg agggcgcggt acccaagcaa ggaacggagg aaacttgcgg   4140
ggcccgaaac ctagtgataa aaggcatatc atccacacga tgaagatctg acggaccata   4200
tctcccacca cggaaagcca tcagacgagg atcagacggc caggaaggaa ccctagcgcc   4260
cgccggtgcc aatataaagc gccactctct ctcgtcttaa gccccagcct ctccattccc   4320
ctctccctct cgccgccgcc gtctccttct cctactccct tcgaggtgtg ttgttcatcc   4380
gtcccgaatc catccatccc ctcttcagat gtgttgttca tggctctaat agctctagat   4440
ctgcttgttt gtgttgttta gctctagatc tactcgcgcg cgcttctctc tcgatctcct   4500
gtagaacaat tttggttggt tttttgtgca tatccatggt aattttgtct gcaatatgga   4560
ggaggctttc taagctccta cgtagcatcg atctttagaa ttccctcggt ttctgtttat   4620
ttcttcgcga gggctctctg ttatctgtag gagtagctgt aagcgcggtt cgttacggat   4680
taatcgtcat gcttagttga acctatcggt cgaaggattt gtgtgggttg tcgtgtagaa   4740
ttgacaccat ctacttactg tactgatatg ccgatctgta ggatactctt cattactttt   4800
gtttactgct agttgtggtg tagatttagc attctcaaac ccatgctgta gcgtttctaa   4860
tattgttaca tagatctacc ggtgcctgtt aattgtattc gatcgggcgt ttctacatct   4920
gtccgcccac ctagtttttat atgtggtaat caaaattgcg ttgacttcgt gatgctgtct   4980
gtgtactgtt tttaatcgct cttacttaga tgatcaacat ggtgatggtt acgatttact   5040
gttttctaat ccctgttact tcgatgctgc agtttggatc catggtctcg aaaggagaag   5100
aggtcatcaa agaattttca ggcagcaccc gctggaatcc gactgcagaa caactttctc   5160
tcctcaaaga gctttattac agaaatggga tcagaacccc ttcagcggac cagatacgcc   5220
agataagcgc ccgcttgtcg aggtacggca aaatcgaggg gaagaatgtt ttttactggt   5280
tccaaaacca taaagcgagg gagcggcaga agaaaagact gagcactgtg ggttgtggat   5340
cggcgggatc ggctgccggg tcaggtgaat ttcgccatgt taaaacgctt ccactgtttc   5400
ccttgcataa taatgaagac agcggatcac ttgacctgga gctggagttg ggcttcgctt   5460
```

-continued

```
ccgcgacggc tgctgcaaca tccggctcgc agcgggcgtc ggcgctggat ttgtgccttt      5520
cgctgggaaa tgagagctgc ggtcttcatg acaactgaa                             5559

<210> SEQ ID NO 48
<211> LENGTH: 5583
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
agcttacgcg tgtcgactcg aatttccccg atcgttcaaa catttggcaa taaagtttct       60
taagattgaa tcctgttgcc ggtcttgcga tgattatcat ataatttctg ttgaattacg      120
ttaagcatgt aataattaac atgtaatgca tgacgttatt tatgagatgg gtttttatga      180
ttagagtccc gcaattatac atttaatacg cgatagaaaa caaaatatag cgcgcaaact      240
aggataaatt atcgcgcgcg gtgtcatcta tgttactaga tcgctcgacg cggccgccat      300
ggccagatcg tacccaattc gccctatagt gagtcgtatt acaattcact ggccgtcgtt      360
ttacaacgtc gtgactggga aaaccctggc gttacccaac ttaatcgcct tgcagcacat      420
ccccctttcg ccagctggcg taatagcgaa gaggcccgca ccgatcgccc ttcccaacag      480
ttgcgcagcc tgaatggcga atggaaattg taagcgttaa tattttgtta aaattcgcgt      540 taaattttg ttaaatcagc tcattttta accataggc cgaaatcggc aaaatccctt         600
ataaatcaaa agaatagacc gagatagggt tgagtgttgt tccagtttgg aacaagagtc      660
cactattaaa gaacgtggac tccaacgtca aagggcgaaa aaccgtctat cagggcgatg      720
gcccactacg tgaaccatca ccctaatcaa gttttttggg gtcgaggtgc cgtaaagcac      780
taaatcggaa ccctaaaggg agcccccgat ttagagcttg acgggaaag ccggcgaacg       840 tggcgagaaa ggaagggaag aaagcgaaag gagcgggcgc tagggcgctg gcaagtgtag      900
cggtcacgct gcgcgtaacc accacacccg ccgcgcttaa tgcgccgcta cagggcgcgt      960
caggtggcac ttttcgggga atgtgcgcg gaacccctat ttgtttattt ttctaaatac      1020
attcaaatat gtatccgctc atgagacaat aaccctgata aatgcttcaa taatattgaa     1080
aaaggaagag tatgagtatt caacatttcc gtgtcgccct tattcccttt tttgcggcat     1140
tttgccttcc tgtttttgct cacccagaaa cgctggtgaa agtaaaagat gctgaagatc     1200
agttgggtgc acgagtgggt tacatcgaac tggatctcaa cagcggtaag atccttgaga     1260
gttttcgccc cgaagaacgt tttccaatga tgagcacttt taaagttctg ctatgtggcg     1320
cggtattatc ccgtattgac gccgggcaag agcaactcgg tcgccgcata cactattctc     1380
agaatgactt ggttgagtac tcaccagtca cagaaaagca tcttacggat ggcatgacag     1440
taagagaatt atgcagtgct gccataacca tgagtgataa cactgcggcc aacttacttc     1500
tgacaacgat cggaggaccg aaggagctaa ccgcttttttt gcacaacatg ggggatcatg     1560
taactcgcct tgatcgttgg gaaccggagc tgaatgaagc cataccaaac gacgagcgtg     1620
acaccacgat gcctgtagca atggcaacaa cgttgcgcaa actattaact ggcgaactac     1680
ttactctagc ttcccggcaa caattaatag actggatgga ggcggataaa gttgcaggac     1740
cacttctgcg ctcggccctt ccggctggct ggtttattgc tgataaatct ggagccggtg     1800
agcgtgggtc tcgcggtatc attgcagcac tggggccaga tggtaagccc tcccgtatcg     1860
tagttatcta cacgacgggg agtcaggcaa ctatggatga acgaaataga cagatcgctg     1920
```

-continued

```
agataggtgc ctcactgatt aagcattggt aactgtcaga ccaagtttac tcatatatac    1980
tttagattga tttaaaactt catttttaat ttaaaaggat ctaggtgaag atcctttttg    2040
ataatctcat gaccaaaatc ccttaacgtg agttttcgtt ccactgagcg tcagaccccg    2100
tagaaaagat caaaggatct tcttgagatc ctttttttct gcgcgtaatc tgctgcttgc    2160
aaacaaaaaa accaccgcta ccagcggtgg tttgtttgcc ggatcaagag ctaccaactc    2220
tttttccgaa ggtaactggc ttcagcagag cgcagatacc aaatactgtc cttctagtgt    2280
agccgtagtt aggccaccac ttcaagaact ctgtagcacc gcctacatac ctcgctctgc    2340
taatcctgtt accagtggct gctgccagtg gcgataagtc gtgtcttacc gggttggact    2400
caagacgata gttaccggat aaggcgcagc ggtcgggctg aacggggggt cgtgcacac    2460 agcccagctt ggagcgaacg acctacaccg aactgagata cctacagcgt gagctatgag    2520
aaagcgccac gcttcccgaa gggagaaagg cggacaggta tccggtaagc ggcagggtcg    2580
gaacaggaga gcgcacgagg gagcttccag ggggaaacgc ctggtatctt tatagtcctg    2640
tcgggtttcg ccacctctga cttgagcgtc gatttttgtg atgctcgtca ggggggcgga    2700
gcctatggaa aaacgccagc aacgcggcct ttttacggtt cctggccttt tgctggcctt    2760
ttgctcacat gttctttcct gcgttatccc ctgattctgt ggataaccgt attaccgcct    2820
ttgagtgagc tgataccgct cgccgcagcc gaacgaccga gcgcagcgag tcagtgagcg    2880
aggaagcgga agagcgccca atacgcaaac cgcctctccc cgcgcgttgg ccgattcatt    2940
aatgcagctg gcacgacagg tttcccgact ggaaagcggg cagtgagcgc aacgcaatta    3000
atgtgagtta gctcactcat taggcacccc aggctttaca ctttatgctt ccggctcgta    3060
tgttgtgtgg aattgtgagc ggataacaat ttcacacagg aaacagctat gaccatgatt    3120
acgccaagct cgaaattaac cctcactaaa gggaacaaaa gctggactag aggcccttaa    3180
ggccttacta gacttcaccg ccattgcaaa aattgtcaat aaatatttag agtgggtggc    3240
atcagaaaaa catctctagt ggactctctt cctatcatag ctactcgggc tgtagataga    3300
acgagggcac aagagttggg tggcgtaggt ttactcgtga cctcaactct tttggctgtg    3360
tcttacgtct aagatgggtt tggcatgtga gaaacatagg tctaagcaat tcatgttagg    3420
gctgttgcat tgttgttgca tcaaccaaat gtccagatag cagttcatgc tacatctagt    3480
tgaaaaccct catcattagg cggaacatgt gttctttttt agcatagtca aagtcagatt    3540
gcggcactcg ctcatccacg gaaagaattt tccctgtgca ggcatctcga tcaaaagacg    3600
caaattaatt tttgaatagc gatataacaa tatctaatta acgtttcttg ttttctgcga    3660
aatgtctttc atcataaaat gagtcatctc gatgagccca agtgacatag cccaacaccc    3720 cacccccacca ataaaagtga agaaacatg ttgggaaaac tataccaagt aaaatacgag    3780
ttgttctaaa gaaaaagtaa agtacgagtt agatcgcacc ctgtcctgga gtgtggcttg    3840
atgatccaac tcctagcatt gtatccctgt ttttggatga tgtaactatt atttacaatg    3900
aataaagagg tgtttactaaa gtaaaaaaat cttgagggga ggagaaaata atggaggtct    3960
tttttcaaac cgatggacta ttatttttag tgaaagagaa taatattatt ggaaaaatta    4020
ttctatccac ttattttata ttggcagaat acaaagaatg gtggggtcca cgcggaactt    4080
gcggcccccg aaacctatcg agggcgcggt acccaagcaa ggaacggagg aaacttgcgg    4140
ggcccgaaac ctagtgataa aaggcatatc atccacacga tgaagatctg acggaccata    4200
tctcccacca cggaaagcca tcagacgagg atcagacggc caggaaggaa ccctagcgcc    4260
cgccggtgcc aatataaagc gccactctct ctcgtcttaa gccccagcct ctccattccc    4320
```

```
ctctccctct cgccgccgcc gtctccttct cctactccct tcgaggtgtg ttgttcatcc      4380
gtcccgaatc catccatccc ctcttcagat gtgttgttca tggctctaat agctctagat      4440
ctgcttgttt gtgttgttta gctctagatc tactcgcgcg cgcttctctc tcgatctcct      4500
gtagaacaat tttggttggt tttttgtgca tatccatggt aattttgtct gcaatatgga      4560
ggaggctttc taagctccta cgtagcatcg atctttagaa ttccctcggt ttctgtttat      4620
ttcttcgcga gggctctctg ttatctgtag gagtagctgt aagcgcggtt cgttacggat      4680
taatcgtcat gcttagttga acctatcggt cgaaggattt gtgtgggttg tcgtgtagaa      4740
ttgacaccat ctacttactg tactgatatg ccgatctgta ggatactctt cattactttt      4800
gtttactgct agttgtggtg tagatttagc attctcaaac ccatgctgta gcgtttctaa      4860
tattgttaca tagatctacc ggtgcctgtt aattgtattc gatcgggcgt ttctacatct      4920
gtccgcccac ctagttttat atgtggtaat caaaattgcg ttgacttcgt gatgctgtct      4980
gtgtactgtt tttaatcgct cttacttaga tgatcaacat ggtgatggtt acgatttact      5040
gttttctaat ccctgttact tcgatgctgc agtttggatc catggtgtct aaaggggaag      5100
aggtcataaa agagttctca ggttctactc gctggaatcc aactgcagaa caactctctc      5160
tcctgaagga gctctactat cggaacggaa tacgcacgcc ttcggcggac caaataaggc      5220
agatttcagc ccgcctgtct agatacggga aaatcgaggg aaagaacgtg ttttattggt      5280
tccaaaacca taaggcaaga gagcggcaga aaaaacggct cagcacagtc ggctgtgggt      5340
cagccggttc ggcggctggc tctggtgaat tccgccacgt caaaaccctg cctctgttcc      5400
cgctccacaa taatgtcgag acacttccct tgttcccgga ggattccggg tctctcgact      5460
tggagctcga attgggcttt gcctctgcca ctgcggcagc gaccagcgga tcacagagag      5520
cctccgcact ggatctgtgc ctgtcacttg gaaatgaatc gtgcggattg cacgacaatt      5580
gaa                                                                    5583
```

<210> SEQ ID NO 49
<211> LENGTH: 5853
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49

```
agcttacgcg tgtcgactcg aatttccccg atcgttcaaa catttggcaa taaagtttct        60
taagattgaa tcctgttgcc ggtcttgcga tgattatcat ataatttctg ttgaattacg       120
ttaagcatgt aataattaac atgtaatgca tgacgttatt tatgagatgg gttttttatga      180 ttagagtccc gcaattatac atttaatacg cgatagaaaa caaaatatag cgcgcaaact       240
aggataaatt atcgcgcgcg gtgtcatcta tgttactaga tcgctcgacg cggccgccat       300
ggccagatcg tacccaattc gccctatagt gagtcgtatt acaattcact ggccgtcgtt       360
ttacaacgtc gtgactggga aaaccctggc gttacccaac ttaatcgcct tgcagcacat       420
ccccctttcg ccagctggcg taatagcgaa gaggcccgca ccgatcgccc ttcccaacag       480
ttgcgcagcc tgaatggcga atggaaattg taagcgttaa tattttgtta aaattcgcgt       540 taaattttg ttaaatcagc tcattttttta accaataggc cgaaatcggc aaaatccctt       600
ataaatcaaa agaatagacc gagatagggt tgagtgttgt tccagtttgg aacaagagtc       660
cactattaaa gaacgtggac tccaacgtca aagggcgaaa aaccgtctat cagggcgatg       720
```

-continued

```
gcccactacg tgaaccatca ccctaatcaa gttttttggg gtcgaggtgc cgtaaagcac      780
taaatcggaa ccctaaaggg agcccccgat ttagagcttg acggggaaag ccggcgaacg      840
tggcgagaaa ggaagggaag aaagcgaaag gagcgggcgc tagggcgctg gcaagtgtag      900
cggtcacgct gcgcgtaacc accacacccg ccgcgcttaa tgcgccgcta cagggcgcgt      960
caggtggcac ttttcgggga aatgtgcgcg gaacccctat ttgtttattt ttctaaatac     1020
attcaaatat gtatccgctc atgagacaat aaccctgata aatgcttcaa taatattgaa     1080
aaaggaagag tatgagtatt caacatttcc gtgtcgccct tattcccttt tttgcggcat     1140
tttgccttcc tgtttttgct cacccagaaa cgctggtgaa agtaaaagat gctgaagatc     1200
agttgggtgc acgagtgggt tacatcgaac tggatctcaa cagcggtaag atccttgaga     1260
gttttcgccc cgaagaacgt tttccaatga tgagcacttt taaagttctg ctatgtggcg     1320
cggtattatc ccgtattgac gccgggcaag agcaactcgg tcgccgcata cactattctc     1380
agaatgactt ggttgagtac tcaccagtca cagaaaagca tcttacggat ggcatgacag     1440
taagagaatt atgcagtgct gccataacca tgagtgataa cactgcggcc aacttacttc     1500
tgacaacgat cggaggaccg aaggagctaa ccgctttttt gcacaacatg ggggatcatg     1560
taactcgcct tgatcgttgg gaaccggagc tgaatgaagc cataccaaac gacgagcgtg     1620
acaccacgat gcctgtagca atggcaacaa cgttgcgcaa actattaact ggcgaactac     1680
ttactctagc ttcccggcaa caattaatag actggatgga ggcggataaa gttgcaggac     1740
cacttctgcg ctcggccctt ccggctggct ggtttattgc tgataaatct ggagccggtg     1800
agcgtgggtc tcgcggtatc attgcagcac tggggccaga tggtaagccc tcccgtatcg     1860
tagttatcta cacgacgggg agtcaggcaa ctatggatga acgaaataga cagatcgctg     1920
agataggtgc ctcactgatt aagcattggt aactgtcaga ccaagtttac tcatatatac     1980
tttagattga tttaaaactt catttttaat ttaaaaggat ctaggtgaag atcctttttg     2040
ataatctcat gaccaaaatc ccttaacgtg agttttcgtt ccactgagcg tcagaccccg     2100
tagaaaagat caaaggatct tcttgagatc ctttttttct gcgcgtaatc tgctgcttgc     2160
aaacaaaaaa accaccgcta ccagcggtgg tttgtttgcc ggatcaagag ctaccaactc     2220
tttttccgaa ggtaactggc ttcagcagag cgcagatacc aaatactgtc cttctagtgt     2280
agccgtagtt aggccaccac ttcaagaact ctgtagcacc gcctacatac ctcgctctgc     2340
taatcctgtt accagtggct gctgccagtg gcgataagtc gtgtcttacc gggttggact     2400
caagacgata gttaccggat aaggcgcagc ggtcgggctg aacggggggt tcgtgcacac     2460
agcccagctt ggagcgaacg acctacaccg aactgagata cctacagcgt gagctatgag     2520
aaagcgccac gcttcccgaa gggagaaagg cggacaggta tccggtaagc ggcagggtcg     2580
gaacaggaga gcgcacgagg gagcttccag ggggaaacgc ctggtatctt tatagtcctg     2640
tcgggtttcg ccacctctga cttgagcgtc gatttttgtg atgctcgtca ggggggcgga     2700
gcctatggaa aaacgccagc aacgcggcct ttttacggtt cctggccttt tgctggcctt     2760
ttgctcacat gttctttcct gcgttatccc ctgattctgt ggataaccgt attaccgcct     2820
ttgagtgagc tgataccgct cgccgcagcc gaacgaccga gcgcagcgag tcagtgagcg     2880
aggaagcgga agagcgccca atacgcaaac cgcctctccc cgcgcgttgg ccgattcatt     2940
aatgcagctg gcacgacagg tttcccgact ggaaagcggg cagtgagcgc aacgcaatta     3000
atgtgagtta gctcactcat taggcacccc aggctttaca ctttatgctt ccggctcgta     3060
```

```
tgttgtgtgg aattgtgagc ggataacaat ttcacacagg aaacagctat gaccatgatt    3120
acgccaagct cgaaattaac cctcactaaa gggaacaaaa gctggactag aggcccttaa    3180
ggccttacta gacttcaccg ccattgcaaa aattgtcaat aaatatttag agtgggtggc    3240
atcagaaaaa catctctagt ggactctctt cctatcatag ctactcgggc tgtagataga    3300
acgagggcac aagagttggg tggcgtaggt ttactcgtga cctcaactct tttggctgtg    3360
tcttacgtct aagatgggtt tggcatgtga gaaacatagg tctaagcaat tcatgttagg    3420
gctgttgcat tgttgttgca tcaaccaaat gtccagatag cagttcatgc tacatctagt    3480
tgaaaaccct catcattagg cggaacatgt gttctttttt agcatagtca aagtcagatt    3540
gcggcactcg ctcatccacg gaaagaattt tccctgtgca ggcatctcga tcaaaagacg    3600
caaattaatt tttgaatagc gatataacaa tatctaatta acgtttcttg ttttctgcga    3660
aatgtctttc atcataaaat gagtcatctc gatgagccca agtgacatag cccaacaccc    3720
caccccacca ataaaagtga agaaacatg ttgggaaaac tataccaagt aaaatacgag    3780
ttgttctaaa gaaaaagtaa agtacgagtt agatcgcacc ctgtcctgga gtgtggcttg    3840
atgatccaac tcctagcatt gtatccctgt ttttggatga tgtaactatt atttacaatg    3900
aataaagagg tgtttactta gtaaaaaaat cttgagggga ggagaaaata atggaggtct    3960
tttttcaaac cgatggacta ttatttttag tgaaagagaa taatattatt ggaaaaatta    4020
ttctatccac ttatttttata ttggcagaat acaaagaatg gtggggtcca cgcggaactt    4080
gcggcccccg aaacctatcg agggcgcggt acccaagcaa ggaacggagg aaacttgcgg    4140
ggcccgaaac ctagtgataa aaggcatatc atccacacga tgaagatctg acggaccata    4200
tctcccacca cggaaagcca tcagacgagg atcagacggc caggaaggaa ccctagcgcc    4260
cgccggtgcc aatataaagc gccactctct ctcgtcttaa gccccagcct ctccattccc    4320
ctctccctct cgccgccgcc gtctccttct cctactccct tcgaggtgtg ttgttcatcc    4380
gtcccgaatc catccatccc ctcttcagat gtgttgttca tggctctaat agctctagat    4440
ctgcttgttt gtgttgttta gctctagatc tactcgcgcg cgcttctctc tcgatctcct    4500
gtagaacaat tttggttggt tttttgtgca tatccatggt aattttgtct gcaatatgga    4560
ggaggctttc taagctccta cgtagcatcg atctttagaa ttccctcggt ttctgtttat    4620
ttcttcgcga gggctctctg ttatctgtag gagtagctgt aagcgcggtt cgttacggat    4680
taatcgtcat gcttagttga acctatcggt cgaaggattt gtgtgggttg tcgtgtagaa    4740
ttgacaccat ctacttactg tactgatatg ccgatctgta ggatactctt cattactttt    4800
gtttactgct agttgtggtg tagatttagc attctcaaac ccatgctgta gcgtttctaa    4860
tattgttaca tagatctacc ggtgcctgtt aattgtattc gatcgggcgt ttctacatct    4920
gtccgcccac ctagttttat atgtggtaat caaaattgcg ttgacttcgt gatgctgtct    4980
gtgtactgtt tttaatcgct cttacttaga tgatcaacat ggtgatggtt acgatttact    5040
gttttctaat ccctgttact tcgatgctgc agtttggatc catggtgtct aaaggcgaag    5100
aggtcattaa ggagttcagc ggctctacta gatggaatcc aacggccgag caacttagcc    5160
tgctcaaaga actctattat cgcaatggga tacgcacgcc ctctgcagat cagatacgcc    5220
aaatctcagc gcgcctgtcc aggtatggga agattgaggg taaaaacgtc ttttactggt    5280
tccaaaatca caaagcgcgc gagagacaga agaaaagact cagcaccgtt ggttgtgacc    5340
ctgctctcat cgagatgggg aatgttgctt ccctggagtt tggcacagag agcgctttgg    5400
aatcactctc ttccggcccc tcaagcgaac tcagagaggc tcccactcgg aagttttacg    5460
```

-continued

```
agaaaaaaac cgtcggagaa aacagcacga ttatcaaccc cgtcgagcag aactgcaccc      5520
tctcatgcgg cacgtcccag gagtttcagt acgccgtcga ctcgaggaga gtgatgaagg      5580
cgatggagga aaagcaagca actgacgacg agcccgacgg aaacaagtgg actgaatcca      5640
atcgccatgt taaaacgttg cctttgttcc cgctccataa caatgtggag acgttgccac      5700
tcttcccgga ggactcggga tctctggact tggagctgga actgggcttt gcttcggcta      5760
ccgcagcagc cacctcgggt tcccagagag cctcggctct tgatctctgc ctgtcactgg      5820
gtaacgaatc ttgcggactg cacgataatt aga                                  5853
```

```
<210> SEQ ID NO 50
<211> LENGTH: 5922
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
```

```
agcttacgcg tgtcgactcg aatttccccg atcgttcaaa catttggcaa taaagtttct        60
taagattgaa tcctgttgcc ggtcttgcga tgattatcat ataatttctg ttgaattacg       120
ttaagcatgt aataattaac atgtaatgca tgacgttatt tatgagatgg gttttttatga      180 ttagagtccc gcaattatac atttaatacg cgatagaaaa caaaatatag cgcgcaaact       240
aggataaatt atcgcgcgcg gtgtcatcta tgttactaga tcgctcgacg cggccgccat       300
ggccagatcg tacccaattc gccctatagt gagtcgtatt acaattcact ggccgtcgtt       360
ttacaacgtc gtgactggga aaaccctggc gttacccaac ttaatcgcct tgcagcacat       420
ccccctttcg ccagctggcg taatagcgaa gaggcccgca ccgatcgccc ttcccaacag       480
ttgcgcagcc tgaatggcga atggaaattg taagcgttaa tattttgtta aaattcgcgt       540 taaattttt ttaaatcagc tcatttttta accaataggc cgaaatcggc aaaatccctt        600
ataaatcaaa agaatagacc gagatagggt tgagtgttgt tccagtttgg aacaagagtc       660
cactattaaa gaacgtggac tccaacgtca aagggcgaaa aaccgtctat cagggcgatg       720
gcccactacg tgaaccatca ccctaatcaa gttttttggg gtcgaggtgc cgtaaagcac       780
taaatcggaa ccctaaaggg agcccccgat ttagagcttg acggggaaag ccggcgaacg       840
tggcgagaaa ggaagggaag aaagcgaaag gagcgggcgc tagggcgctg gcaagtgtag       900
cggtcacgct gcgcgtaacc accacacccg ccgcgcttaa tgcgccgcta cagggcgcgt       960
caggtggcac ttttcgggga aatgtgcgcg gaacccctat ttgtttattt ttctaaatac      1020
attcaaatat gtatccgctc atgagacaat aaccctgata aatgcttcaa taatattgaa      1080
aaaggaagag tatgagtatt caacatttcc gtgtcgccct tattcccttt tttgcggcat      1140
tttgccttcc tgtttttgct cacccagaaa cgctggtgaa agtaaaagat gctgaagatc      1200
agttgggtgc acgagtgggt tacatcgaac tggatctcaa cagcggtaag atccttgaga      1260
gttttcgccc cgaagaacgt tttccaatga tgagcacttt taaagttctg ctatgtggcg      1320
cggtattatc ccgtattgac gccgggcaag agcaactcgg tcgccgcata cactattctc      1380
agaatgactt ggttgagtac tcaccagtca cagaaaagca tcttacggat ggcatgacag      1440
taagagaatt atgcagtgct gccataacca tgagtgataa cactgcggcc aacttacttc      1500
tgacaacgat cggaggaccg aaggagctaa ccgcttttt gcacaacatg ggggatcatg      1560
taactcgcct tgatcgttgg gaaccggagc tgaatgaagc cataccaaac gacgagcgtg      1620
```

-continued

```
acaccacgat gcctgtagca atggcaacaa cgttgcgcaa actattaact ggcgaactac    1680
ttactctagc ttcccggcaa caattaatag actggatgga ggcggataaa gttgcaggac    1740
cacttctgcg ctcggccctt ccggctggct ggtttattgc tgataaatct ggagccggtg    1800
agcgtgggtc tcgcggtatc attgcagcac tggggccaga tggtaagccc tcccgtatcg    1860
tagttatcta cacgacgggg agtcaggcaa ctatggatga acgaaataga cagatcgctg    1920
agataggtgc ctcactgatt aagcattggt aactgtcaga ccaagtttac tcatatatac    1980
tttagattga tttaaaactt cattttttaat ttaaaaggat ctaggtgaag atcctttttg    2040
ataatctcat gaccaaaatc ccttaacgtg agttttcgtt ccactgagcg tcagaccccg    2100
tagaaaagat caaaggatct tcttgagatc ctttttttct gcgcgtaatc tgctgcttgc    2160
aaacaaaaaa accaccgcta ccagcggtgg tttgtttgcc ggatcaagag ctaccaactc    2220 ttttttccgaa ggtaactggc ttcagcagag cgcagatacc aaatactgtc cttctagtgt    2280
agccgtagtt aggccaccac ttcaagaact ctgtagcacc gcctacatac ctcgctctgc    2340
taatcctgtt accagtggct gctgccagtg gcgataagtc gtgtcttacc gggttggact    2400
caagacgata gttaccggat aaggcgcagc ggtcgggctg aacggggggt tcgtgcacac    2460
agcccagctt ggagcgaacg acctacaccg aactgagata cctacagcgt gagctatgag    2520
aaagcgccac gcttcccgaa gggagaaagg cggacaggta tccggtaagc ggcagggtcg    2580
gaacaggaga gcgcacgagg gagcttccag ggggaaacgc ctggtatctt tatagtcctg    2640
tcgggtttcg ccacctctga cttgagcgtc gatttttgtg atgctcgtca ggggggcgga    2700
gcctatggaa aaacgccagc aacgcggcct ttttacggtt cctggccttt tgctggcctt    2760
ttgctcacat gttctttcct gcgttatccc ctgattctgt ggataaccgt attaccgcct    2820
ttgagtgagc tgataccgct cgccgcagcc gaacgaccga gcgcagcgag tcagtgagcg    2880
aggaagcgga agagcgccca atacgcaaac cgcctctccc cgcgcgttgg ccgattcatt    2940
aatgcagctg gcacgacagg tttcccgact ggaaagcggg cagtgagcgc aacgcaatta    3000
atgtgagtta gctcactcat taggcacccc aggctttaca ctttatgctt ccggctcgta    3060
tgttgtgtgg aattgtgagc ggataacaat ttcacacagg aaacagctat gaccatgatt    3120
acgccaagct cgaaattaac cctcactaaa gggaacaaaa gctggactag aggcccttaa    3180
ggccttacta gacttcaccg ccattgcaaa aattgtcaat aaatatttag agtgggtggc    3240
atcagaaaaa catctctagt ggactctctt cctatcatag ctactcgggc tgtagataga    3300
acgagggcac aagagttggg tggcgtaggt ttactcgtga cctcaactct tttggctgtg    3360
tcttacgtct aagatgggtt tggcatgtga gaaacatagg tctaagcaat tcatgttagg    3420
gctgttgcat tgttgttgca tcaaccaaat gtccagatag cagttcatgc tacatctagt    3480
tgaaaaccct catcattagg cggaacatgt gttcttttttt agcatagtca aagtcagatt    3540
gcggcactcg ctcatccacg gaaagaattt tccctgtgca ggcatctcga tcaaaagacg    3600
caaattaatt tttgaatagc gatataacaa tatctaatta acgtttcttg ttttctgcga    3660
aatgtctttc atcataaaat gagtcatctc gatgagccca agtgacatag cccaacaccc    3720
caccccacca ataaaagtga agaaaacatg ttgggaaaac tataccaagt aaaatacgag    3780
ttgttctaaa gaaaaagtaa agtacgagtt agatcgcacc ctgtcctgga gtgtggcttg    3840
atgatccaac tcctagcatt gtatccctgt ttttggatga tgtaactatt atttacaatg    3900
aataaagagg tgtttttacta gtaaaaaaat cttgaggggga ggagaaaata atggaggtct    3960
```

-continued

```
tttttcaaac cgatggacta ttattttag tgaaagagaa taatattatt ggaaaaatta    4020
ttctatccac ttattttata ttggcagaat acaaagaatg gtggggtcca cgcggaactt    4080
gcggcccccg aaacctatcg agggcgcggt acccaagcaa ggaacggagg aaacttgcgg    4140
ggcccgaaac ctagtgataa aaggcatatc atccacacga tgaagatctg acggaccata    4200
tctcccacca cggaaagcca tcagacgagg atcagacggc caggaaggaa ccctagcgcc    4260
cgccggtgcc aatataaagc gccactctct ctcgtcttaa gccccagcct ctccattccc    4320
ctctccctct cgccgccgcc gtctccttct cctactccct tcgaggtgtg ttgttcatcc    4380
gtcccgaatc catccatccc ctcttcagat gtgttgttca tggctctaat agctctagat    4440
ctgcttgttt gtgttgttta gctctagatc tactcgcgcg cgcttctctc tcgatctcct    4500
gtagaacaat tttggttggt tttttgtgca tatccatggt aattttgtct gcaatatgga    4560
ggaggctttc taagctccta cgtagcatcg atctttagaa ttccctcggt ttctgtttat    4620
ttcttcgcga gggctctctg ttatctgtag gagtagctgt aagcgcggtt cgttacggat    4680
taatcgtcat gcttagttga acctatcggt cgaaggattt gtgtgggttg tcgtgtagaa    4740
ttgacaccat ctacttactg tactgatatg ccgatctgta ggatactctt cattactttt    4800
gtttactgct agttgtggtg tagatttagc attctcaaac ccatgctgta gcgtttctaa    4860
tattgttaca tagatctacc ggtgcctgtt aattgtattc gatcgggcgt ttctacatct    4920
gtccgcccac ctagttttat atgtggtaat caaaattgcg ttgacttcgt gatgctgtct    4980
gtgtactgtt tttaatcgct cttacttaga tgatcaacat ggtgatggtt acgatttact    5040
gttttctaat ccctgttact tcgatgctgc agtttggatc catggtttca aaggggggagg    5100 aggtcataaa agaattttct ggcagcacta gatggaatcc gactgctgag cagttgtctc    5160
tcctcaaaga actttactat aggaacggta tccgcactcc gtccgctgat caaattcgcc    5220
aaatttcggc cagactgtcc agatacggga aaattgaggg aaaaaatgtt ttctactggt    5280
tccagaatca taaggcgcgc gaaaggcaga aaaagagact ttcgaccgtc ggatgtgacc    5340
ctgcacttat cgaaatgggc aatgtcgcgt cgttggagtt tggcaccgaa tccgctctcg    5400
aatctcttag ctcgggcccc tcatcggaac tcagagaggc ccctaccaga aaattttatg    5460
agaaaaagac agtgggagag aactctacaa tcattaaccc cgtcgagcag aactgcacat    5520
tgagctgtgg aacatcgcag gagtttcaat acgcggtgga ttcgcgccgc gttatgaagg    5580
caatggagga gaagcaggca acagatgatg agccagacgg caataaatgg accgaatcta    5640
acagacatgt caagacactg ccacttttcc ctctccacaa caatgtcgag acactccctc    5700
tgtttcccga ggattcggga agcctggatc ttgagctgga acttggcttt gcatcaggtg    5760
gatctgccgg gtcagttgac acgctgccat tgtttcctag agaggctgcg ggttctgggg    5820
aatttgccac tgcggctgcg actagcggat cacagcgcgc atcggcgctc gacctctgcc    5880
tttctttggg taacgagtct tgcggcctgc atgacaactg aa    5922
```

<210> SEQ ID NO 51
<211> LENGTH: 5580
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51

```
agcttacgcg tgtcgactcg aatttccccg atcgttcaaa catttggcaa taaagtttct       60
```

-continued

```
taagattgaa tcctgttgcc ggtcttgcga tgattatcat ataatttctg ttgaattacg      120
ttaagcatgt aataattaac atgtaatgca tgacgttatt tatgagatgg gttttttatga     180 ttagagtccc gcaattatac atttaatacg cgatagaaaa caaaatatag cgcgcaaact      240
aggataaatt atcgcgcgcg gtgtcatcta tgttactaga tcgctcgacg cggccgccat      300
ggccagatcg tacccaattc gccctatagt gagtcgtatt acaattcact ggccgtcgtt      360
ttacaacgtc gtgactggga aaaccctggc gttacccaac ttaatcgcct tgcagcacat      420 cccccttcg ccagctggcg taatagcgaa gaggcccgca ccgatcgccc ttcccaacag       480
ttgcgcagcc tgaatggcga atggaaattg taagcgttaa tattttgtta aaattcgcgt       540
taaatttttg ttaaatcagc tcattttttta accaataggc cgaaatcggc aaaatcccttt     600 ataaatcaaa agaatagacc gagatagggt tgagtgttgt tccagtttgg aacaagagtc      660
cactattaaa gaacgtggac tccaacgtca aagggcgaaa aaccgtctat cagggcgatg      720
gcccactacg tgaaccatca ccctaatcaa gttttttggg gtcgaggtgc cgtaaagcac       780
taaatcggaa ccctaaaggg agcccccgat ttagagcttg acgggaaag ccggcgaacg        840 tggcgagaaa ggaagggaag aaagcgaaag gagcgggcgc tagggcgctg gcaagtgtag      900
cggtcacgct gcgcgtaacc accacacccg ccgcgcttaa tgcgccgcta cagggcgcgt      960
caggtggcac ttttcgggga aatgtgcgcg gaacccctat ttgtttattt ttctaaatac     1020
attcaaatat gtatccgctc atgagacaat aaccctgata aatgcttcaa taatattgaa     1080
aaaggaagag tatgagtatt caacatttcc gtgtcgccct tattcccttt tttgcggcat     1140
tttgccttcc tgtttttgct cacccagaaa cgctggtgaa agtaaaagat gctgaagatc     1200
agttgggtgc acgagtgggt tacatcgaac tggatctcaa cagcggtaag atccttgaga     1260
gttttcgccc cgaagaacgt tttccaatga tgagcacttt taaagttctg ctatgtggcg     1320
cggtattatc ccgtattgac gccgggcaag agcaactcgg tcgccgcata cactattctc     1380
agaatgactt ggttgagtac tcaccagtca cagaaaagca tcttacggat ggcatgacag     1440
taagagaatt atgcagtgct gccataacca tgagtgataa cactgcggcc aacttacttc     1500
tgacaacgat cggaggaccg aaggagctaa ccgcttttttt gcacaacatg ggggatcatg     1560
taactcgcct tgatcgttgg gaaccggagc tgaatgaagc cataccaaac gacgagcgtg     1620
acaccacgat gcctgtagca atggcaacaa cgttgcgcaa actattaact ggcgaactac     1680
ttactctagc ttcccggcaa caattaatag actggatgga ggcggataaa gttgcaggac     1740
cacttctgcg ctcggccctt ccggctggct ggtttattgc tgataaatct ggagccggtg     1800
agcgtgggtc tcgcggtatc attgcagcac tggggccaga tggtaagccc tcccgtatcg     1860
tagttatcta cacgacgggg agtcaggcaa ctatggatga acgaaataga cagatcgctg     1920
agataggtgc ctcactgatt aagcattggt aactgtcaga ccaagtttac tcatatatac     1980
tttagattga tttaaaactt catttttaat ttaaaaggat ctaggtgaag atcctttttg     2040
ataatctcat gaccaaaatc ccttaacgtg agttttcgtt ccactgagcg tcagaccccg     2100
tagaaaagat caaaggatct tcttgagatc ctttttttct gcgcgtaatc tgctgcttgc     2160
aaacaaaaaa accaccgcta ccagcggtgg tttgtttgcc ggatcaagag ctaccaactc     2220
tttttccgaa ggtaactggc ttcagcagag cgcagatacc aaatactgtc cttctagtgt     2280
agccgtagtt aggccaccac ttcaagaact ctgtagcacc gcctacatac ctcgctctgc     2340
taatcctgtt accagtggct gctgccagtg gcgataagtc gtgtcttacc gggttggact     2400
caagacgata gttaccggat aaggcgcagc ggtcgggctg aacggggggt tcgtgcacac     2460
```

-continued

```
agcccagctt ggagcgaacg acctacaccg aactgagata cctacagcgt gagctatgag     2520
aaagcgccac gcttcccgaa gggagaaagg cggacaggta tccggtaagc ggcagggtcg     2580
gaacaggaga gcgcacgagg gagcttccag ggggaaacgc ctggtatctt tatagtcctg     2640
tcgggtttcg ccacctctga cttgagcgtc gattttttgtg atgctcgtca ggggggcgga     2700
gcctatggaa aaacgccagc aacgcggcct ttttacggtt cctggccttt tgctggcctt     2760
ttgctcacat gttctttcct gcgttatccc ctgattctgt ggataaccgt attaccgcct     2820
ttgagtgagc tgataccgct cgccgcagcc gaacgaccga gcgcagcgag tcagtgagcg     2880
aggaagcgga gagcgccca atacgcaaac cgcctctccc cgcgcgttgg ccgattcatt     2940
aatgcagctg gcacgacagg tttcccgact ggaaagcggg cagtgagcgc aacgcaatta     3000
atgtgagtta gctcactcat taggcacccc aggctttaca ctttatgctt ccggctcgta     3060
tgttgtgtgg aattgtgagc ggataacaat ttcacacagg aaacagctat gaccatgatt     3120
acgccaagct cgaaattaac cctcactaaa gggaacaaaa gctggactag aggcccttaa     3180
ggccttacta gacttcaccg ccattgcaaa aattgtcaat aaatatttag agtgggtggc     3240
atcagaaaaa catctctagt ggactctctt cctatcatag ctactcgggc tgtagataga     3300
acgagggcac aagagttggg tggcgtaggt ttactcgtga cctcaactct tttggctgtg     3360
tcttacgtct aagatgggtt tggcatgtga gaaacatagg tctaagcaat tcatgttagg     3420
gctgttgcat tgttgttgca tcaaccaaat gtccagatag cagttcatgc tacatctagt     3480
tgaaaaccct catcattagg cggaacatgt gttctttttt agcatagtca aagtcagatt     3540
gcggcactcg ctcatccacg gaaagaattt tccctgtgca ggcatctcga tcaaaagacg     3600
caaattaatt tttgaatagc gatataacaa tatctaatta acgtttcttg ttttctgcga     3660
aatgtctttc atcataaaat gagtcatctc gatgagccca agtgacatag cccaacaccc     3720
caccccacca ataaaagtga agaaaacatg ttgggaaaac tataccaagt aaaatacgag     3780
ttgttctaaa gaaaaagtaa agtacgagtt agatcgcacc ctgtcctgga gtgtggcttg     3840
atgatccaac tcctagcatt gtatccctgt ttttggatga tgtaactatt atttacaatg     3900
aataaagagg tgttttacta gtaaaaaaat cttgagggga ggagaaaata atggaggtct     3960 ttttcaaac cgatggacta ttattttttag tgaaagagaa taatattatt ggaaaaatta     4020
ttctatccac ttatttata ttggcagaat acaaagaatg gtggggtcca cgcggaactt     4080
gcggcccccg aaacctatcg agggcgcggt acccaagcaa ggaacggagg aaacttgcgg     4140
ggcccgaaac ctagtgataa aaggcatatc atccacacga tgaagatctg acggaccata     4200
tctcccacca cggaaagcca tcagacgagg atcagacggc caggaaggaa ccctagcgcc     4260
cgccggtgcc aatataaagc gccactctct ctcgtcttaa gccccagcct ctccattccc     4320
ctctccctct cgccgccgcc gtctccttct cctactccct tcgaggtgtg ttgttcatcc     4380
gtcccgaatc catccatccc ctcttcagat gtgttgttca tggctctaat agctctagat     4440
ctgcttgttt gtgttgttta gctctagatc tactcgcgcg cgcttctctc tcgatctcct     4500
gtagaacaat tttggttggt tttttgtgca tatccatggt aattttgtct gcaatatgga     4560
ggaggctttc taagctccta cgtagcatcg atctttagaa ttccctcggt ttctgtttat     4620
ttcttcgcga gggctctctg ttatctgtag gagtagctgt aagcgcggtt cgttacggat     4680
taatcgtcat gcttagttga acctatcggt cgaaggattt gtgtgggttg tcgtgtagaa     4740
ttgacaccat ctacttactg tactgatatg ccgatctgta ggatactctt cattactttt     4800
```

-continued

```
gtttactgct agttgtggtg tagatttagc attctcaaac ccatgctgta gcgtttctaa    4860
tattgttaca tagatctacc ggtgcctgtt aattgtattc gatcgggcgt ttctacatct    4920
gtccgcccac ctagttttat atgtggtaat caaaattgcg ttgacttcgt gatgctgtct    4980
gtgtactgtt tttaatcgct cttacttaga tgatcaacat ggtgatggtt acgatttact    5040
gttttctaat ccctgttact tcgatgctgc agtttggatc catggtttcg aaggggggaag   5100 aagtcattaa agagtttttca gggtctacgc gctggaaccc taccgctgaa caagtcaagg   5160
ttttgaggga aatatattac cgcgcgggtc ttaggacgcc atccgcggat cagatccgcc    5220
aaatatcctc acagctgaaa cggtatggaa aggtggaagg aaaaaacgtg ttttattggt    5280
tccagaacca taaagcgcgg gaaagacaaa aaaagcggct cagcaccgtt gggagcgctg    5340
gctcagcagc gggttcaggt gagttcaggc acgttaaaac actgcccttg ttccctttgc    5400
acaataatga agactcaggg agcggtttgg acttggatct gaaccttgag ttgcgcctgt    5460
cggcgactgc tgctgccact tcgggctcac agcgggcgtc tgccctcgat ctggacttgg    5520
agctcagact cggtttcgcg cttggtaatg agtcgtgtgg actgcacgac aactagtgaa    5580
```

```
<210> SEQ ID NO 52
<211> LENGTH: 11544
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
```

```
tttgtaggtg ccaccttcct tttctactgt ccttttgatc aagtgacaga tagctgggca      60
atggaatccg aggaggtttc ccgatattac cctttgttga aaagtctcaa tagccctttg     120
gtcttctgag acttgcaggc aagcaagcat gaatgcctgg gggtctcggc gcgccggaga     180
agaactcgag agggaattgc agatcatgag gcagatggct atttttgtgt cacatatgcg     240
caaaaagaga ggctatattt gtgtccctag gttcttcgtt gtattgcagt ttccatatca     300
atctgacttg gtcgcatgag aaattgatgg ttaaataatt tgaatctctc atgtagtatc     360
aactattaga tattattttc accaaatata tttccatcgg agaagaagag gctacagagg     420
aagcagaaga gaggggtggg agaattttta cacttttgta cacccactta aacagcaaaa     480
tccgtatgaa aacaggccca ccaaaacaat gccacgataa caatccgtag aaacaaaagc     540
ttcatttaac agcggcgcaa caaagcacgc ttatccatgg tagttgtagt ccgtatgcga     600
tccaaagatc acgattcacg cgtgacggac ggacgacgcg tgccacacca caactaacgg     660
catccatggt agttgtagtc cgtatgcgat ccaaagatca cgattcacgc gtgacggacg     720
gacgacgcgc gccacaccac aactaacagc gtgagccagc gtccaaactc cggatggcaa     780
cggggacgaa acccgtcggg tagtcactgc ccaaacccgt ccccgcaacc ttcatcccaa     840
acccgtcccc gttccggtc gcgggtttca gtttttctacc agaccgtcc catcgggtt      900 tttcatcccc gtcgggaaat ccgaacccgc cagcatttca gcaccaagcc aaagttgcag     960
cagcaacatg aataaaaaac aacccgtttc aacaccaaga taaaacaaaa cattataatt    1020
tagacaacat ttcacacgta taacaataac atatagttct cacatataac aacaccattt    1080
cacacataaa acaacaccat ttgggataaa aatatgggct atatcaggcc atttttatgg    1140
gccatattga gttttcgtgg gtttcacagg taccggattt gtagaatgct gaaccgggtt    1200
tgaaccgtaa aatccgcggg tattgaattt gacccaatcc cgtcgtcccc tggtgggta    1260
```

-continued

```
aaaacaccat cttgagtcca aacggccacc aaccaaactc cgacggcaac aaacaaacgg    1320
cgttgctttg ctcctcggta tctccgtgac cgctcaatct cccggctgtt tccccggaat    1380
tgcgtggact ctctcatcca cacgcaaacc gcctctccct cctctctcgt cctatccgcc    1440
ccggtgccgt agcctcacgg gactcttctt cctcccttgc tataaaatcc ccgccccctc    1500
ccgtctcctc tccacacatc caaactctca atcgcaccga gaaaaatctc ctagcgatcg    1560
aagcgaagcc tctcccgatc ctctcaaggt acgcccgttt cccgtcgatc ctcctccttc    1620
cgttcgtgtt ctgtagccga tcgattcgat tcccttacac ccgttcgtgt tctctcgtgg    1680
atcgatcgat tgtttgttgc tagaaggaac tcgtagatct ggcgtttatg aactgtgatt    1740
cgggttagtc cagatcgatt caggtcggtc gtcgttgagc ctctcggcta tgtctggatt    1800
atcgtgtaga tctgctggtt cagttgatta tgttcttcta ggagtaattt cgttgggtca    1860
gcgcgatttc tgcttaatct atgctgctta ttgcgcctgt acctatctac taagctatgt    1920
gcacctgtaa ttttgctaga ttattcgttc atcctcgtag ttggtttgtc acagtaatcc    1980
gtatgggttc tgacgatgtt attgttggtc atacctaggc ttctccagat tttattttgt    2040
taaaattgga tagatctgct actgatagtt gatgatggaa tttggtgctg aatctatgct    2100
atttattgcg cctatacctg atctatcggg ctatgtacgg ctgtagttta ctggattatt    2160
cgttcatcct cggtagttgg ttcatcgttt gggttctgac gataatattg ttgattatgc    2220
gtaggcttct gcagattgtt gttaaaattg gatacatcgg ttactgatgg ttgatgatag    2280
atttgtgctg aacctatctg tttattgctc ctatacctga tctatagggc tatgtatgcc    2340
tgtaatttac cagattattc gttcatcctc gtagttggtt catctctata attcgtatgg    2400
gttcttatga tgttatcgtt gattatgcct agtcttatac agattattgt gtcaagattg    2460
aatatacctg ctactgatcg gtgataattt ggttagtagt ttgcaatctg ctaggaacac    2520
gttaccactg taatctgtaa acatggtttg ccagagtagt ttgttctact actcttgata    2580
tggttgctga ttttagtcgc ctccttttgg atcatgtatt gatgtccttg cagatttccg    2640
tgtacttacc ccggcttttg tgtacttcgt gttaacaggt ttaaacgaag caaacatggc    2700
atctagcatg gctccaaaga agaagaggaa ggtcaacaac ggcacgaaca acttccagaa    2760
tttcattggc atttccagcc tccagaagac gctccgcaac gccctgatcc ccaccgagac    2820
cacgcagcag ttcatcgtga agaacggcat catcaaggag gacgagctgc gcggcgagaa    2880
caggcagatc ctcaaggaca tcatggacga ctactaccgc ggcttcatct ccgagacgct    2940
ctccagcatc gacgacatcg actggacgag cctgttcgag aagatggaga tccagctcaa    3000
gaacggcgac aacaaggaca ccctgatcaa ggagcagacg gagtaccgca aggccatcca    3060
caagaagttc gcgaacgacg acaggttcaa gaacatgttc tccgccaagc tgatcagcga    3120
catcctcccg gagttcgtga tccacaacaa caactactcc gccagcgaga aggaggagaa    3180
gacccaggtc atcaagctct tctcccgctt cgcgacgagc ttcaaggact acttcaagaa    3240
cagggccaac tgcttctccg cggacgacat ctccagctcc agctgccaca ggatcgtgaa    3300
cgacaacgcc gagatcttct tcagcaacgc gctggtgtac cgcaggatcg tcaagtccct    3360
cagcaacgac gacatcaaca agatctccgg cgacatgaag gactccctga aggagatgag    3420
cctcgaggag atctacagct acgagaagta cggcgagttc atcacccagg agggcatctc    3480
cttctacaac gacatctgcg gcaaggtcaa cagcttcatg aacctctact gccagaagaa    3540
caaggagaac aagaacctct acaagctgca gaagctccac aagcagatcc tgtgcatcgc    3600
cgacacgtcc tacgaggtgc cgtacaagtt cgagtccgac gaggaggtgt accagagcgt    3660
```

-continued

```
caacggcttc ctggacaaca tctccagcaa gcacatcgtc gagcgcctca ggaagatcgg   3720
cgacaactac aacggctaca acctggacaa gatctacatc gtgagcaagt tctacgagtc   3780
cgtcagccag aagacctacc gcgactggga gacgatcaac acggcgctgg agatccacta   3840
caacaacatc ctccccggca acggcaagtc caaggccgac aaggtgaaga aggcggtcaa   3900
gaacgacctc cagaagagca tcaccgagat caacgagctg gtgtccaact acaagctctg   3960
cagcgacgac aacatcaagg ccgagacgta catccacgag atctcccaca tcctgaacaa   4020
cttcgaggcg caggagctca agtacaaccc ggagatccac ctggtcgagt ccgagctcaa   4080
ggccagcgag ctgaagaacg tgctcgacgt catcatgaac gcgttccact ggtgcagcgt   4140
gttcatgacc gaggagctgg tcgacaagga caacaacttc tacgccgagc tcgaggagat   4200
ctacgacgag atctaccccg tgatctccct gtacaacctc gtgcgcaact acgtcaccca   4260
gaagccgtac agcacgaaga agatcaagct caacttcggc atcccgaccc tggcggacgg   4320
ctggtccaag agcaaggagt actccaacaa cgcgatcatc ctgatgaggg acaacctgta   4380
ctacctcggc atcttcaacg cgaagaacaa gccggacaag aagatcatcg agggcaacac   4440
gagcgagaac aagggcgact acaagaagat gatctacaac ctcctgccgg gccccaacaa   4500
gatgatcccg aaggtgttcc tctccagcaa gaccggcgtc gagacgtaca agccctccgc   4560
ctacatcctg gagggctaca agcagaacaa gcacatcaag tccagcaagg acttcgacat   4620
caccttctgc cacgacctca tcgactactt caagaactgc atcgcgatcc accccgagtg   4680
gaagaacttc ggcttcgact tctccgacac cagcacgtac gaggacatct ccggcttcta   4740
ccgcgaggtg gagctgcagg gctacaagat cgactggacg tacatcagcg agaaggacat   4800
cgacctcctg caggagaagg gccagctcta cctgttccag atctacaaca aggacttctc   4860
caagaagagc accggcaacg acaacctcca cacgatgtac ctgaagaacc tcttctccga   4920
ggagaacctg aaggacatcg tcctcaagct gaacggcgag gccgagatct tcttcaggaa   4980
gtccagcatc aagaacccga tcatccacaa gaagggcagc atcctcgtga accgcaccta   5040
cgaggcggag gagaaggacc agttcggcaa catccagatc gtcaggaaga acatccccga   5100
gaacatctac caggagctgt acaagtactt caacgacaag tccgacaagg agctgagcga   5160
cgaggccgcg aagctcaaga acgtggtggg ccaccacgag gcggccacca acatcgtgaa   5220
ggactaccgc tacacgtacg acaagtactt cctgcacatg ccgatcacca tcaacttcaa   5280
ggccaacaag acgggcttca tcaacgacag gatcctgcag tacatcgcga aggagaagga   5340
cctccacgtc atcggcatcg accgcggcga gaggaacctc atctacgtgt ccgtcatcga   5400
cacctgcggc aacatcgtgg agcagaagag cttcaacatc gtcaacggct acgactacca   5460
gatcaagctg aagcagcagg agggcgctag gcagatcgcc aggaaggagt ggaaggagat   5520
cggcaagatc aaggagatca aggagggcta cctctccctc gtgatccacg agatcagcaa   5580
gatggtcatc aagtacaacg ccatcatcgc gatggaggac ctctcctacg gcttcaagaa   5640
ggggcgcttc aaggtggaga ggcaggtcta ccagaagttc gagacgatgc tgatcaacaa   5700
gctgaactac ctcgtgttca aggacatcag catcaccgag aacggcggcc tcctgaaggg   5760
ctaccagctg acgtacatcc ccgacaagct caagaacgtg gccaccagt gcggctgcat   5820 cttctacgtc ccggccgcgt acacctccaa gatcgacccc accacgggct cgtgaacat   5880 cttcaagttc aaggacctca cggtcgacgc caagcgcgcg ttcatcaaga gttcgactc   5940 catccgctac gacagcgaga agaacctgtt ctgcttcacc ttcgactaca caacttcat   6000
```

-continued

```
cacccagaac accgtgatgt ccaagtccag ctggagcgtg tacacgtacg gcgtccgcat    6060
caagcgcagg ttcgtcaacg gcaggttctc caacgagagc gacaccatcg acatcacgaa    6120
ggacatggag aagaccctcg agatgacgga catcaactgg agggacggcc acgacctgag    6180
gcaggacatc atcgactacg agatcgtgca gcacatcttc gagatcttcc gcctcaccgt    6240
ccagatgagg aactccctga gcgagctcga ggaccgcgac tacgacaggc tgatctcccc    6300
ggtgctcaac gagaacaaca tcttctacga ctcggctaag gccggcgacg ctctgcccaa    6360
ggacgcggac gccaacggcg cttactgcat cgcgctgaag ggcctctacg agatcaagca    6420
gatcacggag aactggaagg aggacggcaa gttcagccgc gacaagctca agattagcaa    6480
caaggattgg ttcgatttca ttcagaacaa gcggtacctg aagcggccag cggcgactaa    6540
gaaggcgggc caggcaaaga agaagaagtg agtcgaccga tcgttcaaac atttggcaat    6600
aaagtttctt aagattgaat cctgttgccg gtcttgcgat gattatcata taatttctgt    6660
tgaattacgt taagcatgta ataattaaca tgtaatgcat gacgttattt atgagatggg    6720
tttttatgat tagagtcccg caattataca tttaatacgc gatagaaaac aaaatatagc    6780
gcgcaaacta ggataaatta tcgcgcgcgg tgtcatctat gttactagat cgatcccggg    6840
agagaccggg atatcgcggc cgcgtcgttc ggctgcggcg agcggtatca gctcactcaa    6900
aggcggtaat acggttatcc acagaatcag gggataacgc aggaaagaac atgtgagcaa    6960
aaggccagca aaaggccagg aaccgtaaaa aggccgcgtt gctggcgttt ttccataggc    7020
tccgcccccc tgacgagcat cacaaaaatc gacgctcaag tcagaggtgg cgaaacccga    7080
caggactata aagataccag gcgtttcccc ctggaagctc cctcgtgcgc tctcctgttc    7140
cgaccctgcc gcttaccgga tacctgtccg cctttctccc ttcgggaagc gtggcgcttt    7200
ctcatagctc acgctgtagg tatctcagtt cggtgtaggt cgttcgctcc aagctgggct    7260
gtgtgcacga accccccgtt cagcccgacc gctgcgcctt atccggtaac tatcgtcttg    7320
agtccaaccc ggtaagacac gacttatcgc cactggcagc agccactggt aacaggatta    7380
gcagagcgag gtatgtaggc ggtgctacag agttcttgaa gtggtggcct aactacggct    7440
acactagaag gacagtattt ggtatctgcg ctctgctgaa gccagttacc ttcggaaaaa    7500
gagttggtag ctcttgatcc ggcaaacaaa ccaccgctgg tagcggtggt ttttttgttt    7560
gcaagcagca gattacgcgc agaaaaaaag gatctcaaga agatcctttg atcttttcta    7620
cggggtctga cgctcagtgg aacgaaaact cacgttaagg gattttggtc atgagattat    7680
caaaaaggat cttcacctag atccttttaa attaaaaatg aagttttaaa tcaatctaaa    7740
gtatatatga gtaaacttgg tctgacagtt accaatgctt aatcagtgag gcacctatct    7800
cagcgatctg tctatttcgt tcatccatag ttgcctgact ccccgtcgtg tagataacta    7860
cgatacggga gggcttacca tctggcccca gtgctgcaat gataccgcga gaaccacgct    7920
caccggctcc agatttatca gcaataaacc agccagccgg aagggccgag cgcagaagtg    7980
gtcctgcaac tttatccgcc tccatccagt ctattaattg ttgccgggaa gctagagtaa    8040
gtagttcgcc agttaatagt ttgcgcaacg ttgttgccat tgctacaggc atcgtggtgt    8100
cacgctcgtc gtttggtatg gcttcattca gctccggttc ccaacgatca aggcgagtta    8160
catgatcccc catgttgtgc aaaaaagcgg ttagctcctt cggtcctccg atcgttgtca    8220
gaagtaagtt ggccgcagtg ttatcactca tggttatggc agcactgcat aattctctta    8280
ctgtcatgcc atccgtaaga tgcttttctg tgactggtga gtactcaacc aagtcattct    8340
gagaatagtg tatgcggcga ccgagttgct cttgcccggc gtcaatacgg gataataccg    8400
```

```
cgccacatag cagaacttta aaagtgctca tcattggaaa acgttcttcg gggcgaaaac   8460
tctcaaggat cttaccgctg ttgagatcca gttcgatgta acccactcgt gcacccaact   8520
gatcttcagc atctttttact ttcaccagcg tttctgggtg agcaaaaaca ggaaggcaaa   8580
atgccgcaaa aaagggaata agggcgacac ggaaatgttg aatactcata ctcttccttt   8640
ttcaatatta ttgaagcatt tatcagggtt attgtctcat gagcggatac atatttgaat   8700
gtatttagaa aaataaacaa ataggggttc cgcgcacatt tccccgaaaa gtgccacctg   8760
acgcgccctg tagcggcacg tctaattcgg gggatctgga tttttagtact ggattttggt   8820 tttaggaatt agaaatttta ttgatagaag tattttacaa atacaaatac atactaaggg   8880
tttcttatat gctcaacaca tgagcgaaac cctataggaa ccctaattcc cttatctggg   8940
aactactcac acattattat ggagaaactc gagcttgtcg atcgacatga tcagggagct   9000
ctagattatt tgtatagttc atccatgcca tgtgtaatcc cagcagctgt tacaaactca   9060
agaaggacca tgtggtctct cttttcgttg ggatctttcg aaagggcaga ttgtgtggac   9120
aggtaatggt tgtctggtaa aaggacaggg ccatcgccaa ttggagtatt ttgttgataa   9180
tggtctgcta gttgaacgct tccatcttca atgttgtgtc taattttgaa gttaactttg   9240
gttccattct tttgtttgtc tgccatgatg tatacgttgt gggagttgta gttgtattcc   9300
aacttgtggc cgaggatgtt tccgtcctcc ttgaaatcga ttcccttaag ctcgatcctg   9360
ttgacgaggg tgtctccctc aaacttgact tcagcacgtg tcttgtagtt cccgtcgtcc   9420
ttgaagaaga tggtcctctc ctgcacgtat ccctcaggca tggcgctctt gaagaagtcg   9480
tgccgcttca tatgatctgg gtatcttgaa aagcattgta caccataaca gaaagtagtg   9540
acaagtgttg gccaaggaac aggtagtttt ccagtagtgc aaataaattt aagggtaagt   9600
tttccgtatg ttgcatcacc ttcaccctct ccactgacag aaaatttgtg cccattaaca   9660
tcaccatcta attcaacaag aattgggaca actccagtga aaagttcttc tcctttaccc   9720
ataaaaaagg tggcgggatc gcgccctatc gttcgtaaat ggtgaaaatt ttcagaaaat   9780
tgcttttgct ttaaaagaaa tgatttaaat tgctgcaata gaagtagaat gcttgattgc   9840
ttgagattcg tttgttttgt atatgttgtg ttgagaggat cctcaagctt cgacctgcag   9900
aagtaacacc aaacaacagg gtgagcatcg acaaaagaaa cagtaccaag caaataaata   9960
gcgtatgaag gcagggctaa aaaaatccac atatagctgc tgcatatgcc atcatccaag   10020
tatatcaaga tcaaaataat tataaaacat acttgtttat tataatagat aggtactcaa   10080
ggttagagca tatgaataga tgctgcatat gccatcatgt atatgcatca gtaaaaccca   10140
catcaacatg tatacctatc ctagatcgat atttccatcc atcttaaact cgtaactatg   10200
aagatgtatg acacacacat acagttccaa aattaataaa tacaccaggt agtttgaaac   10260
agtattctac tccgatctag aacgaatgaa cgaccgccca accacaccac atcatcacaa   10320
ccaagcgaac aaaagcatct ctgtatatgc atcagtaaaa cccgcatcaa catgtatacc   10380
tatcctagat cgatatttcc atccatcatc ttcaattcgt aactatgaat atgtatggca   10440
cacacataca gatccaaaat taataaatcc accaggtagt ttgaaacaga attctactcc   10500
gatctagaac gaccgcccaa ccagaccaca tcatcacaac caagacaaaa aaaagcatga   10560
aaagatgacc cgacaaacaa gtgcacggca tatattgaaa taaaggaaaa gggcaaacca   10620
aaccctatgc aacgaaacaa aaaaaatcat gaaatcgatc ccgtctgcgg aacggctaga   10680
gccatcccag gattccccaa agagaaacac tggcaagtta gcaatcagaa cgtgtctgac   10740
```

-continued

```
gtacaggtcg catccgtgta cgaacgctag cagcacggat ctaacacaaa cacggatcta   10800
acacaaacat gaacagaagt agaactaccg ggccctaacc atggaccgga acgccgatct   10860
agagaaggta gagaggggg gggaggacga gcggcgtacc ttgaagcgga ggtgccgacg    10920
ggtggatttg ggggagatcc actagttcta gagcggccgc caccgcggtg gaattctcga   10980
ggtcctctcc aaatgaaatg aacttcctta tatagaggaa gggtcttgcg aaggatagtg   11040
ggattgtgcg tcatcccta cgtcagtgga gatatcacat caatccactt gctttgaaga    11100
cgtggttgga acgtcttctt tttccacgat gctcctcgtg ggtgggggtc catctttggg   11160
accactgtcg gcagaggcat cttgaacgat agcctttcct ttatcgcaat gatggcattt   11220
gtaggtgcca ccttcctttt ctactgtcct tttgatcaag tgaccgatag ctgggcaatg   11280
gaatccgagg aggtttcccg atattaccct ttgttgaaaa gtctcaatag ccctttggtc   11340
ttctgagact gtatctttga tattcttgga gtagacgaga gtgtcgtgct ccaccatgtt   11400
atcacatcaa ttcacttgct ttgaagacgt ggttggaacg tcttcttttt ccacgatgct   11460
cctcgtgggt gggggtccat ctttgggacc actgtcggca gaggcatctt gaacgatagc   11520 cttttccttta tcgcaatgat ggca                                        11544

<210> SEQ ID NO 53
<211> LENGTH: 3852
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
ctgacgcgcc ctgtagcggc ctgcagtgca gcgtgacccg gtcgtgcccc tctctagaga     60
taatgagcat tgcatgtcta agttataaaa aattaccaca tatttttttt gtcacacttg    120
tttgaagtgc agtttatcta tctttataca tatatttaaa ctttactcta cgaataatat    180
aatctatagt actacaataa tatcagtgtt ttagagaatc atataaatga acagttagac    240
atggtctaaa ggacaattga gtattttgac aacaggactc tacagtttta tcttttttagt    300 gtgcatgtgt tctccttttt ttttgcaaat agcttcacct atataatact tcatccattt    360
tattagtaca tccatttagg gtttagggtt aatggttttt atagactaat ttttttagta    420 catctattt attctatttt agcctctaaa ttaagaaaac taaaactcta ttttagtttt    480
tttatttaat aatttagata taaaatagaa taaaataaag tgactaaaaa ttaaacaaat    540
accctttaag aaaattaaaaa aactaaggaa acatttttct tgtttcgagt agataatgcc   600
agcctgttaa acgccgtcga tcgacgagtc taacggacac caaccagcga accagcagcg    660
tcgcgtcggg ccaagcgaag cagacggcac ggcatctctg tcgctgcctc tggacccctc    720
tcgagagttc cgctccaccg ttggacttgc tccgctgtcg gcatccagaa attgcgtggc    780
ggagcggcag acgtgagccg gcacggcagg cggcctcctc ctcctctcac ggcaccggca    840
gctacggggg attcctttcc caccgctcct tcgctttccc ttcctcgccc gccgtaataa    900
atagacaccc cctccacacc ctctttcccc aacctcgtgt tgttcggagc gcacacacac    960
acaaccagat ctcccccaaa tccacccgtc ggcacctccg cttcaaggta cgccgctcgt   1020
cctccccccc ccccctctc taccttctct agatcggcgt tccggtccat ggttagggcc   1080
cggtagttct acttctgttc atgtttgtgt tagatccgtg tttgtgttag atccgtgctg   1140
ctagcgttcg tacacggatg cgacctgtac gtcagacacg ttctgattgc taacttgcca   1200
```

-continued

```
gtgtttctct ttggggaatc ctgggatggc tctagccgtt ccgcagacgg gatcgatcta      1260
ggataggtat acatgttgat gtgggtttta ctgatgcata tacatgatgg catatgcagc      1320
atctattcat atgctctaac cttgagtacc tatctattat aataaacaag tatgttttat      1380
aattattttg atcttgatat acttggatga tggcatatgc agcagctata tgtggatttt      1440
tttagccctg ccttcatacg ctatttattt gcttggtact gtttcttttg tcgatgctca      1500
ccctgttgtt tggtgttact tctgcaggga tccaaattac tgatgagtcc gtgaggacga      1560
aacgagtaag ctcgtcgtca aaagaccttt ttaatttcta ctcttgtaga tctcgtcacg      1620
attcccctct ccggccggca tggtcccagc ctcctcgctg gcgccggctg ggcaacatgc      1680
ttcggcatgg cgaatgggac cgatcgttca aacatttggc aataaagttt cttaagattg      1740
aatcctgttg ccggtcttgc gatgattatc atataatttc tgttgaatta cgttaagcat      1800
gtaataatta acatgtaatg catgacgtta tttatgagat gggtttttat gattagagtc      1860
ccgcaattat acatttaata cgcgatagaa aacaaaatat agcgcgcaaa ctaggataaa      1920
ttatcgcgcg cggtgtcatc tatgttacta gatcgatcgt cgttcggctg cggcgagcgg      1980
tatcagctca ctcaaaggcg gtaatacggt tatccacaga atcaggggat aacgcaggaa      2040
agaacatgtg agcaaaaggc cagcaaaagg ccaggaaccg taaaaaggcc gcgttgctgg      2100 cgttttttcca taggctccgc cccccctgacg agcatcacaa aaatcgacgc tcaagtcaga      2160
ggtggcgaaa cccgacagga ctataaagat accaggcgtt ccccctggaa gctccctcg      2220 tgcgctctcc tgttccgacc ctgccgctta ccggatacct gtccgccttt ctcccttcgg      2280
gaagcgtggc gctttctcat agctcacgct gtaggtatct cagttcggtg taggtcgttc      2340
gctccaagct gggctgtgtg cacgaacccc ccgttcagcc cgaccgctgc gccttatccg      2400
gtaactatcg tcttgagtcc aacccggtaa gacacgactt atcgccactg gcagcagcca      2460
ctggtaacag gattagcaga gcgaggtatg taggcggtgc tacagagttc ttgaagtggt      2520
ggcctaacta cggctacact agaagaacag tatttggtat ctgcgctctg ctgaagccag      2580
ttaccttcgg aaaaagagtt ggtagctctt gatccggcaa acaaaccacc gctggtagcg      2640
gtggtttttt tgtttgcaag cagcagatta cgcgcagaaa aaaaggatct caagaagatc      2700
ctttgatctt ttctacgggg tctgacgctc agtggaacga aaactcacgt taagggattt      2760
tggtcatgag attatcaaaa aggatcttca cctagatcct tttaaattaa aaatgaagtt      2820
ttaaatcaat ctaaagtata tatgagtaaa cttggtctga cagttaccaa tgcttaatca      2880
gtgaggcacc tatctcagcg atctgtctat ttcgttcatc catagttgcc tgactccccg      2940
tcgtgtagat aactacgata cgggagggct taccatctgg ccccagtgct gcaatgatac      3000
cgcgagaccc acgctcaccg gctccagatt tatcagcaat aaaccagcca gccggaaggg      3060
ccgagcgcag aagtggtcct gcaactttat ccgcctccat ccagtctatt aattgttgcc      3120
gggaagctag agtaagtagt tcgccagtta atagtttgcg caacgttgtt gccattgcta      3180
caggcatcgt ggtgtcacgc tcgtcgtttg gtatggcttc attcagctcc ggttcccaac      3240
gatcaaggcg agttacatga tcccccatgt tgtgcaaaaa agcggttagc tccttcggtc      3300
ctccgatcgt tgtcagaagt aagttggccg cagtgttatc actcatggtt atggcagcac      3360
tgcataattc tcttactgtc atgccatccg taagatgctt ttctgtgact ggtgagtact      3420
caaccaagtc attctgagaa tagtgtatgc ggcgaccgag ttgctcttgc ccggcgtcaa      3480
tacgggataa taccgcgcca catagcagaa ctttaaaagt gctcatcatt ggaaaacgtt      3540
cttcggggcg aaaactctca aggatcttac cgctgttgag atccagttcg atgtaaccca      3600
```

-continued

```
ctcgtgcacc caactgatct tcagcatctt ttactttcac cagcgtttct gggtgagcaa      3660
aaacaggaag gcaaatgcc gcaaaaagg gaataagggc gacacggaaa tgttgaatac       3720
tcatactctt cctttttcaa tattattgaa gcatttatca gggttattgt ctcatgagcg      3780
gatacatatt tgaatgtatt tagaaaaata aacaaatagg ggttccgcgc acatttcccc      3840
gaaaagtgcc ac                                                          3852
```

```
<210> SEQ ID NO 54
<211> LENGTH: 10427
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
```

```
actgctgcag tgcagcgtga cccggtcgtg cccctctcta gagataatga gcattgcatg        60
tctaagttat aaaaaattac cacatatttt ttttgtcaca cttgtttgaa gtgcagttta       120
tctatcttta tacatatatt taaactttac tctacgaata atataatcta tagtactaca       180
ataatatcag tgttttagag aatcatataa atgaacagtt agacatggtc taaaggacaa       240
ttgagtattt tgacaacagg actctacagt tttatctttt tagtgtgcat gtgttctcct       300
ttttttttgc aaatagcttc acctatataa tacttcatcc attttattag tacatccatt       360
tagggtttag ggttaatggt ttttatagac taatttttt agtacatcta ttttattcta       420
ttttagcctc taaattaaga aaactaaaac tctattttag ttttttttatt taataattta      480 gatataaaat agaataaaat aaagtgacta aaaattaaac aaataccctt taagaaatta       540
aaaaaactaa ggaaacattt ttcttgtttc gagtagataa tgccagcctg ttaaacgccg       600
tcgatcgacg agtctaacgg acaccaacca gcgaaccagc agcgtcgcgt cgggccaagc       660
gaagcagacg gcacggcatc tctgtcgctg cctctggacc cctctcgaga gttccgctcc       720
accgttggac ttgctccgct gtcggcatcc agaaattgcg tggcggagcg gcagacgtga       780
gccggcacgg caggcggcct cctcctcctc tcacggcacc ggcagctacg ggggattcct       840
ttcccaccgc tccttcgctt tcccttcctc gcccgccgta ataaatagac accccctcca       900
caccctcttt ccccaacctc gtgttgttcg gagcgcacac acacacaacc agatctcccc       960
caaatccacc cgtcggcacc tccgcttcaa ggtacgccgc tcgtcctccc cccccccccc      1020
tctctacctt ctctagatcg gcgttccggt ccatggttag ggcccggtag ttctacttct      1080
gttcatgttt gtgttagatc cgtgtttgtg ttagatccgt gctgctagcg ttcgtacacg      1140
gatgcgacct gtacgtcaga cacgttctga ttgctaactt gccagtgttt ctctttgggg      1200
aatcctggga tggctctagc cgttccgcag acgggatcga tctaggatag gtatacatgt      1260
tgatgtgggt tttactgatg catatacatg atggcatatg cagcatctat tcatatgctc      1320
taaccttgag tacctatcta ttataataaa caagtatgtt ttataattat tttgatcttg      1380
atatacttgg atgatggcat atgcagcagc tatatgtgga tttttttagc cctgccttca      1440
tacgctattt atttgcttgg tactgtttct tttgtcgatg ctcaccctgt tgtttggtgt      1500
tacttctgca ggtcgaagct tgaagcaaac atggcatcta gcatggcacc aaagaaaaaa      1560
aggaaagttt ccaaacttga aaaatttaca aactgctact ccctttccaa gacgcttagg      1620
tttaaagcga tccccgttgg caagacccaa gagaatatcg ataacaaaag acttctggtc      1680
gaagatgaaa aaagggccga agactacaag ggggtcaaga agttgctcga tcgctattat      1740
```

-continued

```
ctttccttta tcaacgatgt gcttcattca atcaaactga agaacttgaa taactacatt       1800
agccttttca gaaagaaaac gaggactgaa aaggagaaca aggaacttga gaatcttgaa       1860
ataaaccttc gcaaagaaat tgcaaaagcc ttcaagggga acgaaggata taaatctctt       1920
ttcaaaaaag acattataga aacaattttg cctgagtttc ttgacgacaa ggatgaaatt       1980
gcgctcgtca atagctttaa cggatttaca actgccttca cagggttctt cgacaatagg       2040
gagaatatgt ttagcgagga ggcaaaaagc acatccatcg cattcagatg catcaatgaa       2100
aatcttaccc ggtacatatc gaatatggac atatttgaaa aagtggatgc aatattcgat       2160
aagcacgaag tccaggagat aaaggaaaag atactgaata gcgactatga tgtcgaagat       2220
tttttcgaag gtgagttctt caactttgtc ctgactcaag aaggcattga tgtctataat       2280
gcaataattg gaggttttgt gactgagtct ggcgagaaga taaagggctt gaacgagtat       2340
atcaatctct acaaccagaa gactaagcaa aagttgccta aatttaaacc gctttacaag       2400
caagttttga gcgaccggga aagccttttcc ttttacggtg aaggatacac gagcgatgaa       2460
gaagtcctcg aagtcttccg caacacactc aacaagaact cagaaatctt ttcctcaatt       2520
aaaaaattgg agaagctttt caagaacttc gatgaatact cttcggcggg gattttttgtg      2580 aagaacggcc cggcaattc cacaatatct aaagacattt tcggagaatg gaacgtgata       2640
agagacaagt ggaatgcgga gtatgatgac atacacctga agaagaaggc agttgtgact       2700
gaaaaatacg aagatgacag gagaaaaagc tttaaaaaga tcgggtcctt ttcactggaa       2760
cagctgcagg agtatgccga cgccgatctt tcggttgtcg aaaagctcaa agaaataatt       2820
atccagaagg tcgatgaaat ctacaaggtg tacggctcaa gcgagaagct ctttgatgct       2880
gacttcgtgt tggagaagtc tcttaaaaaa aacgacgcag tcgtcgcgat aatgaaagat       2940
ttgctggatt cagtgaaatc cttcgagaat tatatcaaag ccttcttcgg cgaggggaag       3000
gagacaaaca gggatgagtc cttctatgga gacttcgttc tggcttacga catccttctt       3060
aaggtcgacc acatctatga cgcaattcgg aactatgtga cgcagaagcc gtattcgaaa       3120
gataagttca agctctattt ccaaaaccct caatttatgg gtgggtggga taaagacaaa       3180
gagaccgatt accgggcaac aattttgcgg tacgggtcta atattacct cgctataatg       3240 gataagaaat acgctaaatg tctccagaaa attgacaaag atgacgtcaa cggcaattat       3300
gaaaaaatca attataaact ccttcctggc ccaaataaaa tgctcccgaa ggtgtttttt       3360
tccaaaaagt ggatggccta ttataatcca tcagaggata ttcagaaaat ctataaaaat       3420 gggacccttta agaagggtga catgtttaac ctgaacgatt gccacaagct tatagatttt       3480
ttcaaagact ctattagccg ctatcccaaa tggtctaatg cttatgattt caacttctct       3540
gaaactgaaa agtacaaaga tattgcagga ttctaccgcg aagttgaaga acaaggttat       3600
aaggtttcct ttgagtctgc gtccaagaaa gaggtcgata agttggtcga agaagggaaa       3660
ttgtatatgt ttcaaatta caataaagac ttttccgaca agtcccatgg tacacctaat       3720
ctgcatacca tgtacttcaa actgctgttc gatgagaata atcacggtca gattcgcctg       3780
agcggagggg cggaactctt catgaggaga gcatcgttga aaaagaggga gctcgtcgtg       3840
catccggcta acagccccat tgctaacaag aatccggata atccaaagaa gactactacc       3900
ctctcctatg acgtctataa ggataagaga ttctctgagg accagtacga gttgcacatc       3960
cctattgcga taaataaatg ccctaagaac atctttaaaa tcaatactga ggtcagagtc       4020
ctgcttaagc acgacgacaa cccgtatgtg atcgggattg ataggggtga aaggaacttg       4080
```

-continued

```
ctttatattg tggttgtcga tggaaaaggt aatatagtgg aacaatactc tctgaatgaa    4140
attatcaaca acttcaatgg cattaggatc aagaccgact atcattctct gttggacaag    4200
aaagagaaag agcgcttcga ggcacggcaa aactggacgt ctattgagaa catcaaggag    4260
cttaaggctg gttacatttc tcaggttgtg cacaaaattt gcgaactggt cgagaaatat    4320
gatgccgtta tcgcacttga agatctcaac agcggattta agaattctcg ggtgaaagtc    4380
gaaaaacagg tgtatcaaaa attcgaaaag atgctgatcg acaagctcaa ttatatggtt    4440
gataaaaaga gcaacccatg cgccacgggg ggtgcgctta agggctatca gattacgaac    4500
aaatttgaat ccttcaagtc aatgtcgacg caaaatgggt ttatattcta tataccggcg    4560
tggcttacat ctaaaataga tcctagcact gggttcgtga acctgctgaa aaccaagtac    4620
acttcaatcg cagattctaa aaaatttata agcagcttcg acagaatcat gtatgtgccc    4680
gaggaagacc tcttcgagtt tgcccttgat tacaaaaatt tctcaagaac ggatgcagac    4740
tacataaaga agtggaagct gtactcttat gggaaccgga ttcggatatt cagaaatccg    4800
aaaaaaaaca atgtctttga ttgggaggaa gtttgtctta cctctgctta caaagagctg    4860
ttcaataaat atggcattaa ttaccagcaa ggtgatatcc gggcgctcct ttgcgaacag    4920
tctgacaaag ctttctattc ttcatttatg gcgctcatgt cattgatgct gcagatgagg    4980
aatagcatta cggggaggac tgatgttgac tttctgatct cgcccgtgaa aaattctgat    5040
ggaatcttct acgattccag gaattatgag gcccaggaaa atgctatcct tcccaagaac    5100
gcagacgcaa atggcgcgta caatatagct cgcaaggttt tgtgggctat aggccaattc    5160
aagaaagccg aagacgaaaa gctggacaaa gttaagattg ctatatctaa caaagagtgg    5220
cttgagtatg cgcaaacatc tgttaaacac aaacgccccg cggctacaaa gaaggctggc    5280
caggcaaaga agaagaagtg agtcgaccga tcgttcaaac atttggcaat aaagtttctt    5340
aagattgaat cctgttgccg gtcttgcgat gattatcata taatttctgt tgaattacgt    5400
taagcatgta ataattaaca tgtaatgcat gacgttattt atgagatggg ttttttatgat   5460 tagagtcccg caattataca tttaatacgc gatagaaaac aaaatatagc gcgcaaacta    5520
ggataaatta tcgcgcgcgg tgtcatctat gttactagat cgatcccggg atatcgcggc    5580
cgcgtcgttc ggctgcggcg agcggtatca gctcactcaa aggcggtaat acggttatcc    5640
acagaatcag gggataacgc aggaaagaac atgtgagcaa aaggccagca aaaggccagg    5700
aaccgtaaaa aggccgcgtt gctggcgttt ttccataggc tccgcccccc tgacgagcat    5760
cacaaaaatc gacgctcaag tcagaggtgg cgaaacccga caggactata aagataccag    5820
gcgtttcccc ctggaagctc cctcgtgcgc tctcctgttc cgaccctgcc gcttaccgga    5880
tacctgtccg cctttctccc ttcgggaagc gtggcgcttt ctcatagctc acgctgtagg    5940
tatctcagtt cggtgtaggt cgttcgctcc aagctgggct gtgtgcacga accccccgtt    6000
cagcccgacc gctgcgcctt atccggtaac tatcgtcttg agtccaaccc ggtaagacac    6060
gacttatcgc cactggcagc agccactggt aacaggatta gcagagcgag gtatgtaggc    6120
ggtgctacag agttcttgaa gtggtggcct aactacggct acactagaag gacagtattt    6180
ggtatctgcg ctctgctgaa gccagttacc ttcggaaaaa gagttggtag ctcttgatcc    6240
ggcaaacaaa ccaccgctgg tagcggtggt ttttttgttt gcaagcagca gattacgcgc    6300
agaaaaaaag gatctcaaga agatcctttg atcttttcta cggggtctga cgctcagtgg    6360
aacgaaaact cacgttaagg gattttggtc atgagattat caaaaaggat cttcacctag    6420
atccttttaa attaaaaatg aagttttaaa tcaatctaaa gtatatatga gtaaacttgg    6480
```

```
tctgacagtt accaatgctt aatcagtgag gcacctatct cagcgatctg tctatttcgt   6540
tcatccatag ttgcctgact ccccgtcgtg tagataacta cgatacggga gggcttacca   6600
tctggcccca gtgctgcaat gataccgcga gacccacgct caccggctcc agatttatca   6660
gcaataaacc agccagccgg aagggccgag cgcagaagtg gtcctgcaac tttatccgcc   6720
tccatccagt ctattaattg ttgccgggaa gctagagtaa gtagttcgcc agttaatagt   6780
ttgcgcaacg ttgttgccat tgctacaggc atcgtggtgt cacgctcgtc gtttggtatg   6840
gcttcattca gctccggttc ccaacgatca aggcgagtta catgatcccc catgttgtgc   6900
aaaaaagcgg ttagctcctt cggtcctccg atcgttgtca gaagtaagtt ggccgcagtg   6960
ttatcactca tggttatggc agcactgcat aattctctta ctgtcatgcc atccgtaaga   7020
tgcttttctg tgactggtga gtactcaacc aagtcattct gagaatagtg tatgcggcga   7080
ccgagttgct cttgcccggc gtcaatacgg gataataccg cgccacatag cagaacttta   7140
aaagtgctca tcattggaaa acgttcttcg gggcgaaaac tctcaaggat cttaccgctg   7200
ttgagatcca gttcgatgta acccactcgt gcacccaact gatcttcagc atcttttact   7260
ttcaccagcg tttctgggtg agcaaaaaca ggaaggcaaa atgccgcaaa aaagggaata   7320
agggcgacac ggaaatgttg aatactcata ctcttccttt ttcaatatta ttgaagcatt   7380
tatcagggtt attgtctcat gagcggatac atatttgaat gtatttagaa aaataaacaa   7440
ataggggttc cgcgcacatt tccccgaaaa gtgccacctg acgcgccctg tagcggcacg   7500
tctaattcgg gggatctgga ttttagtact ggattttggt tttaggaatt agaaatttta   7560
ttgatagaag tattttacaa atacaaatac atactaaggg tttcttatat gctcaacaca   7620
tgagcgaaac cctataggaa ccctaattcc cttatctggg aactactcac acattattat   7680
ggagaaactc gagcttgtcg atcgacatga tcagggagct ctcaggtacc tctagacttg   7740
tacagctcgt ccatgccgta caggaacagg tggtggcggc cctcggagcg ctcgtactgt   7800
tccacgatgg tgtagtcctc gttgtgggag gtgatgtcca gcttggtgtc cacgtagtag   7860
tagccgggca gttgcacggg cttcttggcc atgtagatgg tcttgaactc caccaggtag   7920
tggccgccgt ccttcagctt cagggcctgg tggatctcgc ccttcagcac gccgtcgcgg   7980
gggtacaggc gctcggtgga ggcctcccag cccatggtct tcttctgcat tacggggccg   8040
tcggggggga agttggtgcc gcgcatcttc accttgtaga tcagcgtgcc gtcctgcagg   8100
gaggagtcct gggtcacggt caccagaccg ccgtcctcga agttcatcac gcgctcccac   8160
ttgaagccct cggggaagga cagcttcttg taatcgggga tgtcggcggg gtgcttcacg   8220
tacgccttgg agccgtacat gaactggggg gacaggatgt cccaggcgaa gggcaggggg   8280
ccgcccttgg tcaccttcag cttggcggtc tgggtgccct cgtaggggcg ccctcgccc   8340 tcgccctcga tctcgaactc gtggccgttc atggagccct ccatgcgcac cttgaagcgc   8400
atgaactctt tgatgacctc ctcgcccttg ctcaccatgg tggcgggatc gcgccctatc   8460
gttcgtaaat ggtgaaaatt ttcagaaaat tgcttttgct ttaaaagaaa tgatttaaat   8520
tgctgcaata gaagtagaat gcttgattgc ttgagattcg tttgtttttgt atatgttgtg   8580 ttgagaggat cctctagagt cgacctgcag aagtaacacc aaacaacagg gtgagcatcg   8640
acaaaagaaa cagtaccaag caaataaata gcgtatgaag gcagggctaa aaaaatccac   8700
atatagctgc tgcatatgcc atcatccaag tatatcaaga tcaaaataat tataaaacat   8760
acttgtttat tataatagat aggtactcaa ggttagagca tatgaataga tgctgcatat   8820
```

-continued

```
gccatcatgt atatgcatca gtaaaaccca catcaacatg tataccatc ctagatcgat    8880 atttccatcc atcttaaact cgtaactatg aagatgtatg acacacacat acagttccaa    8940
aattaataaa tacaccaggt agtttgaaac agtattctac tccgatctag aacgaatgaa    9000
cgaccgccca accacaccac atcatcacaa ccaagcgaac aaaagcatct ctgtatatgc    9060
atcagtaaaa cccgcatcaa catgtatacc tatcctagat cgatatttcc atccatcatc    9120
ttcaattcgt aactatgaat atgtatggca cacacataca gatccaaaat taataaatcc    9180
accaggtagt ttgaaacaga attctactcc gatctagaac gaccgcccaa ccagaccaca    9240
tcatcacaac caagacaaaa aaaagcatga aaagatgacc cgacaaacaa gtgcacggca    9300
tatattgaaa taaaggaaaa gggcaaacca aaccctatgc aacgaaacaa aaaaaatcat    9360
gaaatcgatc ccgtctgcgg aacggctaga gccatcccag gattccccaa agagaaacac    9420
tggcaagtta gcaatcagaa cgtgtctgac gtacaggtcg catccgtgta cgaacgctag    9480
cagcacggat ctaacacaaa cacggatcta acacaaacat gaacagaagt agaactaccg    9540
ggccctaacc atggaccgga acgccgatct agagaaggta gagagggggg gggaggacga    9600
gcggcgtacc ttgaagcgga ggtgccgacg ggtggatttg ggggagatcc actagttcta    9660
gagcggccgc caccgcggtg gaattctcga ggtcctctcc aaatgaaatg aacttcctta    9720
tatagaggaa gggtcttgcg aaggatagtg ggattgtgcg tcatcccta cgtcagtgga    9780 gatatcacat caatccactt gctttgaaga cgtggttgga acgtcttctt tttccacgat    9840
gctcctcgtg ggtgggggtc catctttggg accactgtcg gcagaggcat cttgaacgat    9900
agcctttcct ttatcgcaat gatggcattt gtaggtgcca ccttcctttt ctactgtcct    9960
tttgatcaag tgaccgatag ctgggcaatg gaatccgagg aggtttcccg atattaccct   10020
ttgttgaaaa gtctcaatag ccctttggtc ttctgagact gtatctttga tattcttgga   10080
gtagacgaga gtgtcgtgct ccaccatgtt atcacatcaa ttcacttgct ttgaagacgt   10140
ggttggaacg tcttcttttt ccacgatgct cctcgtgggt gggggtccat ctttgggacc   10200
actgtcggca gaggcatctt gaacgatagc ctttccttta tcgcaatgat ggcatttgta   10260
ggtgccacct tccttttcta ctgtcctttt gatcaagtga cagatagctg ggcaatggaa   10320
tccgaggagg tttcccgata ttaccctttg ttgaaaagtc tcaatagccc tttggtcttc   10380
tgagacttgc aggcaagcaa gcatgaatgc ctgggcgcgc cgatatc                 10427
```

<210> SEQ ID NO 55
<211> LENGTH: 11516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55

```
gggatatcgc ggccgcgtcg ttcggctgcg gcgagcggta tcagctcact caaaggcggt     60
aatacggtta tccacagaat caggggataa cgcaggaaag aacatgtgag caaaaggcca    120
gcaaaaggcc aggaaccgta aaaaggccgc gttgctggcg tttttccata ggctccgccc    180
ccctgacgag catcacaaaa atcgacgctc aagtcagagg tggcgaaacc cgacaggact    240
ataaagatac caggcgtttc ccctggaag ctccctcgtg cgctctcctg ttccgaccct    300
gccgcttacc ggatacctgt ccgcctttct cccttcggga gcgtggcgc tttctcatag    360 ctcacgctgt aggtatctca gttcggtgta ggtcgttcgc tccaagctgg gctgtgtgca    420
```

-continued

```
cgaacccccc gttcagcccg accgctgcgc cttatccggt aactatcgtc ttgagtccaa    480
cccggtaaga cacgacttat cgccactggc agcagccact ggtaacagga ttagcagagc    540
gaggtatgta ggcggtgcta cagagttctt gaagtggtgg cctaactacg gctacactag    600
aaggacagta tttggtatct gcgctctgct gaagccagtt accttcggaa aaagagttgg    660
tagctcttga tccggcaaac aaaccaccgc tggtagcggt ggttttttg tttgcaagca     720 gcagattacg cgcagaaaaa aaggatctca agaagatcct ttgatctttt ctacggggtc    780
tgacgctcag tggaacgaaa actcacgtta agggatttg gtcatgagat tatcaaaaag     840
gatcttcacc tagatccttt taaattaaaa atgaagtttt aaatcaatct aaagtatata    900
tgagtaaact tggtctgaca gttaccaatg cttaatcagt gaggcaccta tctcagcgat    960
ctgtctattt cgttcatcca tagttgcctg actccccgtc gtgtagataa ctacgatacg   1020
ggagggctta ccatctggcc ccagtgctgc aatgataccg cgagacccac gctcaccggc   1080
tccagattta tcagcaataa accagccagc cggaagggcc gagcgcagaa gtggtcctgc   1140
aactttatcc gcctccatcc agtctattaa ttgttgccgg gaagctagag taagtagttc   1200
gccagttaat agtttgcgca acgttgttgc cattgctaca ggcatcgtgg tgtcacgctc   1260
gtcgtttggt atggcttcat tcagctccgg ttcccaacga tcaaggcgag ttacatgatc   1320
ccccatgttg tgcaaaaaag cggttagctc cttcggtcct ccgatcgttg tcagaagtaa   1380
gttggccgca gtgttatcac tcatggttat ggcagcactg cataattctc ttactgtcat   1440
gccatccgta agatgctttt ctgtgactgg tgagtactca accaagtcat tctgagaata   1500
gtgtatgcgg cgaccgagtt gctcttgccc ggcgtcaata cgggataata ccgcgccaca   1560
tagcagaact ttaaaagtgc tcatcattgg aaaacgttct tcggggcgaa aactctcaag   1620
gatcttaccg ctgttgagat ccagttcgat gtaacccact cgtgcaccca actgatcttc   1680
agcatctttt actttcacca gcgtttctgg gtgagcaaaa acaggaaggc aaaatgccgc   1740
aaaaaaggga ataagggcga cacggaaatg ttgaatactc atactcttcc ttttcaata    1800 ttattgaagc atttatcagg gttattgtct catgagcgga tacatatttg aatgtattta   1860
gaaaaataaa caaataggggg ttccgcgcac atttccccga aaagtgccac ctgacgcgcc   1920
ctgtagcggc acgtctaatt cgggggatct ggattttagt actggatttt ggttttagga   1980
attagaaatt ttattgatag aagtatttta caaatacaaa tacatactaa gggtttctta   2040
tatgctcaac acatgagcga aaccctatag gaaccctaat tcccttatct gggaactact   2100
cacacattat tatggagaaa ctcgagcttg tcgatcgaca tgatcaggga gctctcaggt   2160
acctctagac ttgtacagct cgtccatgcc gtacaggaac aggtggtggc ggccctcgga   2220
gcgctcgtac tgttccacga tggtgtagtc ctcgttgtgg gaggtgatgt ccagcttggt   2280
gtccacgtag tagtagccgg gcagttgcac gggcttcttg gccatgtaga tggtcttgaa   2340
ctccaccagg tagtggccgc cgtccttcag cttcagggcc tggtggatct cgcccttcag   2400
cacgccgtcg cggggtaca ggcgctcggt ggaggcctcc cagcccatgg tcttcttctg     2460
cattacgggg ccgtcggggg ggaagttggt gccgcgcatc ttcaccttgt agatcagcgt    2520
gccgtcctgc agggaggagt cctgggtcac ggtcaccaga ccgccgtcct cgaagttcat    2580
cacgcgctcc cacttgaagc cctcggggaa ggacagcttc ttgtaatcgg ggatgtcggc    2640
ggggtgcttc acgtacgcct tggagccgta catgaactgg ggggacagga tgtcccaggc    2700
gaagggcagg gggccgccct tggtcacctt cagcttggcg gtctgggtgc cctcgtaggg    2760
gcggccctcg ccctcgccct cgatctcgaa ctcgtggccg ttcatggagc cctccatgcg    2820
```

-continued

```
caccttgaag cgcatgaact ctttgatgac ctcctcgccc ttgctcacca tggtggcggg      2880
atcgcgccct atcgttcgta aatggtgaaa attttcagaa aattgctttt gctttaaaag      2940
aaatgattta aattgctgca atagaagtag aatgcttgat tgcttgagat tcgtttgttt      3000
tgtatatgtt gtgttgagag gatcctctag agtcgacctg cagaagtaac accaaacaac      3060
agggtgagca tcgacaaaag aaacagtacc aagcaaataa atagcgtatg aaggcagggc      3120
taaaaaaatc cacatatagc tgctgcatat gccatcatcc aagtatatca agatcaaaat      3180
aattataaaa catacttgtt tattataata gataggtact caaggttaga gcatatgaat      3240
agatgctgca tatgccatca tgtatatgca tcagtaaaac ccacatcaac atgtatacct      3300
atcctagatc gatatttcca tccatcttaa actcgtaact atgaagatgt atgacacaca      3360
catacagttc caaaattaat aaatacacca ggtagtttga aacagtattc tactccgatc      3420
tagaacgaat gaacgaccgc ccaaccacac cacatcatca caaccaagcg aacaaaagca      3480
tctctgtata tgcatcagta aaacccgcat caacatgtat acctatccta gatcgatatt      3540
tccatccatc atcttcaatt cgtaactatg aatatgtatg gcacacacat acagatccaa      3600
aattaataaa tccaccaggt agtttgaaac agaattctac tccgatctag aacgaccgcc      3660
caaccagacc acatcatcac aaccaagaca aaaaaaagca tgaaaagatg acccgacaaa      3720
caagtgcacg gcatatattg aaataaagga aaagggcaaa ccaaacccta tgcaacgaaa      3780 caaaaaaat catgaaatcg atcccgtctg cggaacggct agagccatcc caggattccc      3840
caaagagaaa cactggcaag ttagcaatca gaacgtgtct gacgtacagg tcgcatccgt      3900
gtacgaacgc tagcagcacg gatctaacac aaacacggat ctaacacaaa catgaacaga      3960
agtagaacta ccgggcccta accatggacc ggaacgccga tctagagaag gtagagaggg      4020
ggggggagga cgagcggcgt accttgaagc ggaggtgccg acgggtggat ttgggggaga      4080
tccactagtt ctagagcggc cgccaccgcg gtggaattct cgaggtcctc tccaaatgaa      4140
atgaacttcc ttatatagag gaagggtctt gcgaaggata gtgggattgt gcgtcatccc      4200
ttacgtcagt ggagatatca catcaatcca cttgctttga agacgtggtt ggaacgtctt      4260
ctttttccac gatgctcctc gtgggtgggg gtccatcttt gggaccactg tcggcagagg      4320
catcttgaac gatagccttt cctttatcgc aatgatggca tttgtaggtg ccaccttcct      4380
tttctactgt ccttttgatc aagtgaccga tagctgggca atggaatccg aggaggtttc      4440
ccgatattac cctttgttga aaagtctcaa tagccctttg gtcttctgag actgtatctt      4500
tgatattctt ggagtagacg agagtgtcgt gctccaccat gttatcacat caattcactt      4560
gctttgaaga cgtggttgga acgtcttctt tttccacgat gctcctcgtg ggtgggggtc      4620
catctttggg accactgtcg gcagaggcat cttgaacgat agcctttcct ttatcgcaat      4680
gatggcattt gtaggtgcca ccttcctttt ctactgtcct tttgatcaag tgacagatag      4740 ctggcaatg gaatccgagg aggtttcccg atattaccct ttgttgaaaa gtctcaatag      4800 cccctttggtc ttctgagacc tgcaggcaag caagcatgaa tgcctgggcg cgccggagaa      4860
gaactcgaga gggaattgca gatcatgagg cagatggcta tttttgtgtc acatatgcgc      4920
aaaaagagag gctatatttg tgtccctagg ttcttcgttg tattgcagtt tccatatcaa      4980
tctgacttgg tcgcatgaga aattgatggt taaataattt gaatctctca tgtagtatca      5040
actattagat attattttca ccaaatatat ttccatcgga gaagaagagg ctacagagga      5100
agcagaagag aggggtggga gaattttac acttttgtac acccacttaa acagcaaaat      5160
```

```
ccgtatgaaa acaggcccac caaaacaatg ccacgataac aatccgtaga aacaaaagct    5220
tcatttaaca gcggcgcaac aaagcacgct tatccatggt agttgtagtc cgtatgcgat    5280
ccaaagatca cgattcacgc gtgacggacg gacgacgcgt gccacaccac aactaacggc    5340
atccatggta gttgtagtcc gtatgcgatc caaagatcac gattcacgcg tgacggacgg    5400
acgacgcgcg ccacaccaca actaacagcg tgagccagcg tccaaactcc ggatggcaac    5460
ggggacgaaa cccgtcgggt agtcactgcc caaacccgtc cccgcaacct tcatcccaaa    5520
cccgtccccg tttccggtcg cgggtttcag ttttctacca gacccgtccc catcgggttt    5580
ttcatccccg tcgggaaatc cgaacccgcc agcatttcag caccaagcca aagttgcagc    5640
agcaacatga ataaaaaaca acccgtttca acaccaagat aaaacaaaac attataattt    5700
agacaacatt tcacacgtat aacaataaca tatagttctc acatataaca acaccatttc    5760
acacataaaa caacaccatt tgggataaaa atatgggcta tatcaggcca tttttatggg    5820
ccatattgag ttttcgtggg tttcacaggt accggatttg tagaatgctg aaccgggttt    5880
gaaccgtaaa atccgcgggt attgaatttg acccaatccc gtcgtcccct ggtggggtaa    5940
aaacaccatc ttgagtccaa acggccacca accaaactcc gacggcaaca aacaaacggc    6000
gttgctttgc tcctcggtat ctccgtgacc gctcaatctc ccggctgttt ccccggaatt    6060
gcgtggactc tctcatccac acgcaaaccg cctctccctc ctctctcgtc ctatccgccc    6120
cggtgccgta gcctcacggg actcttcttc ctcccttgct ataaaatccc cgccccctcc    6180
cgtctcctct ccacacatcc aaactctcaa tcgcaccgag aaaaatctcc tagcgatcga    6240
agcgaagcct ctcccgatcc tctcaaggta cgcccgtttc ccgtcgatcc tcctccttcc    6300
gttcgtgttc tgtagccgat cgattcgatt cccttacacc cgttcgtgtt ctctcgtgga    6360
tcgatcgatt gtttgttgct agaaggaact cgtagatctg gcgtttatga actgtgattc    6420
gggttagtcc agatcgattc aggtcggtcg tcgttgagcc tctcggctat gtctggatta    6480
tcgtgtagat ctgctggttc agttgattat gttcttctag gagtaatttc gttgggtcag    6540
cgcgatttct gcttaatcta tgctgcttat tgcgcctgta cctatctact aagctatgtg    6600
cacctgtaat tttgctagat tattcgttca tcctcgtagt tggtttgtca cagtaatccg    6660
tatgggttct gacgatgtta ttgttggtca tacctaggct tctccagatt ttattttgtt    6720
aaaattggat agatctgcta ctgatagttg atgatggaat ttggtgctga atctatgcta    6780
tttattgcgc ctatacctga tctatcgggc tatgtacggc tgtagtttac tggattattc    6840
gttcatcctc ggtagttggt tcatcgtttg ggttctgacg ataatattgt tgattatgcg    6900
taggcttctg cagattgttg ttaaaattgg atacatcggt tactgatggt tgatgataga    6960
tttgtgctga acctatctgt ttattgctcc tatacctgat ctatagggct atgtatgcct    7020
gtaatttacc agattattcg ttcatcctcg tagttggttc atctctataa ttcgtatggg    7080
ttcttatgat gttatcgttg attatgccta gtcttataca gattattgtg tcaagattga    7140
atatacctgc tactgatcgg tgataatttg gttagtagtt tgcaatctgc taggaacacg    7200
ttaccactgt aatctgtaaa catggtttgc cagagtagtt tgttctacta ctcttgatat    7260
ggttgctgat tttagtcgcc tccttttgga tcatgtattg atgtccttgc agatttccgt    7320
gtacttaccc cggcttttgt gtacttcgtg ttaacaggtt taaacgaagc aaacatggca    7380
tctagcatgg ctccaaagaa gaagaggaag gtcaacaacg gcacgaacaa cttccagaat    7440
ttcattggca tttccagcct ccagaagacg ctccgcaacg ccctgatccc caccgagacc    7500
acgcagcagt tcatcgtgaa gaacggcatc atcaaggagg acgagctgcg cggcgagaac    7560
```

-continued

```
aggcagatcc tcaaggacat catggacgac tactaccgcg gcttcatctc cgagacgctc   7620
tccagcatcg acgacatcga ctggacgagc ctgttcgaga agatggagat ccagctcaag   7680
aacggcgaca acaaggacac cctgatcaag gagcagacgg agtaccgcaa ggccatccac   7740
aagaagttcg cgaacgacga caggttcaag aacatgttct ccgccaagct gatcagcgac   7800
atcctcccgg agttcgtgat ccacaacaac aactactccg ccagcgagaa ggaggagaag   7860
acccaggtca tcaagctctt ctcccgcttc gcgacgagct tcaaggacta cttcaagaac   7920
agggccaact gcttctccgc ggacgacatc tccagctcca gctgccacag gatcgtgaac   7980
gacaacgccg agatcttctt cagcaacgcg ctggtgtacc gcaggatcgt caagtccctc   8040
agcaacgacg acatcaacaa gatctccggc gacatgaagg actccctgaa ggagatgagc   8100
ctcgaggaga tctacagcta cgagaagtac ggcgagttca tcacccagga gggcatctcc   8160
ttctacaacg acatctgcgg caaggtcaac agcttcatga acctctactg ccagaagaac   8220
aaggagaaca agaacctcta caagctgcag aagctccaca gcagatcct gtgcatcgcc   8280 gacacgtcct acgaggtgcc gtacaagttc gagtccgacg aggaggtgta ccagagcgtc   8340
aacggcttcc tggacaacat ctccagcaag cacatcgtcg agcgcctcag gaagatcggc   8400
gacaactaca acggctacaa cctggacaag atctacatcg tgagcaagtt ctacgagtcc   8460
gtcagccaga gacctaccg cgactgggag acgatcaaca cggcgctgga gatccactac   8520
aacaacatcc tccccggcaa cggcaagtcc aaggccgaca aggtgaagaa ggcggtcaag   8580
aacgacctcc agaagagcat caccgagatc aacgagctgg tgtccaacta caagctctgc   8640
agcgacgaca acatcaaggc cgagacgtac atccacgaga tctcccacat cctgaacaac   8700
ttcgaggcgc aggagctcaa gtacaacccg gagatccacc tggtcgagtc cgagctcaag   8760
gccagcgagc tgaagaacgt gctcgacgtc atcatgaacg cgttccactg gtgcagcgtg   8820
ttcatgaccg aggagctggt cgacaaggac aacaacttct acgccgagct cgaggagatc   8880
tacgacgaga tctaccccgt gatctccctg tacaacctcg tgcgcaacta cgtcacccag   8940
aagccgtaca gcacgaagaa gatcaagctc aacttcggca tcccgaccct ggcggacggc   9000
tggtccaaga gcaaggagta ctccaacaac gcgatcatcc tgatgaggga caacctgtac   9060
tacctcggca tcttcaacgc gaagaacaag ccggacaaga agatcatcga gggcaacacg   9120
agcgagaaca agggcgacta caagaagatg atctacaacc tcctgccggg cccaacaag   9180 atgatcccga aggtgttcct ctccagcaag accggcgtcg agacgtacaa gccctccgcc   9240
tacatcctgg agggctacaa gcagaacaag cacatcaagt ccagcaagga cttcgacatc   9300
accttctgcc acgacctcat cgactacttc aagaactgca tcgcgatcca ccccgagtgg   9360
aagaacttcg gcttcgactt ctccgacacc agcacgtacg aggacatctc cggcttctac   9420
cgcgaggtgg agctgcaggg ctacaagatc gactggacgt acatcagcga gaaggacatc   9480
gacctcctgc aggagaaggg ccagctctac ctgttccaga tctacaacaa ggacttctcc   9540
aagaagagca ccggcaacga caacctccac acgatgtacc tgaagaacct cttctccgag   9600
gagaacctga aggacatcgt cctcaagctg aacggcgagg ccgagatctt cttcaggaag   9660
tccagcatca agaacccgat catccacaag aagggcagca tcctcgtgaa ccgcacctac   9720
gaggcggagg agaaggacca gttcggcaac atccagatcg tcaggaagaa catccccgag   9780
aacatctacc aggagctgta caagtacttc aacgacaagt ccgacaagga gctgagcgac   9840
gaggccgcga agctcaagaa cgtggtgggc caccacgagg cggccaccaa catcgtgaag   9900
```

-continued

```
gactaccgct acacgtacga caagtacttc ctgcacatgc cgatcaccat caacttcaag        9960
gccaacaaga cgggcttcat caacgacagg atcctgcagt acatcgcgaa ggagaaggac       10020
ctccacgtca tcggcatcga ccgcggcgag aggaacctca tctacgtgtc cgtcatcgac       10080
acctgcggca acatcgtgga gcagaagagc ttcaacatcg tcaacggcta cgactaccag       10140
atcaagctga agcagcagga gggcgctagg cagatcgcca ggaaggagtg gaaggagatc       10200
ggcaagatca aggagatcaa ggagggctac ctctccctcg tgatccacga gatcagcaag       10260
atggtcatca agtacaacgc catcatcgcg atggaggacc tctcctacgg cttcaagaag       10320
gggcgcttca aggtggagag gcaggtctac cagaagttcg agacgatgct gatcaacaag       10380
ctgaactacc tcgtgttcaa ggacatcagc atcaccgaga acggcggcct cctgaagggc       10440
taccagctga cgtacatccc cgacaagctc aagaacgtgg gccaccagtg cggctgcatc       10500
ttctacgtcc cggccgcgta cacctccaag atcgacccca ccacgggctt cgtgaacatc       10560
ttcaagttca aggacctcac ggtcgacgcc aagcgcgagt tcatcaagaa gttcgactcc       10620
atccgctacg acagcgagaa gaacctgttc tgcttcacct tcgactacaa caacttcatc       10680
acccagaaca ccgtgatgtc caagtccagc tggagcgtgt acacgtacgg cgtccgcatc       10740
aagcgcaggt tcgtcaacgg caggttctcc aacgagagcg acaccatcga catcacgaag       10800
gacatggaga agaccctcga gatgacggac atcaactgga gggacggcca cgacctgagg       10860
caggacatca tcgactacga gatcgtgcag cacatcttcg agatcttccg cctcaccgtc       10920
cagatgagga actccctgag cgagctcgag gaccgcgact acgacaggct gatctccccg       10980
gtgctcaacg agaacaacat cttctacgac tcggctaagg ccggcgacgc tctgcccaag       11040
gacgcggacg ccaacggcgc ttactgcatc gcgctgaagg gcctctacga gatcaagcag       11100
atcacggaga actggaagga ggacggcaag ttcagccgcg acaagctcaa gattagcaac       11160
aaggattggt tcgatttcat tcagaacaag cggtacctga agcggccagc ggcgactaag       11220
aaggcgggcc aggcaaagaa gaagaagtga gtcgaccgat cgttcaaaca tttggcaata       11280
aagtttctta agattgaatc ctgttgccgg tcttgcgatg attatcatat aatttctgtt       11340
gaattacgtt aagcatgtaa taattaacat gtaatgcatg acgttattta tgagatgggt       11400
ttttatgatt agagtcccgc aattatacat ttaatacgcg atagaaaaca aaatatagcg       11460
cgcaaactag gataaattat cgcgcgcggt gtcatctatg ttactagatc gatccc          11516
```

```
<210> SEQ ID NO 56
<211> LENGTH: 3852
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Plasmid pGEP1067 sgRNA m7GEP22

<400> SEQUENCE: 56
ctgacgcgcc ctgtagcggc ctgcagtgca gcgtgacccg gtcgtgcccc tctctagaga         60
taatgagcat tgcatgtcta agttataaaa aattaccaca tatttttttt gtcacacttg        120
tttgaagtgc agtttatcta tctttataca tatatttaaa ctttactcta cgaataatat        180
aatctatagt actacaataa tatcagtgtt ttagagaatc atataaatga acagttagac        240
atggtctaaa ggacaattga gtattttgac aacaggactc tacagtttta tctttttagt        300
gtgcatgtgt tctccttttt ttttgcaaat agcttcacct atataatact tcatccattt        360
```

-continued

```
tattagtaca tccatttagg gtttagggtt aatggttttt atagactaat tttttttagta   420 catctatttt attctatttt agcctctaaa ttaagaaaac taaaactcta ttttagtttt   480
tttatttaat aatttagata taaaatagaa taaaataaag tgactaaaaa ttaaacaaat   540 acccttttaag aaattaaaaa aactaaggaa acattttttct tgtttcgagt agataatgcc   600
agcctgttaa acgccgtcga tcgacgagtc taacggacac caaccagcga accagcagcg   660
tcgcgtcggg ccaagcgaag cagacggcac ggcatctctg tcgctgcctc tggacccctc   720
tcgagagttc cgctccaccg ttggacttgc tccgctgtcg gcatccagaa attgcgtggc   780
ggagcggcag acgtgagccg gcacggcagg cggcctcctc ctcctctcac ggcaccggca   840
gctacggggg attcctttcc caccgctcct tcgctttccc ttcctcgccc gccgtaataa   900
atagacaccc cctccacacc ctctttcccc aacctcgtgt tgttcggagc gcacacacac   960
acaaccagat ctcccccaaa tccacccgtc ggcacctccg cttcaaggta cgccgctcgt   1020 cctcccccc cccccctctc taccttctct agatcggcgt tccggtccat ggttagggcc   1080
cggtagttct acttctgttc atgtttgtgt tagatccgtg tttgtgttag atccgtgctg   1140
ctagcgttcg tacacggatg cgacctgtac gtcagacacg ttctgattgc taacttgcca   1200
gtgtttctct ttggggaatc ctgggatggc tctagccgtt ccgcagacgg gatcgatcta   1260
ggataggtat acatgttgat gtgggtttta ctgatgcata tacatgatgg catatgcagc   1320
atctattcat atgctctaac cttgagtacc tatctattat aataaacaag tatgtttttat   1380 aattattttg atcttgatat acttggatga tggcatatgc agcagctata tgtggatttt   1440
tttagccctg ccttcatacg ctatttattt gcttggtact gtttcttttg tcgatgctca   1500
ccctgttgtt tggtgttact tctgcaggga tccaaattac tgatgagtcc gtgaggacga   1560
aacgagtaag ctcgtcgtca aaagaccttt ttaatttcta ctcttgtaga tttcagagca   1620
ctgcagctaa gaggccggca tggtcccagc ctcctcgctg gcgccggctg ggcaacatgc   1680
ttcggcatgg cgaatgggac cgatcgttca aacatttggc aataaagttt cttaagattg   1740
aatcctgttg ccggtcttgc gatgattatc atataaatttc tgttgaatta cgttaagcat   1800
gtaataatta acatgtaatg catgacgtta tttatgagat gggttttttat gattagagtc   1860 ccgcaattat acatttaata cgcgatagaa aacaaaatat agcgcgcaaa ctaggataaa   1920
ttatcgcgcg cggtgtcatc tatgttacta gatcgatcgt cgttcggctg cggcgagcgg   1980
tatcagctca ctcaaaggcg gtaatacggt tatccacaga atcaggggat aacgcaggaa   2040
agaacatgtg agcaaaaggc cagcaaaagg ccaggaaccg taaaaaggcc gcgttgctgg   2100 cgttttttcca taggctccgc cccctgacg agcatcacaa aaatcgacgc tcaagtcaga   2160
ggtggcgaaa cccgacagga ctataaagat accaggcgtt tccccctgga agctccctcg   2220
tgcgctctcc tgttccgacc ctgccgctta ccggatacct gtccgccttt ctcccttcgg   2280
gaagcgtggc gctttctcat agctcacgct gtaggtatct cagttcggtg taggtcgttc   2340
gctccaagct gggctgtgtg cacgaacccc ccgttcagcc cgaccgctgc gccttatccg   2400
gtaactatcg tcttgagtcc aacccggtaa gacacgactt atcgccactg gcagcagcca   2460
ctggtaacag gattagcaga gcgaggtatg taggcggtgc tacagagttc ttgaagtggt   2520
ggcctaacta cggctacact agaagaacag tatttggtat ctgcgctctg ctgaagccag   2580
ttaccttcgg aaaaagagtt ggtagctctt gatccggcaa acaaaccacc gctggtagcg   2640
gtggtttttt tgtttgcaag cagcagatta cgcgcagaaa aaaaggatct caagaagatc   2700
ctttgatctt ttctacgggg tctgacgctc agtggaacga aaactcacgt taagggattt   2760
```

-continued

```
tggtcatgag attatcaaaa aggatcttca cctagatcct tttaaattaa aaatgaagtt    2820
ttaaatcaat ctaaagtata tatgagtaaa cttggtctga cagttaccaa tgcttaatca    2880
gtgaggcacc tatctcagcg atctgtctat ttcgttcatc catagttgcc tgactccccg    2940
tcgtgtagat aactacgata cgggagggct taccatctgg ccccagtgct gcaatgatac    3000
cgcgagaccc acgctcaccg gctccagatt tatcagcaat aaaccagcca gccggaaggg    3060
ccgagcgcag aagtggtcct gcaactttat ccgcctccat ccagtctatt aattgttgcc    3120
gggaagctag agtaagtagt tcgccagtta atagtttgcg caacgttgtt gccattgcta    3180
caggcatcgt ggtgtcacgc tcgtcgtttg gtatggcttc attcagctcc ggttcccaac    3240
gatcaaggcg agttacatga tcccccatgt tgtgcaaaaa agcggttagc tccttcggtc    3300
ctccgatcgt tgtcagaagt aagttggccg cagtgttatc actcatggtt atggcagcac    3360
tgcataattc tcttactgtc atgccatccg taagatgctt ttctgtgact ggtgagtact    3420
caaccaagtc attctgagaa tagtgtatgc ggcgaccgag ttgctcttgc ccggcgtcaa    3480
tacgggataa taccgcgcca catagcagaa ctttaaaagt gctcatcatt ggaaaacgtt    3540
cttcggggcg aaaactctca aggatcttac cgctgttgag atccagttcg atgtaaccca    3600
ctcgtgcacc caactgatct tcagcatctt ttactttcac cagcgtttct gggtgagcaa    3660
aaacaggaag gcaaaatgcc gcaaaaaagg gaataagggc gacacggaaa tgttgaatac    3720
tcatactctt cctttttcaa tattattgaa gcatttatca gggttattgt ctcatgagcg    3780
gatacatatt tgaatgtatt tagaaaaata aacaaatagg ggttccgcgc acatttcccc    3840
gaaaagtgcc ac                                                       3852
```

```
<210> SEQ ID NO 57
<211> LENGTH: 25
<212> TYPE: PRT
<213> ORGANISM: Unknown
<220> FEATURE:
<223> OTHER INFORMATION: Description of Unknown:
      WRC domain conserved motif
<220> FEATURE:
<221> NAME/KEY: MOD_RES
<222> LOCATION: (2)..(10)
<223> OTHER INFORMATION: Any amino acid
<220> FEATURE:
<221> NAME/KEY: MOD_RES
<222> LOCATION: (12)..(21)
<223> OTHER INFORMATION: Any amino acid
<220> FEATURE:
<221> NAME/KEY: MOD_RES
<222> LOCATION: (23)..(24)
<223> OTHER INFORMATION: Any amino acid

<400> SEQUENCE: 57

Cys Xaa Xaa Xaa Xaa Xaa Xaa Xaa Xaa Xaa Cys Xaa Xaa Xaa Xaa Xaa
1               5                   10                  15

Xaa Xaa Xaa Xaa Xaa Cys Xaa Xaa His
            20                  25
```

METHOD FOR RAPID GENOME MODIFICATION IN RECALCITRANT PLANTS

CROSS-REFERENCE TO RELATED APPLICATIONS

This application is a U.S. National Phase of International Patent Application No. PCT/EP2021/054805, filed on Feb. 26, 2021, which claims priority to U.S. Provisional Application No. 62/982,979, filed Feb. 28, 2020. The entire contents of these applications are incorporated herein by reference in their entirety.

SEQUENCE LISTING

The instant application contains a Sequence Listing which has been submitted electronically in ASCII format and is hereby incorporated by reference in its entirety. Said ASCII copy, created on Aug. 30, 2023, is named 245761_000182_SL.txt and is 258,283 bytes in size.

TECHNICAL FIELD

The present invention relates to the field of plant regeneration from single cell origin, in particular in combination with genome engineering or gene editing of a plant cell. The present invention provides a method, wherein modification of a cell is achieved by providing a genome modification or editing system together with at least one regeneration booster, or a combination of regeneration boosters, which is/are transiently active in the cell and/or with at least one epigenetically regulating chemical. Preferably, the effector molecules are introduced by means of particle bombardment. Furthermore, the modified plant cell is regenerated to obtain a plant, which inherits the modification to its progeny. In addition, methods, tools, constructs and strategies are provided to effectively modify the genome of a plant cell or at least one genomic target site in a plant cell, to obtain said modified cell and to regenerate a plant tissue, organ, plant or seed from the modified cell. Finally, the present invention also relates to an improved method of regenerating a plant tissue, organ or a plant from a single plant cell.

BACKGROUND OF INVENTION

To cope with the increasing challenges of climate change, food safety and a growing world population, traditional plant breeding, usually being rather time consuming, has to be supported by new techniques of molecular biology to provide new crop plants having desired traits in a safe manner, but needing less development time.

Having more and more potentially suitable site-specific nuclease tools at hand, transformation or transfection and subsequent regeneration are still the major bottleneck technologies for plant genome engineering, such as transgene insertion or genome editing (GE). To obtain a modified plant, the two events have to fall on the same cell. Some plants or plant genotypes are particularly recalcitrant to transformation and/or subsequent regeneration, which makes it very challenging to introduce traits using GE approaches and to propagate them. Up to date, particle bombardment and Agrobacterium-mediated biomolecule delivery are the most efficient methods for plant transformation. In agrobacterial transformation, the Agrobacteria first find the suitable cells and attach to the plant cell walls, which is generally referred to as "inoculation". Following the inoculation, the Agrobacteria are growing with plant cells under suitable conditions for a period of time—from several hours to several days—to allow T-DNA transfer. Agrobacterium-plant interaction, plant tissue structure, plant cell type, etc. constrain agrobacterial transformation. Limited by plant cell susceptibility and accessibility, it is generally believed that Agrobacterium-mediated transformation is plant species, plant tissue-type and plant cell-type dependent. Conversely, based on physical forces, particle bombardment is—at least in theory—plant species and plant cell-type independent, and is able to transform any cells when appropriate pressure is applied. Still, many plant cells, in particular plant cells freshly isolated from a plant depending on the developmental stage and the tissue they are derived from, suffer severe stress or even cell death when physically bombarded with micro- or nanoparticles of various kinds. Further, bombardment may be associated with low transformation and/or integration frequencies also caused by severe cell damage or rupture. However, physical bombardment per se offers great advantages as it is easy, rapid and versatile and allows for transient and stable expression of the inserted molecules, if desired. Potentially toxic chemicals needed for transfection, or bacterial transformations can be avoided.

It is generally believed that transformed cells are less regenerative than wild type cells. These circumstances may result in poor rates of genome modification such as gene editing in view of the fact that the transformed/transfected material may not be viable enough after the introduction of the GE tools. For example, transformed cells are susceptible to programmed cell death due to the presence of foreign DNA inside of these cells. In addition, stresses arisen from delivery—e.g. bombardment damage—may trigger a cell death as well. Therefore, promoting cell proliferation is especially essential for the regeneration of the transformed cells.

Plant regeneration relies on cell proliferation and development. Addition to direct shoot and embryo culture, organogenesis and embryogenesis are the two alternative plant regeneration pathways that involve re-programming and activating the proliferation of somatic cells. Organogenesis and embryogenesis are through organ (e.g. shoot) and embryo formation respectively, and eventually develop into a complete plantlet.

Genome modification efficiency is controlled largely by host cell statuses. The cells undergoing rapid cell-division, are the most suitable recipients for genetic modification. Promoting cell division may therefore increase DNA accessibility during DNA replication and division process, and thus increase genetic modification efficiency. In order to stimulate cell division and regeneration, so-called regeneration boosters may be co-delivered into the cell with the genome modification tools. However, a continuous activity of the regeneration boosters can negatively impact differentiation and subsequent development of transformed plants. The latter point is caused by the fact that naturally occurring booster proteins are usually transcription factors guiding the progression of cell differentiation at different positions in a precise manner and thus have central roles in plant development.

As disclosed in Lowe et al. (Plant Cell, 2016, 28(9)) there is a problem associated with the use of naturally occurring regeneration boosters in artificial settings of plant genome modifications: the usually growth-stimulating effect of regeneration boosters—if not as precisely controlled as in the natural environment, where the transcription factors are only expressed in a tightly controlled spatio-temporal manner, the ectopic expression of regeneration boosters used in plant genome modification easily leads to pleiotropic effects on plant growth and fertility. These uncertainties and negative effects are, however, not desired for targeted genome editing. To address this problem, Lowe et al. suggests a rather cumbersome technique of integrating and later on inactivating booster activity by removal of the relevant expression cassettes. Another approach is described by Lowe et al. (In Vitro Cellular & Developmental Biology—Plant 54(8) 2018), which relies on specific promoters, that are active only in certain tissues.

In summary, efficient genome modification and subsequent regeneration of plants, in particular recalcitrant plants or plant genotypes, is limited by several factors. At first, an efficient way to introduce a desired modification into a target cell has to be established. Notably, when the tools for genome modification are introduced, the target cell may suffer stress or damage from which it may not be able to recover. If the cell carrying the desired modification does survive, regeneration of a plant from single cell origin is often difficult. This problem can be addressed by co-introduction of regeneration boosters, which stimulate cell proliferation in the early stages of regeneration. A continuous and uncontrolled activity of the boosters, however, negatively affects the differentiation and hampers further development into a plant. Furthermore, pleiotropic effects may impact plant growth and fertility.

In order to overcome the above described problems, novel techniques to efficiently modify plant genomes and to regenerate plants, in particular plants carrying a desired modification, are required. In particular, such methods should be applicable to recalcitrant plants/plant genotypes, which are difficult to transform and/or regenerate. It was thus an object of the present invention to provide means and methods to achieve rapid and highly efficient genome modification with single-cell origin directly in recalcitrant elite plant lines. It should be feasible to regenerate plants from the modified cells by reliable differentiation without adverse effects on further development. The modified T0 plants should be transgene-free, fertile and the modifications should be fully inherited to the T1 progeny.

SUMMARY OF THE INVENTION

In a first aspect the present invention provides a method for plant genome modification, preferably for the targeted modification of at least one genomic target sequence, for obtaining at least one modified cell wherein the method comprises the following steps:
  (a) providing at least one plant cell or a single plant cell;
  (b) introducing into the at least one plant cell or the single plant cell:
    (i) at least one genome modification system, preferably a genome editing system comprising at least one site-directed nuclease, nickase or an inactivated nuclease, preferably a nucleic acid guided nuclease, nickase or an inactivated nuclease, or a sequence encoding the same, and optionally at least one guide molecule, or a sequence encoding the same;
    (ii) at least one regeneration booster, or a sequence encoding the same and/or at least one epigenetically regulating chemical, wherein the at least one regeneration booster is transiently present, transiently active or transiently expressed in the plant cell;
    (iii) and, optionally at least one repair template, or a sequence encoding the same; and (c) cultivating the at least one plant cell or the single plant cell under conditions allowing the expression and/or assembly and/or activation of the at least one genome modification system, preferably the at least one genome editing system, and, optionally of the at least one regeneration booster, and optionally of the at least one guide molecule and/or optionally of the at least one repair template; and
  (d) obtaining at least one modified plant cell; and/or
  (e) obtaining at least one plant tissue, organ, plant or seed regenerated from the at least one modified cell; and
  (f) optionally: screening for at least one plant tissue, organ, plant or seed regenerated from the at least one modified cell in the T0 and/or T1 generation carrying a desired targeted modification.

In one embodiment of the various aspects of the present invention, in the method described above, steps (i) and (ii) take place simultaneously or subsequently, for promoting plant cell proliferation and/or to assist in a targeted modification of at least one genomic target sequence.

In a further embodiment of the various aspects of the present invention, in the method according to any of the embodiments above, at least one regeneration booster is introduced in step (ii) and
  (a) the regeneration booster(s) promote plant cell proliferation and/or assist in the targeted modification and/or provide a positive selection for at least one transiently transformed cell for genome modification and/or for regeneration into at least one modified plant, and/or
  (b) the regeneration booster(s) suppress plant cell differentiation if the cell is stably transformed and provide a negative selection for at least one stably transformed cell for regeneration into one transgenic plant, and/or
  (c) the regeneration booster(s) provide a dual selection according to (a) and (b) for at least one transformed cell.

In another embodiment of the various aspects of the present invention, in the method according to any of the embodiments described above, the at least one plant cell is an immature embryo cell or a meristematic cell, in particular a cell of a zygotic or somatic embryo or meristem or the single plant cell is a diploid cell or a haploid cell, preferably a haploid microspore.

In one embodiment of the various aspects of the present invention, in the method according to any of the embodiments described above, the at least one regeneration booster comprises at least one regeneration booster protein (RBP), wherein the at least one RBP comprises an amino acid sequence selected from the group consisting of SEQ ID NOs: 32, 33, 34, 35, 36, 37, 38 and 39, or a sequence having at least 80%, 81%, 82%, 83%, 84%, 85%, 86%, 87%, 88%, 89%, 90%, 91%, 92%, 93%, 94%, 95%, 96%, 97%, 98% or 99% sequence identity thereto, or a catalytically active fragment thereof, or the at least one RBP is encoded by a sequence selected from the group consisting of SEQ ID NOs: 20, 21, 22, 23, 24, 25, 26 and 27, or a sequence having at least 80%, 81%, 82%, 83%, 84%, 85%, 86%, 87%, 88%, 89%, 90%, 91%, 92%, 93%, 94%, 95%, 96%, 97%, 98% or 99% sequence identity thereto, or a cognate codon-optimized sequence.

In another embodiment of the various aspects of the present invention, in the method according to any of the embodiments described above, the at least one regeneration booster further comprises at least one PLT or RKD4, wherein the at least one PLT or RKD4 comprises an amino acid sequence selected from the group consisting of SEQ ID NOs: 28, 29, 30 and 31, or a sequence having at least 80%, 81%, 82%, 83%, 84%, 85%, 86%, 87%, 88%, 89%, 90%, 91%, 92%, 93%, 94%, 95%, 96%, 97%, 98% or 99% sequence identity thereto, or a catalytically active fragment thereof, or the at least one PLT or RKD4 is encoded by a sequence selected from the group consisting of SEQ ID NOs: 16, 17, 18 and 19, or a sequence having at least 80%, 81%, 82%, 83%, 84%, 85%, 86%, 87%, 88%, 89%, 90%, 91%, 92%, 93%, 94%, 95%, 96%, 97%, 98% or 99% sequence identity thereto, or a cognate codon-optimized sequence.

In a further embodiment of the various aspects of the present invention, in the method according to any of the embodiments described above, at least one further regeneration booster is introduced, wherein the further regeneration booster, or the sequence encoding the same is selected from BBM, WUS, WOX, GRF, LEC, or a variant thereof or the further regeneration booster is a regeneration booster as defined in any of the embodiments above, wherein the further regeneration booster is different from the first regeneration booster.

In yet another embodiment of the various aspects of the present invention, in the method according to any of the embodiments described above, the at least one regeneration booster comprises at least one RBP, wherein the at least one RBP comprises an amino acid sequence selected from the group consisting of SEQ ID NOs: 32, 33, 34, 35, 36, 37, 38 and 39, or a sequence having at least 80%, 81%, 82%, 83%, 84%, 85%, 86%, 87%, 88%, 89%, 90%, 91%, 92%, 93%, 94%, 95%, 96%, 97%, 98% or 99% sequence identity thereto, or a catalytically active fragment thereof, or wherein the at least one RBP is encoded by a sequence selected from the group consisting of SEQ ID NOs: 20, 21, 22, 23, 24, 25, 26 and 27, or a sequence having at least 80%, 81%, 82%, 83%, 84%, 85%, 86%, 87%, 88%, 89%, 90%, 91%, 92%, 93%, 94%, 95%, 96%, 97%, 98% or 99% sequence identity thereto, or a cognate codon-optimized sequence, and the at least one regeneration booster comprises PLT5, wherein the PLT5 comprises an amino acid sequence of SEQ ID NO: 30, or a sequence having at least 80%, 81%, 82%, 83%, 84%, 85%, 86%, 87%, 88%, 89%, 90%, 91%, 92%, 93%, 94%, 95%, 96%, 97%, 98% or 99% sequence identity thereto, or a catalytically active fragment thereof, or wherein the PLT5 is encoded by a nucleic acid sequence of SEQ ID NO: 18, or a sequence having at least 80%, 81%, 82%, 83%, 84%, 85%, 86%, 87%, 88%, 89%, 90%, 91%, 92%, 93%, 94%, 95%, 96%, 97%, 98% or 99% sequence identity thereto, or a cognate codon-optimized sequence.

In a further embodiment of the method according to any of the embodiments described above, at least one epigenetically regulating chemical is introduced in step ii) and the at least one epigenetically regulating chemical is a histone deacetylase inhibitor (HDACI), in particular trichostatin A (TSA) or a TSA like chemical.

In one embodiment of the various aspects of the present invention, in the method according to any of the embodiments described above, the at least one genome modification system, preferably the at least one genome editing system, and the at least one regeneration booster, or the sequences encoding the same and/or the at least one epigenetically regulating chemical, are introduced into the cell by transformation or transfection mediated by biolistic bombardment, *Agrobacterium*-mediated transformation, micro- or nanoparticle delivery, or by chemical transfection, or a combination thereof, preferably the at least one genome modification system, preferably the at least one genome editing system, and the at least one regeneration booster and/or the at least one epigenetically regulating chemical are introduced by biolistic bombardment, preferably wherein the biolistic bombardment comprises a step of osmotic treatment before and/or after bombardment.

In another embodiment of the various aspects of the present invention, in the method according to any of the embodiments described above, at least one site-directed nuclease, nickase or an inactivated nuclease, or a sequence encoding the same, is introduced and is selected from the group consisting of a CRISPR/Cas system, preferably from a CRISPR/MAD7 system, a CRISPR/Cfp1 system, a CRISPR/MAD2 system, a CRISPR/Cas9 system, a CRISPR/CasX system, a CRISPR/CasY system, a CRISPR/Cas13 system, or a CRISPR/Csm system, a zinc finger nuclease system, a transcription activator-like nuclease system, or a meganuclease system, or any combination, variant, or catalytically active fragment thereof.

In a further embodiment of the various aspects of the present invention, in the method according to any of the embodiments described above, at least one genome editing system is introduced, wherein the at least one genome editing system further comprises at least one reverse transcriptase and/or at least one cytidine or adenine deaminase, preferably wherein the at least one cytidine or adenine deaminase is independently selected from an apolipoprotein B mRNA-editing complex (APOBEC) family deaminase, preferably a rat-derived APOBEC, an activation-induced cytidine deaminase (AID), an ACF1/ASE deaminase, an ADAT family deaminase, an ADAR2 deaminase, or a PmCDA1 deaminase, a TadA derived deaminase, and/or a transposon, or a sequence encoding the aforementioned at least one enzyme, or any combination, variant, or catalytically active fragment thereof.

In one embodiment of the various aspects of the present invention, in the method according to any of the embodiments described above, at least one genome editing system is introduced, wherein the at least one genome editing system comprises at least one repair template, and the at least one repair template comprises or encodes a double- and/or single-stranded nucleic acid sequence.

In another embodiment of the various aspects of the present invention, in the method according to any of the embodiments described above, the at least one repair template comprises symmetric or asymmetric homology arms and/or the at least one repair template comprises at least one chemically modified base and/or backbone.

In a further embodiment of the various aspects of the present invention, in the method according to any of the embodiments described above, at least one genome editing system is introduced, wherein the at least one genome editing system, and optionally the at least one repair template, or the respective sequences encoding the same, are introduced transiently or stably, or as a combination thereof.

In one aspect, the present invention relates to the use of a regeneration booster or a combination of regeneration boosters, preferably a regeneration booster or combination of regeneration boosters as defined in any of the embodiments described above, in a method for targeted plant genome modification, preferably in a method according to any of the embodiments described above, to (a) promote plant cell proliferation and/or assist in the targeted modification and/or provide a positive selection for at least one transiently transformed cell for genome modification and/or for regeneration into at least one modified plant, and/or (b) suppress plant cell differentiation if the cell is stably transformed and provide a negative selection for at least one stably transformed cell for regeneration into one transgenic plant, and/or (c) provide a dual selection according to (a) and (b) for at least one transformed cell.

In another aspect, the present invention relates to a plant cell, tissue, organ, plant or seed obtainable by or obtained by a method according to any of the embodiments described above.

In one embodiment of the plant cell, tissue, organ, plant or seed described above, the plant cell, tissue, organ, plant or seed originates from a monocotyledonous or a dicotyledonous plant.

In another embodiment of the plant cell, tissue, organ, plant or seed described above, originates from a genus selected from the group consisting of *Hordeum, Sorghum, Saccharum, Zea, Setaria, Oryza, Triticum, Secale, Triticale, Malus, Brachypodium, Aegilops, Daucus, Beta, Eucalyptus, Nicotiana, Solanum, Coffea, Vitis, Erythrante, Genlisea, Cucumis, Marus, Arabidopsis, Crucihimalaya, Cardamine, Lepidium, Capsella, Olmarabidopsis, Arabis, Brassica, Eruca, Raphanus, Citrus, Jatropha, Populus, Medicago, Cicer, Cajanus, Phaseolus, Glycine, Gossypium, Astragalus, Lotus, Torenia, Allium, Spinacia* or *Helianthus*, preferably, the plant cell, tissue, organ, plant or seed originates from a species selected from the group consisting of *Hordeum vulgare, Hordeum bulbusom, Sorghum bicolor, Saccharum officinarium, Zea* spp., including *Zea mays, Setaria italica, Oryza minuta, Oryza sativa, Oryza australiensis, Oryza alta, Triticum aestivum, Triticum durum, Secale cereale, Triticale, Malus domestica, Brachypodium distachyon, Hordeum marinum, Aegilops tauschii, Daucus glochidiatus, Beta* spp., including *Beta vulgaris, Daucus pusillus, Daucus muricatus, Daucus carota, Eucalyptus grandis, Nicotiana sylvestris, Nicotiana tomentosiformis, Nicotiana tabacum, Nicotiana benthamiana, Solanum lycopersicum, Solanum tuberosum, Coffea canephora, Vitis vinifera, Erythrante guttata, Genlisea aurea, Cucumis sativus, Marus notabilis, Arabidopsis arenosa, Arabidopsis lyrata, Arabidopsis thaliana, Crucihimalaya himalaica, Crucihimalaya wallichii, Cardamine nexuosa, Lepidium virginicum, Capsella bursa pastoris, Olmarabidopsis pumila, Arabis hirsute, Brassica napus, Brassica oleracea, Brassica rapa, Raphanus sativus, Brassica juncacea, Brassica nigra, Eruca vesicaria* subsp. *sativa, Citrus sinensis, Jatropha curcas, Populus trichocarpa, Medicago truncatula, Cicer yamashitae, Cicer bijugum, Cicer arietinum, Cicer reticulatum, Cicer judaicum, Cajanus cajanfolius, Cajanus scarabaeoides, Phaseolus vulgaris, Glycine max, Gossypium* sp., *Astragalus sinicus, Lotus japonicas, Torenia fournieri, Allium cepa, Allium fistulosum, Allium sativum, Allium tuberosum, Helianthus annuus, Helianthus tuberosus* and/or *Spinacia oleracea.*

In a further aspect the present invention relates to an expression construct assembly, comprising (i) at least one vector encoding at least one genome modification system which comprises at least one gene of interest, preferably an exogenous gene of interest, and/or which is preferably at least one genome editing system comprising at least one site-directed nuclease, nickase or an inactivated nuclease of a genome editing system, preferably wherein the genome editing system is as defined in any of the embodiments described above, and (ii) at least one vector encoding at least one regeneration booster, preferably wherein the regeneration booster or boosters is/are as defined in any of the embodiments described above, and (iii) optionally, when the at least one site-directed nuclease, nickase or an inactivated nuclease of a genome editing system is a nucleic acid guided nuclease: at least one vector encoding at least one guide molecule guiding the at least one nucleic acid guided nuclease, nickase or an inactivated nuclease to the at least one genomic target site of interest; and (iv) optionally: at least one vector encoding at least one repair template;

wherein (i), (ii), (iii), and/or (iv) are encoded on the same, or on different vectors.

In one embodiment of the expression construct assembly described above, the assembly further comprises a vector encoding at least one marker.

In yet another aspect the present invention relates to a plant cell, tissue, organ, plant or seed comprising at least one regeneration booster as described above and further below and/or an expression construct assembly as defined in any of the embodiments described above.

In a further aspect the present invention relates to a method for selecting a modified plant cell, plant tissue, organ, plant or seed, wherein the method comprises the steps (a) to (c) as defined in any of the embodiments of the method described above and further comprises the step:

(d1) screening for at least one plant cell carrying a targeted modification, or (d2) screening for at least one plant tissue, organ, plant or seed regenerated from at least one modified plant cell in the T0 or T1 generation carrying a desired targeted modification.

In another aspect the present invention relates to a method for regenerating a plant tissue, organ or plant from at least one plant cell or from a single plant cell, wherein the method comprises:

(i) Introducing into the at least one plant cell or the single plant cell at least one regeneration booster, or a sequence encoding the same, wherein the at least one regeneration booster is transiently present, transiently active or transiently expressed in the plant cell, preferably wherein the at least one regeneration booster(s) is/are as defined in any of the embodiments described above, and (ii) regenerating a plant tissue, organ or plant from at least one plant cell or the single plant cell.

In one embodiment of the method for regenerating a plant tissue, organ or plant from a single plant cell as described above, the at least one plant cell is an immature embryo cell or meristematic cell, in particular a cell of a zygotic or somatic embryo or meristem wherein the single plant cell is a diploid cell or a haploid cell.

In another embodiment of the method for regenerating a plant tissue, organ or plant from a single plant cell as described above, the single plant cell is a haploid microspore.

BRIEF DESCRIPTION OF THE DRAWINGS

Whenever the Figures show black/white pictures of originally fluorescence images, brighter spots represent the accumulation of respective fluorescent protein.

DESCRIPTION OF SEQUENCES

Description of Sequences

Figure 1:
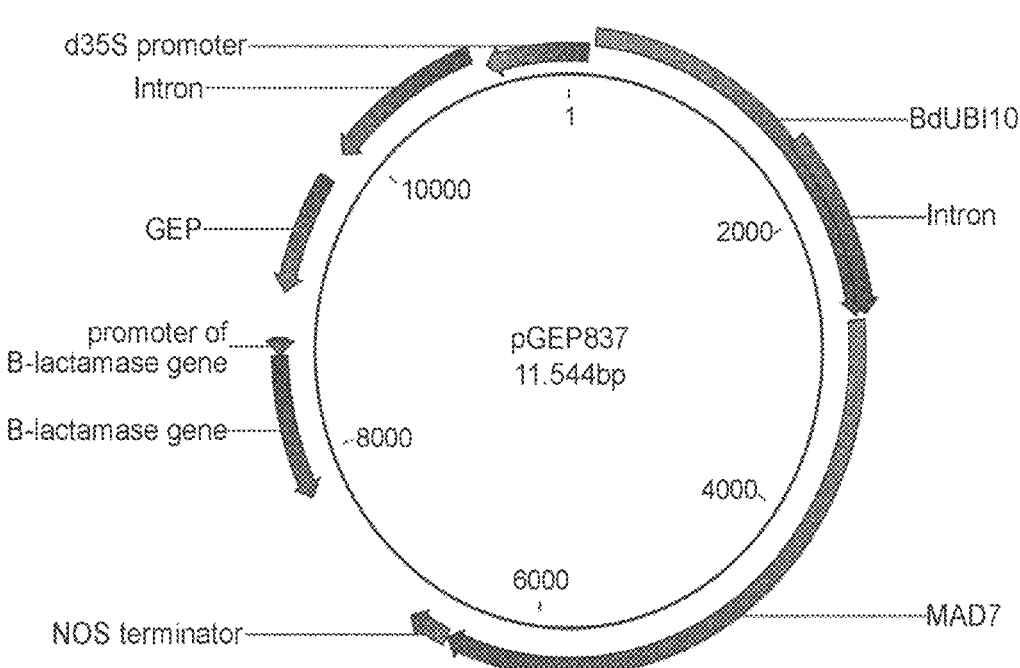
FIG. 1 shows a genome editing nuclease MAD7 expression construct pGEP837 map. A green fluorescent marker was used in this example (indicated as GEP). Any kind of fluorescent protein-encoding marker gene may be used instead depending on the plant target cell/tissue to be transformed and visualized. MAD7 defines the maize codon-optimized CDS of the *Eubacterium rectale* CRISPR/MAD7 gene (Inscripta). BdUB10 defines the *Brachypodium Ubiquitin* 10 promoter. Tnos defines the nos terminator
Figure 3:
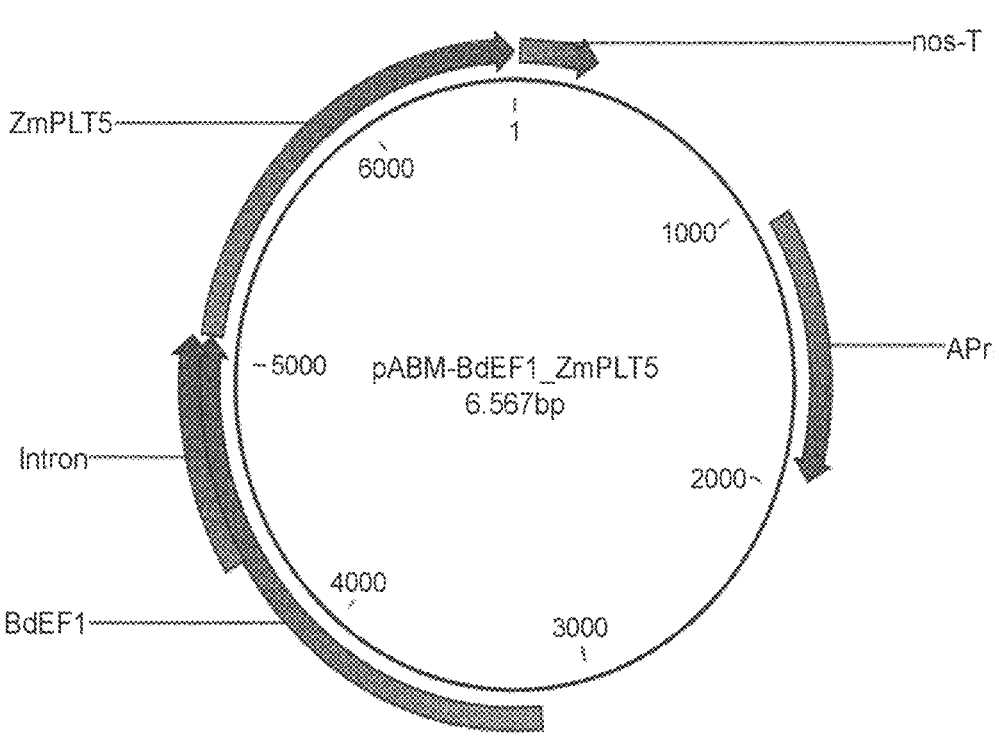
FIG. 3 shows a maize PLT5 expression construct pABM-BdEF1_ZmPLT5 map. ZMPLT5 is driven by the strong constitutive EF1 gene promoter from *Brachypodium* (BdEF1).
Figure 4:
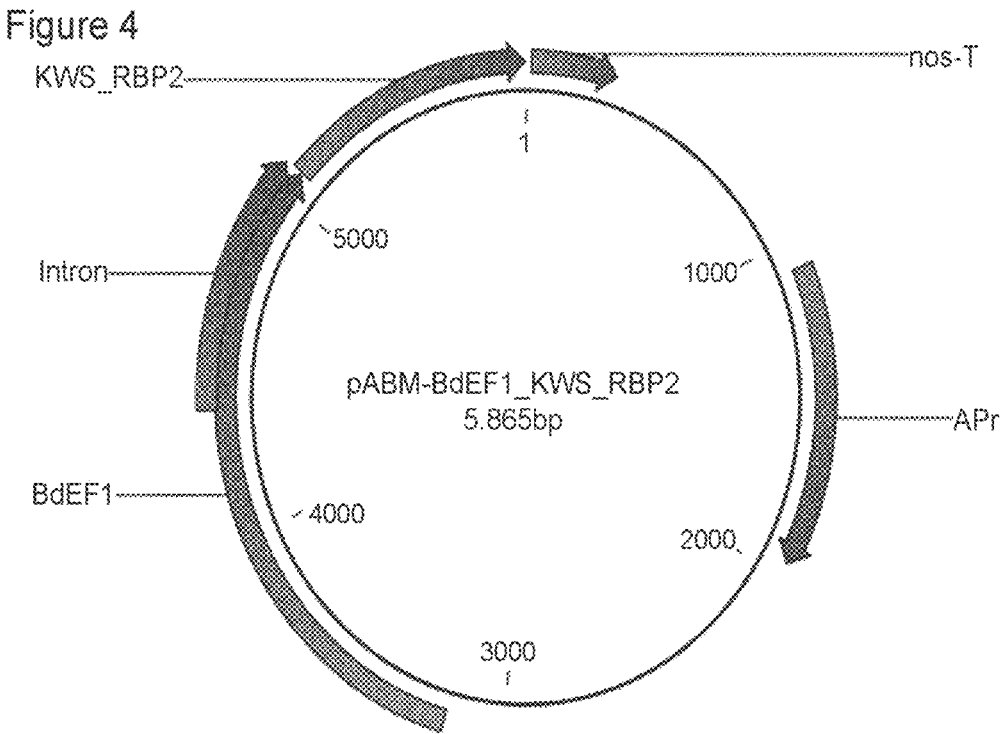
FIG. 4 shows the KWS_RBP2 expression construct pABM-BdEF1_RBP2 map. KWS_RBP2 is driven by the strong constitutive EF1 promoter from *Brachypodium* (BdEF1).
Figure 5:
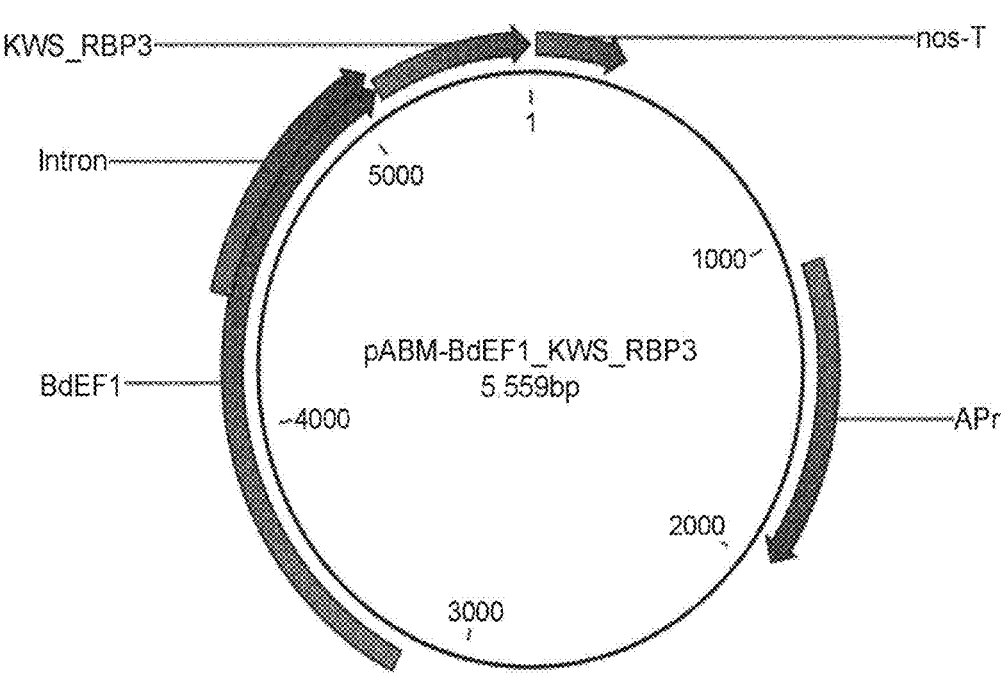
FIG. 5 shows the KWS_RBP3 expression construct pABM-BdEF1_RBP3 map. KWS_RBP3 is driven by the strong constitutive EF1 promoter from *Brachypodium* (BdEF1).
Figure 6:
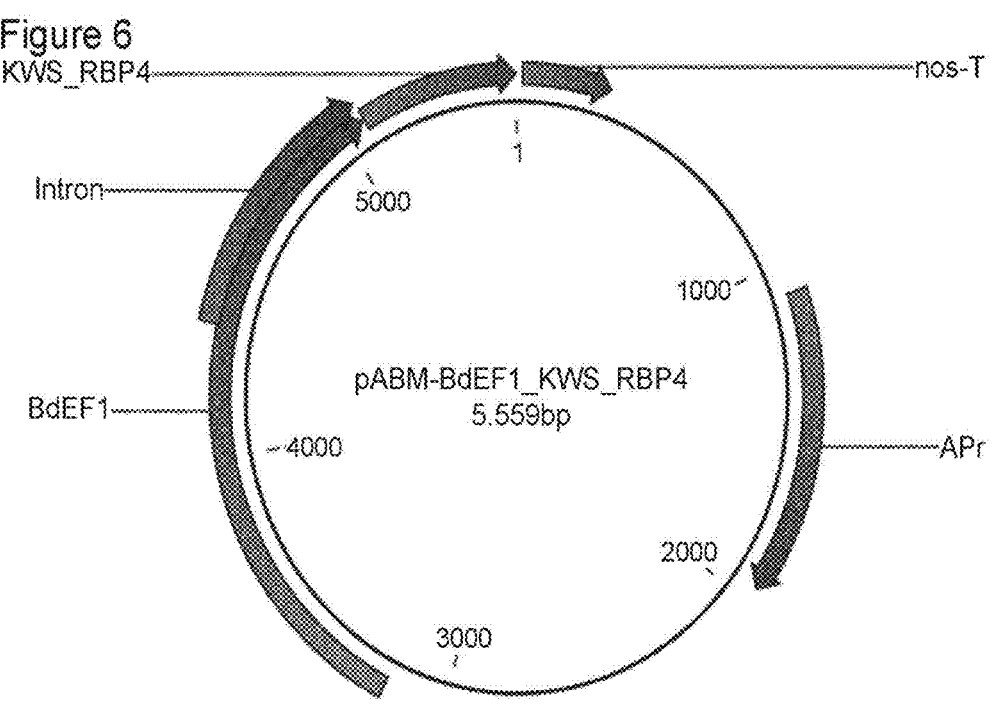
FIG. 6 shows the KWS_RBP4 expression construct pABM-BdEF1_RBP4 map. KWS_RBP4 is driven by the strong constitutive EF1 promoter from *Brachypodium* (BdEF1).
Figure 7:
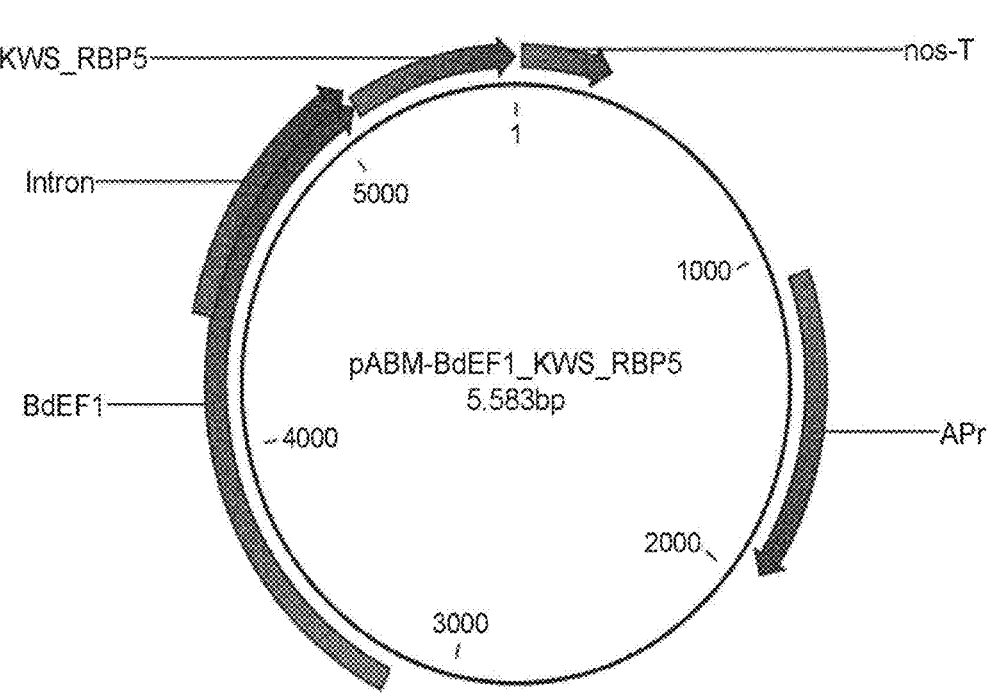
FIG. 7 shows the KWS_RBP5 expression construct pABM-BdEF1_RBP5 map. KWS_RBP5 is driven by the strong constitutive EF1 promoter from *Brachypodium* (BdEF1).
Figure 8:
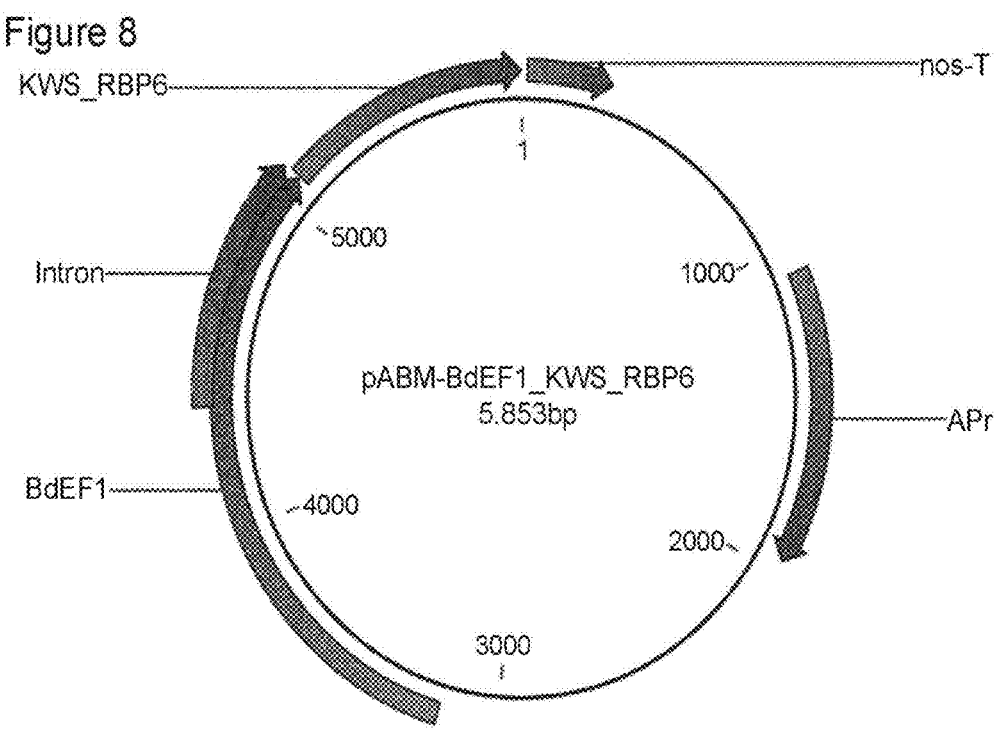
FIG. 8 shows the KWS_RBP6 expression construct pABM-BdEF1_RBP6 map. KWS_RBP6 is driven by the strong constitutive EF1 promoter from *Brachypodium* (BdEF1).
Figure 9:
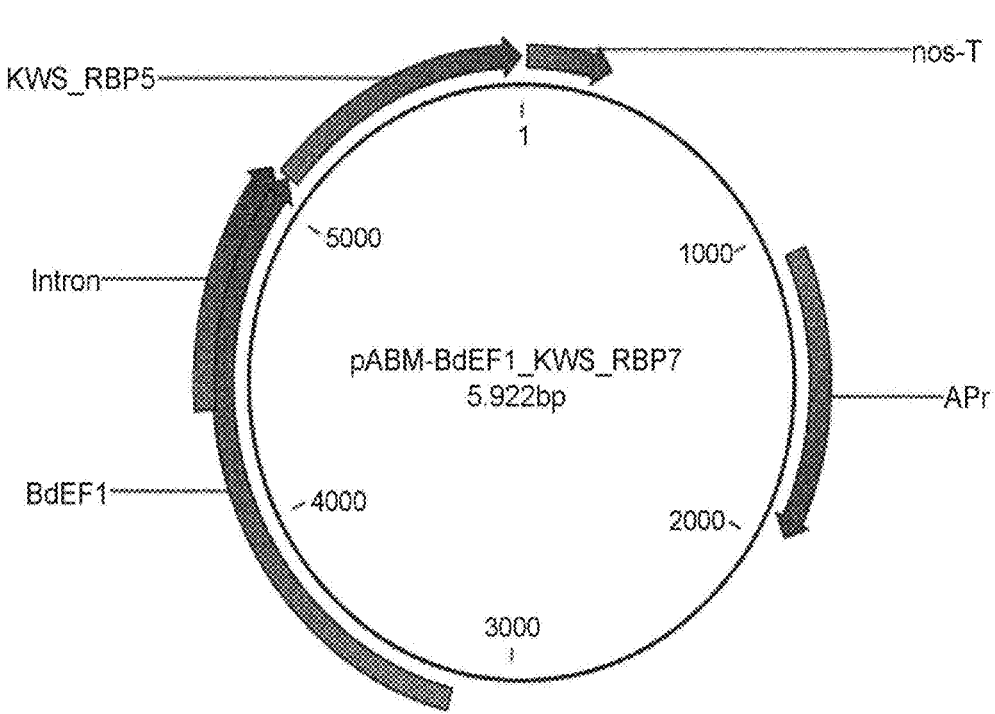
FIG. 9 shows the KWS_RBP7 expression construct pABM-BdEF1_RBP7 map. KWS_RBP7 is driven by the strong constitutive EF1 promoter from *Brachypodium* (BdEF1).
Figure 10:
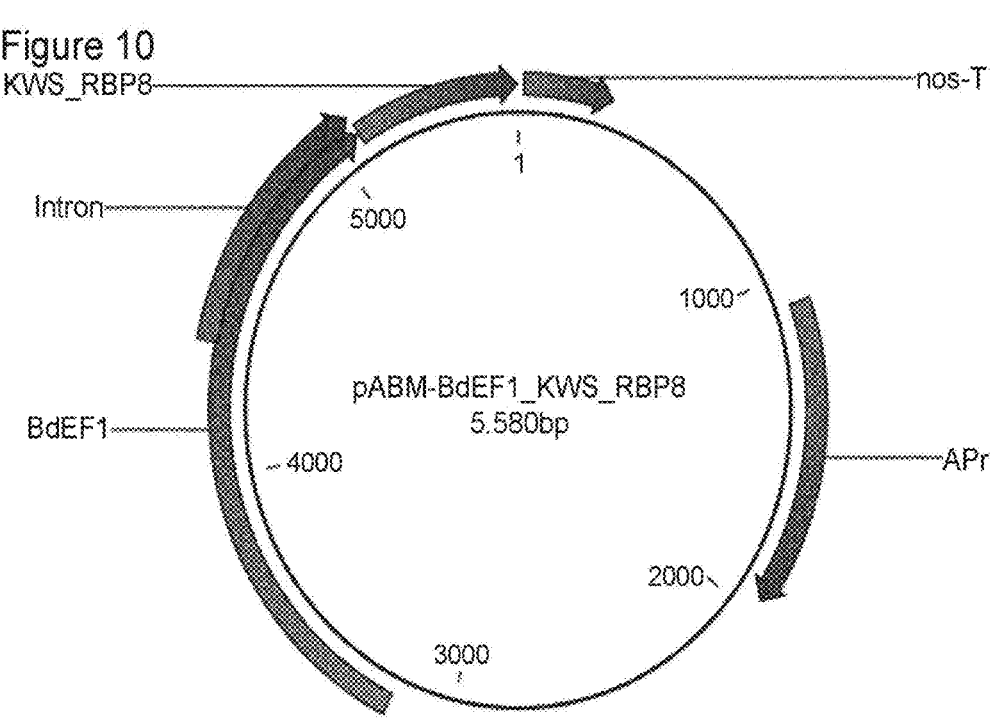
FIG. 10 shows the KWS_RBP8 expression construct pABM-BdEF1_RBP8 map. KWS_RBP8 is driven by the strong constitutive EF1 promoter from *Brachypodium* (BdEF1).

| SEQ ID NO | Brief description |
| --- | --- |
| 1 | A188-HMG13-WT_Full |
| 2 | Maize_HMG13_CDS_B73 CM000781.3 |
| 3 | Maize_HMG13_protein AFW69593.1 high mobility group protein1 [*Zea mays*] |
| 4 | BdEF1_TaRKD4_expression_cassette |
| 5 | BdEF1_ZmPLT3_expression_cassette |
| 6 | BdEF1_ZmPLT5_expression_cassette |
| 7 | BdEF1_ZmPLT7_expression_cassette |
| 8 | BdEF1_KWS_RBP1_expression_cassette |
| 9 | BdEF1_KWS_RBP2_expression_cassette |
| 10 | pABM-BdEF1_RBP3_expression_cassette |
| 11 | pABM-BdEF1_RBP4_Expression_cassette |
| 12 | pABM-BdEF1_RBP5_expression_cassette |
| 13 | pABM-BdEF1_RBP6_expression_cassette |
| 14 | pABM-BdEF1_RBP7_expression_cassette |
| 15 | pABM-BdEF1_RBP8_expression_cassette |
| 16 | TaRKD4_CDS (coding sequence) |
| 17 | ZmPLT3-17207_CDS (coding sequence) |
| 18 | ZmPLT5_CDS (coding sequence) |
| 19 | ZmPLT7_CDS (coding sequence) |
| 20 | RBP1_CDS (coding sequence) |
| 21 | RBP2_CDS (coding sequence) |
| 22 | RBP3_CDS (coding sequence) |
| 23 | RBP4_CDS (coding sequence) |
| 24 | RBP5_CDS (coding sequence) |
| 25 | RBP6_CDS (coding sequence) |
| 26 | RBP7_CDS (coding sequence) |
| 27 | RBP8_CDS (coding sequence) |
| 28 | TaRKD4_PRT (Protein) |
| 29 | ZmPLT3_PRT (Protein) |
| 30 | ZmPLT5_PRT (Protein) |
| 31 | ZmPLT7_PRT (Protein) |
| 32 | RBP1_PRT (Protein) |
| 33 | RBP2_PRT (Protein) |
| 34 | RBP3_PRT (Protein) |
| 35 | RBP4_PRT (Protein) |
| 36 | RBP5_PRT (Protein) |
| 37 | RBP6_PRT (Protein) |
| 38 | RBP7_PRT (Protein) |
| 39 | RBP8_PRT (Protein) |
| 40 | pABM-BdEF1_TaRKD4 |
| 41 | pABM-BdEF1_ZmPLT3 |
| 42 | pABM-BdEF1_ZmPLT5 (FIG. 3) |
| 43 | pABM-BdEF1_ZmPLT7 |
| 44 | pABM-BdEF1_KWS_RBP1 |
| 45 | pABM-BdEF1_KWS_RBP2 (FIG. 4) |
| 46 | pABM-BdEF1_KWS_RBP3 (FIG. 5) |
| 47 | pABM-BdEF1_KWS_RBP4 (FIG. 6) |
| 48 | pABM-BdEF1_KWS_RBP5 (FIG. 7) |
| 49 | pABM-BdEF1_KWS_RBP6 (FIG. 8) |
| 50 | pABM-BdEF1_KWS_RBP7 (FIG. 9) |
| 51 | pABM-BdEF1_KWS_RBP8 (FIG. 10) |
| 52 | pGEP837 (FIG. 1) |
| 53 | pGEP842 (FIG. 2) |
| 54 | pGEP359 (FIG. 13) |
| 55 | pGEP1054 (FIG. 15) |
| 56 | pGEP1067 (FIG. 32) |

Definitions

Unless defined otherwise, technical and scientific terms used herein have the same meaning as commonly understood by one of ordinary skill in the art to which this invention belongs.

A "base editor" as used herein refers to a protein or a fragment thereof having the same catalytic activity as the protein it is derived from, which protein or fragment thereof, alone or when provided as molecular complex, referred to as base editing complex herein, has the capacity to mediate a targeted base modification, i.e., the conversion of a base of interest resulting in a point mutation of interest which in turn can result in a targeted mutation, if the base conversion does not cause a silent mutation, but rather a conversion of an amino acid encoded by the codon comprising the position to be converted with the base editor. Usually, base editors are thus used as molecular complex. Base editors, including, for example, CBEs (base editors mediating C to T conversion) and ABEs (adenine base editors mediating A to G conversion), are powerful tools to introduce direct and programmable mutations without the need for double-stranded cleavage (Komor et al., Nature, 2016, 533(7603), 420-424; Gaudelli et al., Nature, 2017, 551, 464-471). In general, base editors are composed of at least one DNA targeting module and a catalytic domain that deaminates cytidine or adenine. All four transitions of DNA (A→T to G→C and C→G to T→A) are possible as long as the base editors can be guided to the target site. Originally developed for working in mammalian cell systems, both BEs and ABEs have been optimized and applied in plant cell systems. Efficient base editing has been shown in multiple plant species (Zong et al., *Nature Biotechnology*, vol. 25, no. 5, 2017, 438-440; Yan et al., *Molecular Plant*, vol. 11, 4, 2018, 631-634; Hua et al., *Molecular Plant*, vol. 11, 4, 2018, 627-630). Base editors have been used to introduce specific, directed substitutions in genomic sequences with known or predicted phenotypic effects in plants and animals. But they have not been used for directed mutagenesis targeting multiple sites within a genetic locus or several loci to identify novel or optimized traits.

A "CRISPR nuclease", as used herein, is a specific form of a site-directed nuclease and refers to any nucleic acid guided nuclease which has been identified in a naturally occurring CRISPR system, which has subsequently been isolated from its natural context, and which preferably has been modified or combined into a recombinant construct of interest to be suitable as tool for targeted genome engineering. Any CRISPR nuclease can be used and optionally reprogrammed or additionally mutated to be suitable for the various embodiments according to the present invention as long as the original wild-type CRISPR nuclease provides for DNA recognition, i.e., binding properties. CRISPR nucleases also comprise mutants or catalytically active fragments or fusions of a naturally occurring CRISPR effector sequences, or the respective sequences encoding the same. A CRISPR nuclease may in particular also refer to a CRISPR nickase or even a nuclease-dead variant of a CRISPR polypeptide having endonucleolytic function in its natural environment. A variety of different CRISPR nucleases/systems and variants thereof are meanwhile known to the skilled person and include, inter alia, CRISPR/Cas systems, including CRISPR/Cas9 systems (EP2771468), CRISPR/Cpf1 systems (EP3009511B1), CRISPR/C2C2 systems, CRISPR/CasX systems, CRISPR/CasY systems, CRISPR/Cmr systems, CRISPR/MAD systems, including, for example, CRISPR/MAD7 systems (WO2018236548A1) and CRISPR/MAD2 systems, CRISPR/CasZ systems and/or any combination, variant, or catalytically active fragment thereof. A nuclease may be a DNAse and/or an RNAse, in particular taking into consideration that certain CRISPR effector nucleases have RNA cleavage activity alone, or in addition to the DNA cleavage activity.

A "CRISPR system" is thus to be understood as a combination of a CRISPR nuclease or CRISPR effector, or a nickase or a nuclease-dead variant of said nuclease, or a functional active fragment or variant thereof together with the cognate guide RNA (or pegRNA or crRNA) guiding the relevant CRISPR nuclease.

As used herein, the terms "(regeneration) booster", "booster gene", "booster polypeptide", "boost polypeptide", "boost gene" and "boost factor", refer to a protein/peptide(s), or a (poly)nucleic acid fragment encoding the protein/polypeptide, which accelerate cell division and cell proliferation and thus cause improved plant regeneration, in particular of transformed or gene edited plant cells, which may be particularly suitable for improving genome engineering, i.e., the regeneration of a modified plant cell after genome engineering. Such protein/polypeptide may increase the capability or ability of a plant cell, preferably derived from somatic tissue, embryonic tissue, callus tissue or protoplast, to regenerate in an entire plant, preferably a fertile plant. Thereby, they may regulate somatic embryo formation (somatic embryogenesis) and/or they may increase the proliferation rate of plant cells. The regeneration of transformed or gene edited plant cells may include the process of somatic embryogenesis, which is an artificial process in which a plant or embryo is derived from a single somatic cell or group of somatic cells. Somatic embryos are formed from plant cells that are not normally involved in the development of embryos, i.e. plant tissue like buds, leaves, shoots etc. Applications of this process may include: clonal propagation of genetically uniform plant material; elimination of viruses; provision of source tissue for genetic transformation; generation of whole plants from single cells, such as protoplasts; development of synthetic seed technology. Cells derived from competent source tissue may be cultured to form a callus. Further, the term "regeneration booster" may refer to any kind of chemical having a proliferative and/or regenerative effect when applied to a plant cell, tissue, organ, or whole plant in comparison to a no-treated control.

As used herein, "epigenetically regulating chemical" refers to any chemical involved in regulating the epigenetic status of plant cells, e.g., DNA methylation, protein methylation and acetylation. Preferred epigenetically regulating chemicals for use according to the invention are histone deacetylase inhibitors (HDACIs). Histone deacetylase inhibitor (HDACI) refers to any materials that repress histone deacetylase activity as used herein. Such a HDACI may be trichostatin A (TSA), N-Hydroxy-7-(4-dimethylaminobenzoyl)-aminoheptanamide (M344), suberoylanilide hydroxamic acid (SAHA), or others. These HDACIs are selected from hydroxamic acid (HA)-based chemicals, which target to zinc dependent HDACs. TSA suppresses HDAC activities and increases histone acetylation (Yoshida et al, 1995; Finnin et al. 1999).

As used herein, "co-delivery" or "co-deliver" and "co-introduction" or "co-introduce" are used interchangeably. In terms of the present invention, these terms refers to the process, in which at least two different components are delivered into the same plant cell concurrently. Thus, the genome modification components and boost components are introduced together into the same plant cell. Preferably, both types of components, booster and genes of interest, are introduced via separate constructs.

A "genome" as used herein is to be understood broadly and comprises any kind of genetic information (RNA/DNA) inside any compartment of a living cell. In the context of a "genome modification", the term thus also includes artificially introduced genetic material, which may be transcribed and/or translated, inside a living cell, for example, an episomal plasmid or vector, or an artificial DNA integrated into a naturally occurring genome.

The term of "genome engineering" as used herein refers to all strategies and techniques for the genetic modification of any genetic information (DNA and RNA) or genome of a plant cell, comprising genome transformation, genome editing, but also including less site-specific techniques, including TILLING and the like. As such, "genome editing" (GE) more specifically refers to a special technique of genome engineering, wherein a targeted, specific modification of any genetic information or genome of a plant cell. As such, the terms comprise gene editing of regions encoding a gene or protein, but also the editing of regions other than gene encoding regions of a genome. It further comprises the editing or engineering of the nuclear (if present) as well as other genetic information of a plant cell, i.e., of intronic sequences, non-coding RNAs, miRNAs, sequences of regulatory elements like promoter, terminator, transcription activator binding sites, cis or trans acting elements. Furthermore, "genome engineering" also comprises an epigenetic editing or engineering, i.e., the targeted modification of, e.g., DNA methylation or histone modification, such as histone acetylation, histone methylation, histone ubiquitination, histone phosphorylation, histone sumoylation, histone ribosylation or histone citrullination, possibly causing heritable changes in gene expression.

A "genome modification system" as used herein refers to any DNA, RNA and/or amino acid sequence introduced into the cell, on a suitable vector and/or coated on a particles and/or directly introduced. A "genome editing" system more specifically refers to any DNA, RNA and/or amino acid sequence introduced into the cell, on a suitable vector and/or coated on a particles and/or directly introduced, wherein the "genome editing system" comprises at least one component being, encoding, or assisting a site-directed nuclease, nickase or inactivated variant thereof in modifying and/or repairing a genomic target site.

A "genomic target sequence" as used herein refers to any part of the nuclear and/or organellar genome of a plant cell, whether encoding a gene/protein or not, which is the target of a site-directed genome editing or gene editing experiment.

A "plant material" as used herein refers to any material which can be obtained from a plant during any developmental stage. The plant material can be obtained either in planta or from an in vitro culture of the plant or a plant tissue or organ thereof. The term thus comprises plant cells, tissues and organs as well as developed plant structures as well as sub-cellular components like nucleic acids, polypeptides and all chemical plant substances or metabolites which can be found within a plant cell or compartment and/or which can be produced by the plant, or which can be obtained from an extract of any plant cell, tissue or a plant in any developmental stage. The term also comprises a derivative of the plant material, e.g., a protoplast, derived from at least one plant cell comprised by the plant material. The term therefore also comprises meristematic cells or a meristematic tissue of a plant.

As used herein "a preselected site", "predetermined site" or "predefined site" indicates a particular nucleotide sequence in the genome (e.g. the nuclear genome, or the organellar genome, including the mitochondrial or chloroplast genome) at which location it is desired to insert, replace and/or delete one or more nucleotides. The predetermined site is thus located in a "genomic target sequence/ site" of interest and can be modified in a site-directed manner using a site- or sequence-specific genome editing system.

The terms "plant", "plant organ", or "plant cell" as used herein refer to a plant organism, a plant organ, differentiated and undifferentiated plant tissues, plant cells, seeds, and derivatives and progeny thereof. Plant cells include without limitation, for example, cells from seeds, from mature and immature embryos, meristematic tissues, seedlings, callus tissues in different differentiation states, leaves, flowers, roots, shoots, male or female gametophytes, sporophytes, pollen, pollen tubes and microspores, protoplasts, macroalgae and microalgae. The different eukaryotic cells, for example, animal cells, fungal cells or plant cells, can have any degree of ploidy, i.e. they may either be haploid, diploid, tetraploid, hexaploid or polyploid.

The term "plant parts" as used herein includes, but is not limited to, isolated and/or pre-treated plant parts, including organs and cells, including protoplasts, callus, leaves, stems, roots, root tips, anthers, pistils, seeds, grains, pericarps, embryos, pollen, sporocytes, ovules, male or female gametes or gametophytes, cotyledon, hypocotyl, spike, floret, awn, lemma, shoot, tissue, petiole, cells, and meristematic cells.

A "Prime Editing system" as used herein refers to a system as disclosed in Anzalone et al. (2019). Search-and-replace genome editing without double-strand breaks (DSBs) or donor DNA. Nature, 1-1). Base editing as detailed above, does not cut the double-stranded DNA, but instead uses the CRISPR targeting machinery to shuttle an additional enzyme to a desired sequence, where it converts a single nucleotide into another. Many genetic traits in plants and certain susceptibility to diseases caused by plant pathogens are caused by a single nucleotide change, so base editing offers a powerful alternative for GE. But the method has intrinsic limitations, and is said to introduce off-target mutations which are generally not desired for high precision GE. In contrast, Prime Editing (PE) systems steer around the shortcomings of earlier CRISPR based GE techniques by heavily modifying the Cas9 protein and the guide RNA. The altered Cas9 only "nicks" a single strand of the double helix, instead of cutting both. The new guide RNA, called a pegRNA (prime editing extended guide RNA), contains an RNA template for a new DNA sequence, to be added to the genome at the target location. That requires a second protein, attached to Cas9 or a different CRISPR effector nuclease: a reverse transcriptase enzyme, which can make a new DNA strand from the RNA template and insert it at the nicked site. To this end, an additional level of specificity is introduced into the GE system in view of the fact that a further step of target specific nucleic acid::nucleic acid hybridization is required. This may significantly reduce off-target effects. Further, the PE system may significantly increase the targeting range of a respective GE system in view of the fact that BEs cannot cover all intended nucleotide transitions/ mutations (C→A, C→G, G→C, G→T, A→C, A→T, T→A, and T→G) due to the very nature of the respective systems, and the transitions as supported by BEs may require DSBs in many cell types and organisms.

As used herein, a "regulatory sequence", or "regulatory element" refers to nucleotide sequences which are not part of the protein-encoding nucleotide sequence, but mediate the expression of the protein-encoding nucleotide sequence. Regulatory elements include, for example, promoters, cis-regulatory elements, enhancers, introns or terminators. Depending on the type of regulatory element it is located on the nucleic acid molecule before (i.e., 5' of) or after (i.e., 3' of) the protein-encoding nucleotide sequence. Regulatory elements are functional in a living plant cell.

An "RNA-guided nuclease" is a site-specific nuclease, which requires an RNA molecule, i.e. a guide RNA, to recognize and cleave a specific target site, e.g. in genomic DNA or in RNA as target. The RNA-guided nuclease forms a nuclease complex together with the guide RNA and then recognizes and cleaves the target site in a sequence-dependent matter. RNA-guided nucleases can therefore be programmed to target a specific site by the design of the guide RNA sequence. The RNA-guided nucleases may be selected from a CRISPR/Cas system nuclease, including CRISPR/ Cpf1 systems, CRISPR/C2C2 systems, CRISPR/CasX systems, CRISPR/CasY systems, CRISPR/Cmr systems, CRISPR/Cms systems, CRISPR/MAD7 systems, CRISPR/ MAD2 systems and/or any combination, variant, or catalytically active fragment thereof. Such nucleases may leave blunt or staggered ends. Further included are nickase or nuclease-dead variants of an RNA-guided nuclease, which may be used in combination with a fusion protein, or protein complex, to alter and modify the functionality of such a fusion protein, for example, in a base editor or Prime Editor.

The terms "SDN-1", "SDN-2", and "SDN-3" as used herein are abbreviations for the platform technique "site-directed nuclease" 1, 2, or 3, respectively, as caused by any site directed nuclease of interest, including, for example, Meganucleases, Zinc-Finger Nucleases (ZFNs), Transcription Activator Like Effector Nucleases (TALENs), and CRISPR nucleases. SDN-1 produces a double-stranded or single-stranded break in the genome of a plant without the addition of foreign DNA. A "site-directed nuclease" is thus able to recognize and cut, optionally assisted by further molecules, a specific sequence in a genome or an isolate genomic sequence of interest. For SDN-2 and SDN-3, an exogenous nucleotide template is provided to the cell during the gene editing. For SDN-2, however, no recombinant foreign DNA is inserted into the genome of a target cell, but the endogenous repair process copies, for example, a mutation as present in the template to induce a (point) mutation. In contrast, SDN-3 mechanism use the introduced template during repair of the DNA break so that genetic material is introduced into the genomic material.

A "site-specific nuclease" herein refers to a nuclease or an active fragment thereof, which is capable to specifically recognize and cleave DNA at a certain location. This location is herein also referred to as a "target sequence". Such nucleases typically produce a double-strand break (DSB), which is then repaired by non-homologous end-joining (NHEJ) or homologous recombination (HR). Site-specific nucleases include meganucleases, homing endonucleases, zinc finger nucleases, transcription activator-like nucleases and CRISPR nucleases, or variants including nickases or nuclease-dead variants thereof.

The terms "transformation", "transfection", "transformed", and "transfected" are used interchangeably herein for any kind of introduction of a material, including a nucleic acid (DNA/RNA), amino acid, chemical, metabolite, nanoparticle, microparticle and the like into at least one cell of interest by any kind of physical (e.g., bombardment), chemical or biological (e.g., *Agrobacterium*) way of introducing the relevant at least one material.

The term "transgenic" as used according to the present disclosure refers to a plant, plant cell, tissue, organ or material which comprises a gene or a genetic construct, comprising a "transgene" that has been transferred into the plant, the plant cell, tissue organ or material by natural means or by means of transformation techniques from another organism. The term "transgene" comprises a nucleic acid sequence, including DNA or RNA, or an amino acid sequence, or a combination or mixture thereof. Therefore, the term "transgene" is not restricted to a sequence commonly identified as "gene", i.e. a sequence encoding a protein. It can also refer, for example, to a non-protein encoding DNA or RNA sequence, or part of a sequence. Therefore, the term "transgenic" generally implies that the respective nucleic acid or amino acid sequence is not naturally present in the respective target cell, including a plant, plant cell, tissue, organ or material. The terms "transgene" or "transgenic" as used herein thus refer to a nucleic acid sequence or an amino acid sequence that is taken from the genome of one organism, or produced synthetically, and which is then introduced into another organism, in a transient or a stable way, by artificial techniques of molecular biology, genetics and the like.

As used herein, the term "transient" implies that effectors, including all kinds of nucleic acid (RNA and/or DNA) and polypeptide-based molecules optionally including chemical carrier molecules, are only temporarily introduced and/or expressed and/or activated and, e.g. afterwards degraded by the cell, whereas "stable" implies that at least one of the effectors is integrated into the nuclear and/or organellar genome of the cell to be modified and therefore inherited to the progeny. "Transient expression" refers to the phenomenon where the transferred protein/polypeptide and/or nucleic acid fragment encoding the protein/polypeptide is expressed, present and/or active transiently in the cells, and turned off and/or degraded shortly with the cell growth. Transient expression thus also implies a stably integrated construct, for example, under the control of an inducible promoter as regulatory element, to regulate expression in a fine-tuned manner by switching expression on or off.

The terms "vector", or "plasmid (vector)" refer to a construct comprising, inter alia, plasmids or (plasmid) vectors, cosmids, artificial yeast- or bacterial artificial chromosomes (YACs and BACs), phagemides, bacterial phage based vectors, *Agrobacterium* compatible vectors, an expression cassette, isolated single-stranded or double-stranded nucleic acid sequences, comprising sequences in linear or circular form, or amino acid sequences, viral vectors, viral replicons, including modified viruses, and a combination or a mixture thereof, for introduction or transformation, transfection or transduction into any eukaryotic cell, including a plant, plant cell, tissue, organ or material according to the present disclosure. A "nucleic acid vector, for instance, is a DNA or RNA molecule, which is used to deliver foreign genetic material to a cell, where it can be transcribed and optionally translated. Preferably, the vector is a plasmid comprising multiple cloning sites. The vector may further comprise a "unique cloning site" a cloning site that occurs only once in the vector and allows insertion of DNA sequences, e.g. a nucleic acid cassette or components thereof, by use of specific restriction enzymes. A "flexible insertion site" may be a multiple cloning site, which allows insertion of the components of the nucleic acid cassette according to the invention in an arrangement, which facilitates simultaneous transcription of the components and allows activation of the RNA activation unit.

Whenever the present disclosure relates to the percentage of the homology or identity of nucleic acid or amino acid sequences to each other over the entire length of the sequences to be compared to each other, wherein these identity or homology values define those as obtained by using the EMBOSS Water Pairwise Sequence Alignments (nucleotide) programme nucleic acids or the EMBOSS Water Pairwise Sequence Alignments (protein) programme for amino acid sequences. Those tools provided by the European Molecular Biology Laboratory (EMBL) European Bioinformatics Institute (EBI) for local sequence alignments use a modified Smith-Waterman algorithm (see ebi.ac.uk/Tools/psa/and Smith, T. F. & Waterman, M. S. "Identification of common molecular subsequences" *Journal of Molecular Biology,* 1981 147 (1):195-197). When conducting an alignment, the default parameters defined by the EMBL-EBI are used. Those parameters are (i) for amino acid sequences: Matrix=BLOSUM62, gap open penalty=10 and gap extend penalty=0.5 or (ii) for nucleic acid sequences: Matrix=DNAfull, gap open penalty=10 and gap extend penalty=0.5.

DETAILED DESCRIPTION

The present invention provides methods for rapid and highly efficient genome modification in a single cell as well as regeneration of a plant from a single cell. The invention describes nucleotides/proteins of regeneration boosters and methods to increase regeneration capabilities of plant cells; when co-delivered with genome modification machinery, genome modification is promoted. Using the regeneration boosters or combinations of regeneration boosters, it is possible to positively select transient expression delivery of the boosters and negatively select stable transgenic cells continuously expressing the boosters during regeneration. This "dual selection" allows on the one hand to profit from the improved genome modification efficiency and enhanced proliferation and regeneration provided by the regeneration boosters but on the other hand to exclude plants, which continuously express the boosters negatively impacting differentiation and subsequent development. The modification is stably inherited to the progeny of the regenerated plant while the modification tools are preferably only transiently present or expressed in the cell to be modified and are no longer present in the regenerated plant. Thus, it is possible to obtain a fertile transgene-free plant carrying the modification with minimal somatic variation.

Another type of effectors, which can promote genetic modification and increase genome editing SDN1 efficiency, are epigenetically regulating chemicals.

The basic structural and functional unit of genetic material is the nucleosome, in which negatively charged DNA wraps around a positively charged histone octamer and associated linker histones. Nucleosome units further fold and pack into chromatin (Andrews, A. J., and Luger, K. 2011. Nucleosome structure(s) and stability: Variations on a theme. Annu. Rev. Biophys. 40: 99-117.). DNA accessibility largely depends on compactness of the nucleosomes and chromatins. Chromatin-remodeling enzymes dynamically modify lysine or other amino acids of histones, which cause changes in their charges and interactions with DNA and other proteins, and result in chromatin folding or unfolding (Bannister A J, Kouzarides T. 2011, Regulation of chromatin by histone modifications. Cell Res. 21: 381-95.). By adding or removing an acetyl group, acetylation and deacetylation of the lysine residue in histone proteins are often involved in the reversible modulation of chromatin structure in eukaryotes, and mediate chromatin accessibility and gene expression. Histone deacetylases (HDACs) are enzymes that remove acetyl groups from lysine resides on the N-terminal tail of histones, which makes the histone more positively charged, and therefore allows the histone wrap DNA more tightly. And thus, inhibition of HDACs may help chromatin unfolding and enable the DNA to be more accessible.

It is assumed that histone deacetylase inhibitors (HAD-CIs) will relax plant chromatin structure and promote the DNA accessibility to the genome modification machinery when it is co-delivered with the modification component(s) in the introduced cells, thus consequently promote genome modification, e.g., genome editing efficiency. Described herein are methods to increase genome modification efficiency, in particularly genome editing SDN-1 efficiency in presence of at least one selected epigenetically regulating chemical, preferably histone deacetylase inhibitors (HDA-CIs).

In one aspect, the present invention provides a method for plant genome modification, preferably for the targeted modification of at least one genomic target sequence, for obtaining at least one modified cell wherein the method comprises the following steps:

(a) providing at least one plant cell or a single plant cell;

(b) introducing into the at least one plant cell or the single plant cell:

(i) at least one genome modification system, preferably a genome editing system comprising at least one site-directed nuclease, nickase or an inactivated nuclease, preferably a nucleic acid guided nuclease, nickase or an inactivated nuclease, or a sequence encoding the same, and optionally at least one guide molecule, or a sequence encoding the same;

(ii) at least one regeneration booster, or a sequence encoding the same and/or at least one epigenetically regulating chemical, wherein the at least one regeneration booster is transiently present, transiently active or transiently expressed in the plant cell;

(iii) and, optionally at least one repair template, or a sequence encoding the same; and (c) cultivating the at least one plant cell or the single plant cell under conditions allowing the expression and/or assembly and/or activation of the at least one genome modification system, preferably the at least one genome editing system, and, optionally of the at least one regeneration booster, and optionally of the at least one guide molecule and/or optionally of the at least one repair template; and (d) obtaining at least one modified plant cell; and/or (e) obtaining at least one plant tissue, organ, plant or seed regenerated from the at least one modified cell; and (f) optionally: screening for at least one plant tissue, organ, plant or seed regenerated from the at least one modified cell in the T0 and/or T1 generation carrying a desired targeted modification.

In the method according to the invention, the use of the regeneration booster(s) provides an increased genome editing efficiency and enhances proliferation of the edited cell to regenerate a plant. The cells, in which the regeneration boosters are only transiently present, transiently active or transiently expressed in the cell, further develop into mature plants.

Transient expression, transient presence or transient activity of the booster(s) in the cell is achieved by introduction of the booster(s) or the nucleic acid sequence encoding the booster(s) into the target cell resulting in gene expression and/or activity without integration of the coding sequence into the genome of the target cell. The regeneration booster genes are expressed transiently, preferably under a strong constitutive promoter and then turned off and/or degraded. For example, the strong constitutive promoter from *Brachypodium* EF1 gene may be used to drive booster gene expression for transient transformation. The booster genes are translated and active transiently, and turned off and degraded shortly with plant cell development or if the expressing conditions are removed.

The epigenetically regulating chemical may be introduced optionally in addition to the regeneration boosters or it may also be introduced without any regeneration boosters to improve the genome editing efficiency.

In one embodiment, the epigenetically regulating chemical is delivered into explant cells via a pre-treatment of the cells as described further below.

In another embodiment, the epigenetically regulating chemical is co-delivered with the genome editing components into explant cells via co-bombardment. This represents the preferred method, which provides a selective mechanism for the co-delivered cells to achieve genome editing and regeneration.

In yet another embodiment, the epigenetically regulating chemical is co-delivered with the genome editing components and at least one regeneration booster gene construct into explant cells via co-bombardment. This represents a highly preferred method for recalcitrant genotypes, which provides a highly selective mechanism for the delivered cells to achieve genome editing and regeneration.

In another embodiment, the epigenetically regulating chemical is delivered via both, pretreatment and co-bombardment.

In one embodiment of the method described above, steps (i) and (ii) take place simultaneously or subsequently, for promoting plant cell proliferation and/or to assist in a targeted modification of at least one genomic target sequence.

Preferably, all exogenously provided elements or tools of a genome or gene editing system as well as the regeneration booster(s), or sequences encoding the same and/or the epigenetically regulating chemical, and optionally provided repair template sequences are provided either simultaneously or subsequently, wherein the terms simultaneously and subsequently refers to the temporal order of introducing the relevant elements, with the proviso that both simultaneous and subsequent introduction guarantee that one and the same cell will comprise the relevant elements in an active and/or expressible manner. Ultimately, all genome or gene editing system elements are thus physically present in one cell. In particular, the boosters being present and active during genome editing assist in the targeted modification making it more efficient and subsequently enhance proliferation regeneration of the modified cell.

In one embodiment of the method according to any of the embodiments described above, at least one regeneration booster is introduced in step (ii) and (a) the regeneration booster(s) promote plant cell proliferation and/or assist in the targeted modification and/or provide a positive selection for at least one transiently transformed cell for genome modification and/or for regeneration into at least one modified plant, and/or (b) the regeneration booster(s) suppress plant cell differentiation if the cell is stably transformed and provide a negative selection for at least one stably transformed cell for regeneration into one transgenic plant, and/or (c) the regeneration booster(s) provide a dual selection according to (a) and (b) for at least one transformed cell.

As explained above, the regeneration booster(s) increase genome editing efficiency and at the same time promote proliferation of transiently transformed cells while suppressing plant cell differentiation of stably transformed cells. This dual selection advantageously allows to regenerate a modified plant, which does not pass on the genome editing tools to its progeny but merely carries the desired modification.

In one embodiment of the method according to any of the embodiments described above, the at least one plant cell is an immature embryo cell or a meristematic cell, in particular a cell of a zygotic or somatic embryo or meristem or the single plant cell is a diploid cell or a haploid cell, preferably a haploid microspore.

An immature embryo represents a suitable state of development, into which a targeted genome modification may be introduced and a modified plant may be regenerated from the embryo cell. Either zygotic embryos or somatic somatic embryos derived from any type of plant material, shoot, hypocotyl, cotyledon, stem, leave, petiole, root, flower, gametophyte or part thereof may be used.

The plant cells into which genome modification/editing components have been introduced are cultured under suitable conditions allowing the genome modification to occur in said plant cell by activity of the genome modification/editing components in the presence of the at least one regeneration booster and/or the at least one epigenetically regulating chemical. The genetically modified plant cells can be regenerated into a whole plant. Thus, the genetic modification of a plant cell is followed by a step of regenerating a plant.

The method according to the invention may therefore comprise the following steps:

1. Prepare plant cells as part of preferably immature embryos (IEs), either zygotic embryos or somatic embryos.
2. The delivery of genome modification components and regeneration boosters and/or the at least one epigenetically regulating chemical e.g. via particle bombardment into the plant cells.

During regeneration, single or multiple cells proliferate and develop into tissues, organs, and eventually entire plants. Accordingly, the regeneration of plant cells as part of the immature embryos (IEs), either zygotic embryos or somatic embryos after the delivery of genome modification/editing components, may comprise the steps of:

a. Plant cell proliferation and embryogenic callus induction for 1-4 weeks, preferably 1-3 weeks, most preferably 7-14 day;
b. Plant organ/embryo development of the calluses from (a) for 1-4 weeks, preferably 1-3 weeks, most preferably 10-18 days
c. Plantlet development of the organs/embryos from (b) for 1-4 weeks, preferably 4-10 days Certain regeneration booster sequences, usually representing transcription factors active during various stages of plant development and also known as morphogenic regulators in plants, are known for long, including the Wuschel (WUS) and babyboom (BBM) class of boosters (Mayer, K. F. et al. Role of WUSCHEL in regulating stem cell fate in the *Arabidopsis* shoot meristem. *Cell* 95, 805-815 (1998); Yadav, R. K. et al. WUSCHEL protein movement mediates stem cell homeostasis in the *Arabidopsis* shoot apex. *Genes Dev* 25, 2025-2030 (2011); Laux, T., Mayer, K. F., Berger, J. & Jügens, G. The WUSCHEL gene is required for shoot and floral meristem integrity in *Arabidopsis*. *Development* 122, 87-96 (1996); Leibfried, A. et al. WUSCHEL controls meristem function by direct regulation of cytokinin-inducible response regulators. *Nature* 438, 1172-1175 (2005); for BBM: Hofmann, A Breakthrough in Monocot Transformation Methods, The Plant Cell, Vol. 28:1989, September 2016). Others, including the RKD (including TaRKD4) and LEC family of transcription factors have been steadily emerging and are meanwhile known to the skilled person (Hofmann, A Breakthrough in Monocot Transformation Methods The Plant Cell, Vol. 28: 1989, September 2016; New Insights into Somatic Embryogenesis: LEAFY COTY-LEDONI, BABY BOOM1 and WUSCHEL-RELATED HOMEOBOX4 Are Epigenetically Regulated in *Coffea canephora*, PLos one August 2013, vol. 8(8), e72160; LEAFY COTYLEDONI-CASEIN KINASE I-TCP15-PHY-TOCHROME INTERACTING FACTOR4 Network Regulates Somatic Embryogenesis by Regulating Auxin Homeostasis Plant Physiology_, December 2015, Vol. 169, pp. 2805-2821; A. Cagliari et al. New insights on the evolution of Leafy cotyledon1 (LEC1) type genes in vascular plants Genomics 103 (2014) 380-387, U.S. Pat. No. 6,825,397B1; U.S. Pat. No. 7,960,612B2, WO2016146552A1).

The Growth-Regulating Factor (GRF) family of transcription factors, which is specific to plants, is also known to the skilled person. At least nine GRF polypeptides have been identified in *Arabidopsis thaliana* (Kim et al. (2003) Plant J 36: 94-104), and at least twelve in *Oryza sativa* (Choi et al. (2004) Plant Cell Physiol 45(7): 897-904). The GRF polypeptides are characterized by the presence in their N-terminal half of at least two highly conserved domains, named after the most conserved amino acids within each domain: (i) a QLQ domain (InterPro accession IPR014978, PFAM accession PF08880), where the most conserved amino acids of the domain are Gln-Leu-Gln; and (ii) a WRC domain (InterPro accession IPR014977, PFAM accession PF08879), where the most conserved amino acids of the domain are TrpArg-Cys. The WRC domain further contains two distinctive structural features, namely, the WRC domain is enriched in basic amino acids Lys and Arg, and further comprises three Cys and one His residues in a conserved spacing (CX9CX10CX2H (SEQ ID NO: 57)), designated as the Effector of Iranscription (ET) domain (Ellerstrom et al. (2005) Plant Molec Biol 59: 663-681). The conserved spacing of cysteine and histidine residues in the ET domain is reminiscent of zinc finger (zinc-binding) proteins. In addition, a nuclear localisation signal (NLS) is usually comprised in the GRF polypeptide sequences.

Another class of potential regeneration boosters, yet not studied in detail for their function in artificial genome/gene editing, is the class of PLETHORS (PLT) transcription factors (Aida, M., et al. (2004). The PLETHORA genes mediate patterning of the *Arabidopsis* root stem cell niche. Cell 119: 109-120; Mahönen, A. P., et al. (2014). PLETHORA gradient formation mechanism separates auxin responses. Nature 515: 125-129). Organ formation in animals and plants relies on precise control of cell state transitions to turn stem cell daughters into fully differentiated cells. In plants, cells cannot rearrange due to shared cell walls. Thus, differentiation progression and the accompanying cell expansion must be tightly coordinated across tissues. PLETHORA (PLT) transcription factor gradients are unique in their ability to guide the progression of cell differentiation at different positions in the growing *Arabidopsis thaliana* root, which contrasts with well-described transcription factor gradients in animals specifying distinct cell fates within an essentially static context. To understand the output of the PLT gradient, the gene set transcriptionally controlled by PLTs were studied and it was revealed how the PLT gradient can regulate cell state by region-specific induction of cell proliferation genes and repression of differentiation. Moreover, PLT targets include major patterning genes and autoregulatory feedback components, enforcing their role as master regulators of organ development (Santuari et al., 2016, DOI: doi.org/10.1105/tpc.16.00656). PLT, also called AIL (AINTEGUMENT-LIKE) genes, are members of the AP2 family of transcriptional regulators. Members of the AP2 family of transcription factors play important roles in cell proliferation and embryogenesis in plants (El Ouakfaoui, S. et al., (2010) Control of somatic embryogenesis and embryo development by AP2 transcription factors. PLANT MOLECULAR BIOLOGY 74(4-5):313-326.). PLT genes are expressed mainly in developing tissues of shoots and roots, and are required for stem cell homeostasis, cell division and regeneration, and for patterning of organ primordia. PLT family comprises an AP2 subclade of six members. Four PLT members, PLT1/AIL3 PLT2/, AIL4, PLT3/A/L6, and BBM/PLT4/AIL2, are expressed partly overlap in root apical meristem (RAM) and required for the expression of QC (quiescent center) markers at the correct position within the stem cell niche. These genes function redundantly to maintain cell division and prevent cell differentiation in root apical meristem. Three PLT genes, PLT3/AIL6, PLT5/AIL5, and PLT7/AIL7, are expressed in shoot apical meristem (SAM), where they function redundantly in the positioning and outgrowth of lateral organs. PLT3, PLT5, and PLT7, regulate de novo shoot regeneration in *Arabidopsis* by controlling two distinct developmental events. PLT3, PLT5, and PLT7 required to maintain high levels of PIN1 expression at the periphery of the meristem and modulate local auxin production in the central region of the SAM which underlies phyllotactic transitions. Cumulative loss of function of these three genes causes the intermediate cell mass, callus, to be incompetent to form shoot progenitors, whereas induction of PLT5 or PLT7 can render shoot regeneration in a hormoneindependent manner. PLT3, PLT5, PLT7 regulate and require the shoot-promoting factor CUPSHAPED COTYLEDON2 (CUC2) to complete the shoot-formation program. PLT3, PLT5, and PLT7, are also expressed in lateral root founder cells, where they redundantly activate the expression of PLT1 and PLT2, and consequently regulate lateral root formation.

Regeneration boosters derived from naturally occurring transcription factors, as, for example, BBM or WUS, and variants thereof, may have the significant disadvantage that uncontrolled activity in a plant cell over a certain period of time will have deleterious effects on a plant cell. Therefore, the present inventors conducted a series of in silico work to create fully artificial regeneration booster proteins after a series of multiple sequence alignment, domain shuffling, truncations and codon optimization for various target plants. By focusing on core consensus motifs, it was an object to identify new variants of regeneration boosters not occurring in nature that are particularly suitable for use in plant regeneration from single cell origin, in particular in the context of genome modifications and gene editing. Various gymnosperm sequences occurring in different species presently not considered as having a regeneration booster activity of described booster genes and proteins were particularly considered in the design process of the new booster sequences.

Based on this work, it was now found that specific regeneration boosters (cf. SEQ ID NOs: 20 to 27, 32 to 39, regeneration booster proteins 1 to 8 (RBP1-8)), as well as certain modified regeneration boosters naturally acting as transcription factors (SEQ ID NOs: 16 to 19, 28 to 31) artificially created perform particularly well in combination with the methods disclosed herein, as they promote regeneration and additionally have the capacity to improve genome or gene editing efficiencies. Further, the artificially created and then stepwise selected and tested regeneration boosters do not show pleiotropic effects and are particularly suitable to be used during any kind of genome modification and/or gene editing. The boosters or booster combinations described herein allow to positively select transient expression delivery and negatively select stable transgenic cells continuously expressing the boosters during regeneration.

In one embodiment of the method according to any of the embodiments described above, the at least one regeneration booster comprises at least one RBP, wherein the at least one RBP comprises an amino acid sequence selected from the group consisting of SEQ ID NOs: 32, 33, 34, 35, 36, 37, 38 and 39, or a sequence having at least 80%, 81%, 82%, 83%, 84%, 85%, 86%, 87%, 88%, 89%, 90%, 91%, 92%, 93%, 94%, 95%, 96%, 97%, 98% or 99% sequence identity thereto, or a catalytically active fragment thereof, or wherein the at least one RBP is encoded by a sequence selected from the group consisting of SEQ ID NOs: 20, 21, 22, 23, 24, 25, 26 and 27, or a sequence having at least 80%, 81%, 82%, 83%, 84%, 85%, 86%, 87%, 88%, 89%, 90%, 91%, 92%, 93%, 94%, 95%, 96%, 97%, 98% or 99% sequence identity thereto, or a cognate codon-optimized sequence.

The artificial regeneration boosters RBP1 to RBP8 may be used in any combination with each other or and/or in combination with other boosters. RBP1 may be used in combination with RBP2, or in combination with RBP3, or in combination with RBP4, or in combination with RBP5, or in combination with RBP6, or in combination with RBP7, or in combination with RBP8. RBP2 may be used in combination with RBP3, or in combination with RBP4, or in combination with RBP5, or in combination with RBP6, or in combination with RBP7, or in combination with RBP8. RBP3 may be used in combination with RBP4, or in combination with RBP5, or in combination with RBP6, or in combination with RBP7, or in combination with RBP8. RBP4 may be used in combination with RBP5, or in combination with RBP6, or in combination with RBP7, or in combination with RBP8. RBP5 may be used in combination with RBP6, or in combination with RBP7, or in combination with RBP8. RBP6 may be used in combination with RBP7, or in combination with RBP8. RBP8 may also be used in combination with RBP7. The artificial regeneration boosters RBP1 to RBP8 may also be used in any combination of two, three, four, five, six, seven or all of the boosters RBP1 to RBP8.

Preferably, RBP1 to RBP8 or any combination thereof are combined with one of a PLT or RKD booster. RBP1 may be used in combination with PLT3, or in combination with PLT5, or in combination with PLT7, or in combination with RKD4. RBP2 may be used in combination with PLT3, or in combination with PLT5, or in combination with PLT7, or in combination with RKD4. RBP3 may be used in combination with PLT3, or in combination with PLT5, or in combination with PLT7, or in combination with RKD4. RBP4 may be used in combination with PLT3, or in combination with PLT5, or in combination with PLT7, or in combination with RKD4. RBP5 may be used in combination with PLT3, or in combination with PLT5, or in combination with PLT7, or in combination with RKD4. RBP6 may be used in combination with PLT3, or in combination with PLT5, or in combination with PLT7, or in combination with RKD4. RBP7 may be used in combination with PLT3, or in combination with PLT5, or in combination with PLT7, or in combination with RKD4. RBP8 may be used in combination with PLT3, or in combination with PLT5, or in combination with PLT7, or in combination with RKD4. In one preferred embodiment of the method according to any of the embodiments described above, the at least one regeneration booster further comprises at least one PLT or RKD4, wherein the at least one PLT or RKD4 comprises an amino acid sequence selected from the group consisting of SEQ ID NOs: 28, 29, 30 and 31, or a sequence having at least 80%, 81%, 82%, 83%, 84%, 85%, 86%, 87%, 88%, 89%, 90%, 91%, 92%, 93%, 94%, 95%, 96%, 97%, 98% or 99% sequence identity thereto, or a catalytically active fragment thereof, or wherein the at least one PLT or RKD4 is encoded by a sequence selected from the group consisting of SEQ ID NOs: 16, 17, 18 and 19, or a sequence having at least 80%, 81%, 82%, 83%, 84%, 85%, 86%, 87%, 88%, 89%, 90%, 91%, 92%, 93%, 94%, 95%, 96%, 97%, 98% or 99% sequence identity thereto, or a cognate codon-optimized sequence.

The artificial regeneration boosters RBP1 to RBP8 or combinations thererof may also be used in combination with one or more boosters selected from BBM, WUS, WOX, GRF or LEC. RBP1 may be used in combination with BBM, or in combination with WUS, or in combination with WOX, or in combination with GRF or in combination with LEC. RBP2 may be used in combination with BBM, or in combination with WUS, or in combination with WOX, or in combination with GRF or in combination with LEC. RBP3 may be used in combination with BBM, or in combination with WUS, or in combination with WOX, or in combination with GRF or in combination with LEC. RBP4 may be used in combination with BBM, or in combination with WUS, or in combination with WOX, or in combination with GRF or in combination with LEC. RBP5 may be used in combination with BBM, or in combination with WUS, or in combination with WOX, or in combination with GRF or in combination with LEC. RBP6 may be used in combination with BBM, or in combination with WUS, or in combination with WOX, or in combination with GRF or in combination with LEC. RBP7 may be used in combination with BBM, or in combination with WUS, or in combination with WOX, or in combination with GRF or in combination with LEC. RBP8 may be used in combination with BBM, or in combination with WUS, or in combination with WOX, or in combination with GRF or in combination with LEC.

In one embodiment of the method according to any of the embodiment described above, a further regeneration booster is introduced, wherein the further regeneration booster, or the sequence encoding the same is selected from BBM, WUS, WOX, GRF, LEC, or a variant thereof or the further regeneration booster is a regeneration booster selected from RBP1 to RBP8, wherein the further regeneration booster is different from the first regeneration booster.

In one embodiment of the method according to any of the embodiments described above, the at least one regeneration booster comprises at least one RBP, wherein the at least one RBP comprises an amino acid sequence selected from the group consisting of SEQ ID NOs: 32, 33, 34, 35, 36, 37, 38 and 39, or a sequence having at least 80%, 81%, 82%, 83%, 84%, 85%, 86%, 87%, 88%, 89%, 90%, 91%, 92%, 93%, 94%, 95%, 96%, 97%, 98% or 99% sequence identity thereto, or a catalytically active fragment thereof, or wherein the at least one RBP is encoded by a sequence selected from the group consisting of SEQ ID NOs: 20, 21, 22, 23, 24, 25, 26 and 27, or a sequence having at least 80%, 81%, 82%, 83%, 84%, 85%, 86%, 87%, 88%, 89%, 90%, 91%, 92%, 93%, 94%, 95%, 96%, 97%, 98% or 99% sequence identity thereto, or a cognate codon-optimized sequence, and the at least one regeneration booster comprises PLT5, wherein the PLT5 comprises an amino acid sequence of SEQ ID NO: 30, or a sequence having at least 80%, 81%, 82%, 83%, 84%, 85%, 86%, 87%, 88%, 89%, 90%, 91%, 92%, 93%, 94%, 95%, 96%, 97%, 98% or 99% sequence identity thereto, or a catalytically active fragment thereof, or wherein the PLT5 is encoded by a nucleic acid sequence of SEQ ID NO: 18, or a sequence having at least 80%, 81%, 82%, 83%, 84%, 85%, 86%, 87%, 88%, 89%, 90%, 91%, 92%, 93%, 94%, 95%, 96%, 97%, 98% or 99% sequence identity thereto, or a cognate codon-optimized sequence.

According to the various embodiments and aspects disclosed herein, it may be preferable to use a naturally occurring regeneration booster in addition to an artificial RBP according to the present invention, wherein the naturally occurring regeneration booster, e.g., BBM, WUS1/2, LEC1/2, GRF, or a PLT may be derived from a target plant to be transformed, or from a closely related species. For monocot plant modifications, for example, a booster protein with monocot origin (e.g., from *Zea mays* (Zm)) may be preferred, whereas for dicot plant modifications, a booster protein with dicot origin (e.g., originating from *Arabidopsis thaliana* (At), or *Brassica napus* (Bn)) may be preferred. The relevant booster sequences can be easily identified by sequence searches within the published genome data. Notably, regeneration boosters from one plant species may show a certain cross-species applicability so that, for example, a wheat-derived booster gene may be used in *Zea mays*, and vice versa, or a *Arabidopsis*- or *Brachypodium*-derived booster gene may be used in *Helianthus*, and vice versa. A PLT, WUS, WOX, BBM, LEC, RKD4, or GRF sequence as used herein, or a protein with a comparable regeneration booster function, may thus be derived from any plant species harbouring a corresponding gene encoding the respective booster in its genome.

The use of at least one regeneration booster in an artificial and controlled context according to the methods disclosed herein thus has the effect of promoting plant cell proliferation. This effect is highly favourable for any kind of plant genome modification, as it promotes cell regeneration after introducing any plasmid or chemical into the at least one plant cell via transformation and/or transfection, as these interventions necessarily always cause stress to a plant cell.

Additionally, or alternatively, the at least one regeneration booster according to the methods disclosed herein may have a specific effect in enhancing plant genome editing efficiency. In particular, this kind of intervention caused by at least one site-specific nuclease, nickase or a variant thereof, causes a certain repair and stress response in a plant. The presence of at least one regeneration booster can thus also improve the efficiency of genome or gene editing by increasing the regeneration rate of a plant cell after a modification of the plant genome.

In one embodiment, at least one regeneration booster, or a sequence encoding the same, or a regeneration booster chemical, can be provided simultaneously with other tools to be inserted, namely the at least one genome modification system, preferably the genome editing system to reduce the number of transformation/transfection acts potentially stressful for a cell. For certain cells sensitive to transformation/transfection, regeneration booster chemicals may thus represent a suitable option, which may be provided before, simultaneously with, or soon after transforming/transfecting further genome or gene editing tools to reduce the cellular stress and to increase transformation and/or editing efficiency by stabilizing a cell and thus by reducing potentially harmful cellular stress responses.

In another embodiment, the at least one genome modification system, preferably the genome editing system and the at least one regeneration booster, or the sequence encoding the same, may be provided subsequently or sequentially. By separating the introduction steps, the editing construct DNA integration of the site-directed nuclease, nickase or an inactivated nuclease encoding sequence can be avoided, where transient outcomes are of interest.

In certain embodiments, it is favourable that the at least one regeneration booster is active in a cell before further tools are introduced to put the cell into a state of low cellular stress before performing genome or gene editing.

For any simultaneous or subsequent introduction of at least one regeneration booster, the regeneration booster and the optional further genome modification or genome editing system should be active, i.e., present in the active protein and/or RNA stage, in one and the same cell to be modified, preferably in the nucleus of the cell, or in an organelle comprising genomic DNA to be modified.

In one embodiment of the methods according to any of the embodiments described above, at least one epigenetically regulating chemical is introduced in step ii) and the at least one epigenetically regulating chemical is a histone deacetylase inhibitor (HDACI), in particular trichostatin A (TSA) or a TSA like chemical.

In one embodiment of the method according to any of the embodiments described above, the at least one genome modification system, preferably the at least one genome editing system, and the at least one regeneration booster, or the sequences encoding the same and/or the at least one epigenetically regulating chemical, are introduced into the cell by transformation or transfection mediated by biolistic bombardment, *Agrobacterium*-mediated transformation, micro- or nanoparticle delivery, or by chemical transfection, or a combination thereof, preferably wherein the at least one genome modification system, preferably the at least one genome editing system, and the at least one regeneration booster and/or the at least one epigenetically regulating chemical are introduced by biolistic bombardment, preferably wherein the biolistic bombardment comprises a step of osmotic treatment before and/or after bombardment.

Particle or biolistic bombardment may be a preferred strategy according to the methods disclosed herein, as it allows the direct and targeted introduction of exogenous nucleic acid and/or amino acid material in a precise manner not relying on the biological spread and expression of biological transformation tools, including *Agrobacterium*.

Particle bombardment or biolistic bombardment refers to a physical delivery method for transferring a coated microparticle or nanoparticle comprising a construct of interest into a target cell or tissue. For use in the present invention, constructs of interest comprise genome modification components and at least one regeneration booster. The transformation via particle bombardment uses a microprojectile of metal covered with the construct(s) of interest, which is then shot onto the target cells using an equipment known as "gene gun" (Sandford et al. 1987) at high velocity fast enough (~1500 km/h) to penetrate the cell wall of a target tissue, but not harsh enough to cause cell death. The coated components on the at least one microprojectile are released into the cell after bombardment. The acceleration of microprojectiles is accomplished by a high voltage electrical discharge or compressed gas (helium). Concerning the metal particles used it is mandatory that they are non-toxic, non-reactive, and that they have a lower diameter than the target cell. The most commonly used are gold or tungsten. There is plenty of information publicly available from the manufacturers and providers of gene-guns and associated system concerning their general use.

The microparticle consists of a non-toxic, non-reactive material. Preferably, the microparticle comprises a metal such as gold or tungsten. The coating with genome modification and boost components can comprise one or more coating layers. For example, a microparticle may contain a first coating layer comprising genome modification component and a second coating layer comprising the regeneration booster compound. The regeneration boosters can be co-delivered with the genome modification components via microcarriers comprising gold particles having a size in a range of 0.4-1.6 micron (μm), preferably 0.4-1.0 μm. Regeneration boosters and genome modification components can be delivered into target cells for example using a Bio-Rad PDS-1000/He particle gun or handheld Helios gene gun system. More than one chemical or booster construct can be co-delivered with genome modification components into target cells simultaneously. In an exemplary process, 10 ng-10 μg of DNA, preferably 50-1000 ng of DNA, coated onto 10-1000 μg of gold particles, preferably 50-500 μg, are used per one bombardment (shot). When a PDS-1000/He particle gun system used, the bombardment rupture pressures are from 450 psi to 2200 psi, preferred from 450-1,500 psi, more preferably 450-1,100 psi. Up to bombardments (shots), preferred 1-4 shots, per one sample plate can be used for the delivery of foreign molecules into plant cells.

According to a preferred embodiment of the method described above, optionally at least one epigenetically regulating chemical can be introduced into at least one plant cell via in vitro pre-treatment of plant materials in a medium containing at least one epigenetically regulating chemical, e.g., TSA. Thus, the method for genetic modification in a plant cell may further comprise a step of pretreatment of the plant cell to be used in step a), said pretreatment comprising culturing the plant cells or plant material comprising same in a medium containing at least an epigenetically regulating chemical or an active derivative thereof, in particular a histone deacetylase inhibitor (HDACI). Exemplary, as for the histone deacetylase inhibitor TSA, the duration of the TSA pre-treatment is from 10 minutes to 2 days, preferred 2.0 to 24 hours. TSA concentration for a pre-treatment is 1.0 nM to 10 mM, preferred 10 nM to 500 nM. Hereafter the treated plant materials are transferred to TSA-free medium and used for TSA co-introduction with the genetic modification components immediately as a prolonged TSA pre-treatment may cause non-selective enhancement of cell regeneration, which may increase difficulty in retrieving the modified cells.

After the optional pretreatment step, the treated plant cells are taken from the medium and used for co-introduction step by microprojectile bombardment.

Preferred is a co-introduction of epigenetically regulating chemical via microprojectile bombardment. In this context, the present invention provides a microparticle coated with (i) at least one genome modification system, preferably a genome editing system comprising at least one site-directed nuclease, nickase or an inactivated nuclease, preferably a nucleic acid guided nuclease, nickase or an inactivated nuclease, or a sequence encoding the same, and optionally at least one guide molecule, or a sequence encoding the same;

(ii) at least one epigenetically regulating chemical, preferably a histone deacetylase inhibitor (HDACI), in particularly trichostatin A (TSA) or one TSA like chemical, and (iii) optionally, at least one regeneration booster, or a sequence encoding the same.

Preferably, the epigenetically regulating chemical and the regeneration booster, are transiently present, transiently active or transiently expressed in at least one transformed cell.

The microparticle consists of a non-toxic, non-reactive material. Preferably, the microparticle comprises a metal such as gold or tungsten. The size of the microparticle may be in a range of 0.4-1.6 micron (μm), preferably 0.4-1.0 μm. The genome modification materials are DNA, RNA, protein, or ribonucleoprotein (RNP). Plant materials are any or any part of any tissues, organs or cells, e.g., shoots, stems, leaves roots, embryos, calluses, and others. The amounts of TSA used for a bombardment with 100 μg of gold particles (approximately, 4.0-5.0×10⁷ 0.6 μm gold particles) are in range of 0.01 ng to 500 ng, preferred 0.1-50 ng. The TSA and genome modification materials are delivered into target cells using a Bio-Rad PDS-1000/He particle gun or hand-held Helios gene gun system.

The coating with components (i) and (ii) can comprise one or more coating layers. For example, a microparticle may contain a first coating layer comprising genome modification components (i) and a second coating layer comprising components (ii) and/or (iii). Alternatively, a microparticle may contain a coating layer comprising genome engineering components (i) and at least one of components (ii) and (iii).

The genome modification, e.g., genome editing efficiency can be analyzed for instance by next Taqman ddPCR and/or generation sequencing (NGS).

According to another aspect of the present invention, the genetically modified plant cells can be regenerated into a whole (fertile) plant. Thus, in a preferred aspect of the invention, the genetic modification of a plant cell is followed by a step of regenerating a plant. Accordingly, the present invention provides a method for producing a genetically modified plant comprising the steps:

a) genetically modifying a plant cell according to the above method for genetic modification in a plant cell, and b) regenerating a plant from the modified plant cell of step a), In one embodiment of the method according to any of the embodiments described above, at least one site-directed nuclease, nickase or an inactivated nuclease, or a sequence encoding the same, is introduced and is selected from the group consisting of a CRISPR/Cas system, preferably from a CRISPR/MAD7 system, a CRISPR/Cfp1 system, a CRISPR/MAD2 system, a CRISPR/Cas9 system, a CRISPR/CasX system, a CRISPR/CasY system, a CRISPR/Cas13 system, or a CRISPR/Csm system, a zinc finger nuclease system, a transcription activator-like nuclease system, or a meganuclease system, or any combination, variant, or catalytically active fragment thereof.

In another embodiment of the method according to any of the embodiments described above, at least one genome editing system is introduced, wherein the at least one genome editing system further comprises at least one reverse transcriptase and/or at least one cytidine or adenine deaminase, preferably wherein the at least one cytidine or adenine deaminase is independently selected from an apolipoprotein B mRNA-editing complex (APOBEC) family deaminase, preferably a rat-derived APOBEC, an activation-induced cytidine deaminase (AID), an ACF1/ASE deaminase, an ADAT family deaminase, an ADAR2 deaminase, or a PmCDA1 deaminase, a TadA derived deaminase, and/or a transposon, or a sequence encoding the aforementioned at least one enzyme, or any combination, variant, or catalytically active fragment thereof.

A variety of suitable genome editing systems that can be employed according to the methods of the present invention, is available to the skilled person and can be easily adapted for use in the methods used herein.

In embodiments, wherein the site-directed nuclease or variant thereof is a nucleic acid-guided site-directed nuclease, the at least one genome editing system additionally includes at least one guide molecule, or a sequence encoding the same. The "guide molecule" or "guide nucleic acid sequence" (usually called and abbreviated as guide RNA, crRNA, crRNA+tracrRNA, gRNA, sgRNA, depending on the corresponding CRISPR system representing a prototypic nucleic acid-guided site-directed nuclease system), which recognizes a target sequence to be cut by the nuclease. The at least one "guide nucleic acid sequence" or "guide molecule" comprises a "scaffold region" and a "target region". The "scaffold region" is a sequence, to which the nucleic acid guided nuclease binds to form a targetable nuclease complex. The scaffold region may comprise direct repeats, which are recognized and processed by the nucleic acid guided nuclease to provide mature crRNA. A pegRNAs may comprise a further region within the guide molecule, the so-called "primer-binding site". The "target region" defines the complementarity to the target site, which is intended to be cleaved. A crRNA as used herein may thus be used interchangeably herein with the term guide RNA in case it unifies the effects of meanwhile well-established CRISPR nuclease guide RNA functionalities. Certain CRISPR nucleases, e.g., Cas9, may be used by providing two individual guide nucleic acid sequences in the form of a tracrRNA and a crRNA, which may be provided separately, or linked via covalent or non-covalent bonds/interactions. The guide RNA may also be a pegRNA of a Prime Editing system as further disclosed below. The at least one guide molecule may be provided in the form of one coherent molecule, or the sequence encoding the same, or in the form of two individual molecules, e.g., crRNA and tracr RNA, or the sequences encoding the same.

In certain embodiments, the genome editing system may be a base editor (BE) system.

In yet another embodiment, the genome editing system may be a Prime Editing system.

Any nucleic acid sequence comprised by, or encoding a genome modification or genome editing system disclosed herein, or a regeneration booster sequence, may be "codon optimized" for the codon usage of a plant target cell of interest. This means that the sequence is adapted to the preferred codon usage in the organism that it is to be expressed in, i.e. a "target cell of interest", which may have its origin in different target plants (wheat, maize, sunflower, sugar beet, for example) so that a different codon optimization may be preferable, even though the encoded effector on protein level may be the same. If a nucleic acid sequence is expressed in a heterologous system, codon optimization increases the translation efficiency significantly.

In certain embodiments according to the methods as disclosed herein, it may be preferable to achieve homology-directed repair (HDR)-mediated genome editing instead of non-homologous end-joining (NHEJ). In certain embodiments according to the various aspects and methods disclosed herein, wherein at least one genome editing system is introduced, the at least one genome editing system comprises at least one repair template (or donor), and the at least one repair template comprises or encodes a double- and/or single-stranded nucleic acid sequence.

In a further embodiment of the genome editing system according to any of the embodiments described above, the system may thus additionally comprise at least one repair template, or a sequence encoding the same. A "repair template", "repair nucleic acid molecule", or "donor (template)" refers to a template exogenously provided to guide the cellular repair process so that the results of the repair are error-free and predictable. In the absence of a template sequence for assisting a targeted homologous recombination mechanism (HDR), the cell typically attempts to repair a genomic DNA break via the error-prone process of non-homologous end-joining (NHEJ).

In one embodiment, the at least one repair template may comprise or encode a double- and/or single-stranded sequence.

In another embodiment, the at least one repair template may comprise symmetric or asymmetric homology arms.

In another embodiment, the at least one repair template may comprise at least one chemically modified base and/or backbone, including a phosphothioate modified backbone, or a fluorescent marker attached to a nucleic acid of the repair template and the like.

In one embodiment, a genome modification or editing system according to any of the embodiments described above, the at least one site-directed nuclease, nickase or an inactivated nuclease, or a sequence encoding the same, and/or optionally the at least one guide nucleic acid, or the sequence encoding the same, and/or optionally the at least one repair template, or the sequence encoding the same, are provided simultaneously, or one after another.

In certain embodiments, the at least one genome editing system, and optionally the at least one repair template, or the respective sequences encoding the same, are introduced transiently or stably, or as a combination thereof. Whereas the stable integration of at least one genome editing system, in particular the site-directed nuclease or variant thereof, but not necessarily including at least one guide RNA, may allow a stable expression of this effector, the methods as disclosed herein can be performed in a full transient way. This implies that the tools as such are not integrated into the genome of a cell to be modified, unless at least one repair template is used. This transient approach may be preferably for a highly controllable gene editing event.

The methods of the present invention may be applied to monocotyledonous or a dicotyledonous plant as described in more detail below.

The generation and use of haploids is one of the most powerful biotechnological means to improve cultivated plants. The advantage of haploids for breeders is that homozygosity can be achieved already in the first generation after dihaploidization, creating doubled haploid plants, without the need of laborious backcrossing steps to obtain a high degree of homozygosity. Furthermore, the value of haploids in plant research and breeding lies in the fact that the founder cells of doubled haploids are products of meiosis, so that resultant populations constitute pools of diverse recombinant and at the same time genetically fixed individuals. The generation of doubled haploids thus provides not only perfectly useful genetic variability to select from with regard to crop improvement, but is also a valuable means to produce mapping populations, recombinant inbreds as well as instantly homozygous mutants and transgenic lines.

Haploid plants can be obtained by interspecific crosses, in which one parental genome is eliminated after fertilization. It was shown that genome elimination after fertilization could be induced by modifying a centromere protein, the centromere-specific histone CENH3 in *Arabidopsis thaliana* (Ravi and Chan, Haploid plants produced by centromere-mediated genome elimination, Nature, Vol. 464, 2010, 615-619). With the modified haploid inducer lines, haploidization occurred in the progeny when a haploid inducer plant was crossed with a wild type plant. Interestingly, the haploid inducer line was stable upon selfing, suggesting that a competition between modified and wild type centromere in the developing hybrid embryo results in centromere inactivation of the inducer parent and consequently in uniparental chromosome elimination.

In one aspect, there is provided a method of producing a haploid or doubled haploid plant cell, tissue, organ, plant, or seed.

In one embodiment, the methods of the present invention thus comprise the generation of at least one haploid cell, tissue or organ having activity of a haploid inducer, preferably wherein the haploid cell, tissue or organ comprises a callus tissue, male gametophyte or microspore. In this embodiment, the methods as disclosed herein may comprise the introduction of a nucleotide or amino acid sequence encoding or being a sequence allowing the generation of a haploid inducer cell, for example a sequence encoding a KINETOCHORE NULL2 (KNL2) protein comprising a SANTA domain, wherein the nucleotide sequence comprises at least one mutation causing in the SANTA domain an alteration of the amino acid sequence of the KNL2 protein and said alteration confers the activity of a haploid inducer (as disclosed in EP 3 159 413 A1) in a method for plant genome modification, preferably for the targeted modification of at least one genomic target sequence, for obtaining a modification of at least one plant cell. In this embodiment, the at least one genome modification system does not comprise a genome editing system, but the sequence allowing the generation of a haploid inducer line, which is introduced into a plant cell to be modified stably or transiently, in a constitutive or inducible manner.

In another embodiment, the modified cell according to the methods of the present invention is a haploid cell, wherein the haploid cell is generated by introducing a genome editing system into at least one cell to be modified, wherein the genome editing system is capable of introducing at least one mutation into the genomic target sequence of interest resulting in a cell having haploid inducer activity.

In yet a further aspect, there is provided a method of producing a haploid or doubled haploid plant cell, tissue, organ, plant, or seed, wherein the method comprises providing at least one regeneration booster, or a specific combination of regeneration boosters, or the sequence(s) encoding the same, to at least one cell to be modified, wherein the at least one cell is preferably a haploid cell, for example, a gametophyte or microspore. These inherently haploid cells of plants produced during the reproduction cycle have the intrinsic characteristic of being very inert to any kind of chromosome doubling and transformation. The methods as disclosed herein can thus be favourably used to introduce or apply at least one regeneration booster, or a sequence encoding the same for promoting the regenerative capacity of a haploid plant cell to increase the capacity of the haploid cell for a conversion during chromosome doubling, as the doubled haploid material is of particular interest for breeding and ultimately cultivating plants. The methods as disclosed herein thus overcome the difficulties in handling haploid plants cells and tissues, including callus tissue, as the frequency of induced and/or spontaneous chromosome doubling can be increased by providing at least one booster sequence, or preferably a specific combination of booster sequences, as disclosed herein.

Various methods for doubling chromosomes in plant biotechnology are available to the skilled person for various cultivars. In one embodiment, chromosome doubling can be achieved by using colchicine treatment. Other chemicals for chromosome doubling, are available for use according to the methods disclosed herein, wherein these chemicals may be selected from antimicrotubule herbicides, including amiprophosmethyl (APM), pronamide, oryzalin, and trifluralin, which are all known for their chromosome doubling activity.

In one aspect, the present invention also relates to the use of a regeneration booster or a combination of regeneration boosters, preferably a regeneration booster or combination of regeneration boosters as described in any of the embodiments above, in a method for targeted plant genome modification, preferably in a method according to any of the embodiments described above, to (a) promote plant cell proliferation and/or assist in the targeted modification and/or provide a positive selection for at least one transiently transformed cell for genome modification and/or for regeneration into at least one modified plant, and/or (b) suppress plant cell differentiation if the cell is stably transformed and provide a negative selection for at least one stably transformed cell for regeneration into one transgenic plant, and/or (c) provide a dual selection according to (a) and (b) for at least one transformed cell.

As mentioned above, the regeneration booster(s) increase genome editing efficiency and at the same time promote proliferation of transiently transformed cells while suppressing plant cell differentiation of stably transformed cells. This dual selection advantageously allows to regenerate a modified plant, which does not pass on the genome editing tools to its progeny but merely carries the desired modification.

In one aspect the present invention relates to a plant cell, tissue, organ, plant or seed obtainable by or obtained by a method according to any of the embodiments described above.

In one embodiment of the plant cell, tissue, organ, plant or seed described above, the plant cell, tissue, organ, plant or seed originates from a monocotyledonous or a dicotyledonous plant selected from the group consisting of *Hordeum, Sorghum, Saccharum, Zea, Setaria, Oryza, Triticum, Secale, Triticale, Malus, Brachypodium, Aegilops, Daucus, Beta, Eucalyptus, Nicotiana, Solanum, Coffea, Vitis, Erythrante, Genlisea, Cucumis, Marus, Arabidopsis, Crucihimalaya, Cardamine, Lepidium, Capsella, Olmarabidopsis, Arabis, Brassica, Eruca, Raphanus, Citrus, Jatropha, Populus, Medicago, Cicer, Cajanus, Phaseolus, Glycine, Gossypium, Astragalus, Lotus, Torenia, Allium, Spinacia* or *Helianthus*, preferably, the plant cell, tissue, organ, plant or seed originates from a species selected from the group consisting of *Hordeum vulgare, Hordeum bulbusom, Sorghum bicolor, Saccharum officinarium, Zea* spp., including *Zea mays, Setaria italica, Oryza minuta, Oryza sativa, Oryza australiensis, Oryza alta, Triticum aestivum, Triticum durum, Secale cereale, Triticale, Malus domestica, Brachypodium distachyon, Hordeum marinum, Aegilops tauschii, Daucus glochidiatus, Beta* spp., including *Beta vulgaris, Daucus pusillus, Daucus muricatus, Daucus carota, Eucalyptus grandis, Nicotiana sylvestris, Nicotiana tomentosiformis, Nicotiana tabacum, Nicotiana benthamiana, Solanum lycopersicum, Solanum tuberosum, Coffea canephora, Vitis vinifera, Erythrante guttata, Genlisea aurea, Cucumis sativus, Marus notabilis, Arabidopsis arenosa, Arabidopsis lyrata, Arabidopsis thaliana, Crucihimalaya himalaica, Crucihimalaya wallichii, Cardamine nexuosa, Lepidium virginicum, Capsella bursa pastoris, Olmarabidopsis pumila, Arabis hirsute, Brassica napus, Brassica oleracea, Brassica rapa, Raphanus sativus, Brassica juncacea, Brassica nigra, Eruca vesicaria* subsp. *sativa, Citrus sinensis, Jatropha*

*curcas, Populus trichocarpa, Medicago truncatula, Cicer yamashitae, Cicer bijugum, Cicer arietinum, Cicer reticulatum, Cicer judaicum, Cajanus cajanfolius, Cajanus scarabaeoides, Phaseolus vulgaris, Glycine max, Gossypium* sp., *Astragalus sinicus, Lotus japonicas, Torenia fournieri, Allium cepa, Allium fistulosum, Allium sativum, Allium tuberosum, Helianthus annuus, Helianthus tuberosus* and/or *Spinacia oleracea.*

In a further aspect, the present invention relates to an expression construct assembly, comprising (i) at least one vector encoding at least one genome modification system which comprises at least one gene of interest, preferably an exogenous gene of interest, and/or which is preferably at least one genome editing system comprising at least one site-directed nuclease, nickase or an inactivated nuclease of a genome editing system, preferably wherein the genome editing system is as defined above, and (ii) at least one vector encoding at least one regeneration booster, preferably wherein the regeneration booster or boosters is/are as defined in any of the embodiments described above, and (iii) optionally, when the at least one site-directed nuclease, nickase or an inactivated nuclease of a genome editing system is a nucleic acid guided nuclease: at least one vector encoding at least one guide molecule guiding the at least one nucleic acid guided nuclease, nickase or an inactivated nuclease to the at least one genomic target site of interest; and (iv) optionally: at least one vector encoding at least one repair template;

wherein (i), (ii), (iii), and/or (iv) are encoded on the same, or on different vectors.

In one embodiment, the expression construct assembly may further comprise a vector encoding at least one marker, preferably wherein the marker is introduced in a transient manner, see, for example, SEQ ID NO: 55.

In one embodiment, the expression construct assembly comprises or encodes at least one regulatory sequence, wherein the regulatory sequence is selected from the group consisting of a core promoter sequence, a proximal promoter sequence, a cis regulatory sequence, a trans regulatory sequence, a locus control sequence, an insulator sequence, a silencer sequence, an enhancer sequence, a terminator sequence, an intron sequence, and/or any combination thereof.

Notably different components of a genome modification or editing system and/or a regeneration booster sequence and/or a guide molecule and/or a repair template present on the same vector of an expression vector assembly may comprise or encode more than one regulatory sequence individually controlling transcription and/or translation.

In one embodiment of the expression construct assembly described above, the construct comprises or encodes at least one regulatory sequence, wherein the regulatory sequence is selected from the group consisting of a core promoter sequence, a proximal promoter sequence, a cis regulatory sequence, a trans regulatory sequence, a locus control sequence, an insulator sequence, a silencer sequence, an enhancer sequence, a terminator sequence, an intron sequence, and/or any combination thereof.

In another embodiment of the expression construct assembly described above, the regulatory sequence comprises or encodes at least one promoter selected from the group consisting of ZmUbil, BdUbi10, ZmEfl, a double 35S promoter, a rice U6 (OsU6) promoter, a rice actin promoter, a maize U6 promoter, PcUbi4, Nos promoter, AtUbi10, BdEF1, MeEF1, HSP70, EsEF1, MdHMGR1, or a combination thereof.

In a further embodiment of the expression construct assembly described above, the at least one intron is selected from the group consisting of a ZmUbi1 intron, an FL intron, a BdUbi10 intron, a ZmEfl intron, a AdH1 intron, a BdEF1 intron, a MeEF1 intron, an EsEF1 intron, and a HSP70 intron.

In one embodiment of the expression construct assembly according to any of the embodiments described above, the construct comprises or encodes a combination of a ZmUbi1 promoter and a ZmUbi1 intron, a ZmUbi1 promoter and FL intron, a BdUbi10 promoter and a BdUbi10 intron, a ZmEfl promoter and a ZmEfl intron, a double 35S promoter and a AdH1 intron, or a double 35S promoter and a ZmUbil intron, a BdEF1 promoter and BdEF1 intron, a MeEF1 promoter and a MeEF1 intron, a HSP70 promoter and a HSP70 intron, or of an EsEF1 promoter and an EsEF1 intron.

In addition, the expression construct assembly may comprise at least one terminator, which mediates transcriptional termination at the end of the expression construct or the components thereof and release of the transcript from the transcriptional complex.

In one embodiment of the expression construct assembly according to any of the embodiments described above, the regulatory sequence may comprise or encode at least one terminator selected from the group consisting of nosT, a double 35S terminator, a ZmEfl terminator, an AtSac66 terminator, an octopine synthase (ocs) terminator, or a pAG7 terminator, or a combination thereof. A variety of further suitable promoter and/or terminator sequences for use in expression constructs for different plant cells are well known to the skilled person in the relevant field.

Exemplary elements of an expression vector assembly of the present invention, which may be individually combined, may comprise a suitable vector backbone, wherein a variety of suitable vectors are available in plant biotechnology, an expression cassette, i.e., a cassette encoding a sequence of an effector, for example, at least one regeneration booster as disclosed herein, for example, according to any one of SEQ ID NOs: 4 to 15; an expression construct, i.e., a construct including an expression cassette and at least one further vector element, for example, as represented in any one of SEQ ID NOs: 40 to 51; a vector or expression construct comprising or encoding at least one site-directed nuclease, for example, as represented in any one of SEQ ID NOs: 52 or 54; a suitable vector encoding a guide molecule, in case a nucleic acid-guided site directed nuclease is used, specific for a genomic target sequence of interest, for example, a sequence according to SEQ ID NO: 53, wherein the respective guide molecule is compatible with the cognate nucleic acid-guided site directed nuclease, or variant thereof, wherein the guide molecule comprised or encoded can be easily replaced by another guide molecule targeting a different genomic target site of interest; a vector encoding at least one repair template sequence of interest; and/or a vector or expression construct comprising or encoding at least one expressible marker gene, preferably a marker gene, which can be easily detected macroscopically, or microscopically, like a fluorescent marker gene as encoded by, for example, SEQ ID NO: 55. A variety of suitable fluorescent marker proteins and fluorophores applicable over the whole spectrum, i.e., for all fluorescent channels of interest, for use in plant biotechnology for visualization of metabolites in different compartments are available to the skilled person, which may be used according to the present invention.

Examples are GFP from *Aequoria victoria*, fluorescent proteins from *Anguilla japonica*, or a mutant or derivative thereof), a red fluorescent protein, a yellow fluorescent protein, a yellow-green fluorescent protein (e.g., mNeonGreen derived from a tetrameric fluorescent protein from the cephalochordate *Branchiostoma lanceolatum*), an orange, a red or far-red fluorescent protein (e.g., tdTomato (tdT), or DsRed), and any of a variety of fluorescent and coloured proteins may be used depending on the target tissue or cell, or a compartment thereof, to be excited and/or visualized at a desired wavelength.

All elements of the expression vector assembly can be individually combined. Further, the elements can be expressed in a stable or transient manner, wherein a transient introduction may be preferably. In certain embodiments, individual elements may not be provided as part of a yet to be expressed (transcribed and/or translated) expression vector, but they may be directly transfected in the active state, simultaneously or subsequently, and can form the expression vector assembly within one and the same cell of interest to be modified. For example, it may be reasonable to first transform part of the expression vector assembly encoding a site-directed nuclease, which takes some time until the construct is expressed, wherein the cognate guide molecule is then transfected in its active RNA stage and/or at least one repair template is then transfected in its active DNA stage in a separate and subsequent introduction step to be rapidly available. The at least one regeneration booster sequence and/or the at least one genome modification or editing system and/or the at least one marker may also be transformed as part of one vector, as part of different vectors, simultaneously, or subsequently. The use of too many individual introduction steps should be avoided, and several components can be combined in one vector of the expression vector assembly, to reduce cellular stress during transformation/transfection. In certain embodiments, the individual provision of elements of the at least one regeneration booster sequence and/or the at least one genome modification or editing system and/or the at least one marker and/or the at least one guide molecule and/or the at least one repair template on several vectors and in several introduction steps may be preferable in case of complex modifications relying on all elements so that all elements are functionally expressed and/or present in a cell to be active in a concerted manner.

In one aspect, the present invention also relates to a plant cell, tissue, organ, plant or seed comprising the at least one regeneration booster as described above or the expression construct assembly as described above.

In another aspect, the present invention relates to a method for selecting a modified plant cell, plant tissue, organ, plant or seed, wherein the method comprises the steps (a) to (c) as defined in the method for plant genome modification according to any of the embodiments described above and further comprises the step:

(d1) screening for at least one plant cell carrying a targeted modification, or (d2) screening for at least one plant tissue, organ, plant or seed regenerated from at least one modified plant cell in the T0 or T1 generation carrying a desired targeted modification.

The method for selecting a modified plant cell, plant tissue, organ, plant or seed may be without a conventional selection step. A conventional selection step refers to any processes to select and purify the transformed cells from wild-type cells by using an integrated selection marker, e.g. antibiotic (e.g. kanamycin, hygromycin), or herbicide (e.g.

phosphinothricin, glyphosate) resistance gene. Without a conventional selection, such a plant or seed may not have any of the genome modification components integrated, and thus leads to transgene-free genetic modified plants.

The positive impact of the regeneration booster on plant cell division and stem cell identity endows a selective regeneration of the transformed cells at the initiation stage of regeneration, whereas the boosting effect of a booster on stem cell identity, which negatively impacts cell differentiation, allows a negative selection for the cells with continuous activity of the booster (i.e. stably transformed cells) at the subsequent regeneration.

The regeneration boosters and combination of boosters described herein significantly improve the regeneration capabilities of plant from single cell origin. In particular, plants/plant genotypes that are considered recalcitrant to regeneration can be regenerated efficiently.

In a further aspect, the present invention also relates to a method for regenerating a plant tissue, organ or plant from at least one plant cell or a single plant cell, wherein the method comprises:

(i) Introducing into the at least one plant cell or the single plant cell at least one regeneration booster, or a sequence encoding the same, wherein the at least one regeneration booster is transiently present, transiently active or transiently expressed in the plant cell, preferably wherein the at least one regeneration booster(s) is/are as defined in any of the embodiments described above, and (ii) regenerating a plant tissue, organ or plant from at least one plant cell or the single plant cell.

In one embodiment of the method for regenerating a plant tissue, organ or plant from a single plant cell, the at least one regeneration booster comprises at least one RBP, wherein the at least one RBP comprises an amino acid sequence selected from the group consisting of SEQ ID NOs: 32, 33, 34, 35, 36, 37, 38 and 39, or a sequence having at least 80%, 81%, 82%, 83%, 84%, 85%, 86%, 87%, 88%, 89%, 90%, 91%, 92%, 93%, 94%, 95%, 96%, 97%, 98% or 99% sequence identity thereto, or a catalytically active fragment thereof, or wherein the at least one RBP is encoded by a sequence selected from the group consisting of SEQ ID NOs: 20, 21, 22, 23, 24, 25, 26 and 27, or a sequence having at least 80%, 81%, 82%, 83%, 84%, 85%, 86%, 87%, 88%, 89%, 90%, 91%, 92%, 93%, 94%, 95%, 96%, 97%, 98% or 99% sequence identity thereto, or a cognate codon-optimized sequence.

The artificial regeneration boosters RBP1 to RBP8 may be used in any combination with each other or and/or in combination with other boosters as disclosed above in the context of the method for plant genome modification. Preferably, RBP1 to RBP8 or any combination thereof are combined with one of a PLT or RKD booster.

In one preferred embodiment of the method for regenerating a plant tissue, organ or plant from a single plant cell according to any of the embodiments described above, the at least one regeneration booster further comprises at least one PLT or RKD4, wherein the at least one PLT or RKD4 comprises an amino acid sequence selected from the group consisting of SEQ ID NOs: 28, 29, 30 and 31, or a sequence having at least 80%, 81%, 82%, 83%, 84%, 85%, 86%, 87%, 88%, 89%, 90%, 91%, 92%, 93%, 94%, 95%, 96%, 97%, 98% or 99% sequence identity thereto, or a catalytically active fragment thereof, or wherein the at least one PLT or RKD4 is encoded by a sequence selected from the group consisting of SEQ ID NOs: 16, 17, 18 and 19, or a sequence having at least 80%, 81%, 82%, 83%, 84%, 85%, 86%, 87%, 88%, 89%, 90%, 91%, 92%, 93%, 94%, 95%, 96%, 97%, 98% or 99% sequence identity thereto, or a cognate codon-optimized sequence.

The artificial regeneration boosters RBP1 to RBP8 or combinations thereof may also be used in combination with one or more boosters selected from BBM, WUS, WOX, GRF or LEC.

In one embodiment of the method for regenerating a plant tissue, organ or plant from a single plant cell according to any of the embodiment described above, a further regeneration booster is introduced, wherein the further regeneration booster, or the sequence encoding the same is selected from BBM, WUS, WOX, GRF, LEC, or a variant thereof or the further regeneration booster is a regeneration booster selected from RBP1 to RBP8, wherein the further regeneration booster is different from the first regeneration booster.

In one embodiment of the method for regenerating a plant tissue, organ or plant from a single plant cell according to any of the embodiments described above, the at least one regeneration booster comprises at least one RBP, wherein the at least one RBP comprises an amino acid sequence selected from the group consisting of SEQ ID NOs: 32, 33, 34, 35, 36, 37, 38 and 39, or a sequence having at least 80%, 81%, 82%, 83%, 84%, 85%, 86%, 87%, 88%, 89%, 90%, 91%, 92%, 93%, 94%, 95%, 96%, 97%, 98% or 99% sequence identity thereto, or a catalytically active fragment thereof, or wherein the at least one RBP is encoded by a sequence selected from the group consisting of SEQ ID NOs: 20, 21, 22, 23, 24, 25, 26 and 27, or a sequence having at least 80%, 81%, 82%, 83%, 84%, 85%, 86%, 87%, 88%, 89%, 90%, 91%, 92%, 93%, 94%, 95%, 96%, 97%, 98% or 99% sequence identity thereto, or a cognate codon-optimized sequence, and the at least one regeneration booster comprises PLT5, wherein the PLT5 comprises an amino acid sequence of SEQ ID NO: 30, or a sequence having at least 80%, 81%, 82%, 83%, 84%, 85%, 86%, 87%, 88%, 89%, 90%, 91%, 92%, 93%, 94%, 95%, 96%, 97%, 98% or 99% sequence identity thereto, or a catalytically active fragment thereof, or wherein the PLT5 is encoded by a nucleic acid sequence of SEQ ID NO: 18, or a sequence having at least 80%, 81%, 82%, 83%, 84%, 85%, 86%, 87%, 88%, 89%, 90%, 91%, 92%, 93%, 94%, 95%, 96%, 97%, 98% or 99% sequence identity thereto, or a cognate codon-optimized sequence.

As already mentioned above, the generation of haploids is highly desirable for plant breeders as homozygosity can already be obtained in the first generation. However, it is often difficult to regenerate a plant from the haploid cells, in particular from microspores. The booster and booster combinations disclosed herein offer a significant improvement in the regeneration capabilities of haploid plants.

In one embodiment of the method for regenerating a plant tissue, organ or plant described above, the at least one plant cell is an immature embryo cell or meristematic cell, in particular a cell of a zygotic or somatic embryo or meristem or the single plant cell is a diploid cell or a haploid cell, in particular a haploid microspore.

The present invention is further illustrated by the following non-limiting examples.

EXAMPLES

Transformation and transgene expression may be monitored by use of a report gene, such as a green fluorescent gene (GEP) in construct pGEP837 (FIG. 1), which encodes a bright monomeric green fluorescent protein with excitation maximum at 506 nm and emission maximum at 517 nm.

Another report gene used in the present invention is the red fluorescent report gene tdTomato in construct pGEP359 (FIG. 13), which encodes an exceptionally bright red fluorescent protein with excitation maximum at 554 nm and emission maximum at 581 nm. The genome editing efficiency can be analyzed for instance by marker capillary electrophoresis analysis, qPCR, or Digital PCR. Site-specific modification was further conformed by next generation sequencing (NGS), Sanger sequencing, or Sanger sequencing trace decomposition analysis.

Unless stated otherwise in the examples, all recombinant DNA techniques are carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Cray, jointly published by BIOS Scientific Publications Ltd (UK) and Blackwell Scientific Publications, UK. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR-Basics: From Background to Bench, First Edition, Springer Verlag, Germany.

Example 1: A Toolbox of Different Regeneration Boosters Stimulate Cell Proliferation and Regeneration (FIGS. 1 to 11)

Gene Cloning and Construct Generation

Maize ZmPLT5 gene was cloned by RT-PCR using total RNA isolated from maize A188 immature embryos. KWS_RBP genes (KWS_RBP2-8) were maize-codon optimized from its protein sequence, and synthesized by Integrated DNA Technologies (IDT, San Diego, CA, USA). The boost gene fragments are cloned into expression vector pABM-BdEF1 at the cloning site of BamHI and HindIII, and expressing under the control of BdEF1 promoter (BdFE1) and nos terminator (nos-T). The BdFE1 promoter is a strong constitutive promoter from *Brachypodium*. The sequencing-confirmed construct maps are shown in FIGS. 3 to 10.

Preparation of Maize Immature Embryo for Bombardment 9-12 days post pollination, maize ears with immature embryos size 0.5 to 2.5 mm, preferred 0.8-1.5 mm were harvested. The ears were sterilized with 70% ethanol for 10-15 minutes. After a brief air-dry in a laminar hood, remove top ~⅓ of the kernels from the ears with a shark scalpel, and pull the immature embryos out of the kernels carefully with a spatula. The fresh isolated embryos were placed onto the bombardment target area in an osmotic medium plate (N60SM medium) with scutellum-side up. Wrap the plates with parafilm and incubated them at 25° C. in dark for 4-20 hours (preferred 4 hours) before bombardment.

Particle Bombardment

Figure 2:
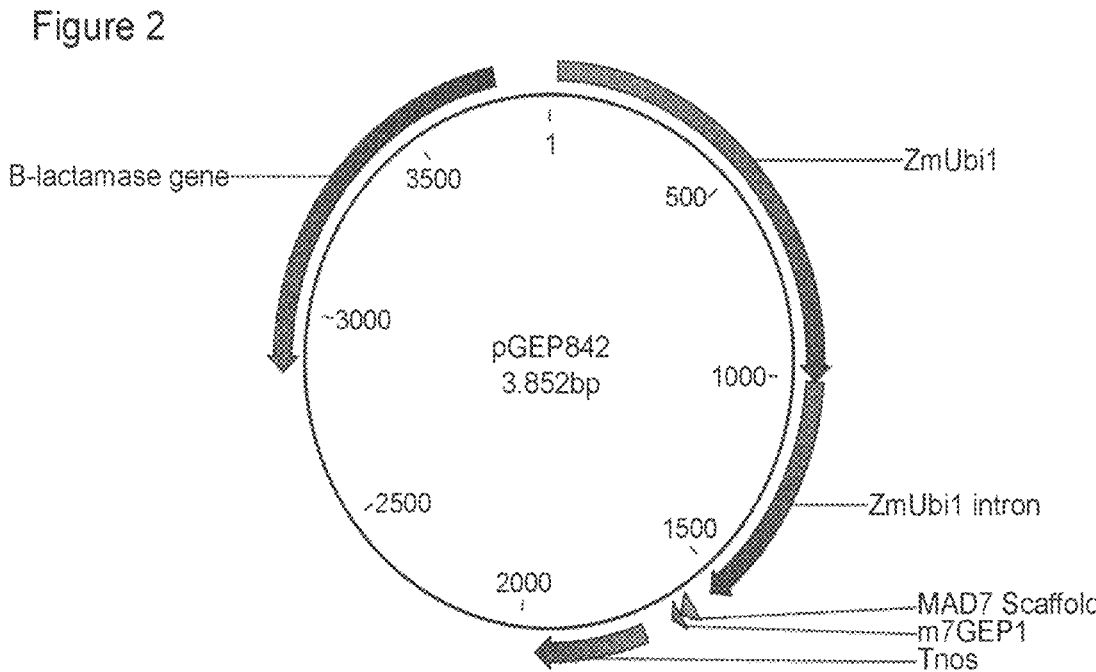
FIG. 2 shows a genome editing sgRNA construct pGEP842 map. m7GEP1 defines the crRNA, which target to maize HMG13 gene. ZmUbi1 defines the promoter and intron from maize Ubiquitin 1 gene. Tnos defines the nos terminator.

Construct pGEP837 (SEQ ID NO: 52) contains the expression cassettes of CRISPR nuclease MAD7 and green fluorescence report gene GEP (FIG. 1), while pGEP842 (SEQ ID NO: 53) harbors the expression cassette of CRISPR crRNA m7GEP1, which targets to maize endogenous HMG13 gene (FIG. 2). Per bombardment, 100 ng of plasmid pGEP837 and 150 ng of plasmid pGEP842 were co-coated with 100 ng of different boost constructs onto 100 μg of 0.4 μm gold particles using calcium-spermidine method. Three bombardments (shots) per sample plate were performed. For 10 shots, 1 mg of gold particle in 50% (v/v) glycerol (100 μg of gold particles per shot) in a total volume of 100 microliter (μl) was pipetted into a clear low-retention microcentrifuge tube. Sonicate for 15 seconds to suspend the gold particles. While vortex at a low speed, add the following in order to each 100 μl of gold particles:

Up to 10 μl of DNA (1.0-10.0 μg total DNA of pre-mixed, 100-1000 ng per each shot)

100 μl of 2.5 M $CaCl_2$ (pre-cold on ice)

40 μl of 0.1 M cold spermidine

Close the lid and vortex the tube for 2-30 minutes at 0-10° C., and spin down the DNA-coated gold particles. After washing in 500 μl of 100% ethanol for two times, the pellet was resuspended in 120 μl of 100% ethanol. While vortexing at a low speed, pipet 10 μl of co-coated gold particles with a wide open 20 μl tip from the tube onto the center of the macrocarrier evenly since the particles tend to form clumps at this point, get the gold particles onto the macrocarriers as soon as possible. Air dry. Bombardment was conducted using a Bio-Rad PDS-1000/He particle gun. The bombardment conditions are: 28-30 mm/Hg vacuum, 450 or 650 psi rupture disc, 6 mm gap distance, the specimen platform is in the second position from the bottom in the chamber at a distance of 60 mm, three shots per sample plate (for maize immature embryos). Keep the coated gold particles at low temperature (e.g. 0-10° C.) as much as possible. The prepared macro-carriers with coated gold particles should be bombard into plant cells within 3 hours after preparation.

Embryogenic Callus Induction

After bombardment the embryos were remained on the osmotic medium (N60SM) for another 16-20 hours. Transient transformation was examined using a fluorescence microscope for the fluorescence report gene expression at excitation maximum 506 nm and emission maximum 517 n. The embryos were transferred from the osmotic medium onto embryogenic callus induction medium (e.g. N6_5Ag) in a petri dish plate (100×25 mm) with scutellum-face-up, at a density of 12-15 embryos per plate. The embryos were incubated at 27° C. in dark for the embryogenic callus induction for 7-14 days.

Figure 11:
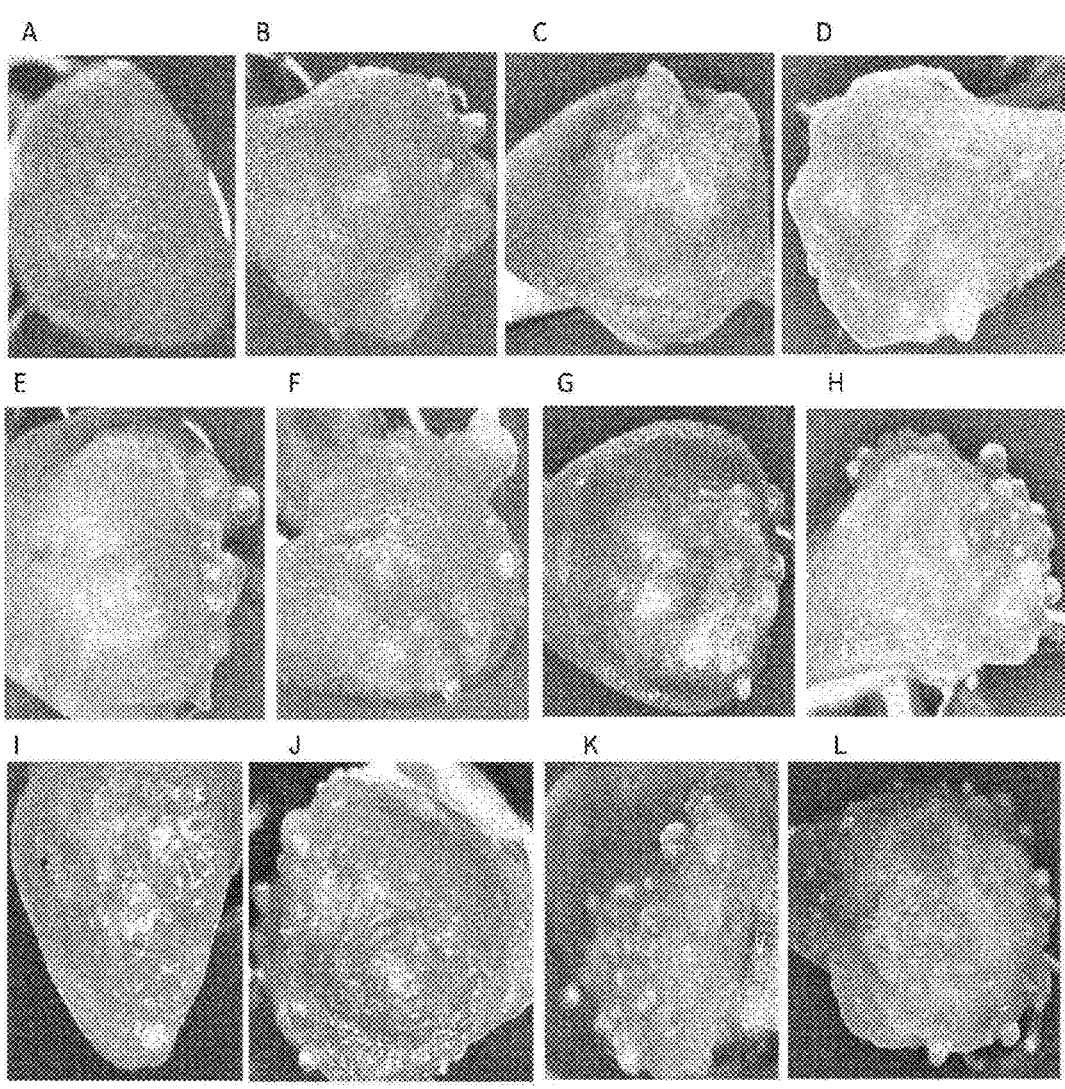
FIG. 11 shows how different regeneration boosters stimulate cell proliferation in the scutellum surfaces of maize immature embryos after the co-bombardment of genome editing constructs pGEP837 (FIG. 1) and pGEP842 (FIG. 2) with the boosters and cultured for 4 days in the embryogenic callus induction medium. (A) to (H): the embryos from maize recalcitrant elite 16V-2015 bombarded with the genome editing constructs only (A), or con-bombarded with the boosters of ZmPLT5 and KWS_RBP2 (B), ZmPLT5 and KWS_RBP3 (C), ZmPLT5 and KWS_RBP4 (D), ZmPLT5 and KWS_RBP5 (E), ZmPLT5 and KWS_RBP6 (F), ZmPLT5 and KWS_RBP7 (G), or ZmPLT5 and KWS_RBP8 (H). (I) to (L): the embryos from maize recalcitrant elite 4V-40214 bombarded with the genome editing constructs only (I), or co-bombarded with the boosters of ZmPLT5 and RBP2 (J), ZmPLT5 and RBP5 (K), or ZmPLT5 and RBP8 (L).

Four days after embryogenic callus induction the cell proliferation and embryogenesis from the scutellum surface of immature embryos were examined under a Zeiss stereo microscope. The representative results were showed in FIG. 11. Without a regeneration booster the immature embryos from the recalcitrant maize elites did not produce any regenerating structures (FIGS. 11A and I). Compared to the control without a booster, multiple embryogenic cell structures were induced from the embryos co-bombarded with different regeneration boosters (compare FIGS. 11A to B-H, and I to J-L). The boosters significantly promote cell proliferation and embryogenic callus induction in maize elites (FIG. 11). The regeneration boosters offer a positive selection for the transformed cells in cell proliferation and regeneration.

Media:

N6OSM:

N6 salt, N6 vitamin, 1.0 mg/L of 2, 4-D, 100 mg/L of Caseine, 0.7 g/L of L-proline, 0.2 M Mannitol (36.4 g/L), 0.2 M sorbitol (36.4 g/L), 20 g/L sucrose, 15 g/L of Bacto-agar, pH 5.8.

N6_5Ag:

N6 salt, N6 vitamin, 1.0 mg/L of 2, 4-D, 100 mg/L of Caseine, 2.9 g/L of L-prolin, 20 g/L sucrose, 5 g/L of glucose, 5 mg/L of AgNO3, 8 g/L of Bacto-agar, pH 5.8.

Example 2: A Toolbox of Different Boosters Promote Rapid Genetic Transformation of Plant Cells (FIG. 12)

The expression cassette of green fluorescence report gene GEP in construct pGEP837 (SEQ ID NO: 52) was co-bombarded with plasmid pGEP842 (SEQ ID NO: 53) and different constructs encode for the expression cassette of a specific booster as indicated. For immature embryo isolation, bombardment, and embryogenic callus induction, please see the description in Example 1.

Green fluorescence report gene expression in the scutellum surface cells of the bombarded immature embryos was examined using a stereo fluorescence microscope at excitation maximum 506 nm and emission maximum 517 nm after bombardment and cultured in embryogenic callus induction for 4 days. The representative results are present in FIG. 12.

Figure 12:
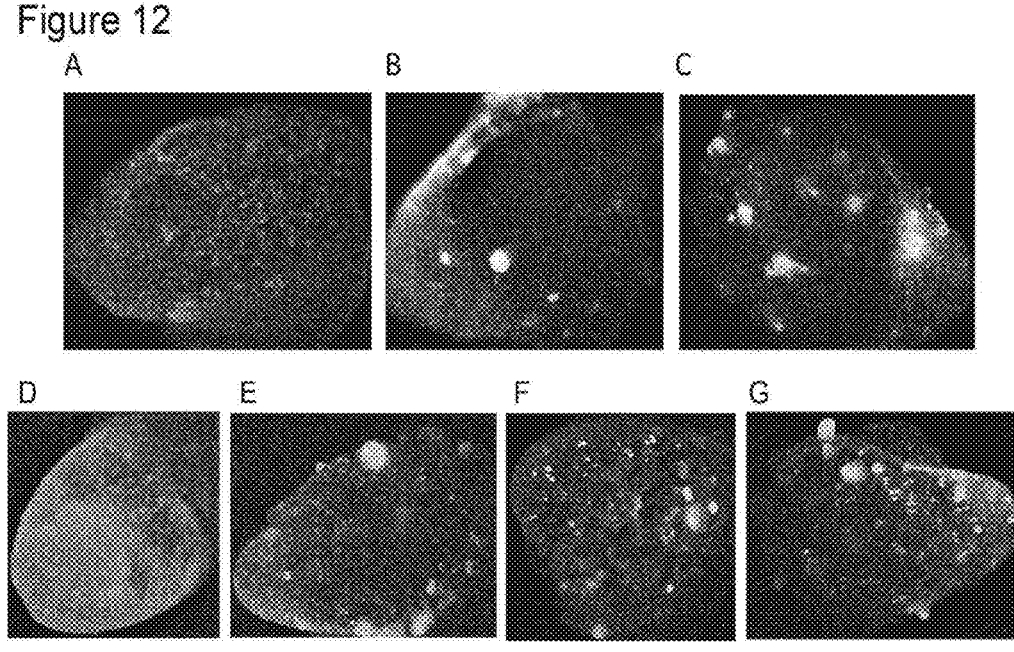
FIG. 12 shows how different regeneration boosters promote rapid genome transformation in maize immature embryos after the co-bombardment of genome editing constructs pGEP837 (FIG. 1) and pGEP842 (FIG. 2) with the boosters and cultured for 4 days in the embryogenic callus induction medium. (A) to (C): the embryos from maize recalcitrant elite WA4-29814 bombarded with the genome editing constructs only (A), or co-bombarded with the boosters of ZmPLT5 and KWS_RBP2 (B), or ZmPLT5 and KWS_RBP8 (C). (D) to (G): the embryos from maize recalcitrant elite 4V-40214 bombarded with the genome editing constructs only (D), or co-bombarded with the boosters of ZmPLT5 and KWS_RBP2 (E), ZmPLT5 and KWS_RBP5 (F), or ZmPLT5 and KWS_RBP8 (G).

Without a booster the immature embryos from maize recalcitrant elite WA4-29814 and 4V-40214 did not produce a green fluorescent cell cluster (FIGS. 12A and D). Contrast to the control without a booster, multiple embryogenic structures with strong and uniformed green fluorescence signals appeared from the embryos co-bombarded with different regeneration boosters after bombardment and cultured for 4 days (FIGS. 12. B to C, and E to G). Strong and uniformed expression of green fluorescent report gene in regenerated tissues, e.g. embryogenic callus, indicates the integration and stable transformation of the foreign gene.

In a regular plant transformation system, it takes a few rounds of selection to identify and purify the cells with stable DNA integration to recover a homogenous transgenic plant. The selection process normally take a few weeks, e.g. 6-8 weeks for maize, depends on the speed of cell proliferation. It takes generally more than 3 month to obtain a stable transformation event in maize. The results present here reveal that boosters remarkably promote rapid stable transformation in maize elites.

Figure 13:
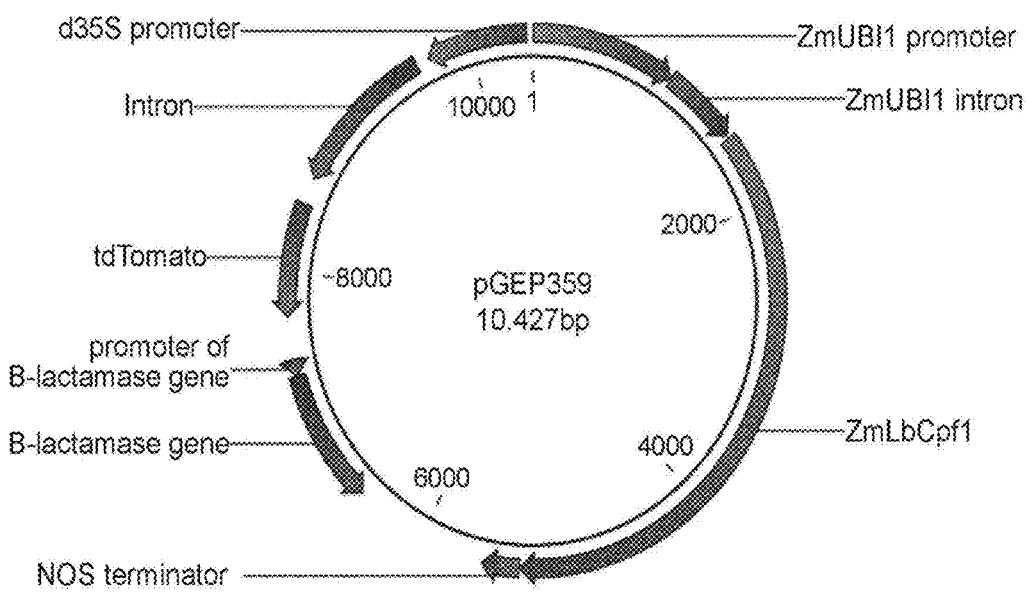
FIG. 13 shows a genome editing nuclease LbCpf1 expression construct pGEP359 map. tDT defines the tdTomato gene. ZmLpCpf1 defines the maize codon-optimized CDS of the Lachnospiraceae bacterium CRISPR/Cpf1 (LbCpf1) gene.
Figures 14, 15:
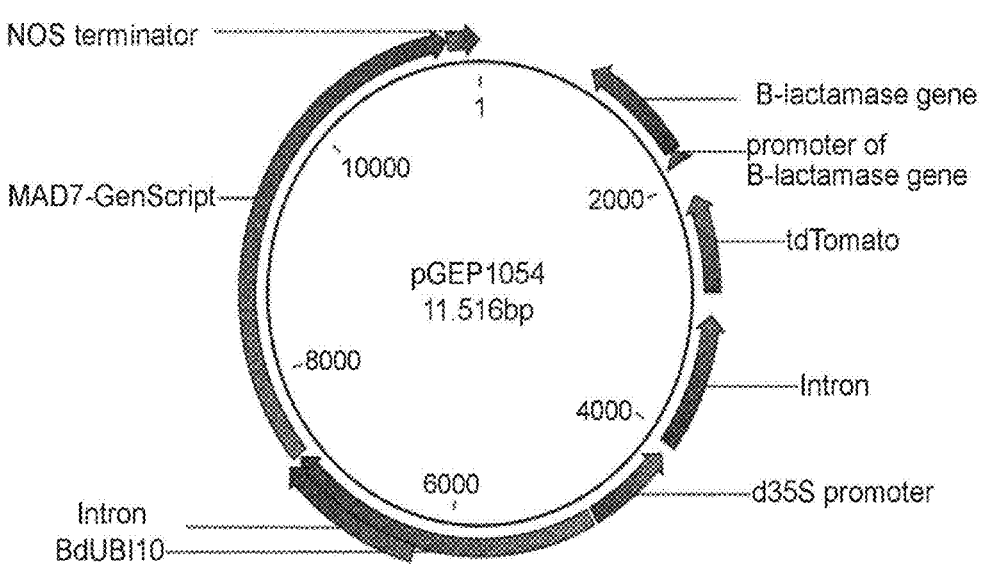
FIG. 14 shows how cell differentiation and subsequent regeneration are negatively impacted by the continuous boosting activity of ZmPLT5 (FIG. 3) and KWS_RBP4 (FIG. 6) as indicated by the co-delivered report gene tDTomato from construct pGEP359 (FIG. 13) in maize elite 4V-40171. tDTomatonegative embryogenic calluses were developed into mature embryos (A), while the embryo maturation were inhibited in the tDTomato-positive calluses in (B) and (C) after incubated in the embryo maturation medium for 10 day. Grey shades of the tissue in (B) and (C) indicate a red coloration, which is due to tDTomato expression.
FIG. 15 shows a genome editing nuclease MAD7 expression construct pGEP1054 map. tdTomato defines tdTomato report gene. MAD7 defines the maize codon-optimized CDS of MAD7 nuclease (Inscripta). BdUBI10 defines the *Brachypodium Ubiquitin* 10 promoter. Tnos defines the nos terminator.

Example 3. Continuous Expression of Boosters Negatively Impact Cell Differentiation and Plant Regeneration in Maize Recalcitrant Elite 4V-40171 (FIGS. 13 to 14)

For immature embryo isolation, osmotic treatment, bombardment, and embryogenic callus induction, please see the description in Example 1. Specifically, construct pGEP359 (SEQ ID NO: 54) that contains the expression cassette of red fluorescence report gene tDTomato (FIG. 13) was co-bombarded with the regeneration boosters of ZmPLT5 and KWS_RBP4. For each bombardment, 100 ng of plasmid pGEP359 were co-coated with 100 ng each of the two boost constructs onto 100 μg of 0.4 μm gold particles using calcium-spermidine method. Three bombardments (shots) per sample plate were performed. Embryogenic calluses were transferred onto embryo maturation medium MRM1 (please see below) after embryogenic callus induction for 12 days in N6_5Ag medium.

Strong tDTomato expression is visible by grey shades on the tissue representing red color (FIG. 14), which allow to distinguish tDTomato-positive tissues from the negative ones. tDTomate-positive calluses also indicates stable transformation of the report gene in the regenerated cells. Due to the nature of co-bombardment, the boost genes are likely co-present with tDTomato, and thus the expression of tDTomato can be used as a report for the presence of the co-bombarded boosters.

After cultured on embryo maturation medium (e.g. MRM1) for 10 days, tDTomato-negative embryogenic calluses were developed into mature embryos (FIG. 14A), while the tDTomato-positive calluses (in red color) generally remained as embryogenic calluses, but not developed into a mature embryo (FIGS. 14B and C). These results revealed a negative impact of the boosters on the further development of transformed cells in subsequent regeneration process if the booster is stably expressed and active.

The regeneration boosters stimulate cell proliferation and offer a positive selection for the initial regeneration of transformed cell. However, continuous expression of boosters negatively impact plant cell differentiation and the subsequent regeneration, and thus provide a negative selection for the stable transformed cells during plant regeneration.

Taken together, the results demonstrate that the regeneration boosters offer a "dual selection" for the transformed cells, namely positively selects transient expression delivery and negatively selects stable transgenic cells during regeneration.

Media

MRM1:

MS Salts, MS vitamins, 100 mg/L of myoinositol, 6% sucrose, 9 g/L of Bactoagar, pH 5.8.

Example 4. Regeneration Boosters Enhance Genome Editing in Maize A188 Immature Embryos (Table 1, FIGS. 15 to 17, 32 and 33)

Cell environment (e.g. cells at different cycle phases) and epigenetic status and chromatin structure of cell genome influences genetic modification. It is generally believed that highly dividing cells are the best recipients for genetic modification, e.g. stable transformation. Regeneration boosters promote cell division and rapid stable transformed as demonstrated above. However, it was further assessed whether the boosters enhance genome editing as well.

For immature embryo isolation, bombardment, and embryogenic callus induction post bombardment, please see the description in Example 1.

Figure 16:
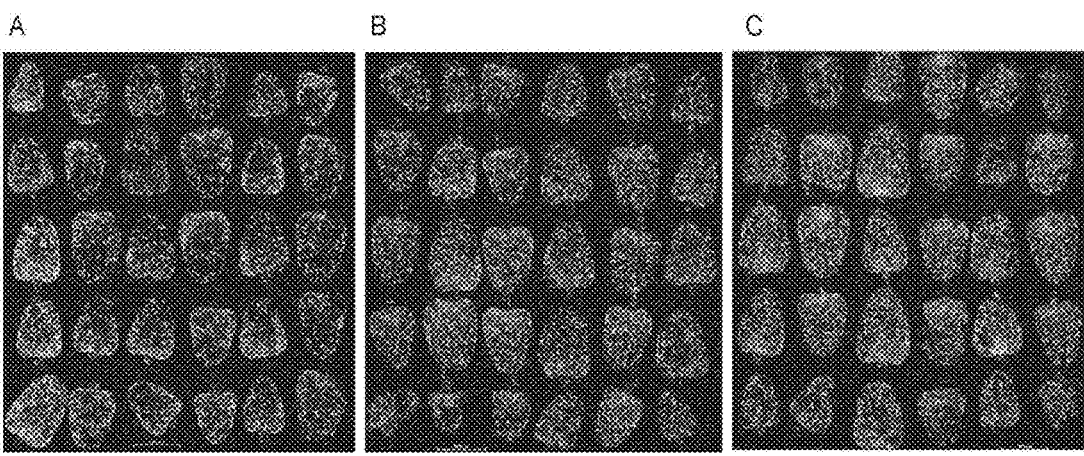
FIG. 16 shows tDTomato fluorescence images of maize A188 immature embryos 16 hour after bombardment. The immature embryos were bombarded with plasmid pGEP1054 only, which contains CRISPR nuclease MAD7 and tDTomato expression cassettes (A), or co-bombarded with plasmids of pGEP1054 and pGEP842 that contains crRNA m7GEP1 expression cassette (B), or co-bombarded with plasmids of pGEP1054, pGEP842, and booster KWS_RBP2 (C).

Specifically, 100 ng of booster KWS_RBP2 construct (FIG. 4) were co-delivered with 100 ng of plasmid pGEP1054 [containing the expression cassettes of CRISPR nuclease MAD7 and report gene tDTomato (SEQ ID NO: 55, FIG. 15)] and 300 ng of plasmid pGEP842 [containing CRISPR guide RNA m7GEP1 expression cassette, which target to maize HMG13 gene (SEQ ID NO: 53, FIG. 2) into maize A188 immature embryos by particle bombardment. tDTomato expression in the bombarded embryos was examined using a stereo fluorescence microscope at excitation 554 nm and emission 581 nm 16 hours bombardment, and results were showed in FIG. 16. The bombarded embryos were sampled at the time points as indicated (see e.g. FIG. 17). SDN-1 efficiency in the sampled embryos was analyzed by Tagman ddPCR.

Figure 17:
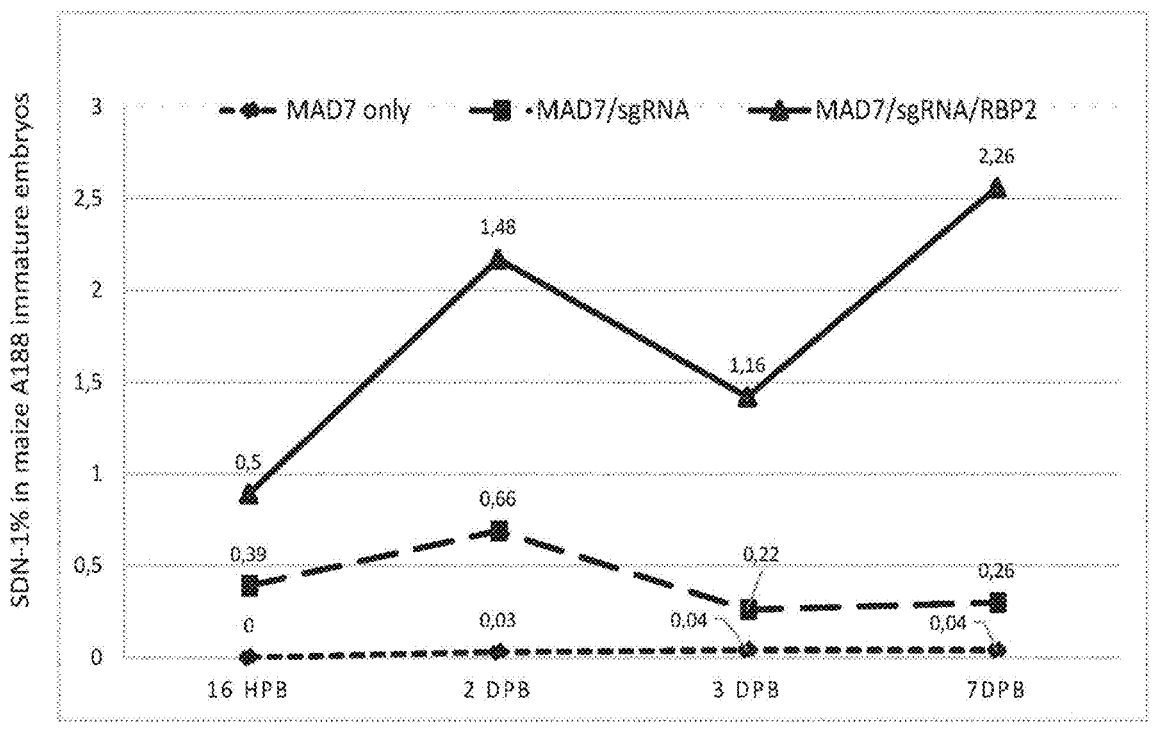
FIG. 17 shows SDN-1 efficiency in bombarded maize A188 immature embryos sampled at the time as indicated (Avg of three experiments). The immature embryos were bombarded with 200 ng plasmid pGEP1054 only, which contains the CRISPR nuclease MAD7 and tDTomato expression cassettes (MAD7 only), or co-bombarded with 200 ng of plasmid pGEP1054 and 300 ng of plasmid pGEP842 that contains the guide RNA m7GEP1 expression cassette (MAD7/sgRNA), or co-bombarded with 200 ng of plasmid pGEP1054 and 300 ng of plasmid pGEP842, plus 100 ng of plasmid KWS_RBP2 (MAD7/sgRNA/RBP2). The bombarded embryos were sampled at the time as indicated, and the SDN1 were analyzed by ddPCR,. HPB: hours post bombardment; DPB: days post bombardment.

The SDN-1 efficiencies are present in Table 1 and FIG. 17. Considering the time needed for gene expression of the bombarded constructs, SDN-1 efficiencies in the embryos 16 hours after bombardment are likely demonstrating the original editing activity in transformed cells without an influence from cell proliferation. The results suggest that the booster KWS_RBP2 enhances genome editing itself, not just as a result from the promoting effect on cell division.

One separate experiment with a focus on booster effect on genome editing SDN-1 efficiency at two CRISPR targets 48 hours after bombardment were further conducted. 200 ng of booster ZmPLT5 (FIG. 3), or 100 ng of booster KWS_RBP2, or the combination of 200 ng ZmPLT5 and 100 ng KWS_RBP2 were co-delivered with 100 ng of plasmid pGEP1054 and 150 ng of plasmid pGEP842 or with 100 ng of pGEP1054 and 150 ng of plasmid pGEP1067 [containing CRISPR guide RNA m7GEP22 expression cassette, which target to maize HMG13 gene (SEQ ID: 56, FIG. 33)] into maize A188 immature embryos by particle bombardment. The bombarded embryos were sampled 48 hours after bombardment.

Figure 33:
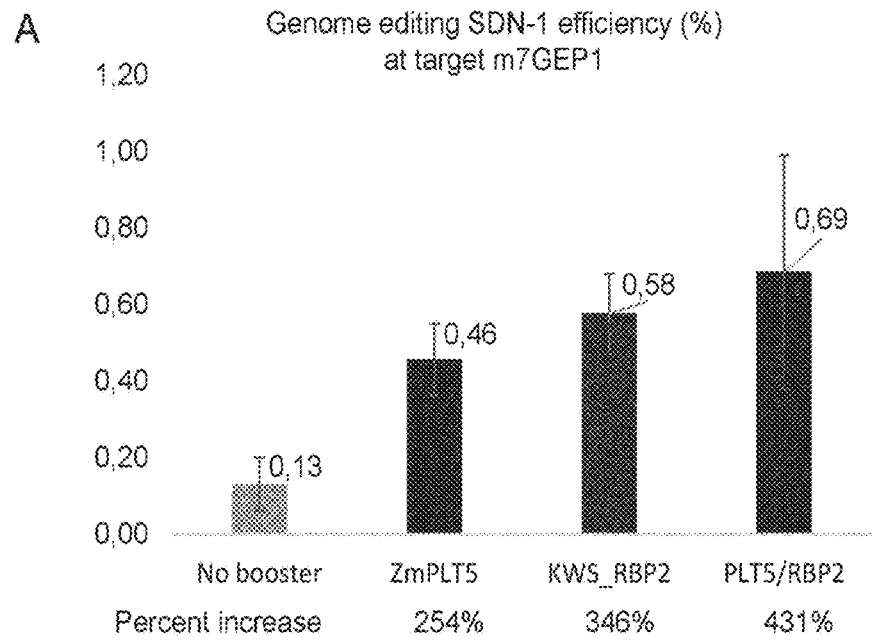
FIG. 33: Regeneration boosters promote genome editing SDN-1 efficiency 48 hours after co-introduced with the editing constructs into corn A188 immature embryos (n=6). A: shows genome editing SDN-1 efficiencies at CRISPR target m7GEP1, or at target m7GEP22 in B. No booster: bombarded with the editing plasmids only (100 ng of plasmid pGEP1054 and 150 ng of plasmid pGEP842 in A or 100 ng of plasmid pGEP1054 and 150 ng of plasmid pGEP1067 in B). The immature embryos were cobombarded with the same amounts of the CRISPR plasmids as those used in "No booster", and plus 200 ng of plasmid ZmPLT5 (ZmPLT5) or 100 ng of plasmid KWS_RBP2 (KWS_RBP2), or 200 ng of plasmid ZmPLT5 and 100 ng of plasmid KWSRBP2 (PLT5/RBP2). Error bar=standard deviation. The SDN-1 were analyzed by Taqman ddPCR.
Figure 33:
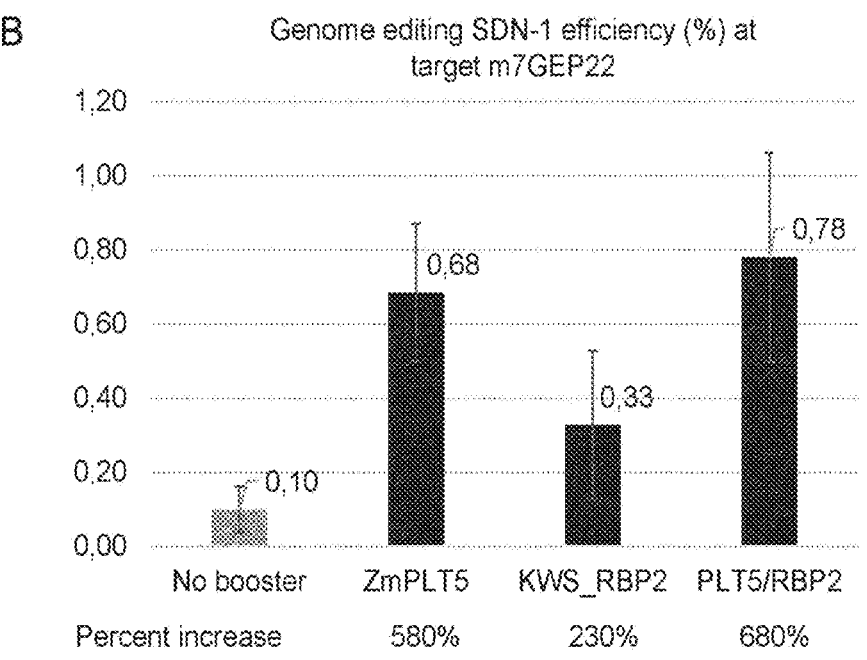

Genome editing SDN-1 efficiencies in the sampled embryos were analyzed by Tagman ddPCR and shown in FIG. 33. Compared to the control without a booster (No booster), an increase within a range of 230% to 680% in the SDN-1 efficiency at the two CRISPR target sites were observed. The best boosting effect were noted when the CRISPR editing constructs were co-introduced with the combination of the two boosters of ZmPLT5 and KWS_RBP2 (FIG. 33, PLT5/RBP2). These results further 0.4 μm gold particles using calcium-spermidine method. Three bombardments (shots) per sample plate were performed.

After bombardment the embryos were remained on the osmotic medium (N60SM) for another 16-20 hours. The embryos were transferred from the osmotic medium onto embryogenic callus induction medium (e.g. N6_5Ag) in a petri dish plate (100×25 mm) with scutellum-face-up, at a density of 12-15 embryos per plate. The embryos were incubated at 27° C. in dark for the embryogenic callus induction. After embryogenic callus induction in N6_5Ag medium for 10-14 days the induced calluses were transferred onto embryo maturation medium MRM1 in petro dish (100×25 mm), and cultured at 27° C. in dark for 10 days, and then at 25° C., weak light (20-50 μmol m$^{-2}$ s$^{-1}$) for 2-4 days. The mature somatic embryos were then transferred onto MSO medium (see below) in phytotray for plant outgrowth and further development for 5-7 days. A 5-10 mm leaf tip from each of the leaves of a $T_0$ plant is collected for DNA extraction. The targeted genome editing SDN-1 in the regenerated $T_0$ plants are screened by TaqMan real-time PCR (qPCR), and further conformed by Sanger sequencing trace decomposition analysis. The SDN-1 results are showed in Table 2 and FIG. 18.

TABLE 2

| | Different boosters enhance genome editing in maize A188. | | | | | | |
|---|---|---|---|---|---|---|---|
| Boosters | Total IEs | Total Events | Bi-SDN-1 | Mon-SDN-1 | Total SDN-1 | % SDN-1/ Event | % SDN-1/ IE |
| No booster | 130 | 312 | 2 | 0 | 2 | 0.6% | 1.5% |
| RBP2 | 150 | 237 | 20 | 14 | 34 | 14.3% | 22.7% |
| PLT5/RBP4 | 51 | 108 | 8 | 4 | 12 | 11.1% | 23.5% |
| RBP5 | 47 | 224 | 8 | 3 | 11 | 4.9% | 23.4% |
| RBP7 | 31 | 50 | 5 | 1 | 6 | 12.0% | 19.4% |
| RBP8 | 23 | 67 | 5 | 4 | 9 | 13.4% | 39.1% |
| Avg with booster | 302 | 686 | 46 | 26 | 72 | 10.5% | 23.8% | support the idea of that boosters promote genome editing SDN-1 at molecular and cell levels.

TABLE 1

SDN-1 efficiencies in the bombarded maize
A188 immature embryos sampled at a time as indicated

| | 16 HPB | 2 DPB | 3 DPB | 7 DPB |
|---|---|---|---|---|
| MAD7 only | 0 | 0.03 | 0.04 | 0.04 |
| MAD7 & sgRNA | 0.39 | 0.66 | 0.22 | 0.26 |
| MAD7, sgRNA & KWS_RBP2 | 0.50 | 1.48 | 1.16 | 2.26 |

Example 5. A Toolbox of Different Boosters
Enhance Genome Editing in to Plants of Maize
A188 (Table 2, FIG. 18)

For immature embryo isolation, bombardment, and embryogenic callus induction post bombardment, please see the description in Example 1.

Figure 18:
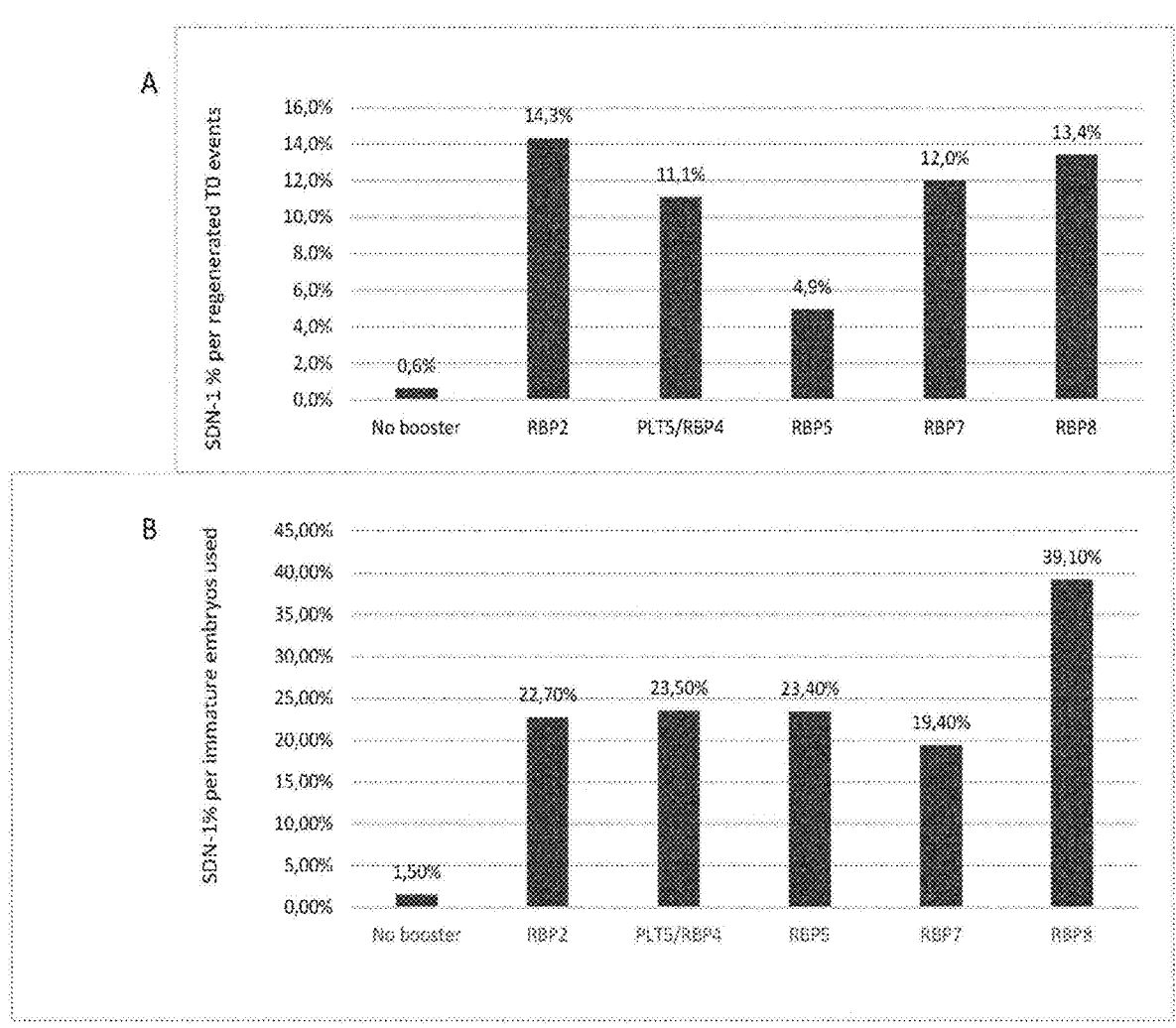
FIG. 18 shows how different regeneration boosters enhance genome editing in the regenerated T0 plants of maize A188. A: SDN-1 efficiency per regenerated T0 event; B: SDN-1 efficiency per immature embryo (IE) initially used. The regeneration boosters were co-delivered with the genome editing nuclease MAD7 construct pGEP837 (FIG. 1) and the sgRNA construct pGEP842 (FIG. 2) into maize A188 immature embryos by particle bombardment.

Specifically, construct pGEP837 (SEQ ID NO: 52, FIG. 1) and the crRNA construct pGEP842 (SEQ ID NO: 53, FIG. 2) were co-bombarded with the different boosters as indicated into maize A188 immature embryos by particle bombardment. For each bombardment (shot), 100 ng of plasmid pGEP837 were cocoated with 150 ng of plasmid pGEP842 and 100 ng each of different boost constructs onto 100 μg of Maize A188 is a highly regenerative genotype, and has been widely used as a model for plant study. Using the rapid regeneration system present here we are able to recover genome edited $T_0$ plants without a conventional selection and booster at a feasible efficiency (e.g. 0.6% of SDN-1 per T0 plant or 1.5% of SDN-1 per immature embryo initially used) from maize A188. However, when a booster was co-delivered the SDN-1 efficiency was dramatically increased (e.g. >15 fold increase in average when compared to that without a booster). An average 10% of SDN-1 per regenerated T0 plant or 24% per immature embryo is achieved (Table 2; FIG. 18). These results indicate that boosters promote genome editing and offer a positive selection for plant regeneration of the transformed cells. A toolbox of different boosters for highly efficient genome editing in maize A188 was developed.

Media:
  MSO: MS Salts, MS vitamins, 2 g/L of myoinositol, 2% sucrose, 8 g/L of Bactoagar, pH 5.8

Figure 19:
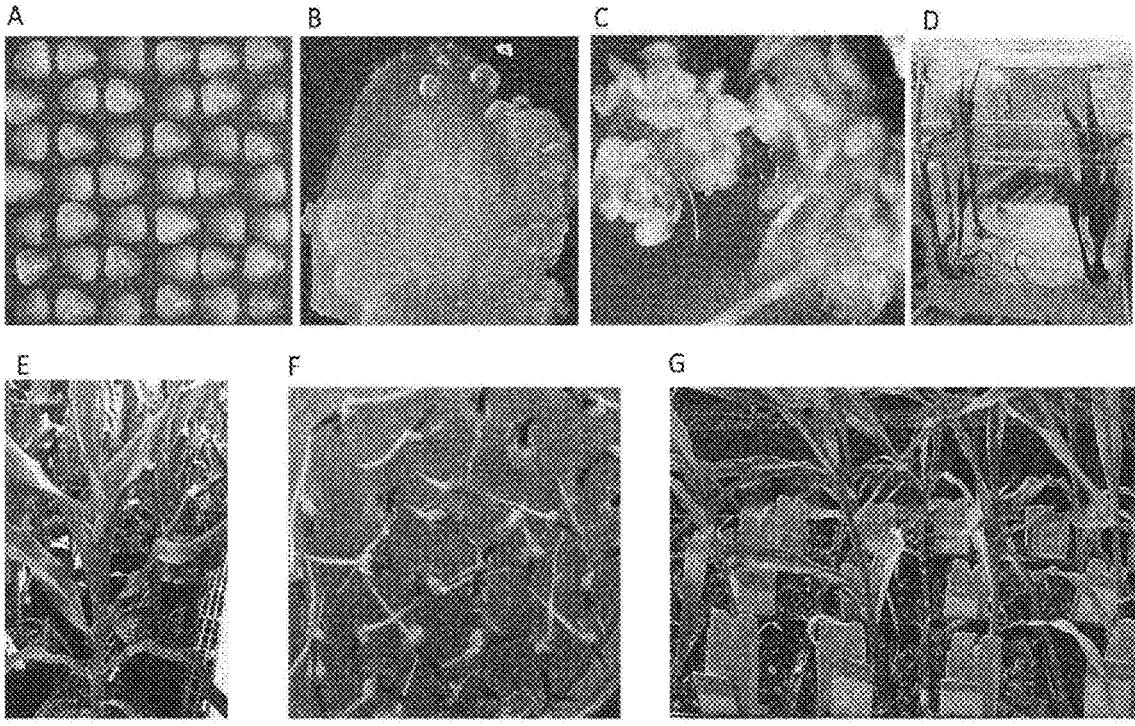
FIG. 19 shows the workflow for rapid plant regeneration and genome modification via particle bombardment of immature embryos (IEs) from maize recalcitrant elite 4V-40290. A: The immature embryos (IEs) in osmotic medium for 4 hours and were ready for particle bombardment; B: embryogenic calluses were induced from the scutellum surface of the IEs after co-bombarded with the boost constructs pABMBdEF1_ZmPLT5 and pABM-BdEF1_RBP8 and cultured on embryogenic callus induction medium for 6 days; (C): embryogenic calluses were matured after cultured on the maturation medium for 10 days; (D): T0 plantlets were developed from the mature embryos after outgrowth on the embryo germination medium for 7 days; (E): T0 plants growing in green house; (F): 14-day-old T1 embryos were germinating on MSO medium for 3 days; G: T1 plants in green house.

Example 6: Using Regeneration Boosters as a
"Dual Selection" for Rapid Regeneration and
Genome Editing Directly in Maize Recalcitrant
Elites (FIG. 19)

For immature embryo isolation, bombardment, and embryogenic callus induction post bombardment, please see the description in Example 1.

Workflow for Rapid Genome Editing in Maize

The rapid regeneration and genome editing in maize comprising the steps:

a) Preparing plant cells as part of preferably immature embryos (IEs), either zygotic embryos or somatic embryos.

b) Delivery of genome modification/editing components via particle bombardment into the plant cells as part of preferably immature embryos (IEs) from a), c) Culturing the plant cells from b) in the conditions allow for genome modification occur, and d) Regenerating a plant from the modified plant cell of step c), comprising of:

i) Plant cell proliferation and embryogenic callus induction, in which the cells from scutellum surface in immature embryos multiple and are organized into regenerative calluses. Specifically, 16-48 hours after particle bombardment, the bombarded immature embryos are transferred onto a embryogenesis callus induction medium containing relatively high concentration of auxin, e.g. 2,4-D (e.g. N6_5Ag, please also see Example 1-6) in petro dish plate (e.g. 25 100 mm), and culture at 15-30° C., dark for 1-4 weeks, preferably 1-3 weeks, most preferably 7-14 day (Note: the boosters offer a positive selection for the transiently transformed cells during this step).

ii) Plant organ/embryo development from the cells in i): separate developing embryogenic calluses from i) into small pieces of 1-10 mm, preferably 2-7 mm in diameter, and transfer the calluses onto a plant organ/embryo development medium in petro dish (e.g. 25×100 mm) depending on different genotypes. An embryo development medium contains high concentration of sucrose (e.g. 6% of sucrose) without plant hormone (e.g. MRM1 medium), while a plant organ development medium contains a high ratio of cytokinin (e.g. 6-Benzylaminopurine, Zeatin) to auxin (e.g. NAA, or IAA), e. g. the shooting medium (see below). Seal the plate with parafilm/surgical tape and culture at 15-30° C., light (50-200 µmol m$^{-2}$ s$^{-1}$) for 1-4 weeks, preferably 1-3 weeks, most preferably 10-18 days [Note: the boosters offer a negative selection for the stably transformed cells during this step; a "dual selection" for the cells with the booster activities only in regeneration step (a) degreed in step (b)]. Please also see Example 6.

iii) Plant development from the organs and embryos regenerated from ii): transfer the developing plantlets from ii) onto a plant development medium in phytotray (e.g. MSO or Rooting medium, see below), and culture at 15-30° C., light (50-200 µmol m$^{-2}$ s$^{-1}$) for 1-4 weeks, preferably 5-20 days. Now the regenerated T0 plants are ready for leaf sampling for molecular analysis or transfer to soil for $T_1$ seed production.

e) Screen for genetic modification events in the regenerated $T_0$ plants A 5-20 mm leaf tip from each of the leaves of a $T_0$ plant is collected for DNA extraction. Genome modification, e.g. genome editing in the regenerated $T_0$ plants are screened for instance by TaqMan realtime PCR (qPCR), marker capillary electrophoresis analysis, and TaqMan Digital Droplet PCR. Sitespecific modification is further conformed by next generation sequencing (NGS), Sanger sequencing, or Sanger sequencing trace decomposition analysis.

f) Grow the modified $T_0$ plants for $T_1$ seed production.

After the molecular screening and confirmation the modified $T_0$ plants are transferred to soil, and grow in a growth chamber or greenhouse under the suitable growth conditions. $T_0$ plants are phenotypically analyzed and grown for $T_1$ seed production by self-cross or back-cross to the maize WT.

g) Molecular analysis for genetic modification in the T1 progeny

Genome modification, for example, target genome editing in the genome of the bombarded immature embryo cells is likely inheritable. The inheritability of a genome editing event is determined by the segregation analysis of the modification in $T_1$ progeny. 10-20 days after pollination the immature $T_1$ embryos from the growing ear in a To plant are isolated by direct pulling the embryos out of the kernels in the ear (starts from the tip of the ear) in planta (Note: DO NOT harvest the ears at this point and leave the ear with remaining kernels in $T_0$ plants for $T_1$ seed production). The DNA from each of the $T_1$ immature embryos are isolated individually, and the modification in $T_1$ progeny are analyzed by TaqMan qPCR, marker capillary electrophoresis analysis, and Digital Droplet PCR. Site-specific modification is further conformed by Sanger sequencing. The segregation analysis of the modification in $T_1$ progeny can also be performed using the mature T1 embryos, or the leaf tissues from the T1 seedlings.

The workflow was also demonstrated in FIG. 19. Using regeneration boosters as a "dual selection" a rapid plant regeneration and genome editing system was established. For maize it takes about 4-6 weeks from immature embryo to T0 plants, or 4-5 months from immature embryos to T1 seeds.

Media

Shooting Medium:

1× MS salt, Ix LS vitamins, Ix FeEDTA, 2.5 mg/L CuSO4.5H2O, 100 mg/L Myo Inosit, 5 mg/L Zeatin, 0.5 g/L of MES, 20 g/L of sucrose, 3 g/L Gelzan, pH: 5.8

Rooting Medium:

1× MS salts, LS vitamins, Ix FeEDTA, 0.5 mg/L MES, 0.5 mg/L IBA, 1.25 mg/L of CuSO4, 20 g/L sucrose, 3 g/L Gelzan Example 7: A Toolbox of Different Boosters Promote Embryogenic Callus Induction and Regeneration in Recalcitrant Elite 4V-40171 (5F1690, FIGS. 20 and 21)

For immature embryo isolation, osmotic treatment, bombardment, and embryogenic callus induction, please see the description in Example 1.

Specifically, genome editing constructs pGEP837 (SEQ ID NO: 52, FIG. 1) and pGEP842 (SEQ ID NO: 53, FIG. 2) were co-bombarded with the different boosters as indicated into the immature embryos of maize elite 4V-40171 by particle bombardment. For each bombardment (shot), 100 ng of plasmid pGEP837 and 150 ng of plasmid pGEP842 were co-coated with 100 ng each of different boost constructs onto 100 µg of 0.4 µm gold particles using calcium-spermidine method. Three bombardments (shots) per sample plate were performed. The bombarded embryos were transformed onto the embryogenic callus induction medium 16-20 hours after bombardment.

Embryogenic callus induction was observed under a Zeiss stereo microscope 4 days and 7 days after bombardment. The representative results were showed in FIG. 20.

Figure 20:
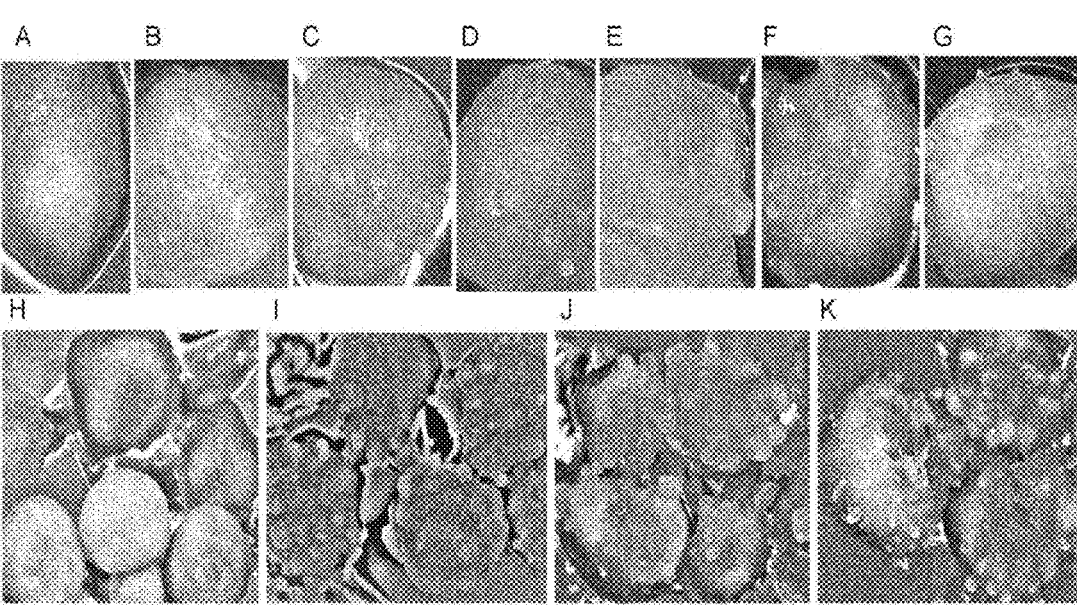
FIG. 20 shows how the regeneration boosters promote embryogenic callus induction from maize recalcitrant elite 4V-40171. (A) to (G): images of embryogenic callus induction for 4 days in a callus induction medium from the embryos bombarded with the genome editing constructs pGEP837 and pGEP842 only (A), or co-bombarded with booster KWS_RBP2 (B), KWS_RBP4 (C), KWS_RBP5 (D), ZmPLT5 and KWS_RBP5 (E), ZmPLT5 and KWS_RBP6 (F), or ZmPLT5 and KWS_RBP7 (G). (H) to (K): images of embryogenic callus induction in a callus induction medium for 7 days from the embryos bombarded with the genome editing constructs pGEP837 and pGEP842 only (H) or co-bombarded with boosters of ZmPLT5 and KWS_RBP2 (I), ZmPLT5 and ZmPLT5 and KWS_RBP3 (J), or ZmPLT5 and KWS_RBP4 (K).
Figure 21:
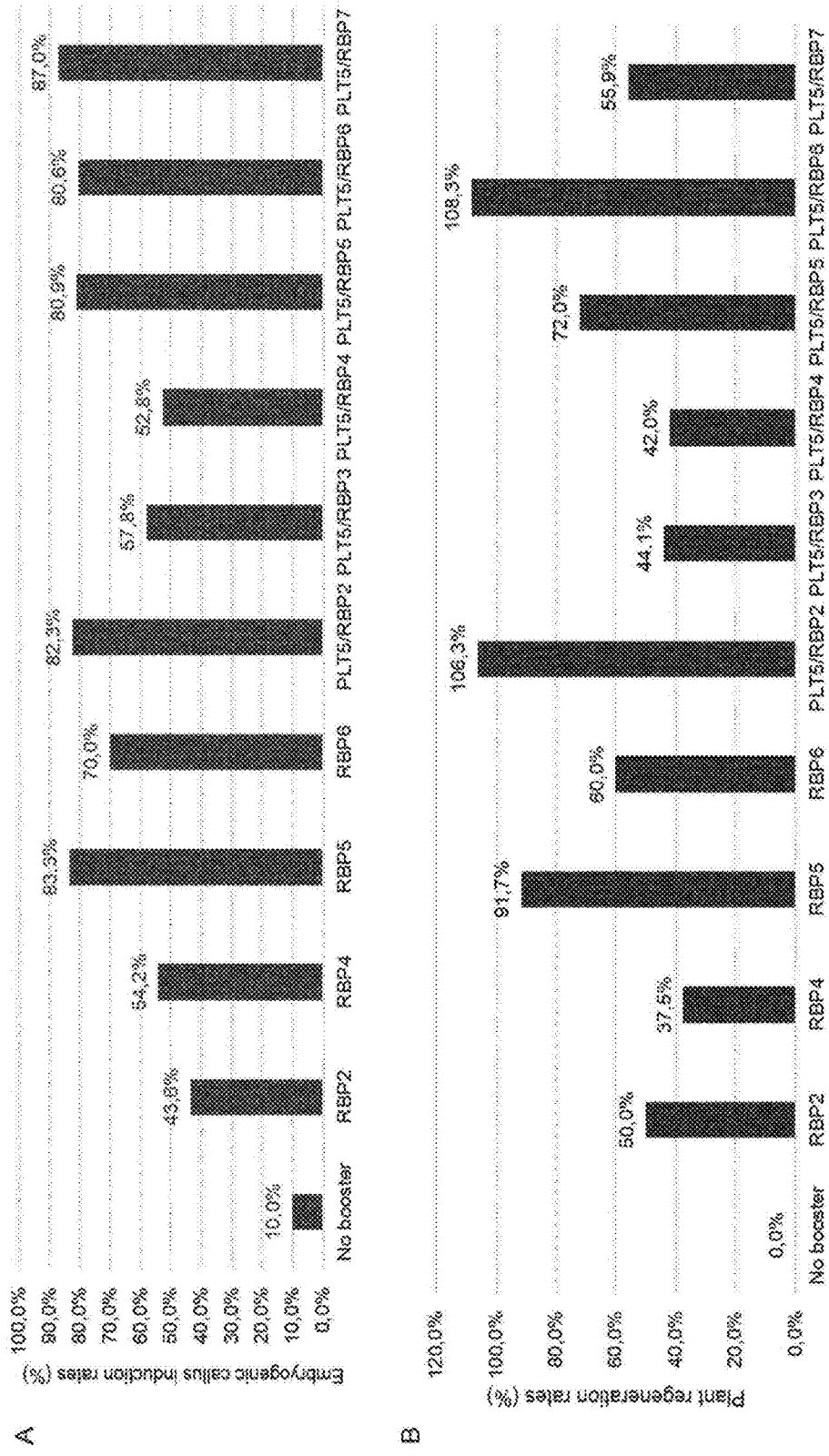
FIG. 21 shows embryogenic callus induction and plant regeneration efficiencies from the recalcitrant maize elite 4V-40171 immature embryos after co-bombarded with boosters as indicated. (A) Embryogenic callus induction rates (the numbers of embryos with at least one embryogenic callus from 100 embryos initially used; results recorded 12 days after bombardment; (B) plant regeneration rates (calculated by the total regenerated T0 events from 100 immature embryos initially used).

Maize elite 4V-40171 is a recalcitrant genotype. Without a regeneration booster the immature embryos from this elite did not produce any regenerating structures when examined in both of 4 days and 7 days after bombardment (FIGS. 20A and H). Compared to the control without a booster, multiple embryogenic cell structures were induced from the embryos co-bombarded with different regeneration boosters (compare the results in FIG. 20A to B-G and FIG. 20 H to K) in both of 4 days and 7 days after bombardment.

Callus induction rates were recorded 12 days after bombardment, which is defined as the numbers of embryos with at least one embryogenic callus from 100 embryos initially used. The callus induction rates were present in FIG. 21A, and plant regeneration rates (the numbers of regenerated T0 events from 100 embryos initially used) were presented in FIG. 21B. Without a booster this elite is generally a recalcitrant genotype, it became regenerative when a booster was applied (FIG. 21B) in our regeneration system. These results demonstrate that the boosters significantly promote cell proliferation and plant regeneration in maize elites.

Figure 22:
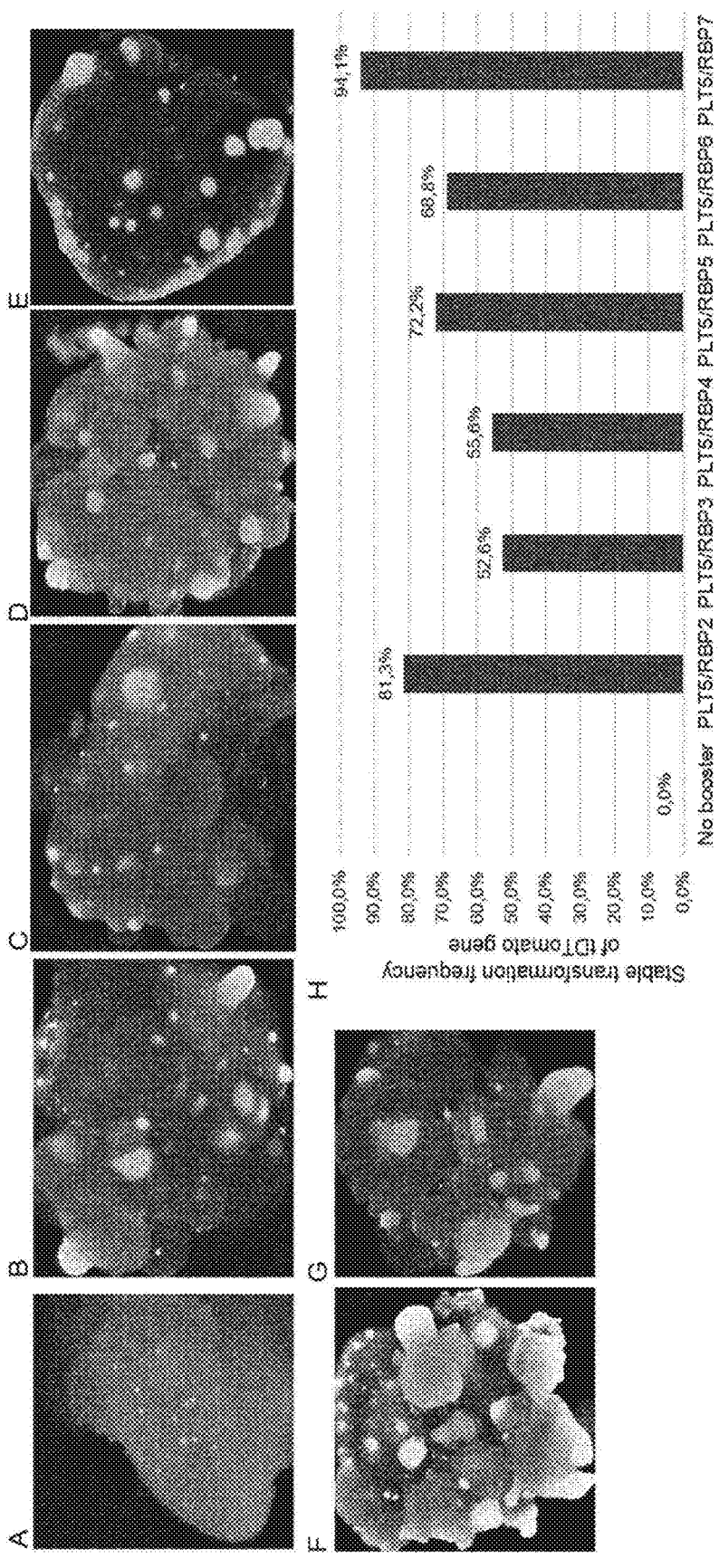
FIG. 22 shows that the regeneration boosters promote stable transformation of the fluorescent report gene tDTomato in maize recalcitrant elite 4V-40171. (A) Fluorescent images of immature embryos in embryogenic callus induction medium for 8 days after bombarded with tDTomato construct pGEP359 (FIG. 13) only (A), or co-bombarded with boosters ZmPLT5 and KWS_RBP2 (B), ZmPLT5 and KWS_RBP3 (C), ZmPLT5 and KWS_RBP4 (D), ZmPLT5 and KWS_RBP5 (E), ZmPLT5 and KWS_RBP6 (F), or ZmPLT5 and KWS_RBP7 (G). (H) Stable transformation frequency of tDTomato report gene (the numbers of embryos with at least one tDTomato-positive structure from 100 embryos initially used). The results were recorded 8 days after co-bombarded with boosters as indicated.

Example 8: A Toolbox of Different Boosters Promote Rapid Transformation in Maize Recalcitrant Elite 4V 40171 (FIG. 22)

For immature embryo isolation, osmotic treatment, bombardment, and embryogenic callus induction, please see the description in Example 1.

Specifically, genome editing constructs pGEP359 (SEQ ID NO: 54, FIG. 13) and pGEP842 (SEQ ID NO: 53, FIG. 2) were co-bombarded with different boosters as indicated into the immature embryos of maize elite 4V-40171 by particle bombardment. For each bombardment (shot), 100 ng of plasmid pGEP359 and 150 ng of plasmid pGEP842 were co-coated with 100 ng each of different boost constructs onto 100 μg of 0.4 μm gold particles using calcium-spermidine method. Three bombardments (shots) per sample plate were performed. The bombarded embryos were transformed onto the embryogenic callus induction medium 16-20 hours after bombardment.

tDTomato gene expression in the scutellum surface cells of the bombarded immature embryos was examined using a stereo fluorescence microscope at excitation 554 nm and emission 581 nm after bombardment and cultured in embryogenic callus induction for 8 days. The representative results are present in FIG. 22.

Without a booster the immature embryos from maize recalcitrant elite 4V-40171 did not produce a red fluorescent cell cluster (FIG. 22A). Contrast to the control without a booster, multiple embryogenic structures with strong and uniformed fluorescence signals appeared from the embryos co-bombarded with different regeneration boosters after bombardment and cultured for 8 days (FIG. 22B to G). Strong and uniformed expression of tDTomato in regenerated tissues, e.g. embryogenic callus, indicates the integration and stable transformation of this foreign gene. The stable transformation frequencies of tDTomato report gene in the co-bombarded immature embryos (defined as the numbers of embryos with at least one tDTomato-positive structure from 100 embryos initially used) were recorded 8 days after bombardment, and showed in FIG. 22H. As a recalcitrant genotype, the immature embryos from maize elite 4V-40171 is generally not responsible to transformation, but they became rapidly responsible and highly transformable when a booster was applied. The results demonstrate that boosters remarkably promote rapid stable transformation in maize elites and offer a positive selection for the transformed cells in cell proliferation and regeneration.

Figure 23:
FIG. 23 shows how different boosters promote genome editing in recalcitrant maize elite 4V-40171. A: SDN-1 efficiency per regenerated T0 event (the number of SDN-1 events per 100 regenerated T0 events); B: SDN-1 efficiency per immature embryo (the number of SDN-1 events per 100 immature embryos initially used). The regeneration boosters were co-delivered with the genome editing constructs pGEP837 (FIG. 1) and the pGEP842 (FIG. 2) into maize immature embryos by particle bombardment.

Example 9: A Toolbox of Different Boosters Promote Genome Editing in to Plants of Maize Recalcitrant Elite 4V-40171 (Table 3; FIG. 23)

The workflow was as described in Example 6. For immature embryo isolation, bombardment, and embryogenic callus induction post bombardment, please see the description in Example 1.

Specifically, genome editing constructs pGEP837 (SEQ ID NO: 52, FIG. 1) and pGEP842 (SEQ ID NO: 53, FIG. 2) were co-bombarded with the different boosters as indicated into the immature embryos of maize elite 4V-40171 by particle bombardment. For each bombardment (shot), 100 ng of plasmid pGEP837 and 150 ng of plasmid pGEP842 were co-coated with 100 ng each of different boost constructs onto 100 μg of 0.4 μm gold particles using calcium-spermidine method. Three bombardments (shots) per sample plate were performed. The bombarded embryos were transformed onto the embryogenic callus induction medium 16-20 hours after bombardment.

For embryogenic callus induction and plant regeneration and genome editing SDN-1 screening and confirmation, please see Example 5.

The immature embryos from maize recalcitrant elite 4V-40171 is generally not responsible to regeneration, but they became regenerative when a booster was co-delivered. An average ~20% of SDN-1 per regenerated T0 plant or 10% per immature embryo is achieved (Table 3; FIG. 23). The results demonstrate that boosters remarkably promote cell regeneration and genome editing in maize elites and offer a positive selection for the regeneration of transformed cells.

TABLE 3

| | Different boosters promote highly efficient genome editing in recalcitrant maize elite 4V-40171 | | | | | | |
| Boosters | Total IE | Total Event | Bi-SDN-1 | Mon-SDN-1 | Total SDN-1 | % SDN-1/ Event | % SDN-1/ IE |
| --- | --- | --- | --- | --- | --- | --- | --- |
| No booster | 16 | 0 | 0 | 0 | 0 | 0 | 0 |
| PLT5/RBP2 | 34 | 14 | 1 | 0 | 1 | 7.1% | 2.9% |
| PLT5/RBP3 | 32 | 15 | 1 | 6 | 7 | 46.7% | 21.9% |
| PLT5/RBP4 | 47 | 19 | 3 | 2 | 5 | 26.3% | 10.6% |
| PLT5/RBP5 | 67 | 39 | 4 | 3 | 7 | 17.9% | 10.4% |
| PLT5/RBP6 | 56 | 68 | 4 | 6 | 10 | 14.7% | 17.9% |

TABLE 3-continued

| | | | | | | | |
|---|---|---|---|---|---|---|---|
| Different boosters promote highly efficient genome editing in recalcitrant maize elite 4V-40171 | | | | | | | |
| Boosters | Total IE | Total Event | Bi-SDN-1 | Mon-SDN-1 | Total SDN-1 | % SDN-1/ Event | % SDN-1/ IE |
| PLT5/RBP8 | 42 | 2 | 1 | 0 | 1 | 50.0% | 2.4% |
| Avg. with boosters | 294 | 157 | 14 | 17 | 31 | 19.7% | 10.5% |

Figure 24:
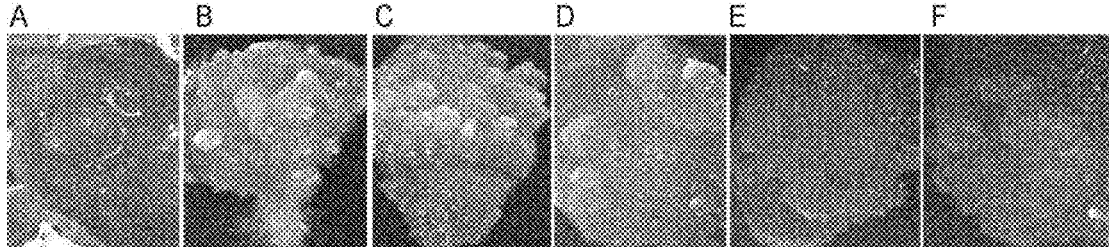
FIG. 24 shows how regeneration boosters promote embryogenic callus induction from the immature embryos of maize recalcitrant elite 2V-20195. The embryos were cultured in callus induction medium for 8 days after the bombarded with the genome editing construct pGEP837 only (A), or co-bombarded with the boosters of ZmPLT5 and KWS_RBP2 (B), ZmPLT5 and KWS_RBP3 (C), ZmPLT5 and KWS_RBP4 (D), ZmPLT5 and KWS_RBP5 (E), or ZmPLT5 and KWS_RBP6 (F). Images were taken 8 days after bombardment.
Figure 25:
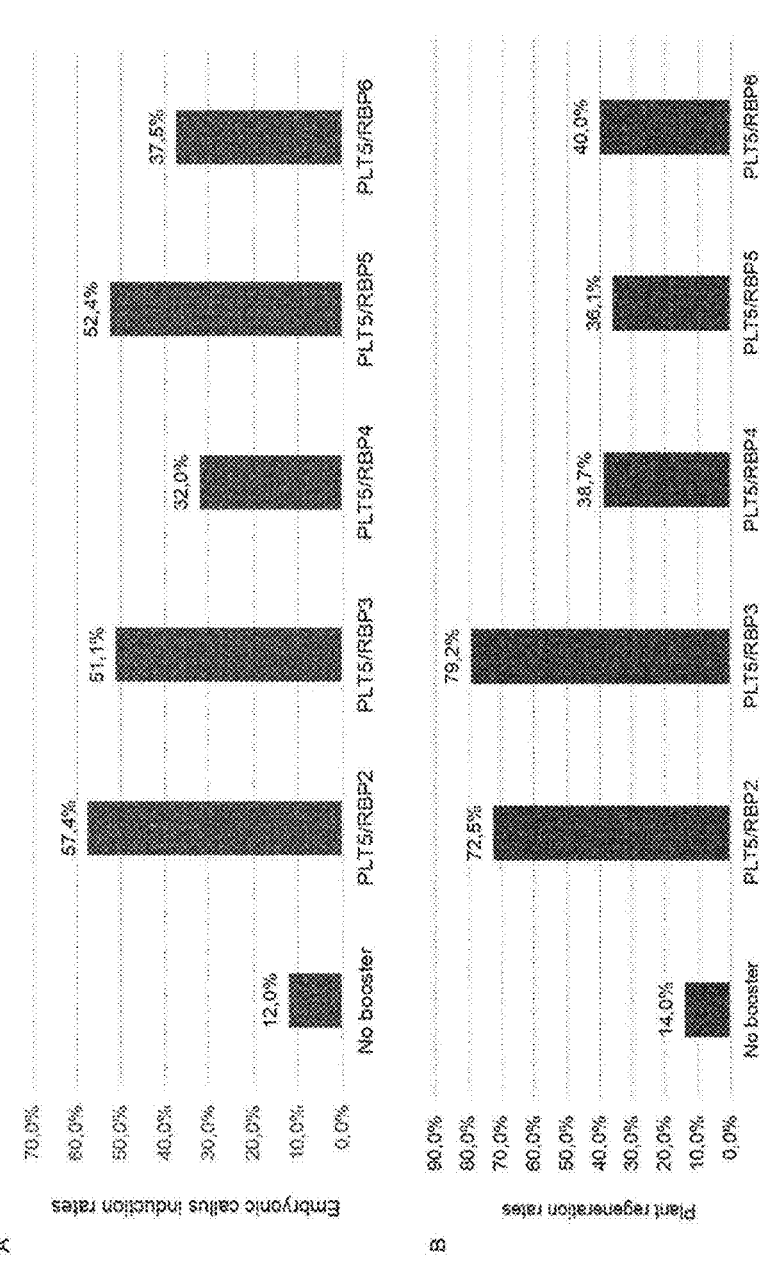
FIG. 25 shows embryogenic callus induction and plant regeneration efficiencies from the recalcitrant maize elite 2V-20195 immature embryos after co-bombarded with boosters as indicated. (A) Embryogenic callus induction rates (the numbers of embryos with at least one embryogenic callus from 100 embryos initially used; results recorded after cultured in the medium for 14 days; (B) plant regeneration rates (calculated by the total regenerated T0 events from 100 immature embryos initially used).

Example 10: A Toolbox of Different Boosters Promote Embryogenic Callus Induction and Regeneration in Recalcitrant Elite 2V-20195 (FIGS. 24 and 25)

For immature embryo isolation, osmotic treatment, bombardment, and embryogenic callus induction, please see the description in Example 1 and Example 7.

Specifically, genome editing constructs pGEP837 (SEQ ID NO: 52, FIG. 1) and pGEP842 (SEQ ID NO: 53, FIG. 2) were co-bombarded with the different boosters as indicated into the immature embryos of maize elite 2V-20195 by particle bombardment. For each bombardment (shot), 100 ng of plasmid pGEP837 and 150 ng of plasmid pGEP842 were co-coated with 100 ng each of different boost constructs onto 100 µg of 0.4 µm gold particles using calcium-spermidine method. Three bombardments (shots) per sample plate were performed. The bombarded embryos were transformed onto the embryogenic callus induction medium 16-20 hours after bombardment.

Embryogenic callus induction was observed under a Zeiss stereo microscope 8 days after bombardment. The representative results were showed in FIG. 24. Without a regeneration booster majority of the immature embryos from the maize recalcitrant elite 2V-20195 did not produce regenerating structures in 8 days after bombardment (FIG. 24 A). Compared to the control without a booster, multiple embryogenic cell structures were induced from the embryos co-bombarded with different regeneration boosters (compare the results in FIG. 24A to B-F) in both of 8 days after bombardment.

Callus induction rates were recorded 14 days after bombardment, which is defined as the numbers of embryos with at least one embryogenic callus from 100 embryos initially used. The callus induction rates were present in FIG. 25A, and plant regeneration rates (defined as the numbers of regenerated T0 events from 100 embryos initially used) were presented in FIG. 25B. Without a booster this elite had a low regeneration rate in both of callus induction and plant regeneration, and the both of regeneration rates increased significantly when a booster was co-delivered in our regeneration system (FIG. 25). These results demonstrate that the boosters significantly promote cell proliferation and plant regeneration in maize elites.

Figure 26:
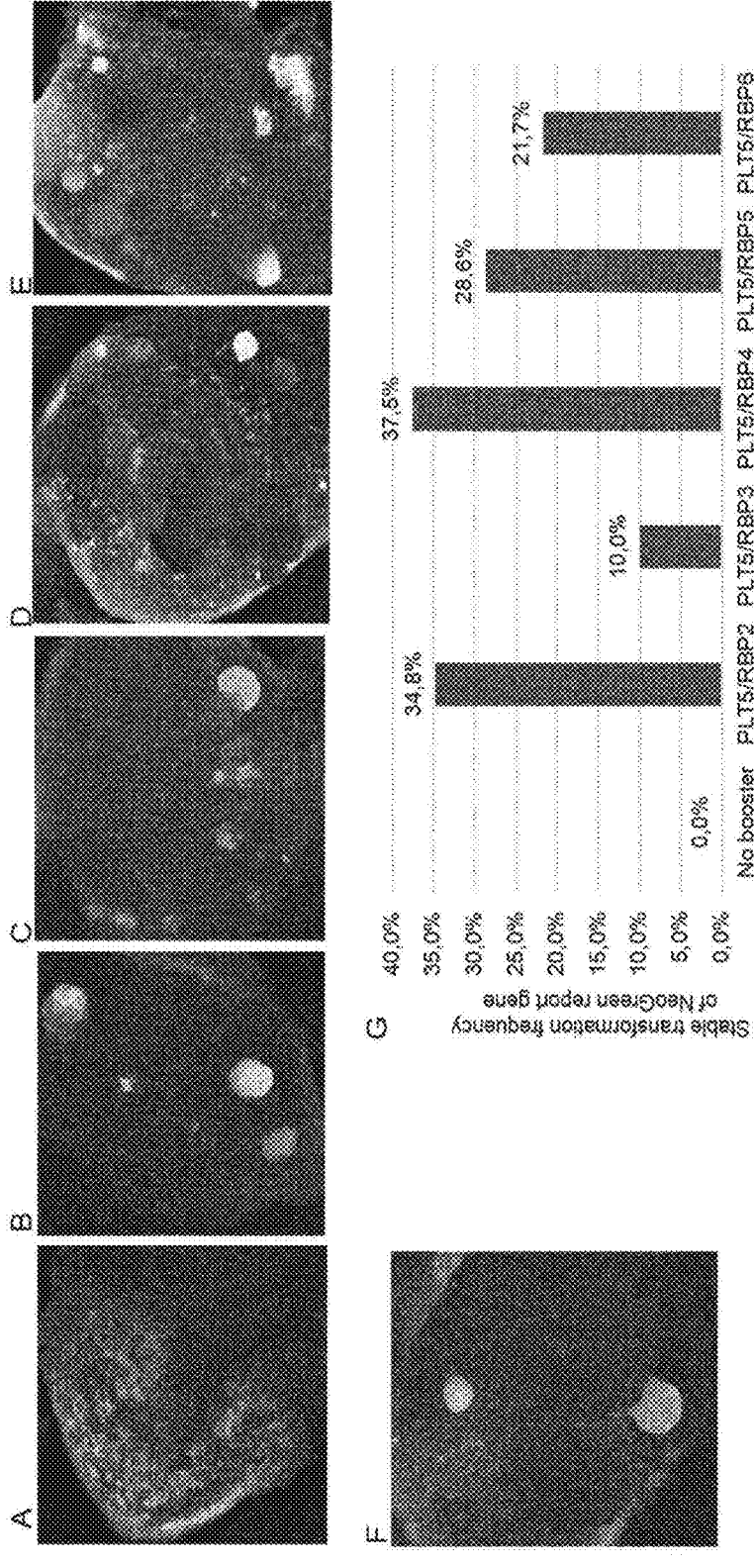
FIG. 26 shows how regeneration boosters promote stable transformation of a green fluorescent report gene (GEP) in maize recalcitrant elite 2V-20195. (A) fluorescent images of immature embryos in callus induction medium for 8 days after bombarded with the GEP construct pGEP837 only (A), or co-bombarded with the boosters of ZmPLT5 and KWS_RBP2 (B), ZmPLT5 and KWS_RBP3 (C), ZmPLT5 and KWS_RBP4 (D), ZmPLT5 and KWS_RBP5 (E), or ZmPLT5 and KWS_RBP6 (F). (H) Stable transformation frequency of the GEP report gene in the immature embryos (the numbers of embryos with at least one tDTomato-positive structure from 100 embryos initially used). The results were recorded 14 days after co-bombarded with the boosters as indicated.

Example 11: A Toolbox of Different Boosters Promote Rapid and Highly Efficient Genetic Transformation in Maize Recalcitrant Elite 2V-20195 (FIG. 26)

For immature embryo isolation, osmotic treatment, bombardment, and embryogenic callus induction, please see the description in Example 1, Example 7, and Example 10.

Specifically, genome editing constructs pGEP837 (SEQ ID NO: 52, FIG. 1) and pGEP842 (SEQ ID NO: 53, FIG. 2) were co-bombarded with the different boosters as indicated into the immature embryos of maize elite 2V-20195 by particle bombardment. For each bombardment (shot), 100 ng of plasmid pGEP837 and 150 ng of plasmid pGEP842 were co-coated with 100 ng each of different boost constructs onto 100 µg of 0.4 µm gold particles using calcium-spermidine method. Three bombardments (shots) per sample plate were performed. The bombarded embryos were transformed onto the embryogenic callus induction medium 16-20 hours after bombardment.

Green fluorescent report gene expression in the scutellum surface cells of the bombarded immature embryos was examined using a stereo fluorescence microscope at excitation maximum 506 nm and emission maximum 517 nm after bombardment and cultured in embryogenic callus induction for 4 days. The representative results are present in FIG. 26.

Without a booster the immature embryos from maize recalcitrant elite 2V-20195 did not produce a green fluorescent cell cluster (FIG. 26 A). Contrast to the control without a booster, multiple embryogenic structures with strong and uniformed green fluorescence signals appeared from the embryos co-bombarded with different regeneration boosters after bombardment and cultured for 8 days (FIG. 26B to F). Strong and uniformed expression of green fluorescent report gene in regenerated tissues, e.g. embryogenic callus, indicates the integration and stable transformation of this foreign gene. The stable transformation frequencies of green fluorescent report gene in the co-bombarded immature embryos (defined as the numbers of embryos with at least one green fluorescent report gene-positive structure from 100 embryos initially used) were recorded 14 days after bombardment and showed in FIG. 26G. The immature embryos from maize elite 2V-20195 is generally not responsible to transformation, but they became rapidly responsible and highly transformable when a booster was applied. The results demonstrate that boosters remarkably promote rapid stable transformation in maize elites and offer a positive selection for the transformed cells in cell proliferation and regeneration.

Figure 27:
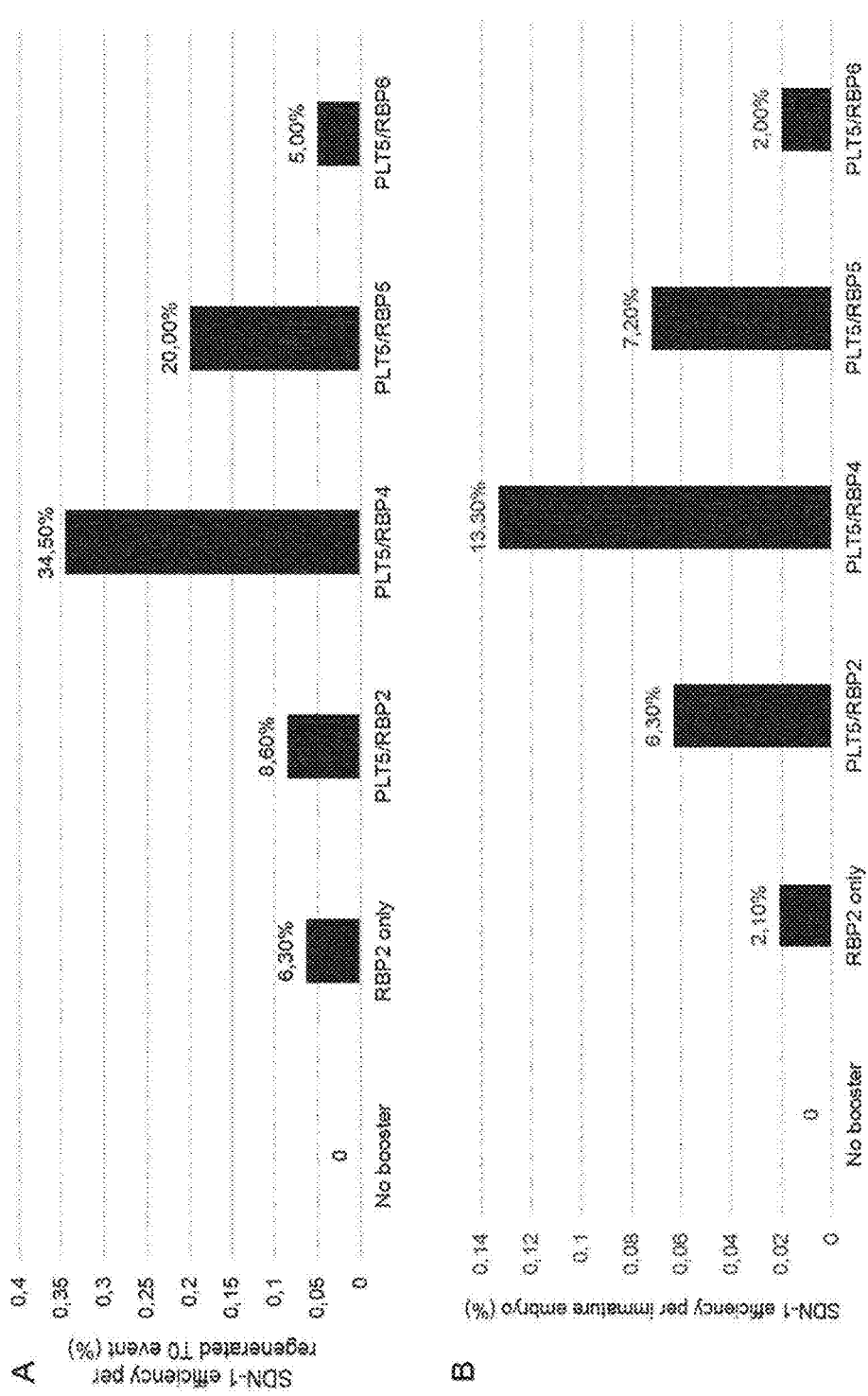
FIG. 27 shows how different boosters promote genome editing in recalcitrant maize elite 2V-20195. A: SDN-1 efficiency per regenerated event (SDN-1 events from 100 regenerated T0 events); B: SDN-1 efficiency per immature embryo (SDN-1 events per 100 immature embryos initially used). The regeneration boosters were co-delivered with the genome editing constructs of pGEP837 and pGEP842 into maize immature embryos by particle bombardment.

Example 12: A Toolbox of Different Boosters Promote Rapid Genome Editing in to Plants of Maize Recalcitrant Elite 2V-20195 (Table 4; FIG. 27)

The workflow was as described in Example 6. For immature embryo isolation, osmotic treatment, and bombardment, please see the description in Example 1. Specifically, genome editing constructs pGEP837 (SEQ ID NO: 52, FIG. 1) and pGEP842 (SEQ ID NO: 53, FIG. 2) were co-bombarded with the different boosters as indicated into the immature embryos of maize elite 2V-20195 by particle bombardment. For each bombardment (shot), 100 ng of plasmid pGEP837 and 150 ng of plasmid pGEP842 were co-coated with 100 ng each of different boost constructs onto 100 µg of 0.4 µm gold particles using calcium-spermidine method. Three bombardments (shots) per sample plate were performed. The bombarded embryos were transformed onto the embryogenic callus induction medium 16-20 hours after bombardment.

For plant regeneration, and genome editing SDN-1 screen and conformation in regenerated T0 plants please see Example 5 and Example 9.

The plant regeneration rate from elite 2V-20195 immature embryos is low in the control experiment without a booster. Only seven T0 plants were regenerated from 50 immature embryos initially bombarded. There was not any editing at the target site identified from the 7 regenerated plants (Table 4). The elite 2V-20195 immature embryos became more regenerative and more responsive to genome editing when a booster was co-delivered. An average 14.5% of SDN-1 per regenerated T0 plant or 6% of SDN-1 per immature embryo is achieved (Table 4; FIG. 27). The results reveal that the boosters promote cell regeneration and genome editing in maize elites and offer a positive selection for the regeneration of transformed cells.

TABLE 4

| | | | | | | Different boosters promote genome editing in T0 plants of maize recalcitrant elite 2V-20195 | |
|---|---|---|---|---|---|---|---|
| Boosters | Total IE | Total Event | Bi- SDN-1 | Mon- SDN-1 | Total SDN-1 | % SDN-1/ Event | % SDN-1/ IE |
| No booster | 50 | 7 | 0 | 0 | 0 | 0 | 0 |
| RBP2 only | 47 | 16 | 1 | 0 | 1 | 6.3% | 2.1% |
| PLT5/RBP2 | 80 | 58 | 2 | 3 | 5 | 8.6% | 6.3% |
| PLT5/RBP4 | 75 | 29 | 8 | 2 | 10 | 34.5% | 13.3% |
| PLT5/RBP5 | 97 | 35 | 6 | 1 | 7 | 20.0% | 7.2% |
| PLT5/RBP6 | 50 | 20 | 1 | 0 | 1 | 5.0% | 2.0% |
| Avg. with boosters | 399 | 165 | 18 | 6 | 24 | 14.5% | 6.0% |

Figure 28:
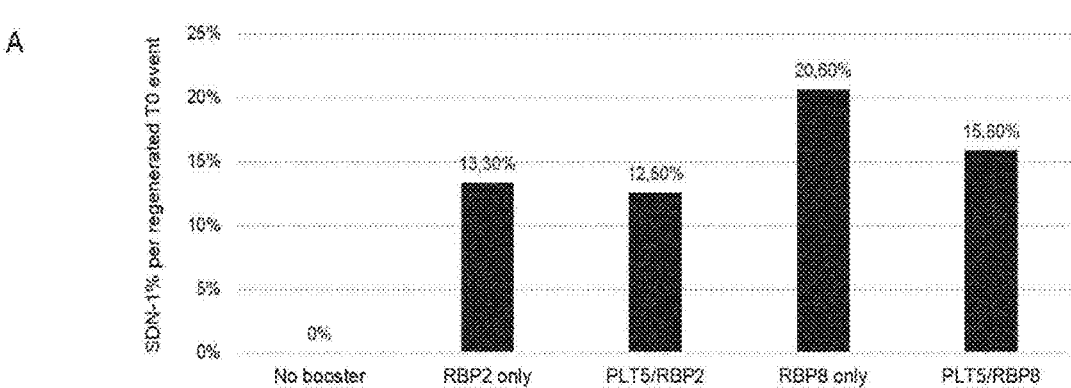
FIG. 28 shows how different boosters promote genome editing in $T_o$ plants of maize recalcitrant elite 4V-40290. A: SDN-1 efficiency per regenerated T0 events (the number of SDN-1 T0 events per 100 regenerated T0 events); B: SDN-1 efficiency per embryo (the number of SDN-1 T0 events per 100 immature embryos initially used).
Figure 28:
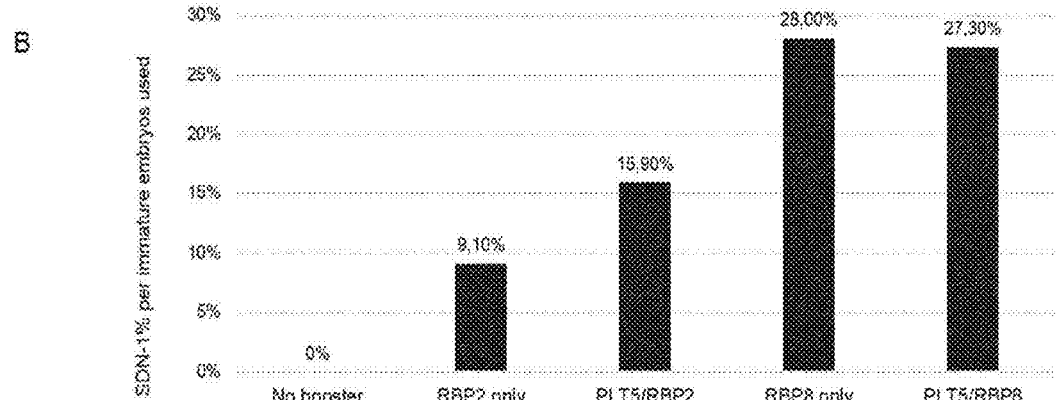

Example 13: A Toolbox of Different Boosters Promote Rapid Genome Editing in to Plants of Maize Recalcitrant Elite 4V-40290 (Table 5; FIG. 28)

The workflow was as described in Example 6. For immature embryo isolation, osmotic treatment, and bombardment, please see the description in Example 1. Specifically, genome editing constructs pGEP837 (SEQ ID NO: 52, FIG. 1) and pGEP842 (SEQ ID NO: 53, FIG. 2) were co-bombarded with the different boosters as indicated into the immature embryos of elite 4V-40290 by particle bombardment. For each bombardment (shot), 100 ng of plasmid pGEP837 and 150 ng of plasmid pGEP842 were cocoated with 100 ng each of different boost constructs onto 100 μg of 0.4 μm gold particles using calcium-spermidine method. Three bombardments (shots) per sample plate were performed. The bombarded embryos were transformed onto the embryogenic callus induction medium 16-20 hours after bombardment.

For plant regeneration, and genome editing SDN-1 screen and conformation in regenerated T0 plants please see Example 5 and Example 9.

The plant regeneration rate from elite 4V-402 90immature embryos is low in the control experiment without a booster. Only five T0 plants were regenerated from 44 immature embryos initially bombarded. There was not any editing at the target site identified from the 5 regenerated plants (Table 5). The elite 4V-40290 immature embryos became more regenerative and more responsive to genome editing when a booster was co-delivered. An average 14% of SDN-1 per both of regenerated T0 plant and per immature embryo is achieved (Table 5; FIG. 28). The results reveal that the boosters promote cell regeneration and genome editing in maize elites and offer a positive selection for the regeneration of transformed cells.

TABLE 5

| | | | | | | Different boosters promote rapid genome editing in $T_0$ plants of maize recalcitrant elite 4V-40290 | |
|---|---|---|---|---|---|---|---|
| Boosters | Total IE | Total Event | Bi- SDN-1 | Mon- SDN-1 | Total SDN-1 | % SDN-1/ Event | % SDN-1/ IE |
| No booster | 44 | 5 | 0 | 0 | 0 | 0% | 0% |
| RBP2 only | 22 | 15 | 2 | 0 | 2 | 13.3% | 9.1% |
| PLT5/RBP2 | 82 | 104 | 3 | 10 | 13 | 12.5% | 15.9% |
| RBP8 only | 25 | 34 | 1 | 6 | 7 | 20.6% | 28.0% |
| PLT5/RBP8 | 22 | 38 | 2 | 4 | 6 | 15.8% | 27.3% |
| Avg. with boosters | 195 | 196 | 8 | 20 | 28 | 14.3% | 14.4% |

Figure 29:
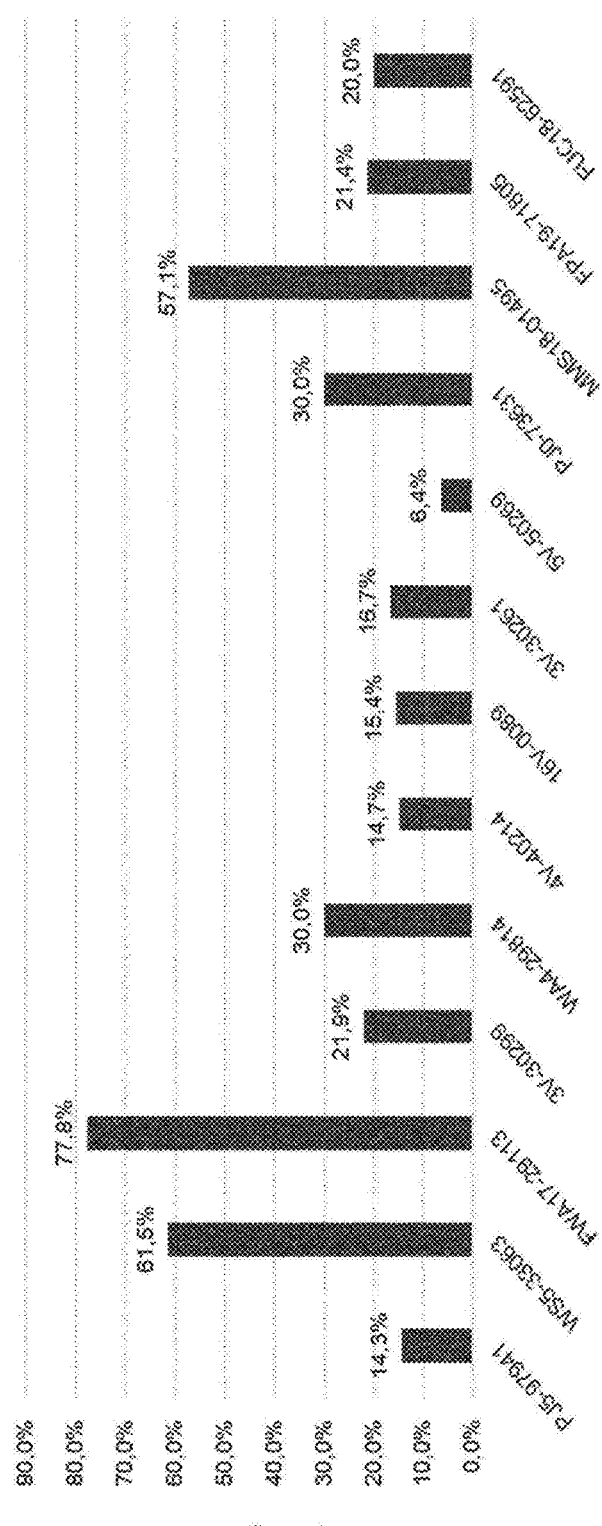
FIG. 29 shows how different boosters enable highly efficient genome editing directly in maize recalcitrant elites.

Example 14: A Toolbox of Different KWS RBPs Enable Highly Efficient Genome Editing Directly in Maize Recalcitrant Elites (Table 6; FIG. 29)

To examine robustness and genotype-independence of using regeneration boosters as a "dual selection" for rapid regeneration and genome editing in maize, 13 additional maize recalcitrant elites were tested.

The workflow was as described in Example 6. For immature embryo isolation, osmotic treatment, and bombardment, please see the description in Example 1. Specifically, genome editing constructs pGEP837 (SEQ ID NO: 52, FIG. 1) and pGEP842 (SEQ ID NO_53, FIG. 2) were co-bombarded with the different boosters as indicated into the immature embryos of elite 4V-40290 by particle bombardment. For each bombardment (shot), 100 ng of plasmid pGEP837 and 150 ng of plasmid pGEP842 were co-coated with 100 ng each of different boost constructs onto 100 μg of 0.4 μm gold particles using calcium-spermidine method. Three bombardments (shots) per sample plate were performed. The bombarded embryos were transformed onto the embryogenic callus induction medium 16-20 hours after bombardment.

For plant regeneration, and genome editing SDN-1 screen and conformation in regenerated T0 plants please see Example 5 and Example 9.

An average genome editing SDN-1 efficiency per regenerated plants with a toolbox of different boosters for the 13 maize recalcitrant elites is list in Table 6, and also demonstrated in FIG. 29. The results further exhibit that the boosters promote cell regeneration and genome editing in maize elites and offer a positive selection for the regeneration of transformed cells. A toolbox of different boosters for highly efficient genome editing in maize recalcitrant elites was developed.

TABLE 6

Different boosters enable highly efficient genome editing in directly in maize recalcitrant elites

| Elite ID | Regen plant | Bi-SDN-1 | Mono-SDN-1 | Total SDN-1 | % SDN-1 |
|---|---|---|---|---|---|
| PJ5-97941 | 56 | 7 | 1 | 8 | 14.3% |
| WS5-33063 | 13 | 6 | 2 | 8 | 61.5% |
| FWA17-29113 | 9 | 6 | 1 | 7 | 77.8% |

TABLE 6-continued

Different boosters enable highly efficient genome editing in directly in maize recalcitrant elites

| Elite ID | Regen plant | Bi-SDN-1 | Mono-SDN-1 | Total SDN-1 | % SDN-1 |
|---|---|---|---|---|---|
| 3V-30299 | 32 | 5 | 2 | 7 | 21.9% |
| WA4-29814 | 10 | 3 | 0 | 3 | 30.0% |
| 4V-40214 | 34 | 3 | 2 | 5 | 14.7% |
| 16V-0089 | 13 | 0 | 2 | 2 | 15.4% |
| 3V-30261 | 36 | 4 | 2 | 6 | 16.7% |
| 5V-50269 | 78 | 3 | 2 | 5 | 6.4% |
| PJ0-73631 | 63 | 13 | 6 | 19 | 30.0% |
| MMS18-01495 | 7 | 4 | 0 | 4 | 57.1% |
| FPA19-71805 | 14 | 0 | 3 | 3 | 21.4% |
| FUC18-62591 | 25 | 3 | 2 | 5 | 20.0% |

Example 15: A Toolbox of Different KWS RBPs Enable Highly Efficient Genome Editing with Single-Cell Origin Directly in Maize Recalcitrant Elites (Table 7)

Without a conventional selection for isolating and purifying the genetic modified cells during the regeneration chimeras may be an issue in the regenerated T0 plants. To address this matter the edited T0 events were analyzed by Sanger sequencing trace decomposition analysis of genome editing. The edited T0 events were generated from the co-bombardment of genome editing constructs of pGEP837 (SEQ ID NO: 52) and pGEP842 (SEQ ID NO: 53) with different boosters. For the workflow and methods to generate the T0 edited plants please see the descriptions in Examples above. The results revealed the majority of the edited $T_0$ plants containing one or two edits, suggesting a mono-allelic or bi-allelic SDN1 event in the $T_0$ plants and the $T_0$ plants are likely regenerated from a single edited cell (the representative results were showed in Table 7).

TABLE 7

The representative results from sanger sequencing trace decomposition analysis of genome editing SDN-1 T0 events in maize

| SDN-1 ID | Genotype | % event 1 | event 1 detail | % event 2 | Event 2 | % event 3 | Event 3 | R square |
|---|---|---|---|---|---|---|---|---|
| xxxx008-T479 | A188 | 46.362 | 2 bp deletion | 44.435 | wild type | 1.579 | 1 bp deletion | 0.960619 |
| xxxx008-T827 | A188 | 45.57 | wild type | 43.69 | 5 bp deletion | 2.248 | 5 bp deletion | 0.960294 |
| xxxx011-T052 | A188 | 42.967 | wild type | 41.21 | 20 bp deletion | 6.149 | 20 bp deletion | 0.955375 |
| xxxx011-T1163 | A188 | 44.017 | wild type | 43.621 | 3 bp deletion | 4.323 | 3 bp deletion | 0.964498 |
| xxxx011-T1567 | A188 | 42.834 | wild type | 42.457 | 2 bp deletion | 4.133 | 3 bp deletion | 0.964653 |
| xxxx011-T695 | A188 | 45.508 | 5 bp deletion | 44.05 | 14 bp deletion | 2.831 | 14 bp deletion | 0.954624 |
| xxxx011-T731 | A188 | 43.83 | 4 bp deletion | 42.935 | 6 bp deletion | 3.247 | 6 bp deletion | 0.966725 |
| xxxx011-T757 | A188 | 95.243 | 10 bp deletion | 1.25 | 10 bp deletion | 10.687 | 10 bp deletion | 0.996223 |

TABLE 7-continued

The representative results from sanger sequencing trace decomposition
analysis of genome editing SDN-1 T0 events in maize

| SDN-1 ID | Genotype | % event 1 | event 1 detail | % event 2 | Event 2 | % event 3 | Event 3 | R square |
|---|---|---|---|---|---|---|---|---|
| xxxx011-T850 | A188 | 44.982 | 9 bp deletion | 43.588 | 23 bp deletion | 1.68 | 9 bp deletion | 0.951346 |
| xxxx021-T363 | A188 | 44.102 | 5 bp deletion | 42.323 | 7 bp deletion | 7.132 | 7 bp deletion | 0.962038 |
| xx0245-T-358 | A188 | 98.595 | 5 bp deletion | 0.784 | 5 bp deletion | 0.113 | 7 bp deletion | 0.998456 |
| xx0245-T-379 | A188 | 44.611 | 5 bp deletion | 33.949 | 34 bp deletion | 8.401 | 34 bp deletion | 0.940991 |
| xxxx016-T018 | 4V-40290 | 62.07 | 8 bp deletion | 32.566 | 8 bp deletion | 1.342 | 28 bp deletion | 0.958118 |
| xxxx016-T028 | 4V-40290 | 94.437 | 5 bp deletion | 0.799 | 25 bp deletion | 0.72 | 69 bp deletion | 0.956733 |
| xxxx016-T106 | 4V-40290 | 49.409 | 3 bp deletion | 41.984 | 2 bp deletion | 1.124 | 2 bp deletion | 0.955874 |
| xxxxx0254-T009 | PJ5-97941 | 39.42 | 29 bp deletion | 36.296 | 11 bp deletion | 6.505 | 11 bp deletion | 0.949311 |
| xxxxx0254-T011 | PJ5-97941 | 39.327 | 12 bp deletion | 35.518 | 8 bp deletion | 5.555 | 8 bp deletion | 0.958839 |
| xxxxx0254-T016 | PJ5-97941 | 43.116 | 8 bp deletion | 39.967 | 6 bp deletion | 4.636 | 8 bp deletion | 0.958694 |
| xxxxx0254-T017 | PJ5-97941 | 44.7 | 5 bp deletion | 44.557 | wild type | 2.476 | 5 bp deletion | 0.956408 |
| xxxxx0254-T032 | PJ5-97941 | 40.917 | 2 bp deletion | 19.311 | 9 bp deletion | 12.967 | 9 bp deletion | 0.928388 |
| xxxxx0254-T037 | PJ5-97941 | 64.819 | 34 bp deletion | 8.279 | 34 bp deletion | 8.223 | 34 bp deletion | 0.949046 |
| xx0255-T005 | WS5-33063 | 46.88 | wild type | 36.695 | 7 bp deletion | 7.569 | 7 bp deletion | 0.954609 |
| xx0255-T006 | WS5-33063 | 44.519 | 7 bp deletion | 18.525 | 12 bp deletion | 18.215 | 12 bp deletion | 0.964447 |

Figure 30:
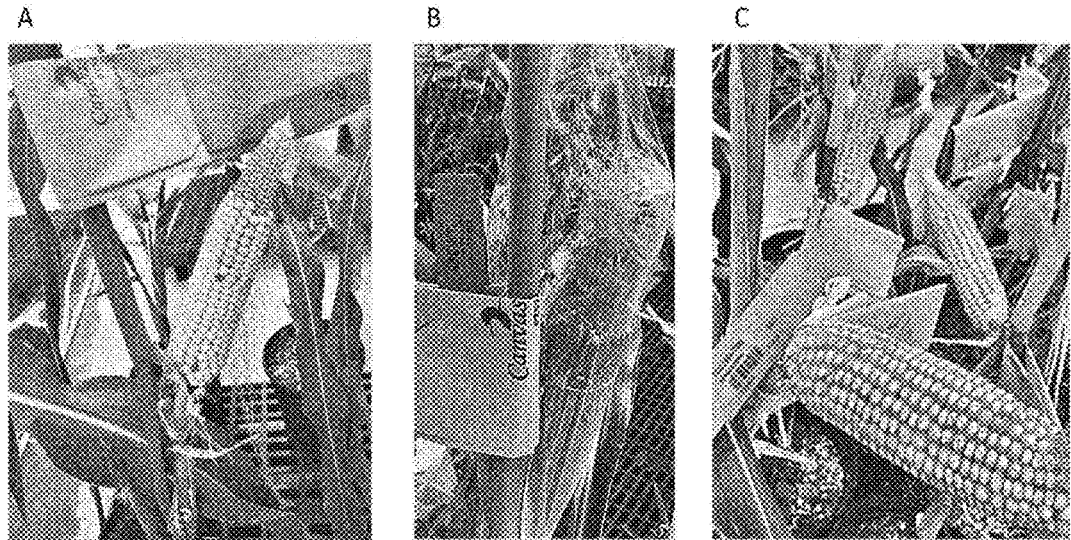
FIG. 30 shows the edited T0 maize elite plants in green house. The regenerated T0 plants from maize recalcitrant elite 4V-4071 (A), 2V-20195 (B), or 4V-40290 (C).

Example 16: The Edited $T_0$ Plants are Normal, Fertile, and Transgene-Free (FIG. 30)

The edited $T_0$ plants were transferred into soil and growing in greenhouse for genotyping, phenotyping, and $T_1$ seed production. The foreign DNA integration were analyzed by qPCR and WGS. $T_0$ plants are general normal and fertile (FIG. 30). There were only six $T_0$ plants showing foreign DNA integration from an analysis of total 642 regenerated $T_0$ plants, while no foreign DNA integration was detected from an analysis of 1471 $T_1$ progeny derived from 35 independent edited lines, and up to 99% of the edited T0 plants are transgene-free.

Example 17: The edits are full inheritable from T0 to T1 progeny (FIG. 31; Table 8)

Figure 31:
FIG. 31 shows the T1 progeny of maize recalcitrant elite 4V-4071 growing in green house.

T1 seeds are produced by selfing, which requires viable male and female gametes from T0 plants. T1 seed germination and growth in green house were normal (FIG. 31). Editing segregation in T1 progeny was analyzed by Tagman qPCR. A full match of the actual segregation of an editing event in the T1 progeny to the expected Mendel's Law of Segregation for a mono- or bi-allelic event was observed (Table 8). These results suggest that the edits are full transmittable/inheritable from T0 to T1 progeny, and also further support the idea of that the T0 plants are derived from single edited cells.

TABLE 8

The representative results from genome editing
SDN-1 segregation analysis in T1 progeny in the maize elites

| Genotype | Event | SDN-1 in T0 | SDN-1 in T1 Total (WT:Mono-:Bi-) |
|---|---|---|---|
| 4V-40171 | xxx223-T-050 | Bi-allelic | 20  (0:0:20) |
| 4V-40171 | xxx230-T-088 | Bi-allelic | 20  (0:0:20) |
| 4V-40171 | xxx232-T-077 | Mono-alleic | 20  (5:8:7) |
| 4V-40171 | xxx232-T-103 | Mono-alleic | 19  (1:13:5) |
| 2V-20195 | xxx231-T-006 | Mono-alleic | 16  (2:10:4) |
| 2V-20195 | xxx231-T-071 | Mono-alleic | 15  (4:7:4) |
| 2V-20195 | xxx231-T-082 | Bi-allelic | 18  (0:0:18) |
| 2V-20195 | xxx231-T-113 | Bi-allelic | 17  (0:0:17) |
| 4V-40290 | xxxD004-T016 | Bi-allelic | 20  (0:0:20) |
| 4V-40290 | xxxD004-T031 | Bi-allelic | 20  (0:0:20) |
| 4V-40290 | xxxD004-T086 | Mono-llelic | 19  (3:10:6) |
| 4V-40290 | xxxD006-T085 | Mono-allelic | 19  (7:8:4) |
| PJ5-97941 | xxx254-T-009 | Bi-allelic | 8  (0:0:8) |
| PJ5-97941 | xxx254-T-016 | Bi-allelic | 19  (0:0:19) |
| PJ5-97941 | xxx254-T-017 | monoallelic | 9  (2:3:3) |
| PJ5-97941 | xxx254-T-041 | Biallelic (back-cross to WT) | 7  (3:4:0) |

Figure 34:
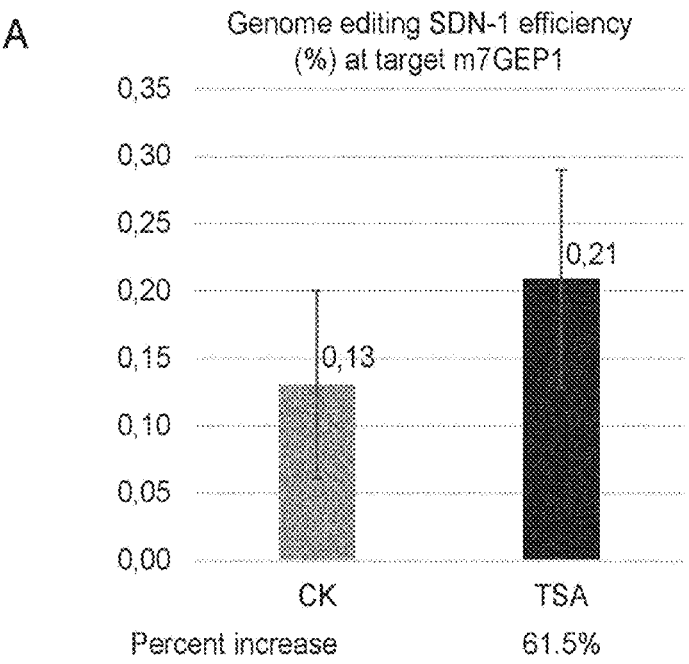
FIG. 34: Trichostatin A (TSA) promotes genome editing SDN-1 efficiency 48 hours after co-introduced with the editing plasmids (n=6). A: shows SDN-1 efficiencies at the CRISPR target m7GEP1 and B shows the SDN-1 efficiencies at target m7GP22. CK: the immature embryos were bombarded with the editing constructs only (100 ng of plasmid pGEP1054 and 150 ng of plasmid pGEP842 in A or 100 ng of plasmid pGEP1054 and 150 ng of plasmid pGEP1067 in B). TSA: the immature embryos were co-bombarded with the editing plasmids and 15 ng of TSA. Error bar=standard deviation. The SDN-1 were analyzed by Taqman ddPCR.
Figure 34:
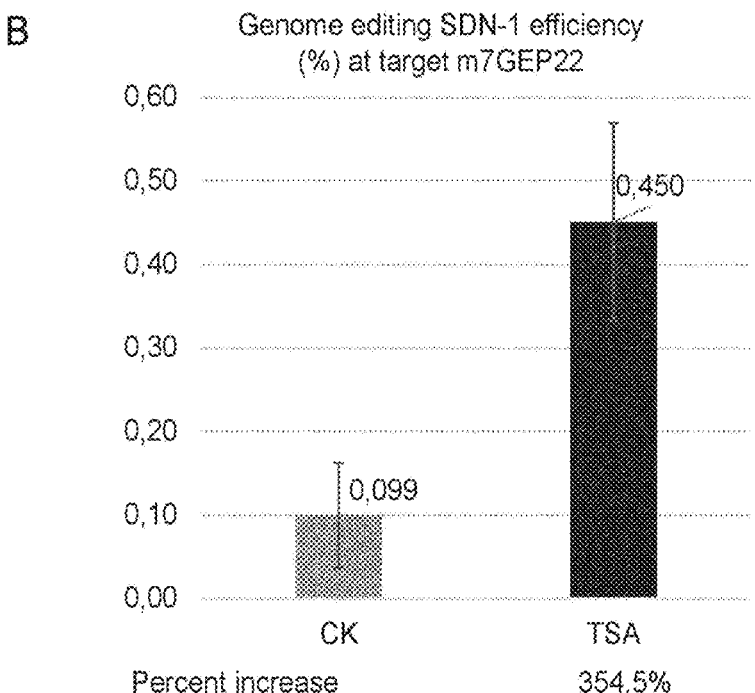

Example 18: Co-Delivery of Trichostatin a (TSA) with Genome Editing Constructs The co-delivery by microprojectile bombardment increased genome editing SDN-1 efficiency in corn A188 immature embryos (FIG. 34).

Procedure:

For immature embryo isolation, bombardment, and embryogenic callus induction post bombardment, please see the description in Example 1.

Figure 32:
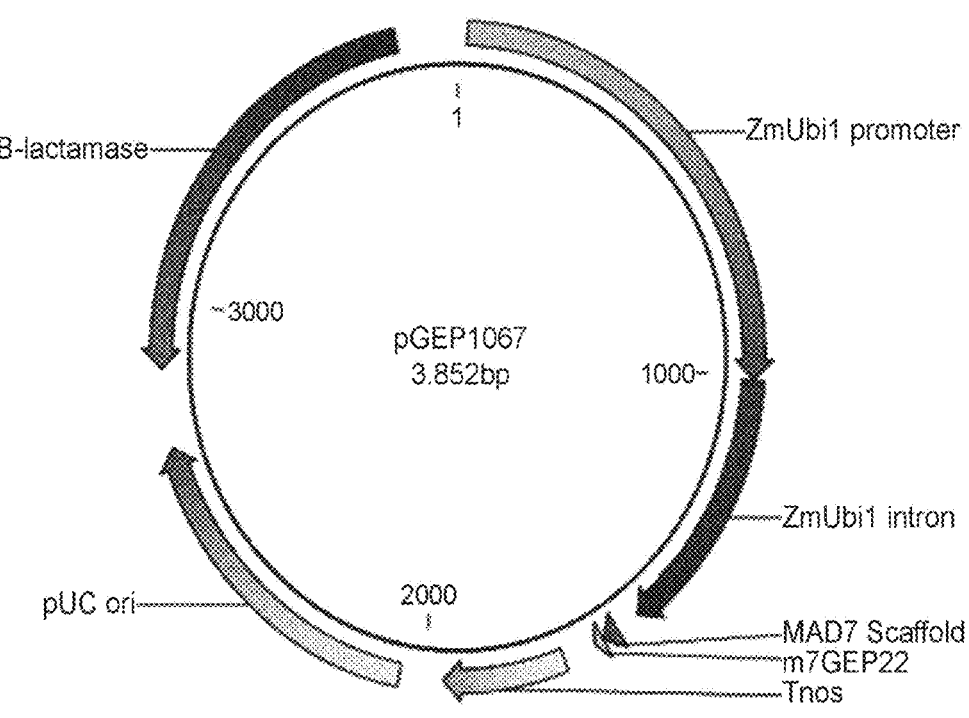
FIG. 32 shows a genome editing guide RNA construct pGEP1067 map. m7GEP22 defines the crRNA, which target to maize HMG13 gene. ZmUbi1 defines the promoter and intron from maize Ubiquitin 1 gene. Tnos defines the nos terminator.

The amounts of TSA used for a bombardment with 100 μg of gold particles (approximately, $4.0$-$5.0 \times 10^7$ gold particles size of 0.6 micron) is 15 ng. Specifically, the plasmid DNA and TSA were co-coated onto gold particles for bombardment as follows. For 10 shots, 100 microlite (μl) of 10 mg/ml 0.6 μm gold particle in 50% (v/v) glycerol particle stock solution (1.0 mg of the gold particles in total for 10 shots, and 100 μg per shot) was pipetted into a clear low-retention microcentrifuge tube. Sonicate for 15 seconds to suspend the gold particles. While vortex at a low speed, add the following in order:

1.0 μg of pGEP1054 (FIG. 15), 1.5 μg of pGEP842 (FIG. 2) or pGEP1067 (FIG. 32)

100 μl of 2.5 M CaCl₂ (pre-cold on ice)

40 μl of 0.1 M cold spermidine

Close the lid and vortex the tube for 5 minutes at room temperature and spin down the DNA-coated gold particles. After washing in 1000 μl of 100% ethanol (pre-cold at −20° C.) for two times, the pellet was resuspended in 120 μl of 100% ethanol. Finally, 150 ng of TSA was added into the resuspended gold particle solution carefully. While vertexing at a low speed, pipet 10 μl of TSA co-coated gold particles with a wide open 20 μl tip from the tube onto the center of the macrocarrier evenly. Since the particles tend to form clumps at this point, get the gold particles onto the macrocarriers as soon as possible. Brief air dry in a clear laminar hood.

Bombardment was conducted using a Bio-Rad PDS-1000/He particle gun. The bombardment conditions are: 28-30 mm/Hg vacuum, 450 psi rupture disc, 6 mm gap distance, the specimen platform is in the second position from the bottom in the chamber at a distance of 60 mm, and three shots per sample plate. After bombardment the embryos were remained on the osmotic plate for another 16 hours, and then removed onto an embryogenic callus induction medium plate (N6_5Ag). 48 hours after bombardment, the bombarded embryos were sampled for DNA extraction and genome editing SDN-1 analysis by Taqman ddPCR.

Co-delivery of 15 ng TSA and genome editing components in corn immature embryos by microprojectile bombardment significantly improves the genome editing SDN-1 efficiency at two CRISPR target sites from 6 repeats. Compared to the control without TSA (CK), a 61.5% (FIG. 34 A) and 354.5% (FIG. 34 B) increase in the SDN-1 efficiency was detected at the target m7GEP1 and m7GEP22, respectively. These results clearly demonstrate the epigenetically regulating chemical, specifically the histone deacetylase inhibitor (HDACI) trichostatin A (TSA) enhances genome editing SDN-1 efficiency, which might be achieved through its roles in relaxing chromatin and increasing the target accessibility.

The invention claimed is:

1. A method for plant genome modification of at least one genomic target sequence, for obtaining at least one modified cell wherein the method comprises the following steps:

(a) providing at least one plant cell or a single plant cell;

(b) introducing into the at least one plant cell or the single plant cell:

(i) at least one genome modification system comprising at least one nucleic acid guided nuclease, nickase or an inactivated nuclease, or a sequence encoding the same, and optionally at least one guide molecule, or a sequence encoding the same;

(ii) at least one regeneration booster, or a sequence encoding the same and/or at least one epigenetically regulating chemical, wherein the at least one regeneration booster is transiently present, transiently active or transiently expressed in the plant cell;

(iii) and, optionally at least one repair template, or a sequence encoding the same; and (c) cultivating the at least one plant cell or the single plant cell under conditions allowing the expression and/or assembly and/or activation of the at least one genome modification system, and, optionally of the at least one regeneration booster, and optionally of the at least one guide molecule and/or optionally of the at least one repair template; and (d) obtaining at least one modified plant cell; and/or (e) obtaining at least one plant tissue, organ, plant or seed regenerated from the at least one modified cell; and (f) optionally: screening for at least one plant tissue, organ, plant or seed regenerated from the at least one modified cell in the T0 and/or T1 generation carrying a desired targeted modification, wherein the at least one regeneration booster comprises at least one regeneration booster protein (RBP), wherein the at least one RBP comprises the amino acid sequence of SEQ ID NO: 36, or wherein the at least one RBP is encoded by the nucleic acid sequence of SEQ ID NO: 24, or a cognate codon-optimized sequence.

2. The method of claim 1, wherein steps (i) and (ii) take place simultaneously or subsequently, for promoting plant cell proliferation and/or to assist in a targeted modification of at least one genomic target sequence.

3. The method of claim 1, wherein at least one regeneration booster is introduced in step (ii) and (a) the regeneration booster(s) promote plant cell proliferation and/or assist in the targeted modification and/or provide a positive selection for at least one transiently transformed cell for genome modification and/or for regeneration into at least one modified plant, and/or (b) the regeneration booster(s) suppress plant cell differentiation if the cell is stably transformed and provide a negative selection for at least one stably transformed cell for regeneration into one transgenic plant, and/or (c) the regeneration booster(s) provide a dual selection according to (a) and (b) for at least one transformed cell.

4. The method of claim 1, wherein the at least one plant cell is a cell of a zygotic or somatic embryo or meristem or wherein the single plant cell is a diploid cell or a haploid cell.

5. The method of claim 1, wherein the at least one regeneration booster further comprises at least one PLETHORA (PLT), wherein the at least one PLT comprises the amino acid sequence of SEQ ID NO: 30, or wherein the at least one PLT is encoded by the nucleic acid sequence of SEQ ID NO: 18 or a cognate codon-optimized sequence.

6. The method of claim 1, wherein at least one further regeneration booster is introduced, wherein the further regeneration booster, or the sequence encoding the same comprises babyboom (BBM), WUSCHEL (WUS), WUSCHEL-related homeobox (WOX), growth-regulating factor (GRF), and leafy cotyledon (LEC), or a variant thereof or wherein the further regeneration booster is selected from RBP1 to RBP8, and wherein the at least one further regeneration booster is different from the at least one regeneration booster.

7. The method of claim 1, wherein at least one epigenetically regulating chemical is introduced in step ii) and wherein the at least one epigenetically regulating chemical is a histone deacetylase inhibitor (HDACI), trichostatin A (TSA) or a TSA like chemical.

8. The method of claim 1, wherein the at least one genome modification system, and the at least one regeneration booster, or the sequences encoding the same and/or the at least one epigenetically regulating chemical, are introduced into the cell by transformation or transfection mediated by biolistic bombardment, *Agrobacterium*-mediated transformation, micro- or nanoparticle delivery, or by chemical transfection, or a combination thereof, wherein when the at least one genome modification system, and the at least one regeneration booster and/or the at least one epigenetically regulating chemical are introduced by biolistic bombardment, the biolistic bombardment comprises a step of osmotic treatment before and/or after bombardment.

9. The method of claim 1, wherein the at least nucleic acid guided nuclease, nickase or an inactivated nuclease, or a sequence encoding the same, is selected from the group consisting of a CRISPR/MAD7 system, a CRISPR/Cfp1 system, a CRISPR/MAD2 system, a CRISPR/Cas9 system, a CRISPR/CasX system, a CRISPR/CasY system, a CRISPR/Cas13 system, or a CRISPR/Csm system, a zinc finger nuclease system, a transcription activator-like nuclease system, and a meganuclease system, or any combination or variant thereof.

10. The method of claim 1, wherein the at least one genome modification system further comprises at least one reverse transcriptase and/or at least one cytidine or adenine deaminase, wherein the at least one cytidine or adenine deaminase is independently selected from an apolipoprotein B mRNA-editing complex (APOBEC) family deaminase, an activation-induced cytidine deaminase (AID), an ACF1/ASE deaminase, an ADAT family deaminase, an ADAR2 deaminase, or a PmCDA1 deaminase, a TadA derived deaminase, and/or a transposon, or a sequence encoding the aforementioned at least one enzyme, or any combination or variant thereof.

11. The method of claim 1, wherein the at least one genome modification system comprises at least one repair template, and wherein the at least one repair template comprises or encodes a double- and/or single-stranded nucleic acid sequence.

12. The method of claim 11, wherein the at least one repair template comprises symmetric or asymmetric homology arms and/or wherein the at least one repair template comprises at least one chemically modified base and/or backbone.

13. The method of claim 1, wherein the at least one genome modification system, and optionally the at least one repair template, or the respective sequences encoding the same, are introduced transiently or stably, or as a combination thereof.

14. A method of using a first regeneration booster or a combination of regeneration boosters, in a method for targeted plant genome modification according to claim 1, to (a) promote plant cell proliferation and/or assist in the targeted modification and/or provide a positive selection for at least one transiently transformed cell for genome modification and/or for regeneration into at least one modified plant, and/or (b) suppress plant cell differentiation if the cell is stably transformed and provide a negative selection for at least one stably transformed cell for regeneration into one transgenic plant, and/or (c) provide a dual selection according to (a) and (b) for at least one transformed cell, wherein the first regeneration booster or combination of regeneration boosters comprise:

(i) at least one RBP, wherein the at least one RBP comprises the amino acid sequence of SEQ ID NO: 36, or wherein the at least one RBP is encoded by the nucleic acid sequence SEQ ID NO: 24, or a cognate codon-optimized sequence, and/or (ii) at least one PLT, wherein the at least one PLT comprises the amino acid sequence of SEQ ID NO: 30, or wherein the at least one PLT is encoded by the nucleic acid sequence of SEQ ID NO: 18, or a cognate codon-optimized sequence, and/or (iii) at least one further regeneration booster, wherein the further regeneration booster, or the sequence encoding the same comprises BBM, WUS, WOX, GRF, LEC, or a variant thereof or wherein the further regeneration booster selected from RBP1 to RBP8, wherein the further regeneration booster is different from the first regeneration booster.

15. A method for selecting a modified plant cell, plant tissue, organ, plant or seed, wherein the method comprises the steps (a) to (c) as defined in claim 1 and further comprises the step:

(d1) screening for at least one plant cell carrying a targeted modification, or (d2) screening for at least one plant tissue, organ, plant or seed regenerated from at least one modified plant cell in the T0 or T1 generation carrying a desired targeted modification.

16. A method for regenerating a plant tissue, organ or plant from at least one plant cell or a single plant cell, wherein the method comprises:

(i) introducing into the at least one plant cell or the single plant cell at least one regeneration booster, or a sequence encoding the same, wherein the at least one regeneration booster is transiently present, transiently active or transiently expressed in the plant cell, and (ii) regenerating a plant tissue, organ or plant from at least one plant cell or the single plant cell, wherein the at least one regeneration booster comprises:

(a) at least one RBP, wherein the at least one RBP comprises the amino acid sequence of SEQ ID NO: 36, or wherein the at least one RBP is encoded by the sequence of SEQ ID NO: 24, or a cognate codon-optimized sequence, and/or (b) at least one PLT, wherein the at least one PLT comprises the amino acid sequence of SEQ ID NO: 30, or wherein the at least one PLT is encoded by the sequence of SEQ ID NO: 18, or a cognate codon-optimized sequence, and/or (c) at least one further regeneration booster, wherein the further regeneration booster, or the sequence encoding the same is selected from BBM, WUS, WOX, GRF, LEC, or a variant thereof or wherein the further regeneration booster selected from RBP1 to RBP8, wherein the further regeneration booster is different from the first regeneration booster.

17. The method of claim 16, wherein the at least one plant cell is an immature embryo cell or meristematic cell, in particular a cell of a zygotic or somatic embryo or meristem wherein the single plant cell is a diploid cell or a haploid cell.

18. The method of claim 17, wherein the single plant cell is a haploid microspore.

\* \* \* \* \*